US008108046B2

(12) United States Patent
Giftakis et al.

(10) Patent No.: US 8,108,046 B2
(45) Date of Patent: Jan. 31, 2012

(54) SYSTEM AND METHOD FOR USING CARDIAC EVENTS TO TRIGGER THERAPY FOR TREATING NERVOUS SYSTEM DISORDERS

(75) Inventors: Jonathon E. Giftakis, Maple Grove, MN (US); Nina M. Graves, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 1094 days.

(21) Appl. No.: 11/766,886

(22) Filed: Jun. 22, 2007

(65) Prior Publication Data
US 2007/0260289 A1 Nov. 8, 2007

Related U.S. Application Data

(63) Continuation-in-part of application No. 11/380,462, filed on Apr. 27, 2006, which is a continuation-in-part of application No. 11/311,043, filed on Dec. 19, 2005, now Pat. No. 7,865,244, which is a continuation-in-part of application No. 11/311,200, filed on Dec. 19, 2005, and a continuation-in-part of application No. 11/311,393, filed on Dec. 19, 2005, and a continuation-in-part of application No. 11/311,456, filed on Dec. 19, 2005, now Pat. No. 7,945,316.

(60) Provisional application No. 60/636,929, filed on Dec. 17, 2004.

(51) Int. Cl.
*A61N 1/00* (2006.01)
(52) U.S. Cl. .......................................... 607/45
(58) Field of Classification Search ...................... 607/45
See application file for complete search history.

(56) References Cited

U.S. PATENT DOCUMENTS

| 4,374,382 A | 2/1983 | Markowitz |
| 4,485,813 A | 12/1984 | Anderson et al. |
| 4,495,950 A | 1/1985 | Schneider |
| 4,503,857 A | 3/1985 | Boute et al. |
| 4,556,063 A | 12/1985 | Thompson et al. |
| 4,567,892 A | 2/1986 | Plicchi et al. |
| 4,596,251 A | 6/1986 | Plicchi et al. |
| 4,702,254 A | 10/1987 | Zabara |
| 4,862,144 A | 8/1989 | Tao |

(Continued)

FOREIGN PATENT DOCUMENTS
EP 0512577 11/1992
(Continued)

OTHER PUBLICATIONS

U.S. Appl. No. 11/311,200 Notice of Allowance mailed Dec. 5, 2009, 3 pgs.

(Continued)

*Primary Examiner* — Eric D. Bertram
(74) *Attorney, Agent, or Firm* — Fredrikson & Byron, PA

(57) ABSTRACT

A method of treating a neurological disorder in a patient. In some embodiments, the method includes obtaining a neurological event detection signal, obtaining a cardiac event detection signal, analyzing the timing relationships between the detected neurological and cardiac events to identify matched events, using the matched events to determine whether the cardiac event detection signal facilitates detection of neurological events, delivering a therapy to the patient in response to a cardiac event if the cardiac event detection signal is determined to facilitate detection of neurological events, and changing the therapy delivered based on sensed brain signals from the patient.

79 Claims, 57 Drawing Sheets

U.S. PATENT DOCUMENTS

| | | |
|---|---|---|
| 4,867,164 A | 9/1989 | Zabara |
| 4,903,701 A | 2/1990 | Moore et al. |
| 4,987,897 A | 1/1991 | Funke |
| 5,003,976 A | 4/1991 | Alt |
| 5,025,807 A | 6/1991 | Zabara |
| 5,052,388 A | 10/1991 | Sivula et al. |
| 5,113,859 A | 5/1992 | Funke |
| 5,127,404 A | 7/1992 | Wyborny et al. |
| 5,168,759 A | 12/1992 | Bowman |
| 5,203,326 A | 4/1993 | Collins |
| 5,271,395 A | 12/1993 | Wahlstrand et al. |
| 5,312,451 A | 5/1994 | Limousin et al. |
| 5,314,430 A | 5/1994 | Bardy |
| 5,336,244 A | 8/1994 | Weijand |
| 5,354,316 A | 10/1994 | Keimel |
| 5,354,318 A | 10/1994 | Taepke |
| 5,409,009 A | 4/1995 | Olson |
| 5,509,927 A | 4/1996 | Epstein et al. |
| 5,545,186 A | 8/1996 | Olson et al. |
| 5,554,177 A | 9/1996 | Kievel et al. |
| 5,560,368 A | 10/1996 | Berger |
| 5,562,711 A | 10/1996 | Yerich et al. |
| 5,626,622 A | 5/1997 | Cooper |
| 5,645,068 A | 7/1997 | Mezack et al. |
| 5,683,432 A | 11/1997 | Goedeke et al. |
| 5,684,460 A | 11/1997 | Scanlon |
| 5,713,923 A | 2/1998 | Ward et al. |
| 5,749,900 A | 5/1998 | Schroeppel et al. |
| 5,752,976 A | 5/1998 | Duffin et al. |
| 5,782,891 A | 7/1998 | Hassler et al. |
| 5,836,988 A | 11/1998 | Cooper et al. |
| 5,871,517 A | 2/1999 | Abrams |
| 5,928,272 A | 7/1999 | Adkins et al. |
| 5,987,352 A | 11/1999 | Klein et al. |
| 5,995,868 A * | 11/1999 | Dorfmeister et al. ......... 600/544 |
| 6,029,087 A | 2/2000 | Wohlgemuth |
| 6,035,233 A | 3/2000 | Schroeppel et al. |
| 6,067,473 A | 5/2000 | Greeninger et al. |
| 6,083,248 A | 7/2000 | Thompson |
| 6,115,630 A | 9/2000 | Stadler et al. |
| 6,128,526 A | 10/2000 | Stadler et al. |
| 6,134,474 A | 10/2000 | Fischell et al. |
| 6,155,267 A | 12/2000 | Nelson |
| 6,185,459 B1 | 2/2001 | Mehra et al. |
| 6,200,265 B1 | 3/2001 | Walsh et al. |
| 6,263,237 B1 | 7/2001 | Rise |
| 6,280,461 B1 | 8/2001 | Glegyak et al. |
| 6,337,997 B1 | 1/2002 | Rise |
| 6,341,236 B1 | 1/2002 | Osorio et al. |
| 6,353,754 B1 | 3/2002 | Fischell et al. |
| 6,360,122 B1 | 3/2002 | Fischell et al. |
| 6,363,274 B1 | 3/2002 | Scalisi et al. |
| 6,366,813 B1 | 4/2002 | DiLorenzo |
| 6,415,174 B1 | 7/2002 | Bebehani |
| 6,427,086 B1 | 7/2002 | Fischell et al. |
| 6,463,328 B1 | 10/2002 | John |
| 6,466,822 B1 | 10/2002 | Pless |
| 6,473,639 B1 | 10/2002 | Fischell et al. |
| 6,480,743 B1 | 11/2002 | Kirkpatrick et al. |
| 6,496,175 B1 | 12/2002 | Fukuo |
| 6,496,715 B1 | 12/2002 | Lee et al. |
| 6,505,067 B1 | 1/2003 | Lee et al. |
| 6,512,940 B1 | 1/2003 | Brabec et al. |
| 6,512,949 B1 | 1/2003 | Combs et al. |
| 6,522,915 B1 | 2/2003 | Ceballos et al. |
| 6,549,804 B1 | 4/2003 | Osorio et al. |
| 6,556,859 B1 | 4/2003 | Wohlgemuth et al. |
| 6,572,542 B1 | 6/2003 | Houben et al. |
| 6,587,727 B2 | 7/2003 | Osorio et al. |
| 6,622,036 B1 | 9/2003 | Suffin |
| 6,647,292 B1 | 11/2003 | Bardy et al. |
| 6,650,938 B2 | 11/2003 | Boute |
| 6,656,125 B2 | 12/2003 | Misczynski |
| 6,671,555 B2 | 12/2003 | Gielen et al. |
| 6,671,556 B2 | 12/2003 | Osorio et al. |
| 6,719,701 B2 | 4/2004 | Lade |
| 6,721,599 B2 | 4/2004 | De Vries |
| 6,745,076 B2 | 6/2004 | Wohlgemuth et al. |
| 6,920,357 B2 | 7/2005 | Osorio et al. |
| 6,934,580 B1 | 8/2005 | Osorio et al. |
| 6,961,618 B2 | 11/2005 | Osorio et al. |
| 7,103,412 B1 | 9/2006 | Kroll |
| 7,146,218 B2 | 12/2006 | Esteller et al. |
| 7,162,304 B1 | 1/2007 | Bradley |
| 7,174,206 B2 | 2/2007 | Frei et al. |
| 7,177,674 B2 | 2/2007 | Echauz et al. |
| 7,207,948 B2 | 4/2007 | Coyle |
| 7,242,983 B2 | 7/2007 | Frei et al. |
| 7,324,845 B2 | 1/2008 | Mietus |
| 2001/0051819 A1 | 12/2001 | Fischell |
| 2002/0072778 A1 | 6/2002 | Guck |
| 2002/0099412 A1 | 7/2002 | Fischell et al. |
| 2002/0107553 A1 | 8/2002 | Hill et al. |
| 2002/0169485 A1 | 11/2002 | Pless et al. |
| 2003/0004548 A1 | 1/2003 | Warkentin |
| 2003/0073917 A1 | 4/2003 | Echauz et al. |
| 2003/0083716 A1 | 5/2003 | Nicolelis |
| 2003/0149457 A1 | 8/2003 | Tcheng et al. |
| 2003/0195574 A1 | 10/2003 | Osorio et al. |
| 2003/0195588 A1 | 10/2003 | Fischell et al. |
| 2003/0236474 A1 | 12/2003 | Singh |
| 2004/0006264 A1 | 1/2004 | Mojarradi et al. |
| 2004/0102816 A1 | 5/2004 | Mazar |
| 2004/0116974 A1 | 6/2004 | Obel |
| 2004/0133119 A1 | 7/2004 | Osorio et al. |
| 2004/0133120 A1 | 7/2004 | Frei et al. |
| 2004/0133248 A1 | 7/2004 | Frei et al. |
| 2004/0133390 A1 | 7/2004 | Osorio et al. |
| 2004/0138516 A1 | 7/2004 | Osorio et al. |
| 2004/0138517 A1 | 7/2004 | Osorio et al. |
| 2004/0138518 A1 | 7/2004 | Rise et al. |
| 2004/0138536 A1 | 7/2004 | Frei et al. |
| 2004/0138580 A1 | 7/2004 | Frei et al. |
| 2004/0138581 A1 | 7/2004 | Frei et al. |
| 2004/0138647 A1 | 7/2004 | Osorio et al. |
| 2004/0138711 A1 | 7/2004 | Osorio et al. |
| 2004/0138721 A1 | 7/2004 | Osorio et al. |
| 2004/0152958 A1 | 8/2004 | Frei et al. |
| 2004/0158119 A1 | 8/2004 | Osorio et al. |
| 2004/0176817 A1 | 9/2004 | Wahlstrand et al. |
| 2004/0181263 A1 | 9/2004 | Balzer et al. |
| 2004/0199482 A1 | 10/2004 | Wilson |
| 2004/0215240 A1 | 10/2004 | Lovett |
| 2004/0230105 A1 | 11/2004 | Geva et al. |
| 2004/0267152 A1 | 12/2004 | Pineda |
| 2005/0010265 A1 | 1/2005 | Baru Fassio et al. |
| 2005/0081847 A1 | 4/2005 | Lee et al. |
| 2005/0115561 A1 | 6/2005 | Stahmann et al. |
| 2005/0197590 A1 | 9/2005 | Osorio et al. |
| 2005/0216071 A1 | 9/2005 | Devlin et al. |
| 2006/0058856 A1 | 3/2006 | Morell |
| 2006/0094970 A1 | 5/2006 | Drew |
| 2006/0094972 A1 | 5/2006 | Drew |
| 2006/0135877 A1 | 6/2006 | Giftakis et al. |
| 2006/0135881 A1 | 6/2006 | Giftakis et al. |
| 2006/0136006 A1 | 6/2006 | Giftakis et al. |
| 2006/0195144 A1 | 8/2006 | Giftakis et al. |
| 2006/0206159 A1 | 9/2006 | Moffitt |
| 2006/0224067 A1 | 10/2006 | Giftakis et al. |
| 2006/0241725 A1 | 10/2006 | Libbus et al. |
| 2007/0100392 A1 | 5/2007 | Maschino |
| 2007/0161919 A1 | 7/2007 | DiLorenzo |
| 2007/0238939 A1 | 10/2007 | Giftakis |
| 2007/0239054 A1 | 10/2007 | Giftakis |
| 2007/0239060 A1 | 10/2007 | Giftakis |
| 2007/0239230 A1 | 10/2007 | Giftakis |
| 2007/0260147 A1 | 11/2007 | Giftakis |
| 2007/0260286 A1 | 11/2007 | Giftakis |
| 2007/0265536 A1 | 11/2007 | Giftakis |
| 2007/0265677 A1 | 11/2007 | Giftakis |
| 2008/0033490 A1 | 2/2008 | Giftakis |
| 2008/0269842 A1 | 10/2008 | Giftakis |

FOREIGN PATENT DOCUMENTS

| | | |
|---|---|---|
| WO | 02/34332 | 5/2002 |
| WO | WO 02/36003 | 5/2002 |

| | | |
|---|---|---|
| WO | WO 02/49500 | 6/2002 |
| WO | 2004/091720 | 10/2004 |
| WO | WO 9726823 | 8/2008 |

OTHER PUBLICATIONS

U.S. Appl. No. 11/311,043 Notice of Allowance mailed Dec. 21, 2009, 1 pgs.
U.S. Appl. No. 11/796,576 Office Action mailed Jan. 8, 2010, 7 pgs.
U.S. Appl. No. 11/796,575 Office Action mailed Mar. 12, 2010, 8 pgs.
U.S. Appl. No. 11/796,577 Office Action mailed Mar. 9, 2010, 8 pgs.
U.S. Appl. No. 11/380,462 Office Action mailed Mar. 15, 2010, 12 pgs.
Notification of Transmittal of the International Search and the Written Opinion, dated Jan. 7, 2008 for corresponding PCT Application No. PCT/US2007/067625 (15 pages).
U.S. Appl. No. 11/380,462 Non Final Office Action mailed Apr. 8, 2009, 13 pgs.
Vaughn, et al., "Monitoring Heart Period Variability changes During Seizures. II. Diversity and Trends", J. Epilepsy, 1996, p. 27-34, vol. 9.
Pacemaker Stops Epilepsy Deaths, Dec. 2004, BBC News World Edition.
Jones, et al., Heart Rate Responses to Selective Stimulation of Cardiac Vagal C Fibres in Anaesthetized Cats, Rats and Rabbits, 1995, pp. 203-214, J. Physiol. 489.1, London.
Asconape et al., Early Experience with Vagus Nerve Stimulation for the Treatment of Epilepsy: Cardiac Complications, No. 6.058—Abstract from American Epilepsy Society, Epilepsia, 1998, vol. 39, Supp. 6.
Kamath, et al., Neurocardiac responses to Vagoaferent Electrostimulation in Humans, 1992, pp. 1581-1687, PACE, vol. 15.
U.S. Appl. No. 10/997,540, filed Nov. 24, 2004 entitled "A Method and System for Logging Quantitative Seizure Information and Assessing Efficacy of Therapy Using Cardiac Signals".
International Search and the Written Opinion, dated May 3, 2006 for PCT Application No. PCT/US2005/045656 8 pages).
International Search and the Written Opinion, dated May 3, 2006 for PCT Application No. PCT/US2005/045648 8 pages).
International Search and the Written Opinion, dated May 8, 2006 for PCT Application No. PCT/US2005/047628 7 pages).
International Search and the Written Opinion, dated May 8, 2006 for PCT Application No. PCT/US2005/045902 8 pages).
International Search and the Written Opinion, dated May 8, 2006 for PCT Application No. PCT/US2007/067625 13 pages).
U.S. Appl. No. 11/311,200 Non Final Office Action mailed Aug. 25, 2009, 7 pgs.
U.S. Appl. No. 11/311,043 Non Final Office Action mailed Dec. 23, 2008, 8 pgs.
U.S. Appl. No. 11/311,043 Notice of Allowance mailed Aug. 10, 2009, 4 pgs.
U.S. Appl. No. 11/796,576 Non Final Office Action mailed Jun. 17, 2009, 8 pgs.
U.S. Appl. No. 11/796,382 Non Final Office Action mailed Nov. 23, 2009, 30 pgs.
U.S. Appl. No. 11/380,462 Final Office Action mailed Nov. 9, 2009, 12 pgs.
Frei MG, Osorio I. Left vagus nerve stimulation with the neurocybernetic prosthesis has complex effects on heart rate and on its variability in humans. Epilepsia. Aug. 2001;42(8):1007-1016. Presented in part at the American Epilepsy Society Annual Meetings San Francisco, CA, 1996, and San Diego, CA, 1998).
Sunderam S, Osorio I, Frei MG, Watkins III JF. Stochastic modeling and prediction of experimental seizures in sprague-dawley rats. J Clin Neurophysiol. May 2001;18(3):275-282.
Osorio I, Harrison MAF, Frei MG, Lai YC. Observations on the application of the correlation dimension and correlation integral to the prediction of seizures. J Clin Neurophysiol. May 2001;18(3):269-274.
Ingram J, Sunderam S, Frei MG, Osorio, I. Autonomic regulation during complex partial seizures: A thermographic study. Abstract; Epilepsia. 41(S7);59. Proceedings of the 54th Annual Meeting of the American Epilepsy Society, Los Angeles, CA, Dec. 1-6, 2000.

Sunderam S, Watkins III JF, Frei MG, and Osorio I. A stochastic analysis of ictal-interictal transitions during experimental seizures: Seizure duration depends on the duration of preceding ictal and interictal states. Abstract; Epilepsia. 41(S7);49. Proceedings of the 54th Annual Meeting of the American Epilepsy Society, Los Angeles, CA, Dec. 1-6, 2000.
DiTeresi CA, Thompson M, Frei MG, Sunderam S, and Osorio I. Loss of function during partial seizures: A quantitative study in humans. Abstract; Epilepsia. 41(S7);237. Proceedings of the 54th Annual Meeting of the American Epilepsy Society, Los Angeles, CA, Dec. 1-6, 2000.
Nagaraddi V, Wilkinson SB, Osorio I. The effect of one hertz stimulation on kindled seizures in rats. Abstract; Proceeding of the 54th Annual Meeting of the American Epilepsy Society, Los Angeles, CA, Dec. 1-6, 2000.
Frei MG, Davidchack R, Osorio I. Least squares acceleration filtering for estimating signal derivatives and Sharpness at extrema. IEEE. Aug. 1999; 46(8):971-977.
Osorio I, Frei MG, Wilkinson SB. Real time automated detection and quantitative analysis of seizures and short term predictions of clinical onset. Epilepsia. 1998;39(S16):615-627.
Thomas CV, Angel CA, Watkins JM, Frei MG, Bunag RD, Osorio I. Effects of vagal and sciatic stimulation on 3-MPA-induced seizures in rats. Epilepsia. 1998;39(S6):29.
Frei MG, Haas SM, Ingram JL, Osorio I. Filter design methods for improved seizure detection. Epilepsia. 1998;39 (S6):108.
Powell J, Frei MG, Davidchak R, Watkins JM, Wilkinson SB, Osorio I. Ictal tachycardia does not closely correlate with electrographic onset of ictal ECoG frequency changes. Epilepsia. 1998;39(S6):112.
Frei MG, Davidchack R, Osorio I. Effects of vagal stimulation on human ECG. Epilepsia. 1998:39(S6):200.
Frei MG, Osorio I, Davidchack R. A reappraisal of the value of EKG in the detection of epileptic seizures. Abstract; Epilepsia. 1996:37(S5). Poster presentation, 50th Annual Meeting of the American Epilepsy Society, San Francisco, CA., Dec. 8, 1996.
Han P, Frei MG, Osorio I. Probable mechanisms of action of vagus nerve stimulation in humans with epilepsy: Is the heart a window into the brain? Abstract; Epilepsia. 1996:37(55):83. Platform presentation, 50th Annual Meeting of the American Epilepsy Society, San Francisco, CA, Dec. 8, 1996.
Frei MG, Osorio I, Wilkinson SB. Quantitative analysis of inter-ictal vs. ictal ECoG signals. Abstract; Epilepsia. 1995:36 (S4):5. Poster presentation, 49th Annual Meeting of the American Epilepsy Society, Baltimore, MD, Dec. 4, 1995.
Osorio I, Frei MG, Lerner D, Wilkinson S. A method for accurate automated real time seizure detection. Abstract; Epilepsia. 1995:36(S4):4. Poster presentation, 49th Annual Meeting of the American Epilepsy Society, Baltimore, MD, Dec. 4, 1995.
Ingram J, Osorio I, Frei MG, Wilkinson SB, Troster A. Temporospatial behavior of seizures of temporal lobe origin. Abstract; Epilepsia. 1995:36(S4):9. Poster presentation, 49th Annual Meeting of the American Epilepsy Society, Baltimore, MD, Dec. 4, 1995.
Hayden R, Lerner D, Osorio I, Lai YC, Frei MG.Correlation dimension does not distinguish ictal from interictal activity or noise. Abstract; Epilepsia. 1995:36(S4):5. Poster presentation, 49th Annual Meeting of the American Epilepsy Society, Baltimore, MD, Dec. 4, 1995.
Osorio I, Frei MG, Lerner D, Wilkinson SB. Automated rapid seizure detection in the human ECoG. Abstract in Proceedings of the IEEE Computer-Based Medical Systems, Lubbock, TX, Jun. 9-12, 1995.
Blum M, Floyd R, Vaughan P, Rivest R, Tarjan R. Linear Time Bounds for Median Computations. Abstract in, Aug. 1971.
Hastad J. Median finding. Advanced Algorithms. Lecture 11: May 3, 1995.
Leutmezer, et al., "Electrocardiographic Changes at Seizure Onset," Epilepsia, 2003, pp. 348-354, 44(3).
Rocamora, et al., "Cardiac Asystole in Epilepsy: Clinical and Neurophysiologic Features," Epilepsia, 2003, pp. 179-185, 44(2).
Tavernor, et al., "Electrocardiograph QT Lengthening Associated with Epileptiform EEG Discharges—a Role in Sudden Unexplained Death in Epilepsy," Seizure, Mar. 1996, pp. 79-83, 5(1).
Devinsky, "Effects of Seizures on Autonomic and Cardiovascular Function," Epilepsy Currents, Mar./Apr. 2004, pp. 43-46, 4(2).

Donner, et al., "Sudden Unexplained Death in Children with Epilepsy," Neurology, 2001, pp. 430-434, 57.
Nei, et al., "EEG and ECG in Sudden Unexplained Death in Epilepsy," Epilepsia, 2004, pp. 338-345, 45(4).
U.S. Appl. No. 11/311,043 Notice of Allowance mailed May 5, 2010, 4 pgs.
U.S. Appl. No. 11/311,200 Notice of Allowance mailed Apr. 20, 2010, 1 pgs.
U.S. Appl. No. 11/796,382 Office Action mailed May 20, 2010, 10 pages.
U.S. Appl. No. 11/311,456 Office Action mailed May 28, 2010, 11 pages.
U.S. Appl. No. 11/311,393 Office Action mailed Jun. 4, 2010, 10 pages.
U.S. Appl. No. 11/311,200 Office Communication mailed Jul. 26, 2010, 6 pgs.
U.S. Appl. No. 11/796,576 Office Action mailed Aug. 20, 2010, 7 pgs.
U.S. Appl. No. 11/796,575 Office Action mailed Aug. 31, 2010, 10 pgs.
U.S. Appl. No. 11/741,103 Office Action mailed Aug. 31, 2010, 11 pgs.
U.S. Appl. No. 11/741,109 Office Action mailed Sep. 29, 2010, 10 pgs.
U.S. Appl. No. 11/311,393 Notice of Allowance mailed Oct. 1, 2010, 3 pgs.
U.S. Appl. No. 11/380,462 Final Office Action mailed Nov. 1, 2010, 13 pgs.
U.S. Appl. No. 11/311,456 Notice of Allowance mailed Oct. 20, 2010, 1 page.
U.S. Appl. No. 11/311,043 Notice of Allowance mailed Oct. 19, 2010, 4 pages.
U.S. Appl. No. 11/311,200 Notice of Allowance mailed Oct. 12, 2010, 4 pages.
U.S. Appl. No. 11/796,577 Final Office Action mailed Nov. 15, 2010, 9 pgs.
U.S. Appl. No. 11/796,382 Final Office Action mailed Sep. 15, 2010, 10 pages.
U.S. Appl. No. 11/767,054 Office Action mailed Jan. 4, 2011, 8 pages.
U.S. Appl. No. 11/796,575 Final Office Action mailed Mar. 18, 2011, 11 pages.
U.S. Appl. No. 11/741,119 Office Action mailed Mar. 28, 2011, 28 pages.
U.S. Appl. No. 11/796,576 Final Office Action mailed Mar. 30, 2011, 10 pages.
U.S. Appl. No. 11/796,382 Notice of Allowance mailed Mar. 2, 2011, 7 pages.
U.S. Appl. No. 11/741,109 Final Office Action mailed Apr. 12, 2011, 8 pgs.
U.S. Appl. No. 11/380,462 Office Action mailed Apr. 13, 2011, 7 pgs.
U.S. Appl. No. 11/741,103 Office Action mailed Apr. 13, 2011, 10 pgs.
U.S. Appl. No. 11/796,577 Notice of Allowance mailed May 5, 2011, 13 pgs.
U.S. Appl. No. 11/767,054 Office Action mailed Jun. 15, 2011, 10 pgs.
U.S. Appl. No. 11/311,393 Notice of Allowance mailed Jun. 13, 2011, 4 pgs.
U.S. Appl. No. 11/311,200 Notice of Allowance mailed Jun. 13, 2011, 3 pages.
U.S. Appl. No. 11/741,109 Notice of Allowance mailed Jul. 5, 2011, 3 pages.
U.S. Appl. No. 11/796,576 Office Action mailed Jul. 8, 2011, 7 pages.
U.S. Appl. No. 11/741,126 Office Action mailed Dec. 6, 2011, 24 pgs.
U.S. Appl. No. 11/741,111 Office Action mailed Dec. 7, 2011, 28 pgs.

* cited by examiner

| Top = Neurological Event Detection  Bottom = Cardiac Event Detection | Category Code | Cardiac Event Timing | CRITERIA |
|---|---|---|---|
| (neuro and cardiac aligned) | TP1 | EQUAL-EQUAL | $((Beg._{card} = START_N)$ & $(Term._{card} = END_N))$ |
| (cardiac starts before, ends within) | TP2 | OUT-IN | $((Beg._{card} <= START_N)$ & $(Term._{card} > START_N)$ & $(Term._{card} <= END_N))$ |
| (cardiac encloses neuro) | TP3 | OUT-OUT | $((Beg._{card} <= START_N)$ & $(Term._{card} >= END_N))$ |
| (cardiac starts within, ends after) | TP4 | IN-OUT | $((Beg._{card} >= START_N)$ & $(Beg._{card} < END_N)$ & $(Term._{card} >= END_N))$ |
| (cardiac within neuro) | TP5 | IN-IN | $((Beg._{card} >= START_N)$ & $(Beg._{card} < END_N)$ & $(Term._{card} > START_N)$ & $(Term._{card} <= END_N))$ |
| (cardiac ends at neuro start) | TP6 | OUT-EQUAL | $((Beg._{card} < START_N)$ & $(Term._{card} = START_N))$ |
| (cardiac starts at neuro end) | TP7 | EQUAL-OUT | $((Beg._{card} = END_N)$ & $(Term._{card} > END_N))$ |
| (cardiac after neuro within window) | TP8 | OUT-OUT AFTER DETECT | $((Beg._{card} > END_N)$ & $(Beg._{card} - WinSize <= END_N))$  Beg.$_{card}$ within window after neuro event end. |
| (cardiac before neuro within window) | TP9 | OUT-OUT BEFORE DETECT | $((Term._{card} < START_N)$ & $(Term._{card} + WinSize >= START_N))$  Term.$_{card}$ within window prior to neuro event start. |
| (neuro only) | FN | OUT-OUT | FALSE NEGATIVE (UN-MATCHED NEURO EVENT DETECTION) |
| (cardiac only) | FP | ---------- | FALSE POSITIVE (UN-MATCHED CARDIAC EVENT DETECTION) |

FIG. 64

SYSTEM AND METHOD FOR USING CARDIAC EVENTS TO TRIGGER THERAPY FOR TREATING NERVOUS SYSTEM DISORDERS

RELATED APPLICATIONS

This application is a continuation-in-part of U.S. application Ser. No. 11/380,462, filed Apr. 27, 2006, published as U.S. Application Publication 2006/0224067, which is still pending and a continuation-in-part of U.S. application Ser. No. 11/311,043, filed Dec. 19, 2005, published as U.S. Application Publication 2006/0195144, now U.S. Pat. No. 7,865,244; a continuation-in-part of U.S. application Ser. No. 11/311,200, filed Dec. 19, 2005, published as U.S. Application Publication 2006/0136006, which is still pending; a continuation-in-part of U.S. application Ser. No. 11/311,393, filed Dec. 19, 2005, published as U.S. Application Publication 2006/0135877, which is still pending; a continuation-in-part of U.S. application Ser. No. 11/311,456, filed Dec. 19, 2005, published as U.S. Application Publication 2006/0135881, now U.S. Pat. No. 7,945,316, each of which claims the benefit of U.S. Provisional Application Ser. No. 60/636,929, filed Dec. 17, 2004, and all of which are incorporated herein by reference.

FIELD OF THE INVENTION

This invention relates generally to medical devices, systems and methods, and more particularly to the monitoring of cardiac signals associated with neurological events.

BACKGROUND OF THE INVENTION

Nervous system disorders affect millions of people, causing death and a degradation of life. Nervous system disorders include disorders of the central nervous system, peripheral nervous system, and mental health and psychiatric disorders. Such disorders include, for example without limitation, epilepsy, Parkinson's disease, essential tremor, dystonia, and multiple sclerosis (MS). Additionally, nervous system disorders include mental health disorders and psychiatric disorders which also affect millions of individuals and include, but are not limited to, anxiety (such as general anxiety disorder, panic disorder, phobias, post traumatic stress disorder (PTSD), and obsessive compulsive disorder (OCD)), mood disorders (such as major depression, bipolar depression, and dysthymic disorder), sleep disorders (narcolepsy), eating disorders such as obesity, and anorexia. As an example, epilepsy is the most prevalent serious neurological disease across all ages. Epilepsy is a group of neurological conditions in which a person has or is predisposed to recurrent seizures. A seizure is a clinical manifestation resulting from excessive, hypersynchronous, abnormal electrical or neuronal activity in the brain. A neurological event is an activity that is indicative of a nervous system disorder. A seizure is a type of a neurological event. This electrical excitability of the brain may be likened to an intermittent electrical overload that manifests with sudden, recurrent, and transient changes of mental function, sensations, perceptions, or involuntary body movement. Because the seizures are unpredictable, epilepsy affects a person's employability, psychosocial life, and ability to operate vehicles or power equipment. It is a disorder that occurs in all age groups, socioeconomic classes, cultures, and countries.

There are various approaches to treating nervous system disorders. Treatment therapies can include any number of possible modalities alone or in combination including, for example, electrical stimulation, magnetic stimulation, drug infusion, or brain temperature control. Each of these treatment modalities may use open loop treatment where neither the timing of the therapy nor treatment parameters are automatically set or revised based on information coming from a sensed signal. Each of these treatment modalities may also be operated using closed-loop feedback control. Such closed-loop feedback control techniques may receive from a monitoring element a brain signal (such as EEG, ECoG, intracranial pressure, change in quantity of neurotransmitters) that carries information about a symptom or a condition of a nervous system disorder and is obtained from the head or brain of the patient.

For example, U.S. Pat. No. 5,995,868 discloses a system for the prediction, rapid detection, warning, prevention, or control of changes in activity states in the brain of a patient. Use of such a closed-loop feed back system for treatment of a nervous system disorder may provide significant advantages in that treatment can be delivered before the onset of the symptoms of the nervous system disorder.

While much work has been done in the area of detecting nervous system disorders by processing EEG signals, less has been done in the area of the brain-heart relationship as it pertains to these disorders. The relationship between the heart and the brain is complex and not fully understood. While some references discuss monitoring cardiac and brain activity, the question of what the device or system should do once it receives those signals has not been fully explored.

Sudden unexpected death in epilepsy, or SUDEP, is just one example of a nervous system disorder that involves a relationship between the brain and the heart. SUDEP, is defined as sudden, unexpected, often unwitnessed, non-traumatic and non-drowning death in patients for which no cause has been found except for the individual having a history of seizures. Depending on the cohort studied, SUDEP is responsible for 2% to 18% of all deaths in patients with epilepsy, and the incidence may be up to 40 times higher in young adults with epilepsy than among persons without seizures. Although the pathophysiological mechanisms leading to death are not fully understood, experimental, autopsy and clinical evidence implicate seizure related heart and pulmonary dysfunction or indicators. Pulmonary events may include obstructive sleep apnea (OSA), central apnea, and neurogenic pulmonary edema. Cardiac events may include cardiac arrhythmic abnormalities including sinus arrhythmia, sinus pause, premature atrial contraction (PAC), premature ventricular contraction (PVC), irregular rhythm (wandering pacemaker, multifocal atrial tachycardia, atrial fibrillation), asystole or paroxysmal tachycardia. Cardiac events may also include conduction abnormalities including AV-block (AVB) and bundle branch block (BBB) and repolarization abnormalities including T-wave inversion and ST-elevation or depression. Lastly, hypertension, hypotension and vaso-vagal syncope (VVS) are common in epilepsy patients.

Epileptic seizures are associated with autonomic neuronal dysfunction that results in a broad array of abnormalities of cardiac and pulmonary function. Different pathophysiological events may contribute to SUDEP in different patients, and the mechanism is probably multifactorial. Without intervention, respiratory events, including airway obstruction, central apnea and neurogenic pulmonary edema are probably terminal events. In addition, cardiac arrhythmia and anomalies, during the ictal and interictal periods, leading to arrest and acute cardiac failure also plays an important role in potentially terminal events. For example, the paper "Electrocardiographic Changes at Seizure Onset", Leutmezer, et al, Epilepsia 44(3): 348-354, 2003 describes cardiovascular anomalies, such as heart rate variability (HRV), tachycardia and bradycardia, that may precede, occur simultaneous or lag behind EEG seizure onset. "Cardiac Asystole in Epilepsy: Clinical and Neurophysiologic Features", Rocamora, et al, Epilepsia 44(2): 179-185, 2003 reports that cardiac asystole is "provoked" by the seizure. "Electrocardiograph QT Lengthening Associated with Epileptiform EEG Discharges—a Role in Sudden Unexplained Death in Epilepsy", Tavernor, et al, Seizure 5(1): 79-83, March 1996 reports QT lengthening during seizures in SUDEP patients versus control. "Effects of Seizures on Autonomic and Cardiovascular Function", Devinsky Epilepsy Currents 4(2): 43-46, March/April 2004 describes ST segment depression and T-wave inversion, AVB, VPC and BBB during or immediately after a seizure. "Sudden Unexplained Death in Children with Epilepsy", Donner, et al, Neurology 57: 430-434, 2001 reports that bradycardia is frequently preceded by hypoventilation or apnea suggesting that heart rate changes during seizures may be a result of cardiorespiratory reflexes. Lastly, "EEG and ECG in Sudden Unexplained Death in Epilepsy", Nei, et al, Epilepsia 45(4) 338-345, 2004 reports on sinus tachycardia during or after seizures.

With the above broad and, often conflicting, array of neuro-cardiopulmonary physiological anomalies, manifestations and indicators, a device, or array of devices, is desired to allow for better diagnosis, monitoring and/or treatment of nervous system disorders including monitoring of both cardiac and brain signals.

SUMMARY OF THE INVENTION

In an embodiment of the invention, a method is provided for treating a neurological disorder in a patient. The method may include obtaining a neurological event detection signal and a cardiac event detection signal, analyzing timing relationships between cardiac and neurological events, identifying matched events when neurological events are temporally related to cardiac events, determining whether the cardiac event detection signal facilitates detection of neurological events, and delivering a therapy for treating the neurological disorder in response to a detected cardiac event if the cardiac event detection signal is determined to facilitate detection of neurological events. In some embodiments, a medical device system is provided that includes a processor configured to obtain a neurological event detection signal and a cardiac event detection signal, to analyze timing relationships between cardiac and neurological events, to identify matched events when neurological events are temporally related to cardiac events, to determine whether the cardiac event detection signal facilitates detection of neurological events, and to deliver a therapy to the patient in response to a detected cardiac event if the cardiac event detection signal is determined to facilitate detection of neurological events. A system or method according to certain embodiments of the invention may also be adapted to change the therapy delivered to the patient based on sensed brain signals.

BRIEF DESCRIPTION OF THE DRAWINGS

Core Monitor

Full Monitor

Figure 5:
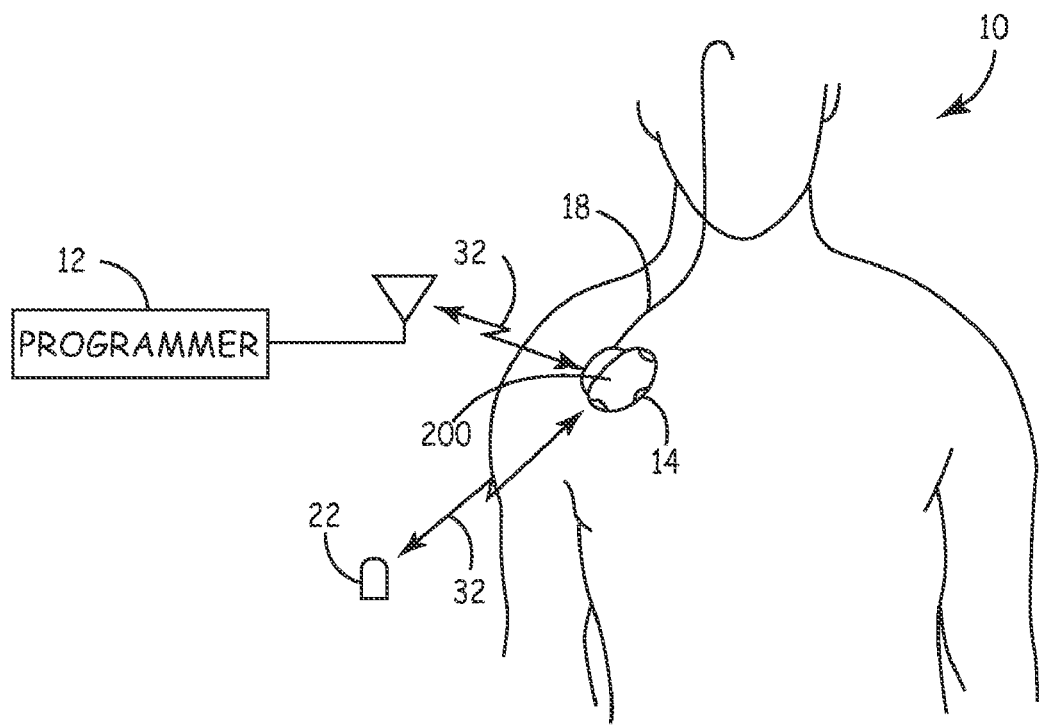

FIG. 5 is a simplified schematic view of an alternative embodiment thoracic leadless and cranial leaded medical device implanted in a patient that monitors cardiac, respiratory and brain parameters relating to nervous system disorder.

Figure 6:
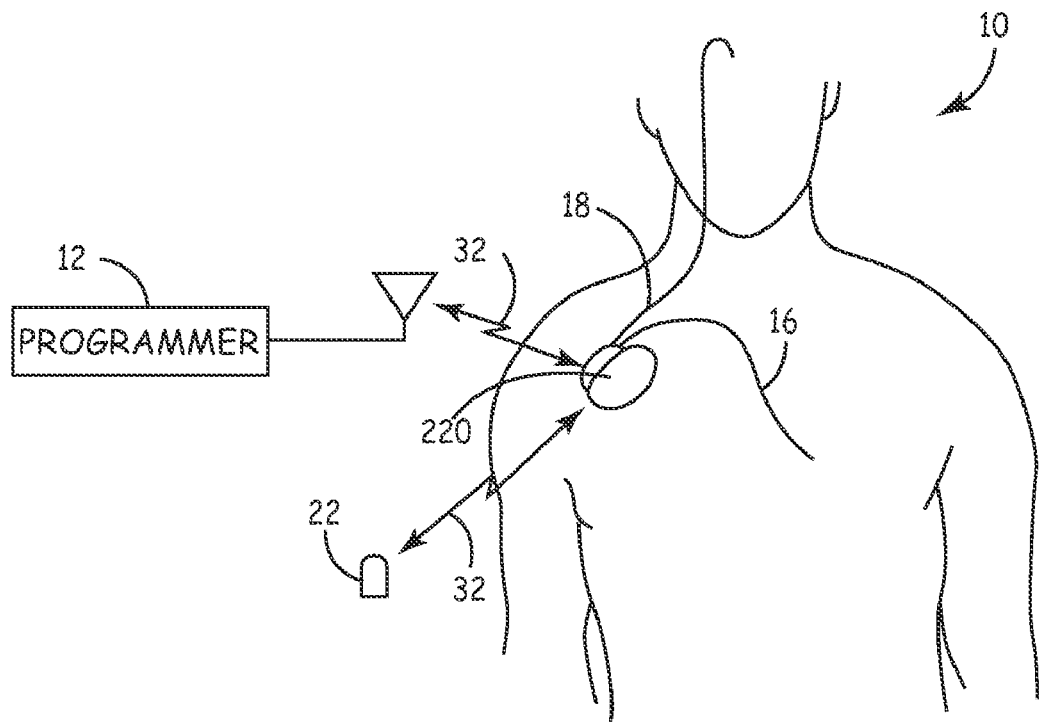

FIG. 6 is a simplified schematic view of an alternative embodiment cardiac and cranial leaded medical device implanted in a patient that monitors cardiac, respiratory and brain parameters relating to nervous system disorder.

Figure 7:
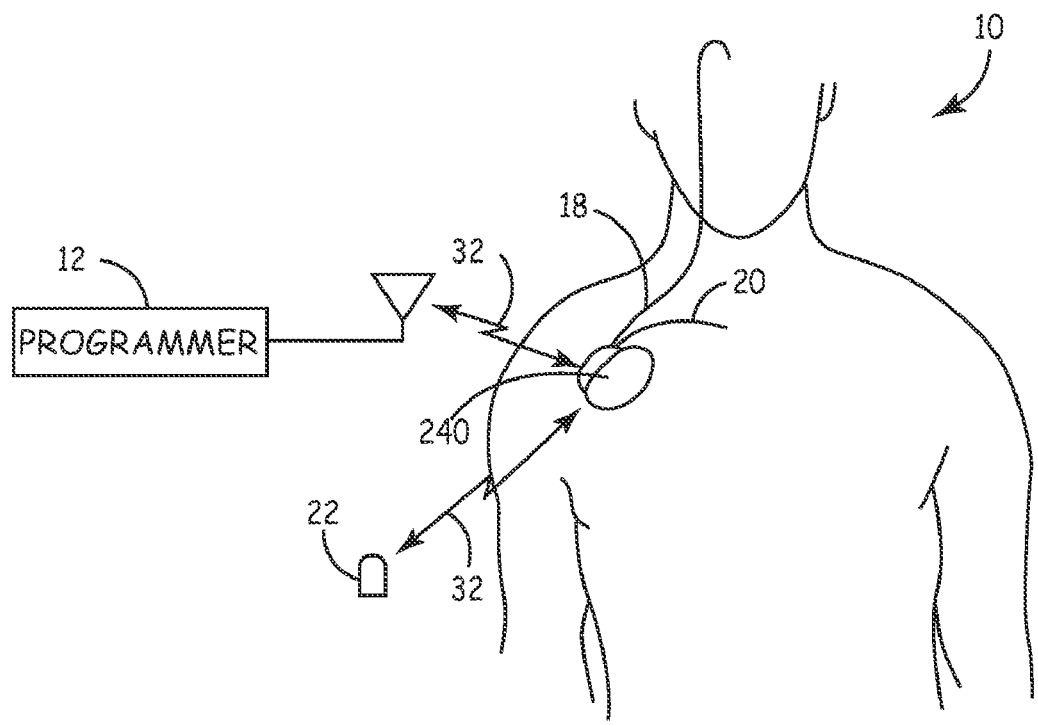

FIG. 7 is a simplified schematic view of an alternative embodiment sensor stub and cranial leaded medical device implanted in a patient that monitors cardiac, respiratory and brain parameters relating to nervous system disorder.

Figure 8:
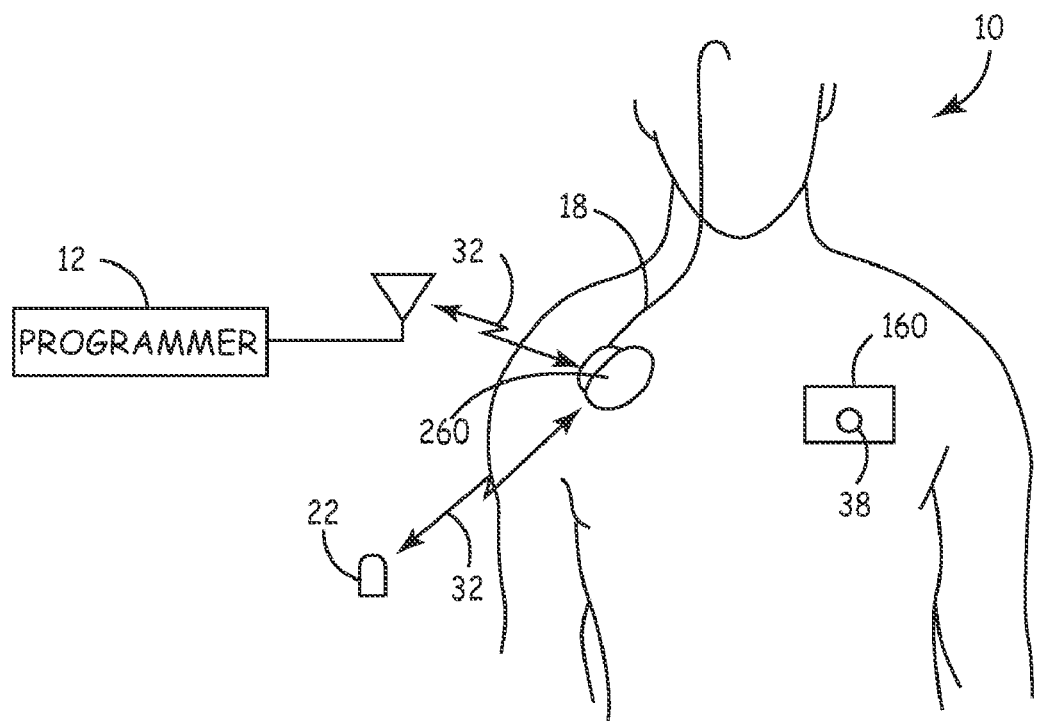

FIG. 8 is a simplified schematic view of an alternative embodiment external patch and cranial leaded medical device implanted in a patient that monitors cardiac, respiratory and brain parameters relating to nervous system disorder.

Figure 9:
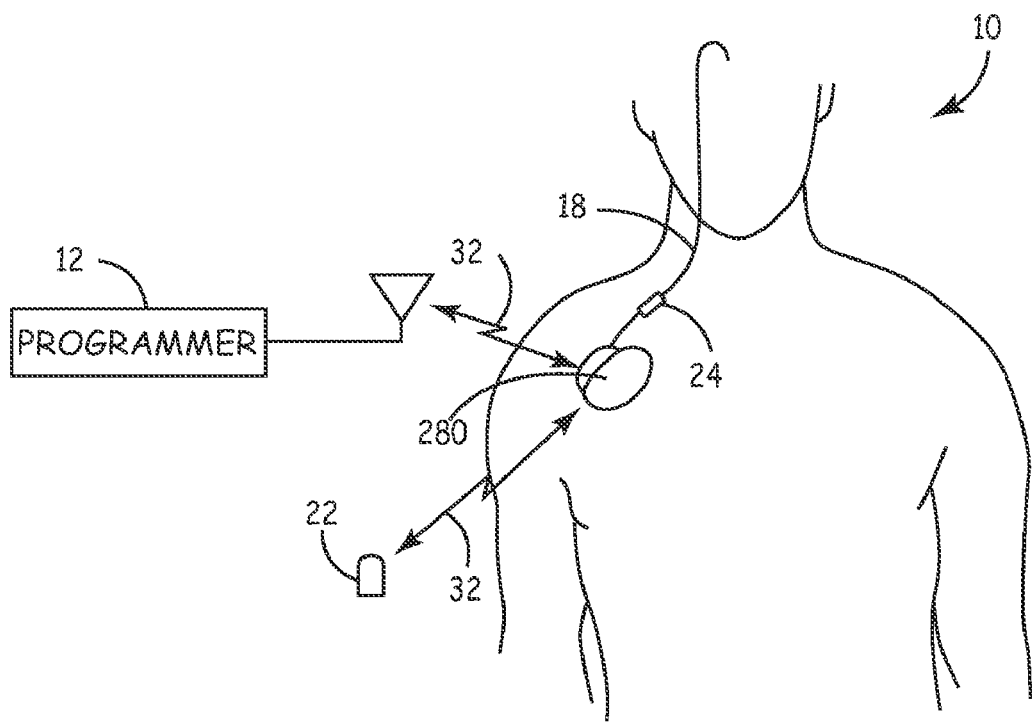

FIG. 9 is a simplified schematic view of an alternative embodiment integrated brain lead medical device implanted in a patient that monitors cardiac, respiratory and brain parameters relating to nervous system disorder.

Figure 10:
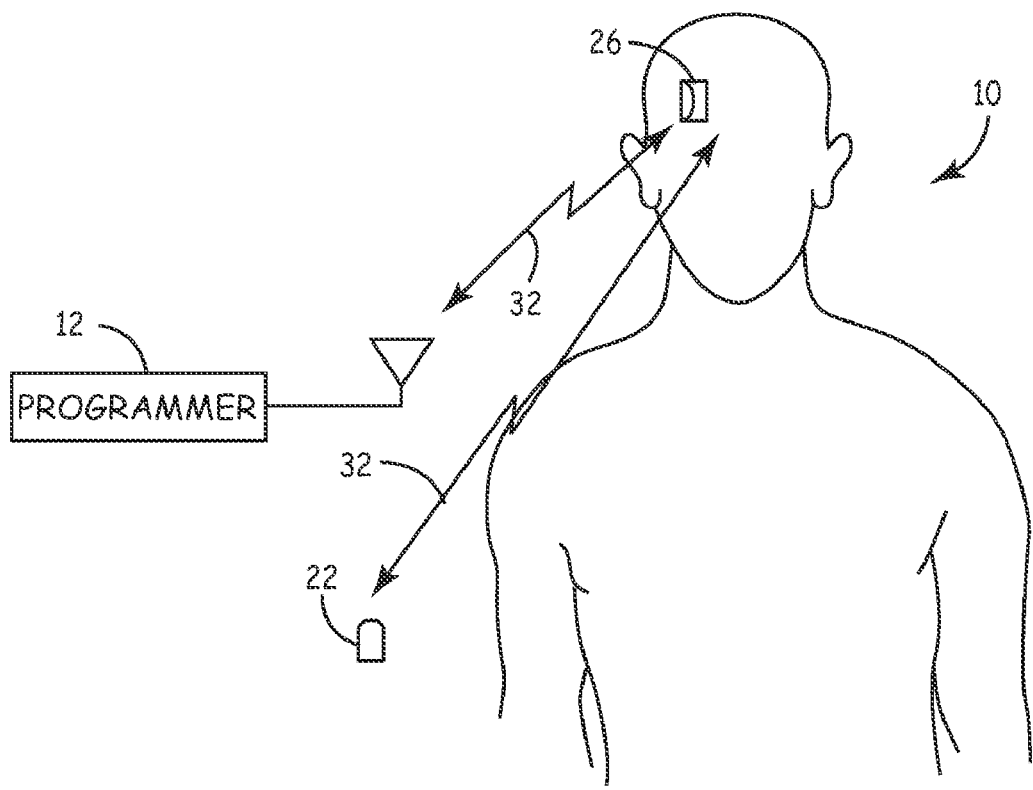

FIG. 10 is a simplified schematic view of an alternative embodiment cranial implant medical device implanted in a patient that monitors cardiac and brain parameters relating to nervous system disorder.

Monitor+Treatment (Brain)

Figure 11:
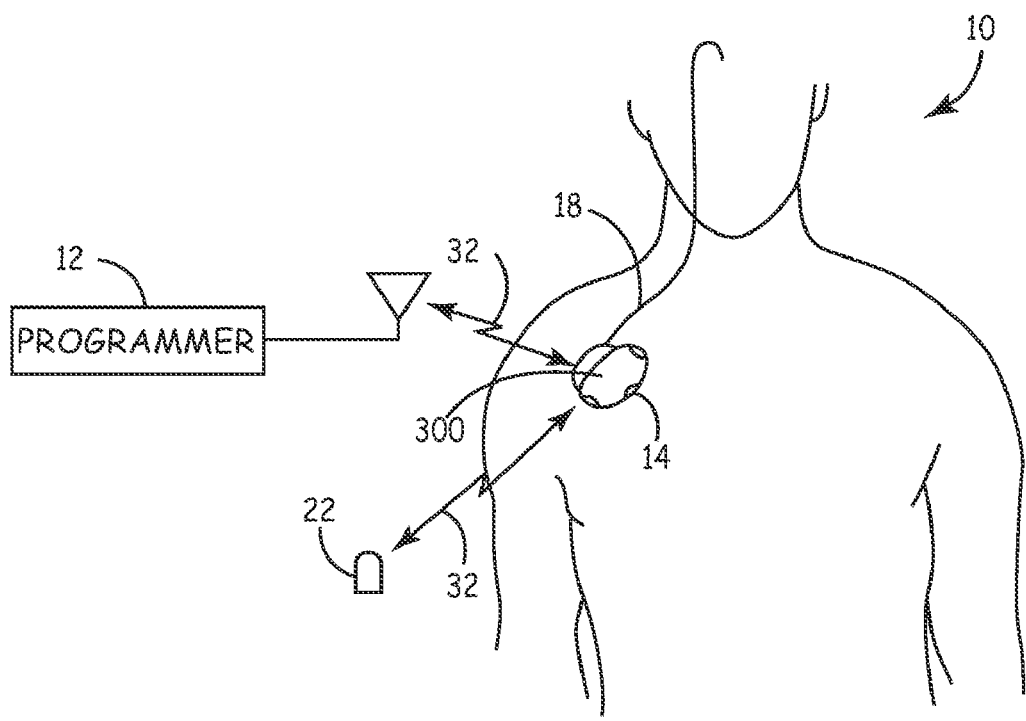

FIG. 11 is a simplified schematic view of an alternative embodiment thoracic leadless and cranial leaded medical device implanted in a patient that monitors cardiac, respiratory and brain parameters relating to nervous system disorders and provides brain treatment.

Figure 12A:
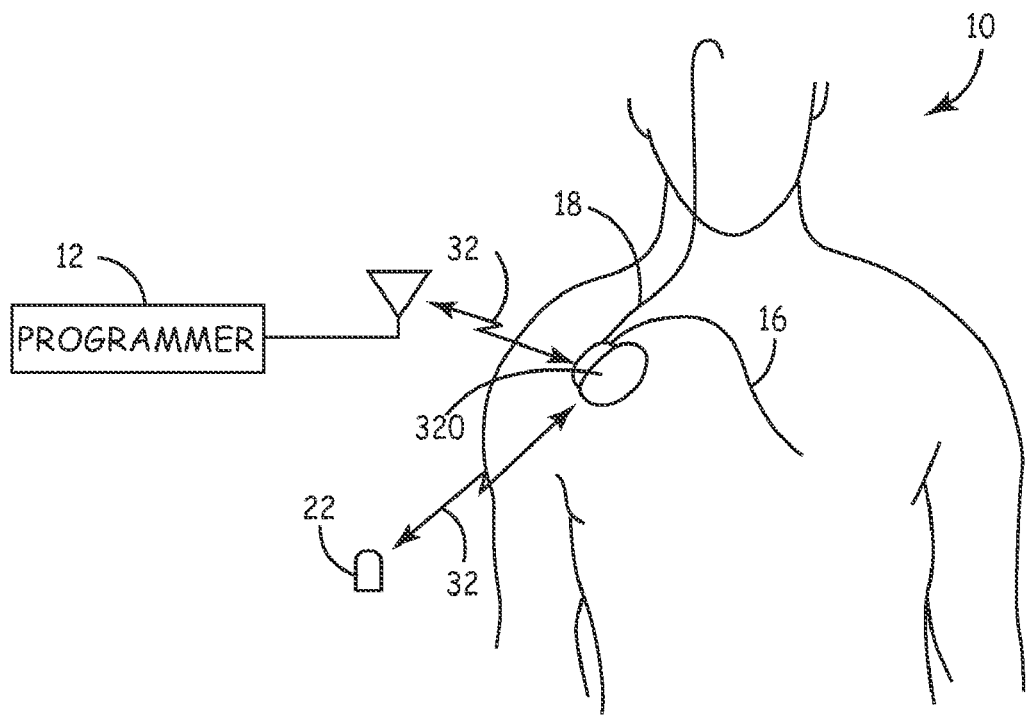

FIG. 12A is a simplified schematic view of an alternative embodiment cardiac and cranial leaded medical device implanted in a patient that monitors cardiac, respiratory and brain parameters relating to nervous system disorders and provides brain treatment.

Figure 12B:
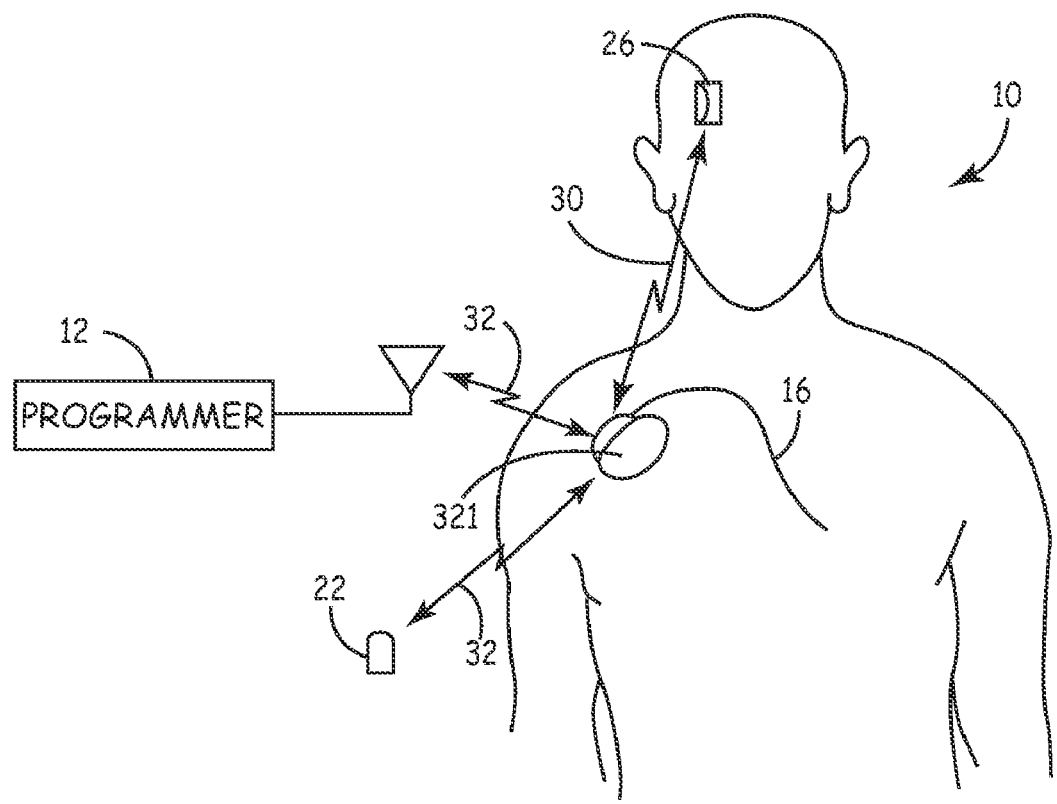

FIG. 12B is a simplified schematic view of an alternative embodiment cardiac and cranial leaded medical device implanted in a patient that monitors cardiac, respiratory and brain parameters relating to nervous system disorders and provides brain treatment.

Figure 13:
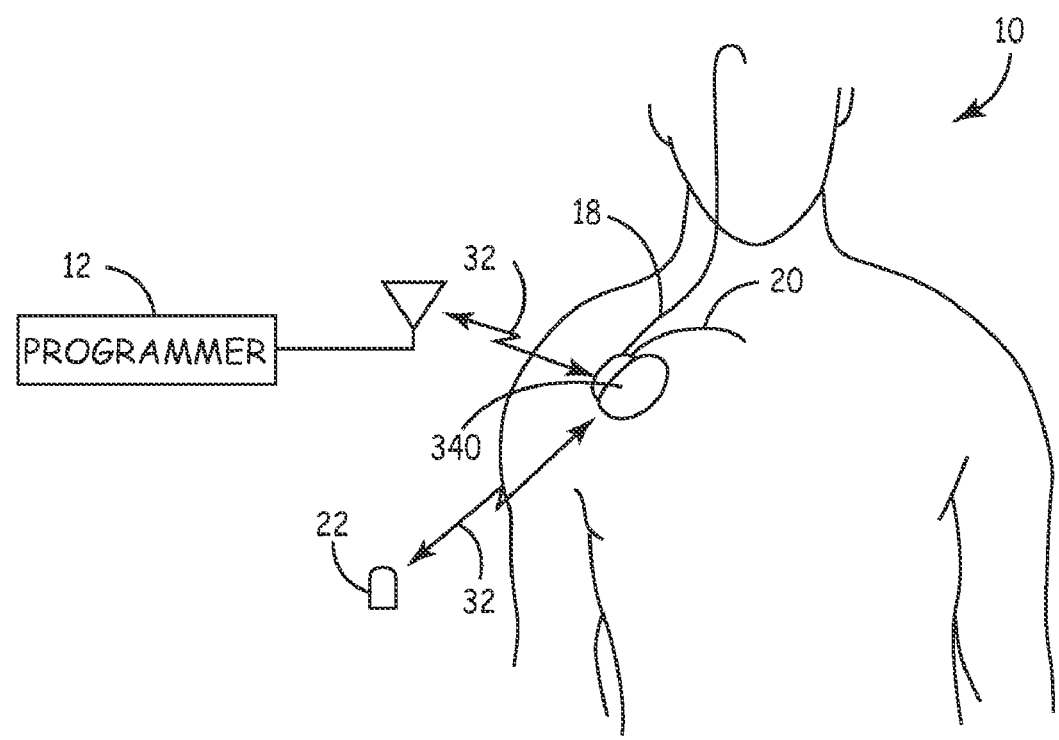

FIG. 13 is a simplified schematic view of an alternative embodiment sensor stub and cranial leaded medical device implanted in a patient that monitors cardiac, respiratory and brain parameters relating to nervous system disorders and provides brain treatment.

Figure 14:
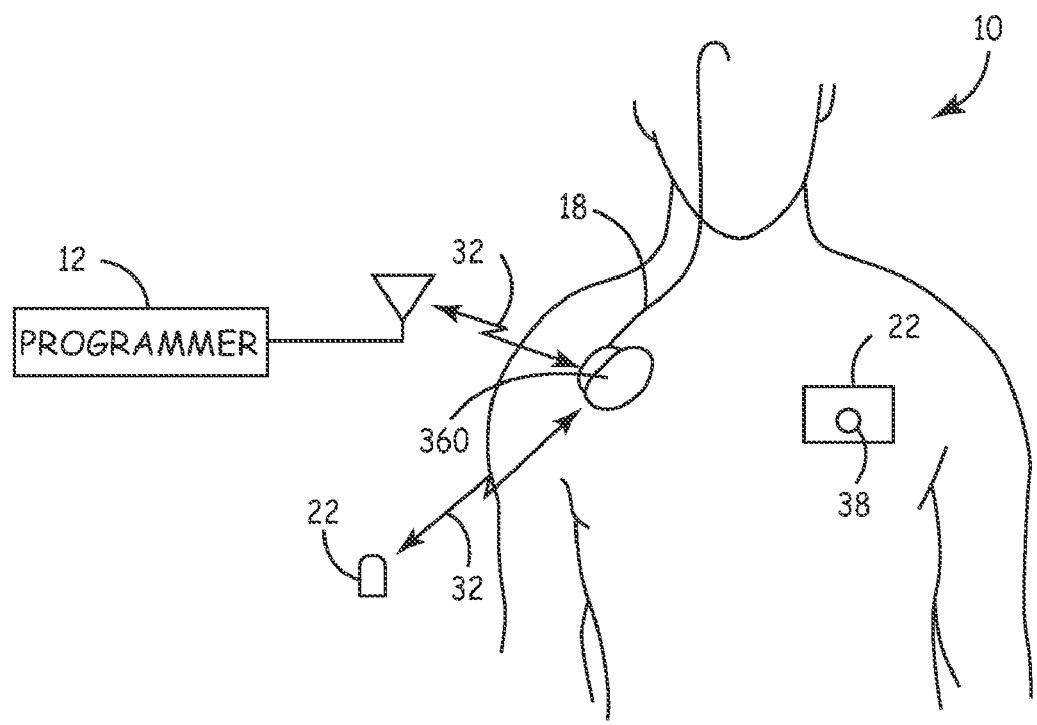

FIG. 14 is a simplified schematic view of an alternative embodiment external patch and cranial leaded medical device implanted in a patient that monitors cardiac, respiratory and brain parameters relating to nervous system disorders and provides brain treatment.

Figure 15:
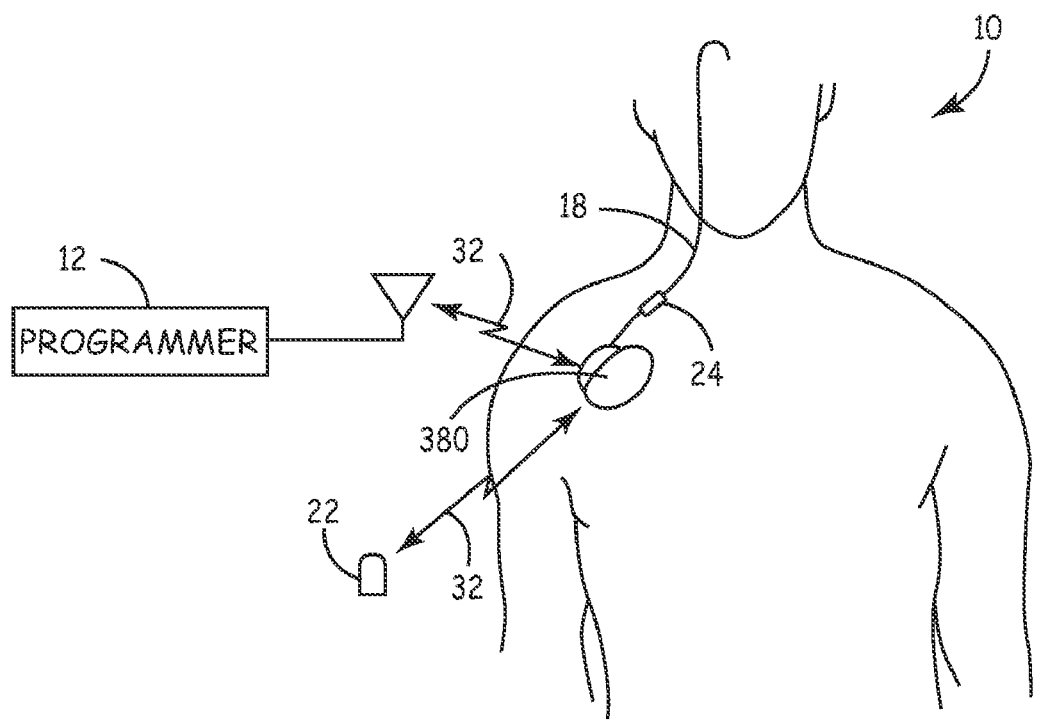

FIG. 15 is a simplified schematic view of an alternative embodiment integrated brain lead medical device implanted in a patient that monitors cardiac, respiratory and brain parameters relating to nervous system disorders and provides brain treatment.

Figure 20:
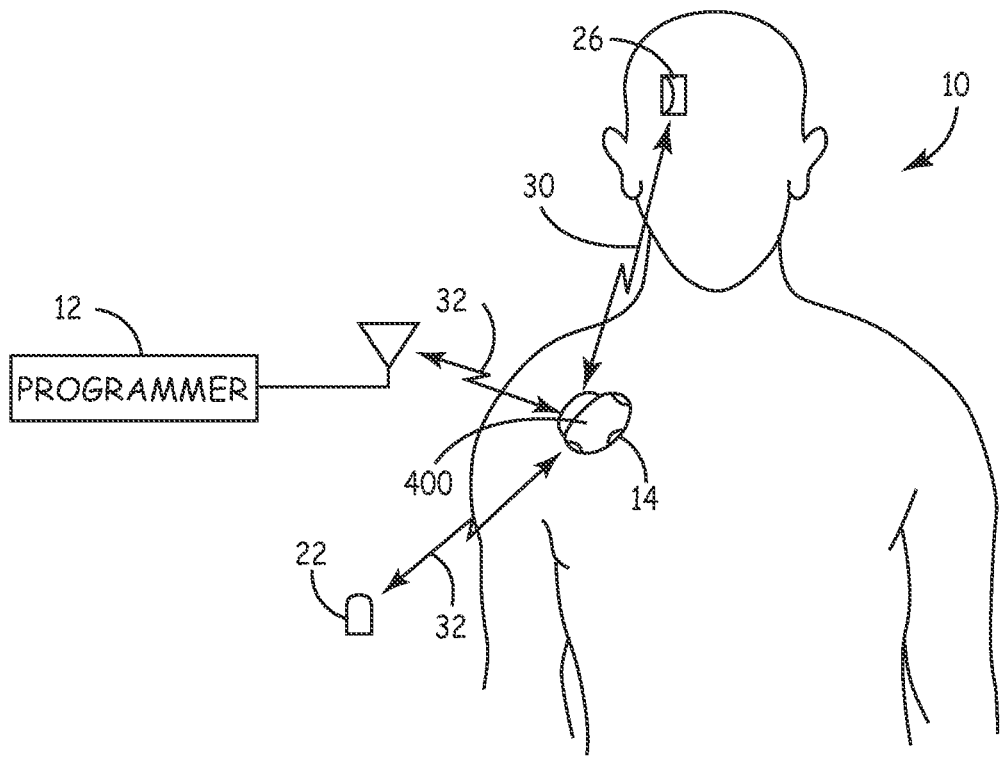

FIG. 20 is a simplified schematic view of an alternative embodiment thoracic leadless device to cranial implant via wireless connect medical device implanted in a patient that monitors cardiac, respiratory and brain parameters relating to nervous system disorders and provides brain treatment.

Figure 21:
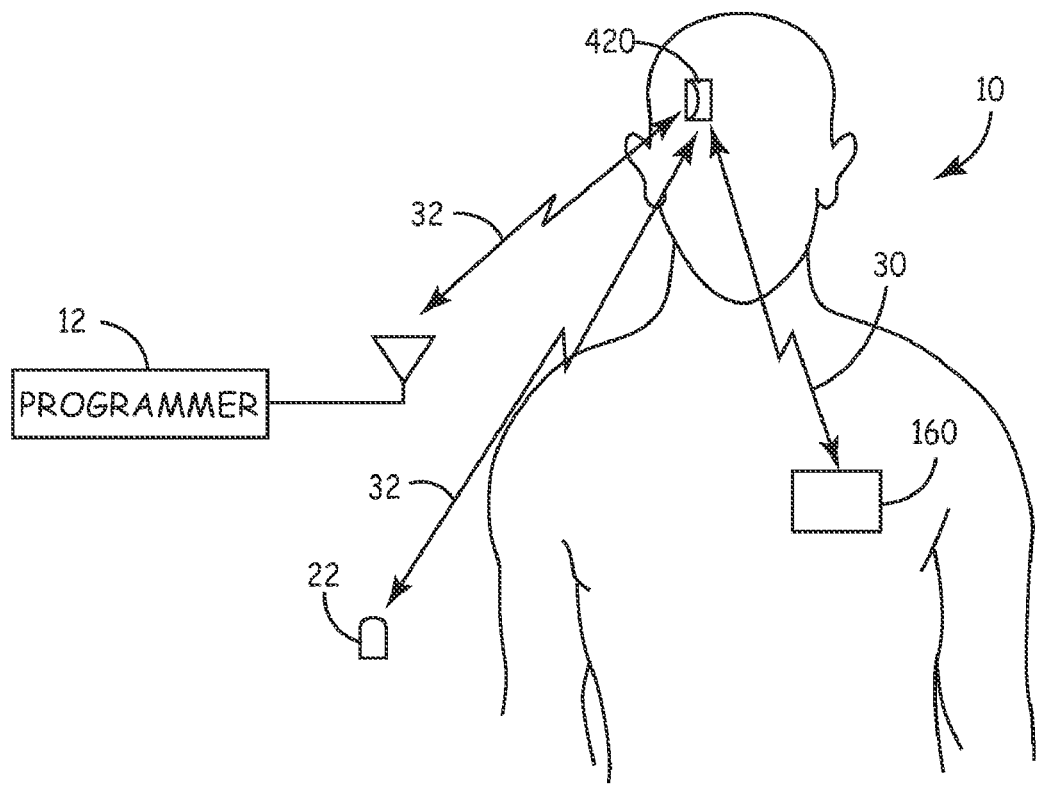

FIG. 21 is a simplified schematic view of an alternative embodiment external patch to cranial implant via wireless connect medical device implanted in a patient that monitors cardiac, respiratory and brain parameters relating to nervous system disorders and provides brain treatment.

Monitor+Treatment (Brain+Respiration)

Figure 16A:
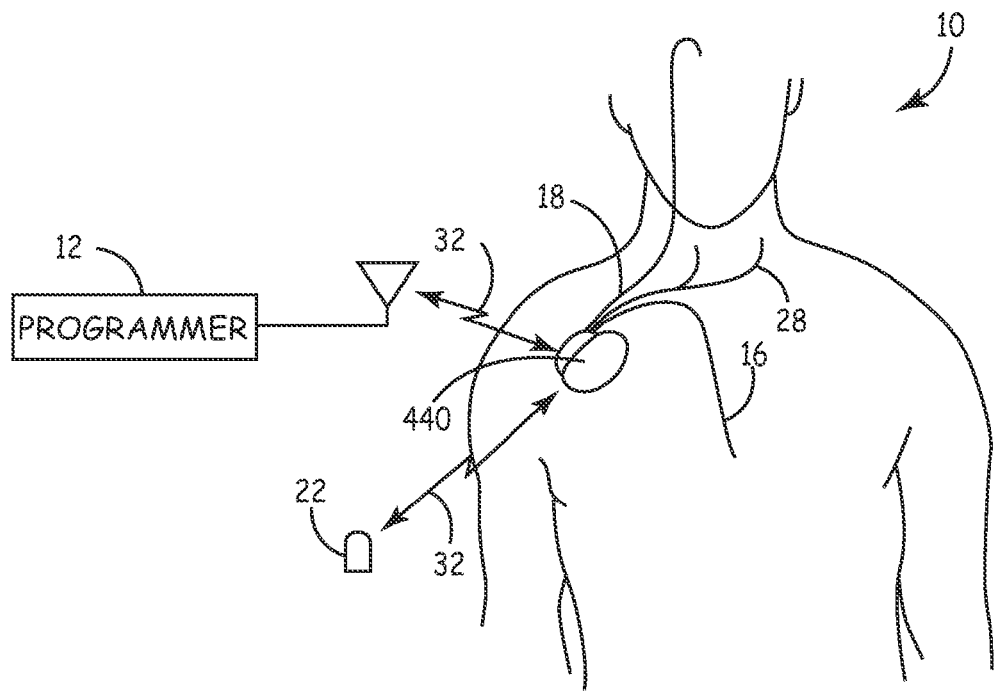

FIG. 16A is a simplified schematic view of an alternative embodiment cardiac, brain and phrenic nerve leaded medical device implanted in a patient that monitors cardiac, respiratory and brain parameters relating to nervous system disorders and provides brain and respiration treatment.

Figure 16B:
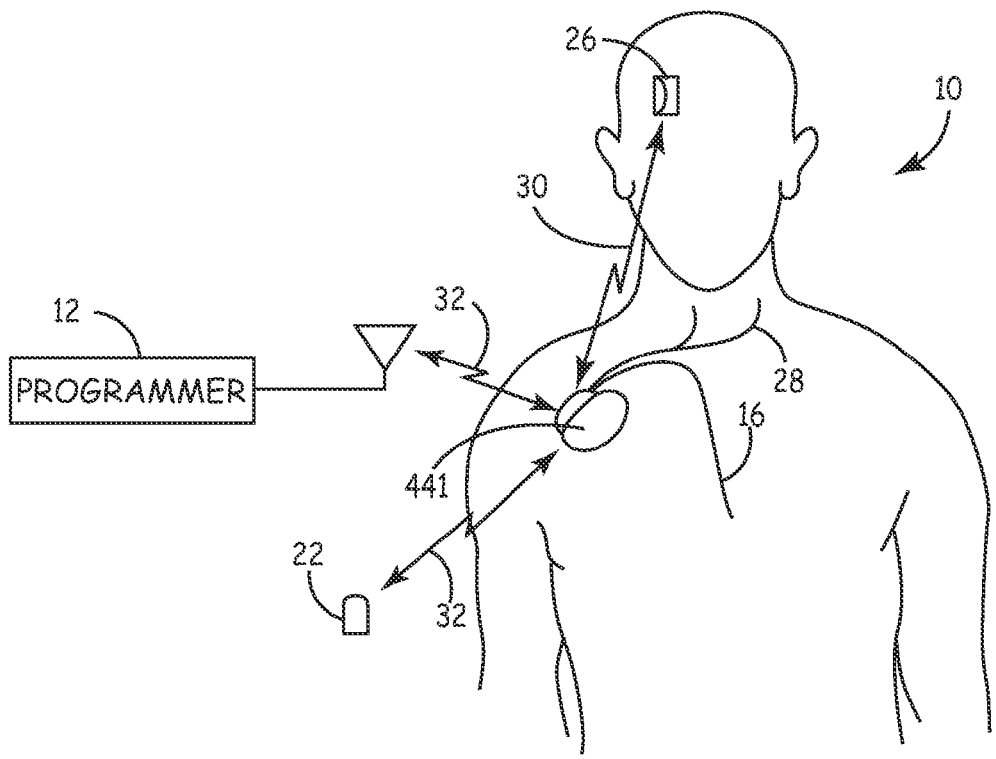

FIG. 16B is a simplified schematic view of an alternative embodiment cardiac, brain and phrenic nerve leaded medical device implanted in a patient that monitors cardiac, respiratory and brain parameters relating to nervous system disorders and provides brain and respiration treatment.

Figure 17:
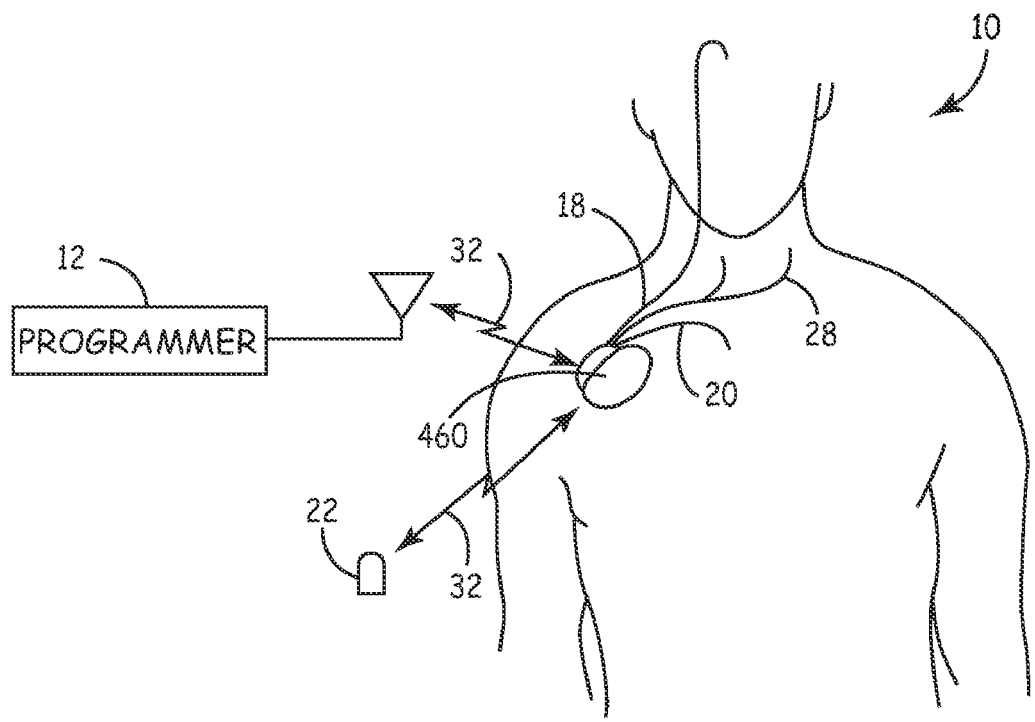

FIG. 17 is a simplified schematic view of an alternative embodiment sensor stub, brain and phrenic nerve leaded medical device implanted in a patient that monitors cardiac, respiratory and brain parameters relating to nervous system disorders and provides brain and respiration treatment.

Figure 18:
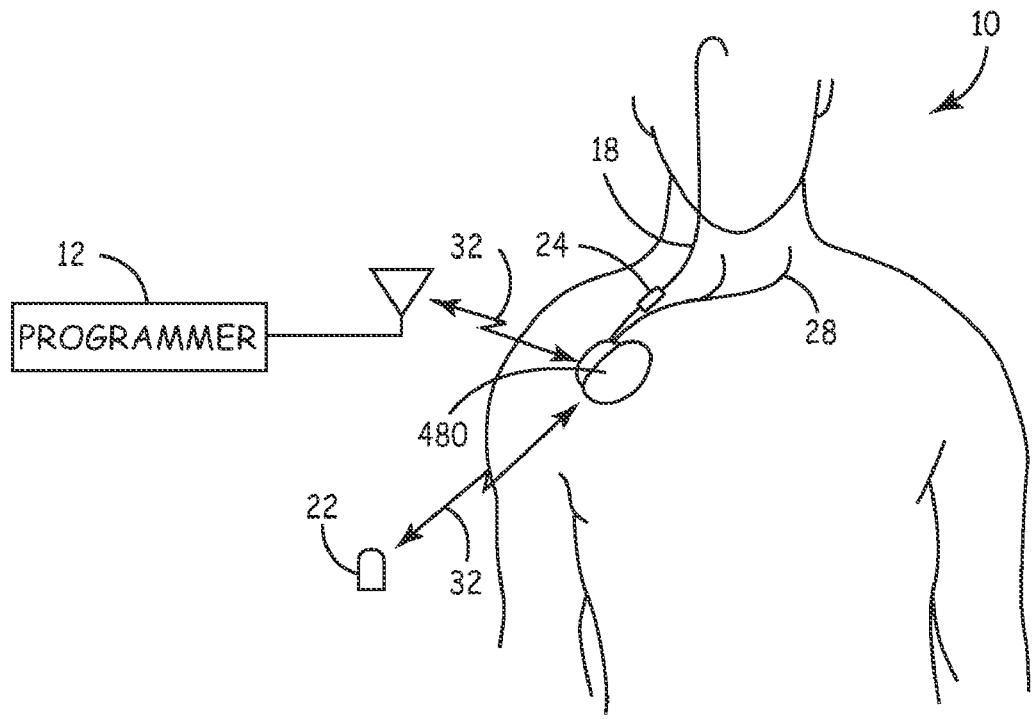

FIG. 18 is a simplified schematic view of an alternative embodiment integrated brain and phrenic nerve leaded medical device implanted in a patient that monitors cardiac, respiratory and brain parameters relating to nervous system disorders and provides brain and respiration treatment.

Figure 19:
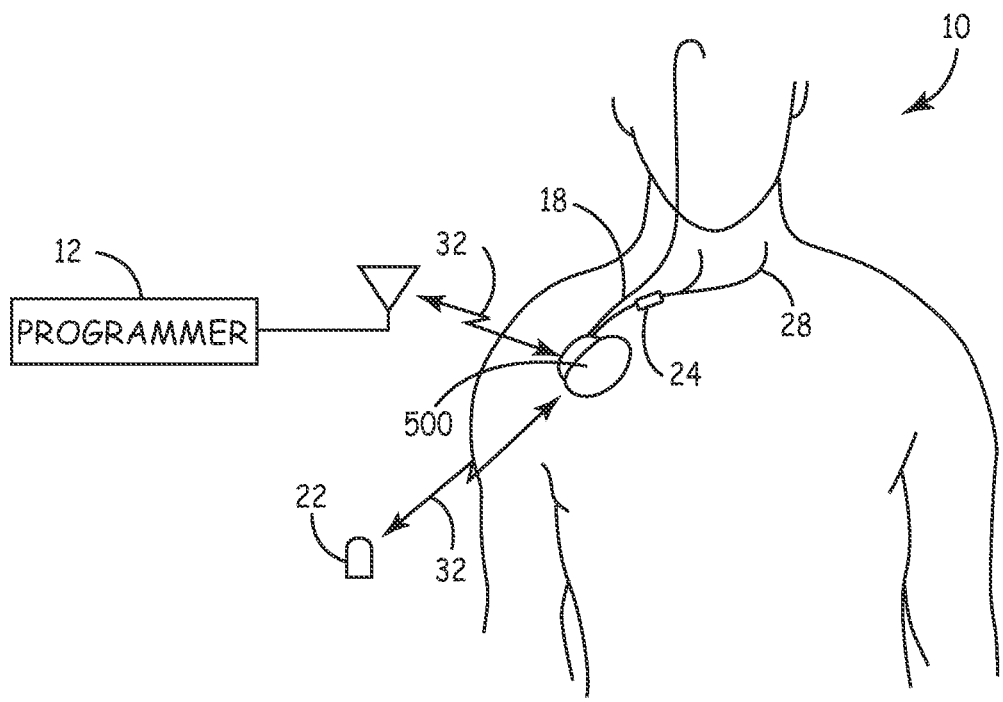

FIG. 19 is a simplified schematic view of an alternative embodiment brain and integrated respiration lead medical device implanted in a patient that monitors cardiac, respiratory and brain parameters relating to nervous system disorders and provides brain and respiration treatment.

Monitor+Treatment (Brain+Cardiac)

Figure 24A:
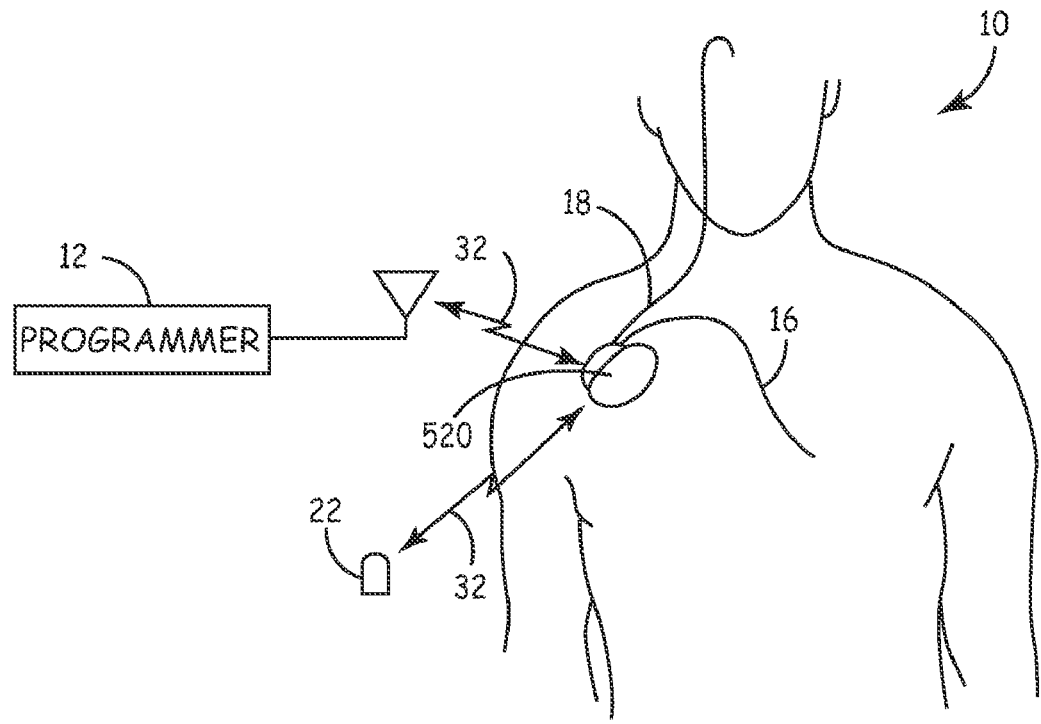

FIG. 24A is a simplified schematic view of an alternative embodiment cardiac and brain leaded medical device implanted in a patient that monitors cardiac, respiratory and brain parameters relating to nervous system disorders and provides brain and cardiac treatment.

Figure 24B:
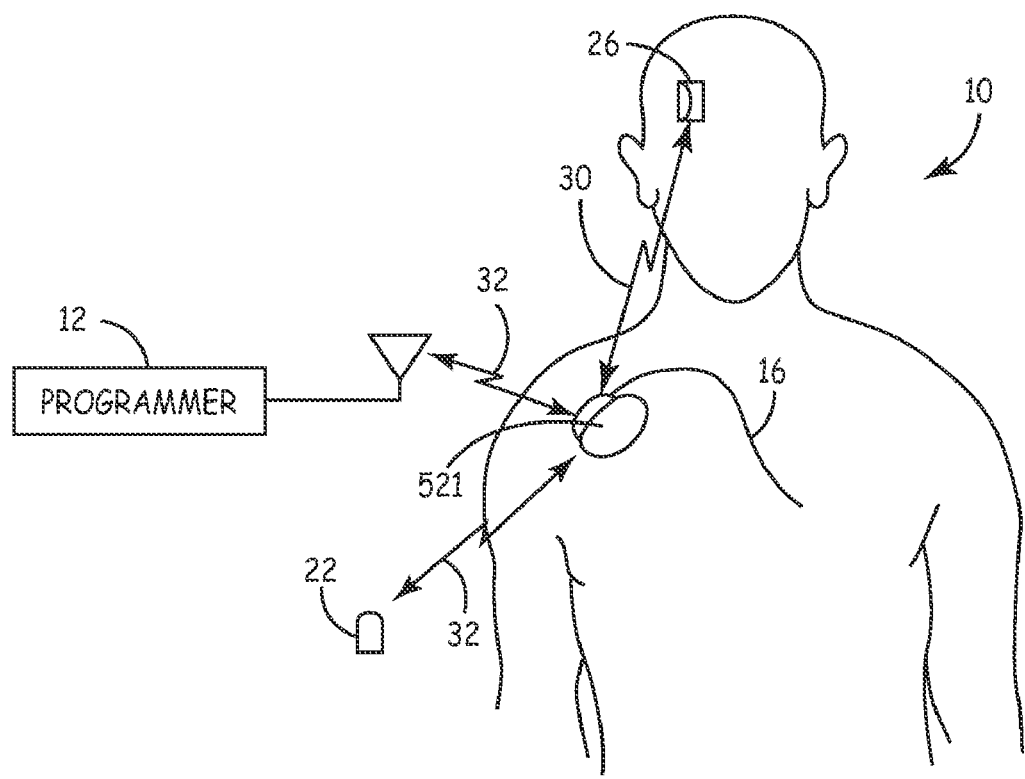

FIG. 24B is a simplified schematic view of an alternative embodiment cardiac and brain leaded medical device implanted in a patient that monitors cardiac, respiratory and brain parameters relating to nervous system disorders and provides brain and cardiac treatment.

Figure 22:
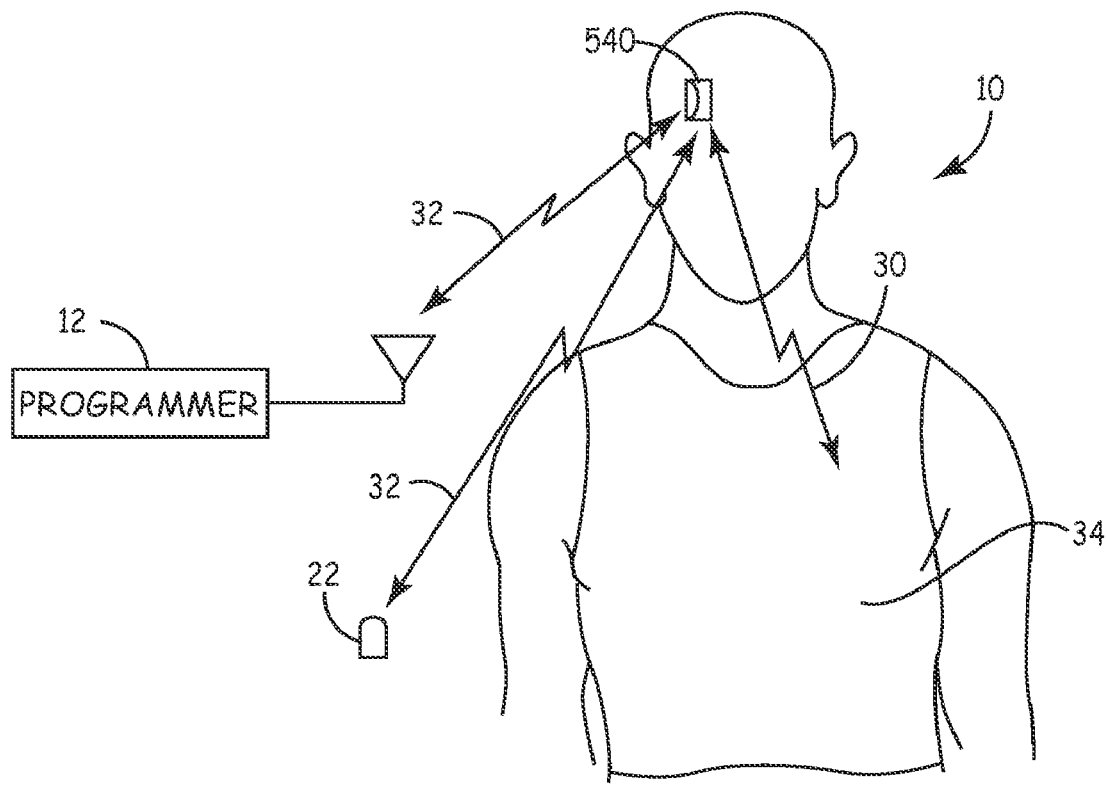

FIG. 22 is a simplified schematic view of an alternative embodiment cranial implant to defibrillator vest via wireless connect medical device used by a patient that monitors cardiac, respiratory and brain parameters relating to nervous system disorders and provides brain and cardiac treatment.

Figure 23:
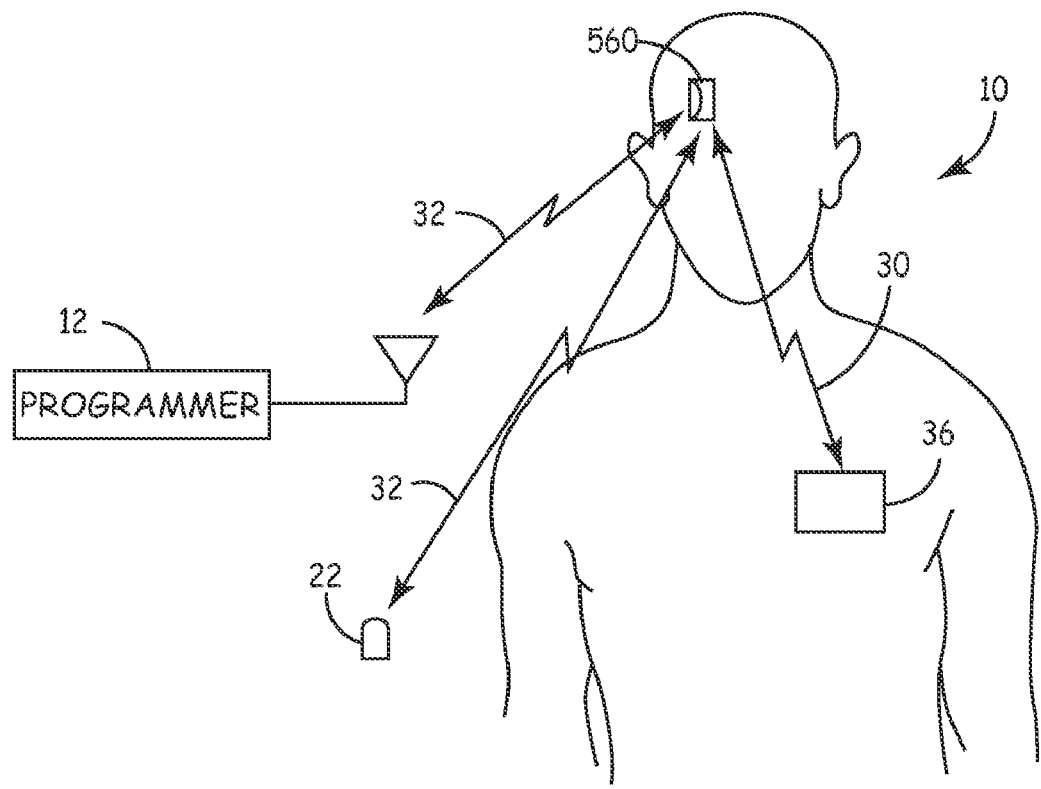

FIG. 23 is a simplified schematic view of an alternative embodiment cranial implant to leadless defibrillator (lifeboat) via wireless connect medical device used by a patient that monitors cardiac, respiratory and brain parameters relating to nervous system disorders and provides brain and cardiac treatment.

Monitor+Treatment (Brain+Respiration+Cardiac)

Figure 25A:
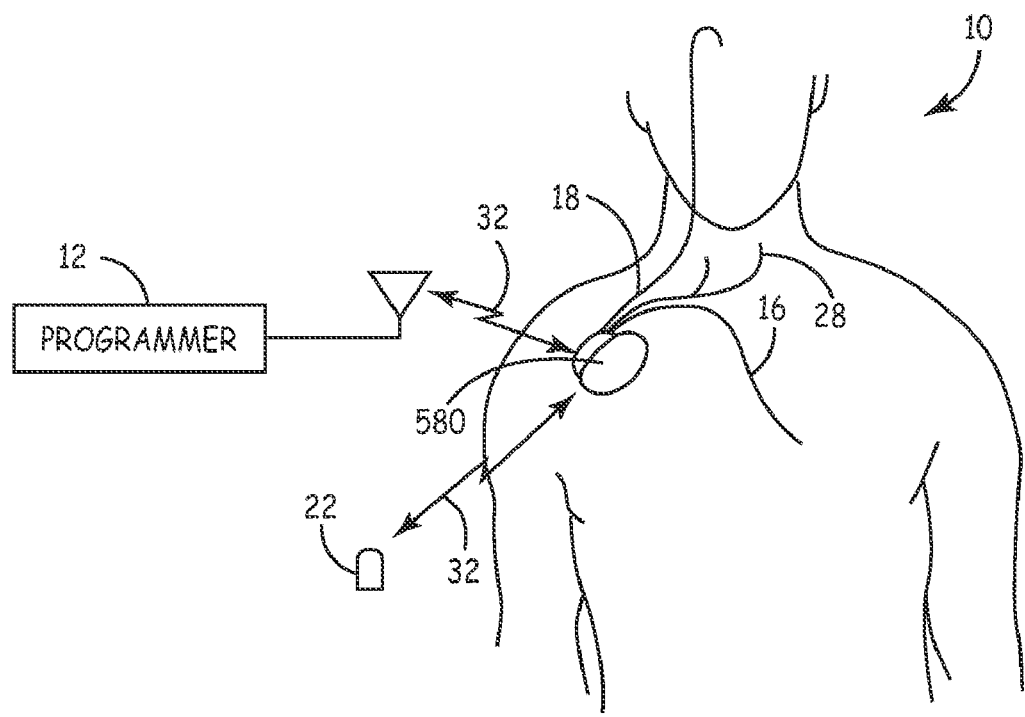

FIG. 25A is a simplified schematic view of an alternative embodiment cardiac, cranial and phrenic nerve leaded medical device implanted in a patient that monitors cardiac, respiratory and brain parameters relating to nervous system disorders and provides brain and respiration and cardiac treatment.

Figure 25B:
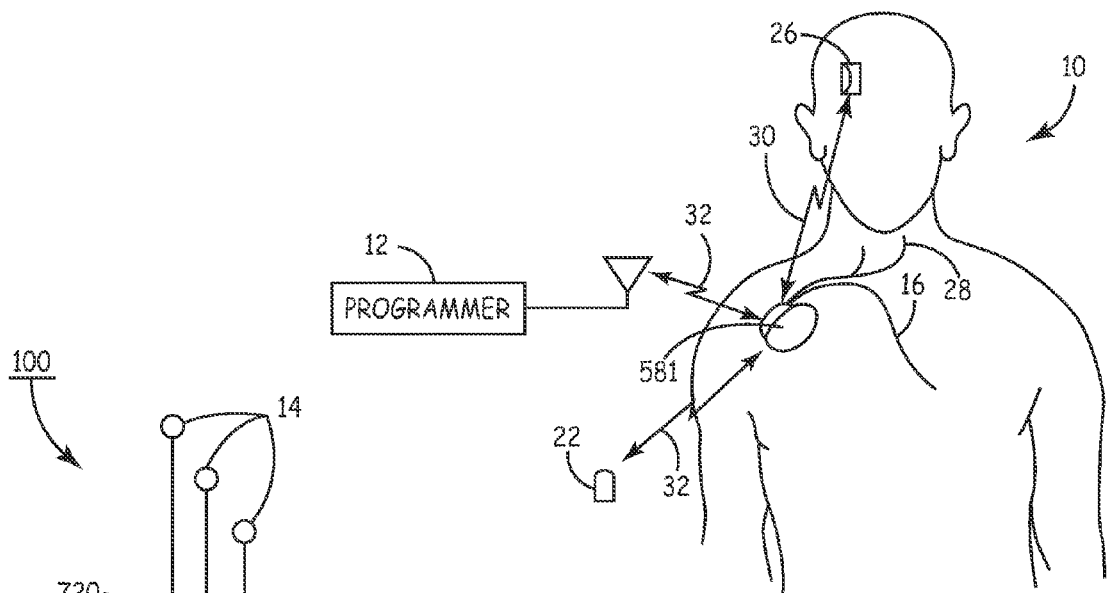

FIG. 25B is a simplified schematic view of an alternative embodiment cardiac, cranial and phrenic nerve leaded medical device implanted in a patient that monitors cardiac, respiratory and brain parameters relating to nervous system disorder and provides brain and respiration and cardiac treatment.

Detailed Design

Figure 1:
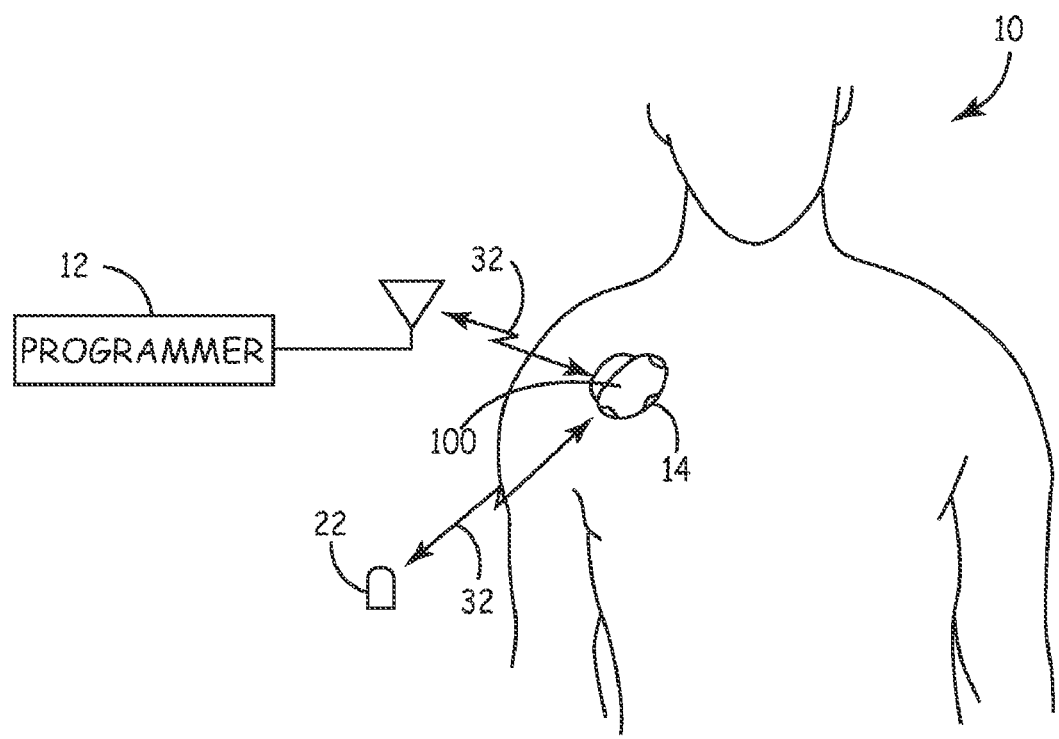
FIG. 1 is a simplified schematic view of a thoracic cavity leadless medical device implanted in a patient that monitors cardiac and respiratory parameters relating to a nervous system disorder.
Figure 26:
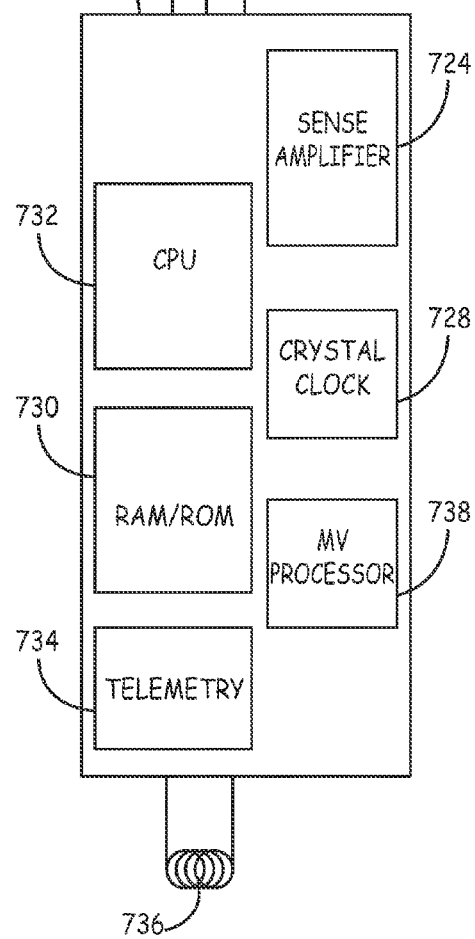

FIG. 26 is a simplified block diagram of a core monitor as shown in FIG. 1 above.

Figure 27:
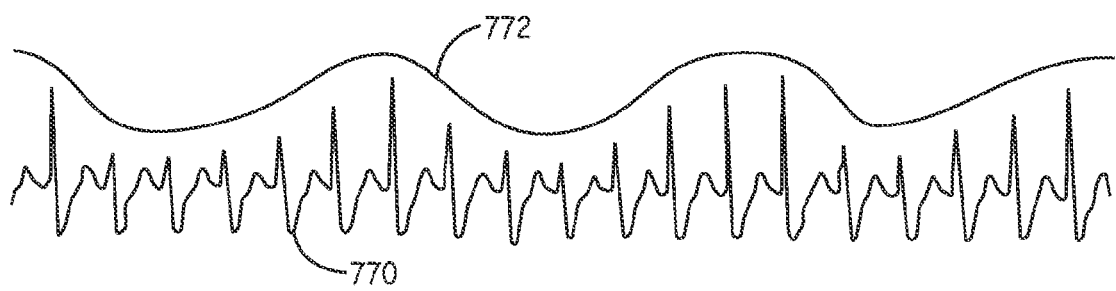

FIG. 27 is a graphical representation of the signals sensed by core monitor as shown in FIG. 1 above.

Figure 2:
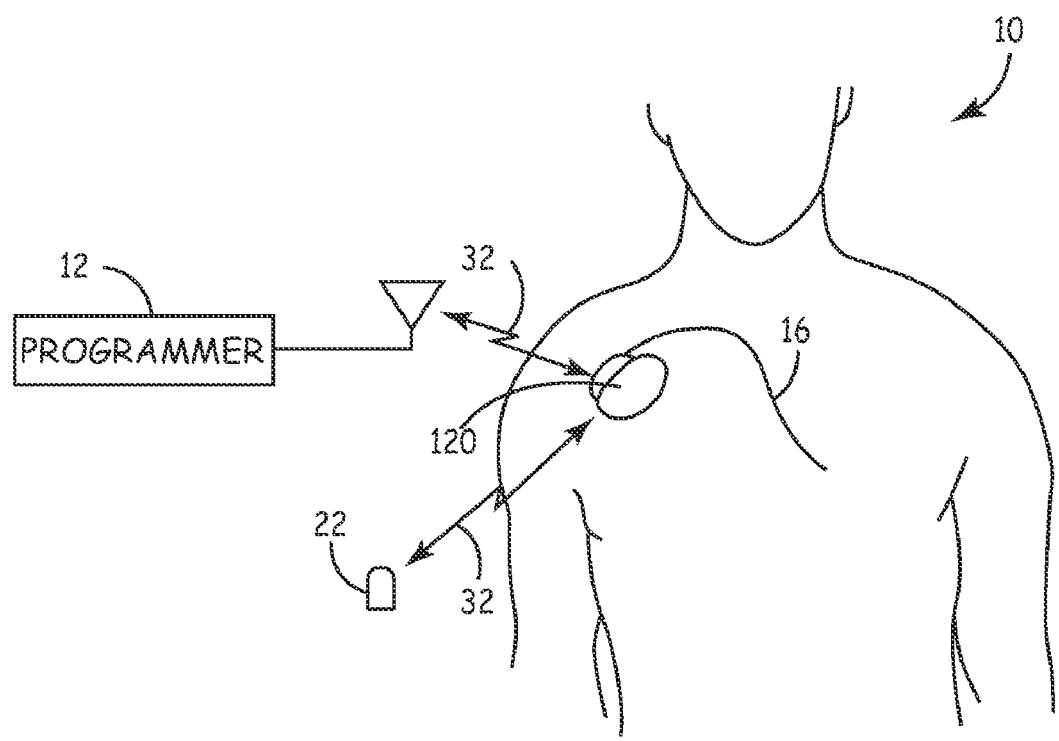
FIG. 2 is a simplified schematic view of an alternative embodiment cardiac leaded medical device implanted in a patient that monitors cardiac and respiratory parameters relating to nervous system disorder.
Figure 28:
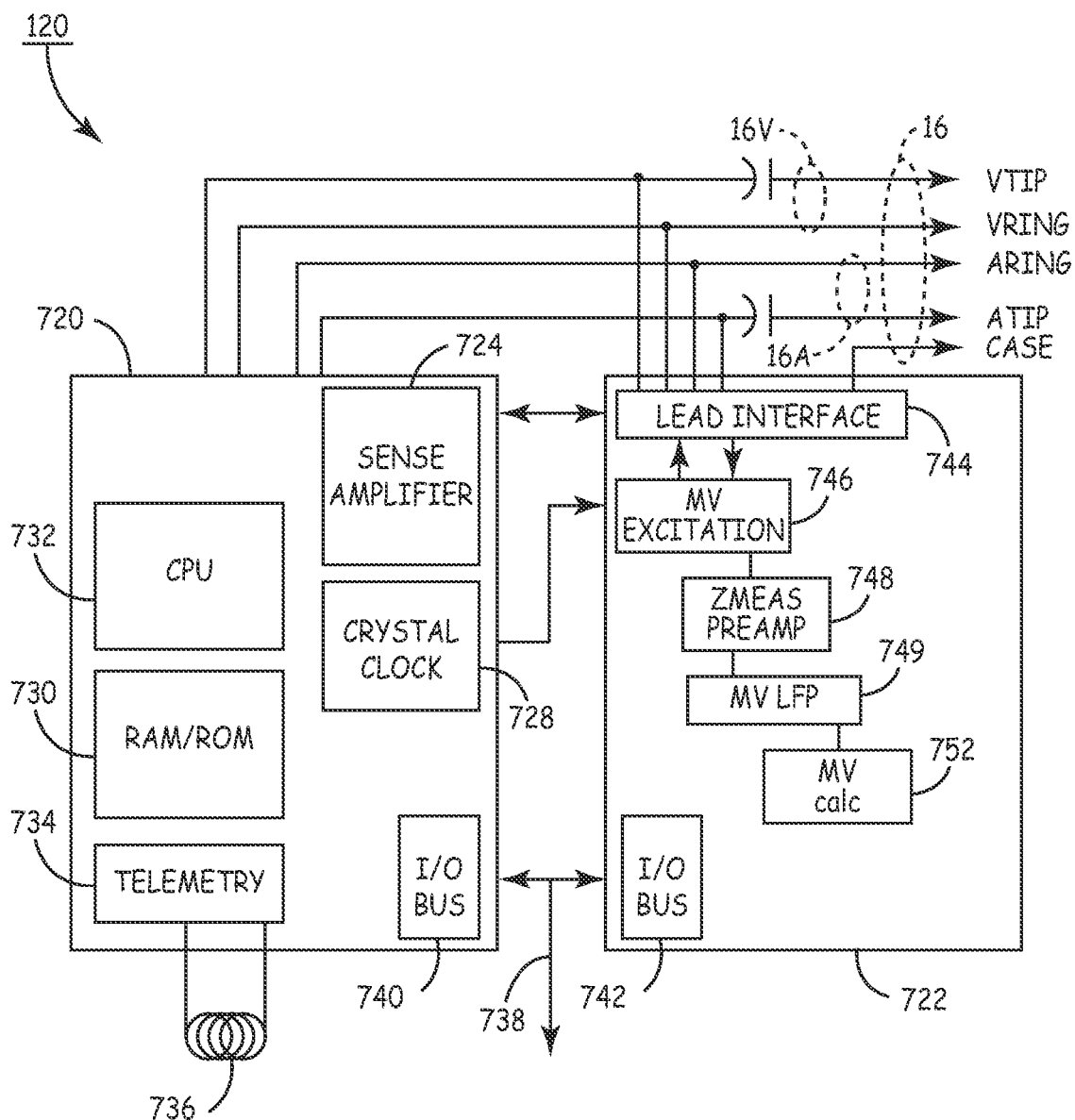

FIG. 28 is a simplified block diagram of a core monitor as shown in FIG. 2 above.

Figure 3:
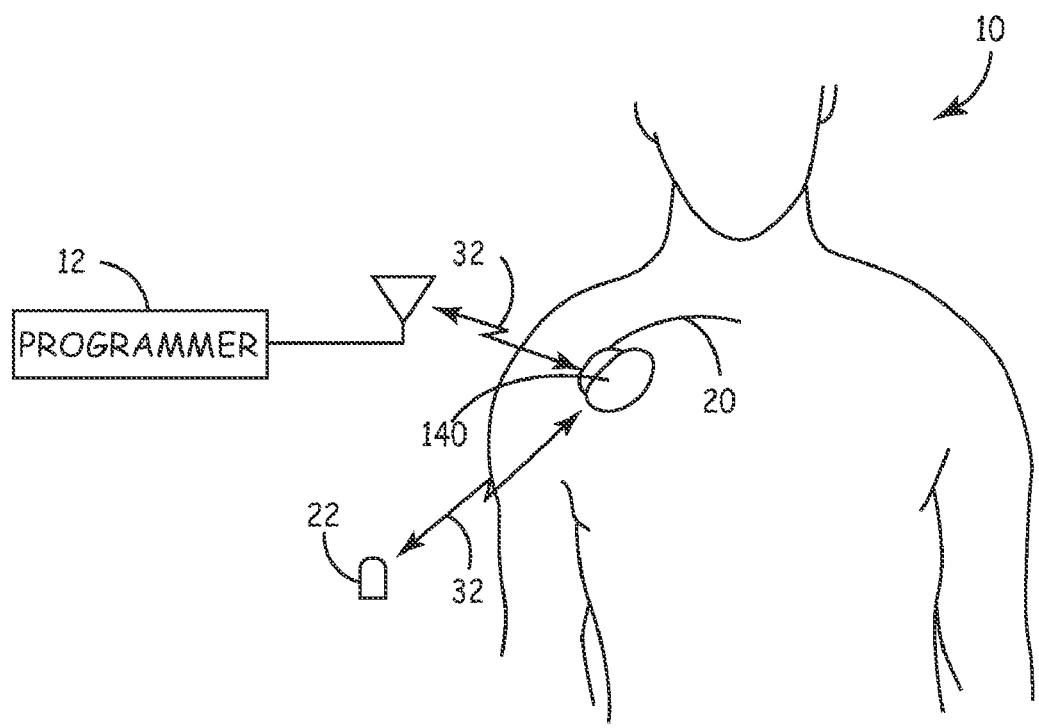
FIG. 3 is a simplified schematic view of an alternative embodiment sensor stub medical device implanted in a patient that monitors cardiac and respiratory parameters relating to nervous system disorder.
Figure 29:
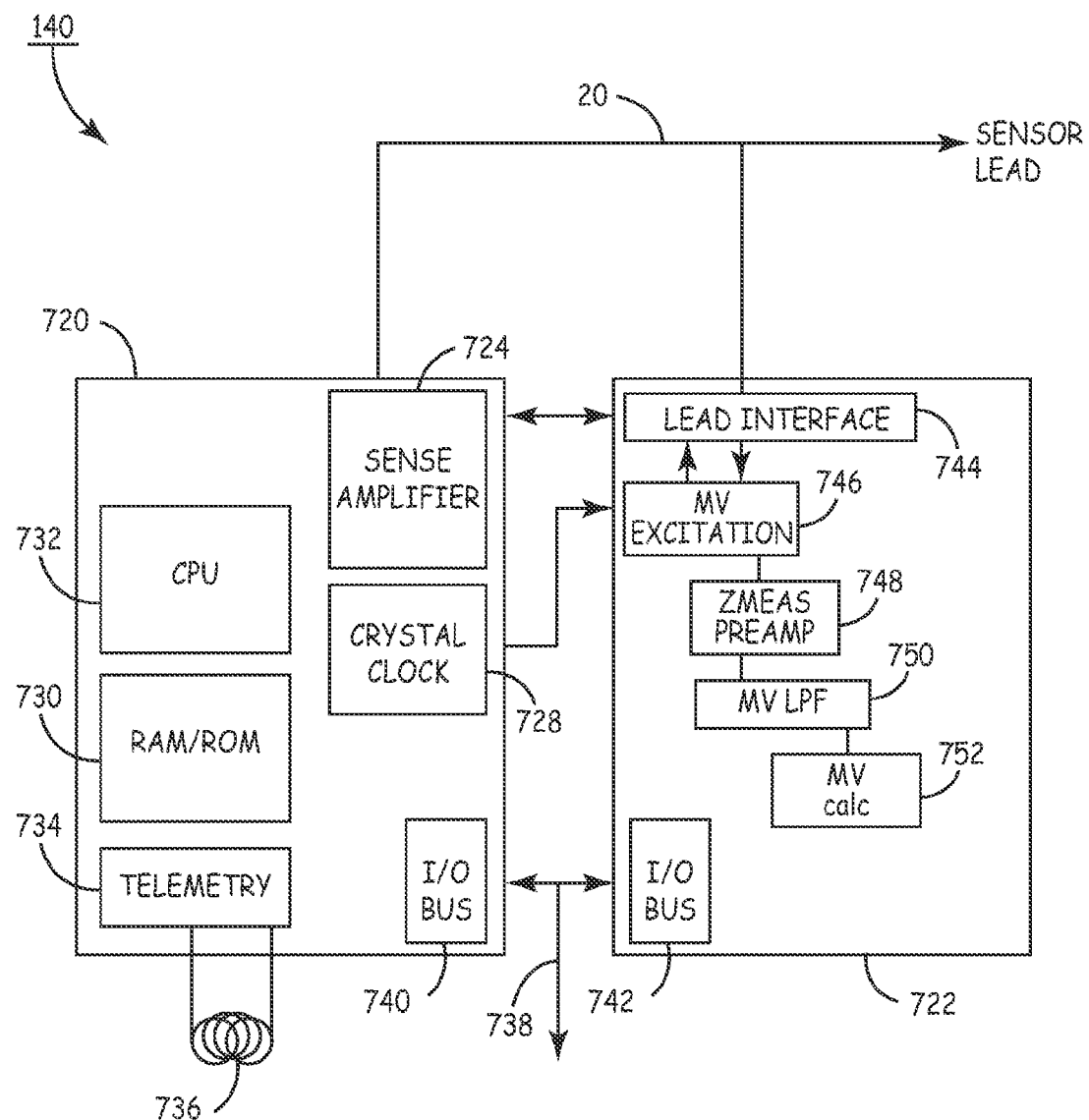

FIG. 29 is a simplified block diagram of a core monitor as shown in FIG. 3 above.

Figure 4:
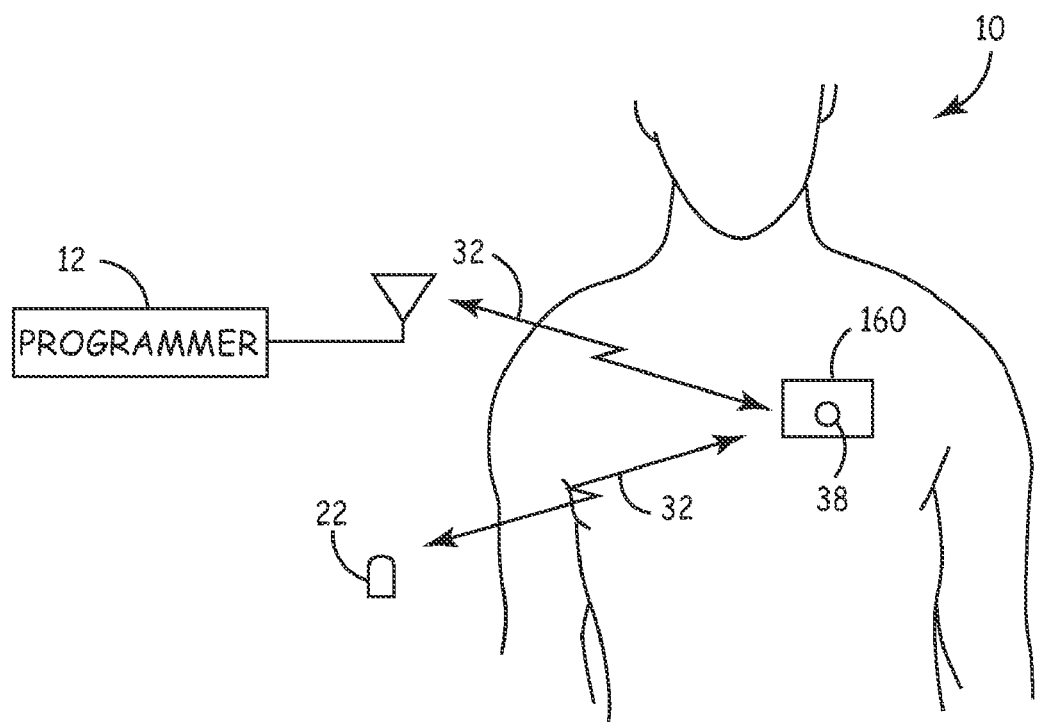
FIG. 4 is a simplified schematic view of an alternative embodiment external patch medical device used by a patient that monitors cardiac and respiratory parameters relating to nervous system disorder.
Figure 30:
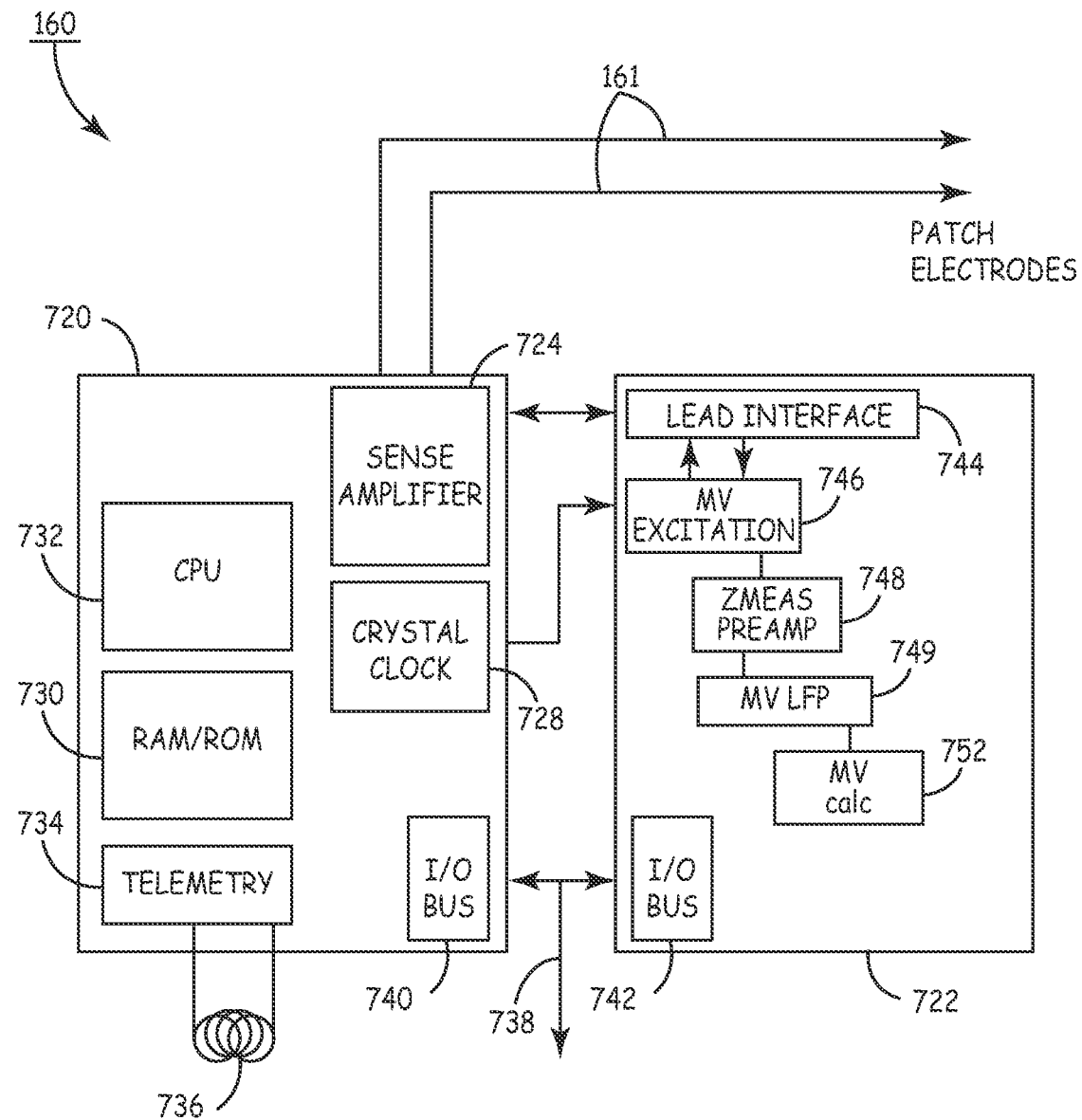

FIG. 30 is a simplified block diagram of a core monitor as shown in FIG. 4 above.

Figure 31:
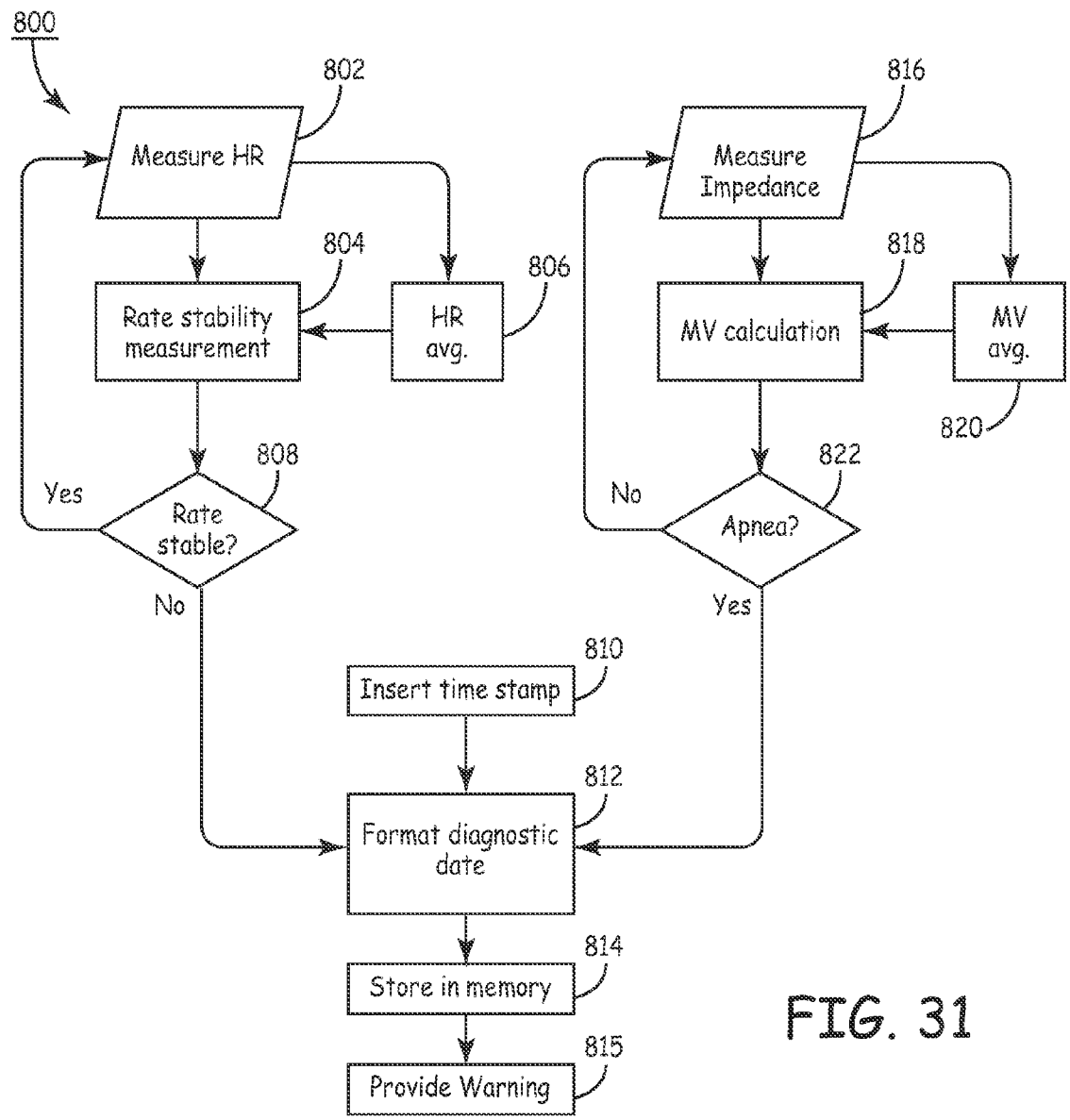

FIG. 31 is a flow diagram showing operation of a core monitor as shown in FIG. 1-4 above.

Figure 32:
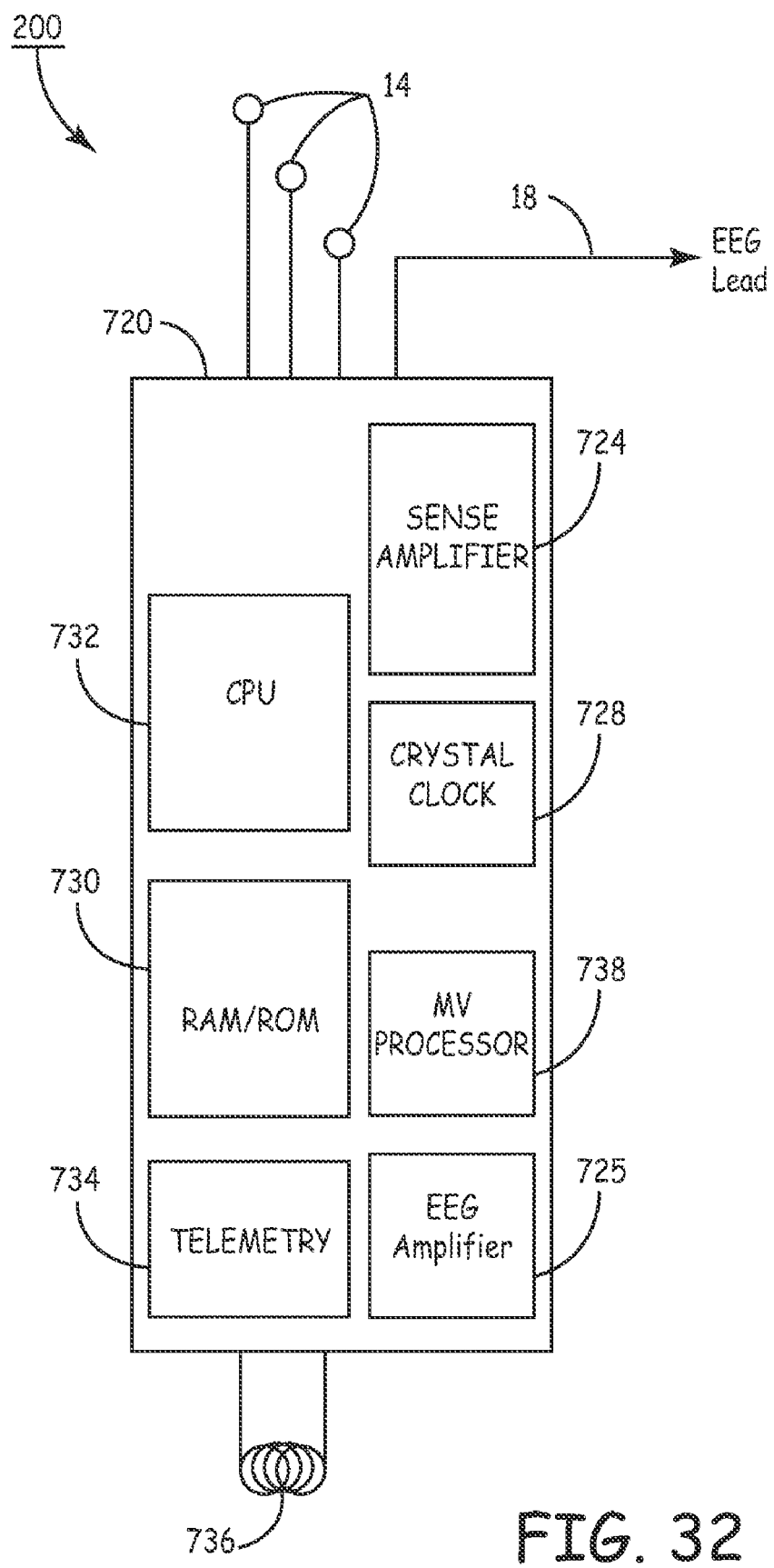

FIG. 32 is a simplified block diagram of a full monitor as shown in FIG. 5 above.

Figure 33:
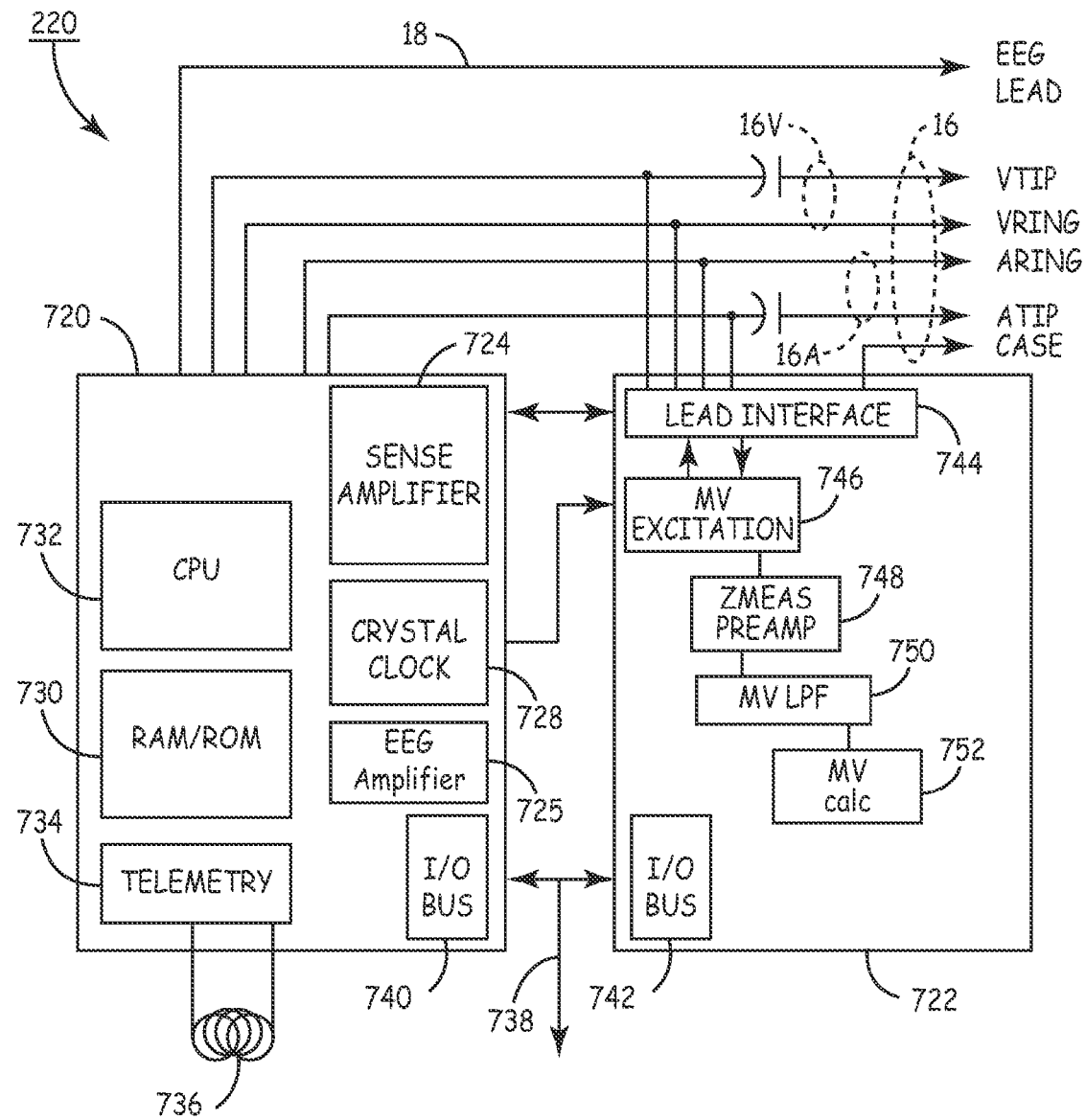

FIG. 33 is a simplified block diagram of a full monitor as shown in FIG. 6 above.

Figure 34:
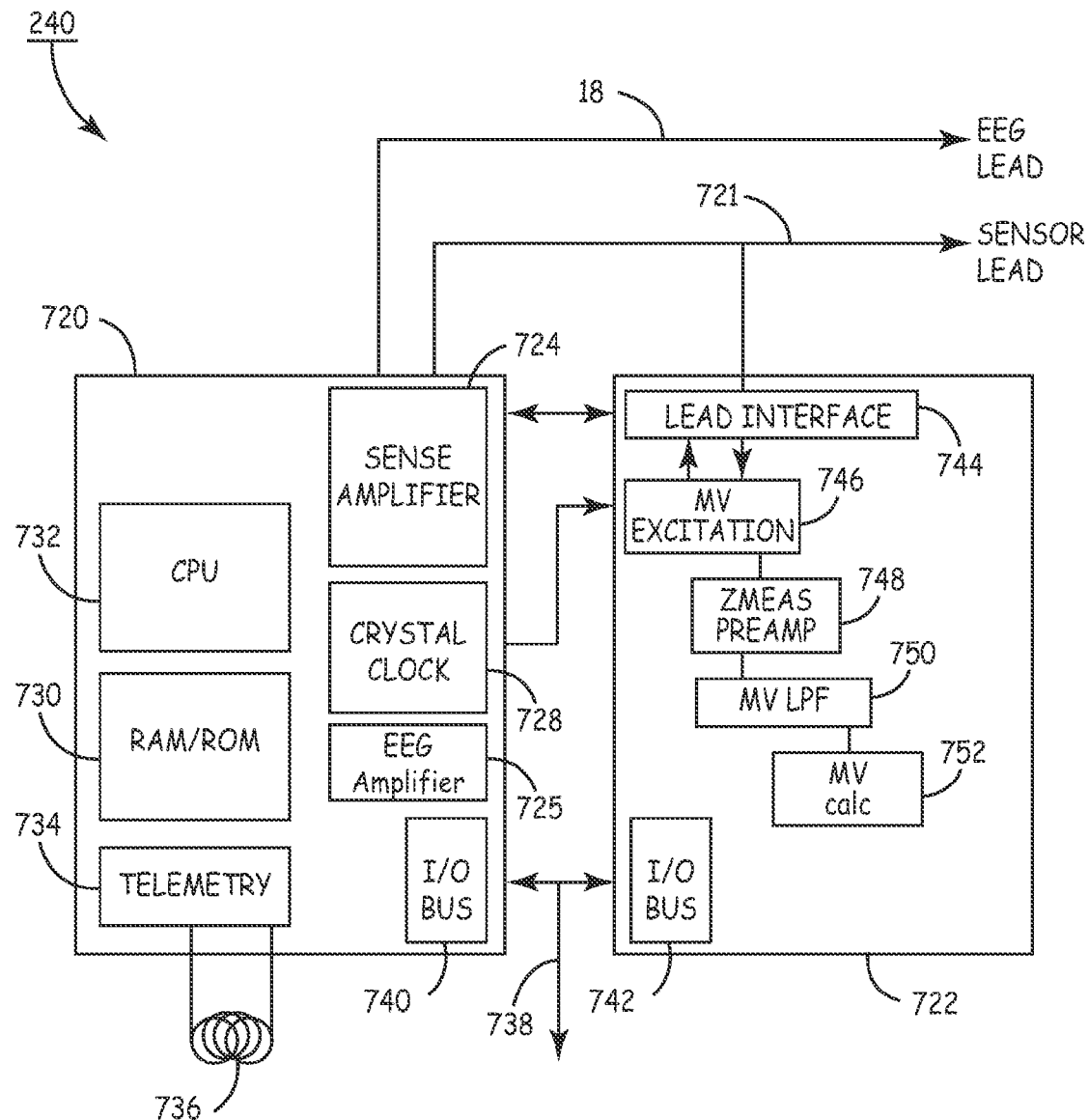

FIG. 34 is a simplified block diagram of a full monitor as shown in FIGS. 7 and 9 above.

Figure 35:
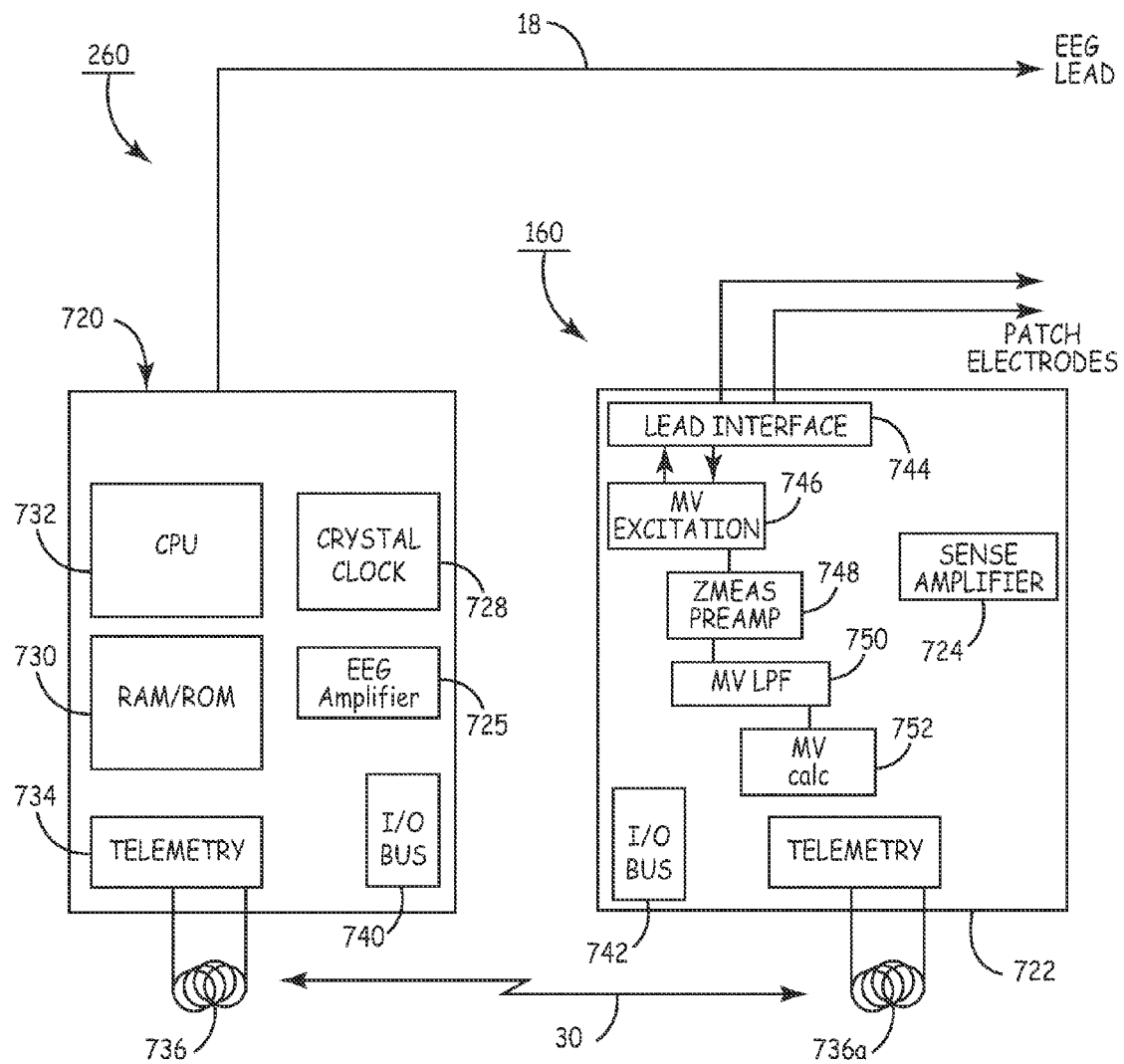

FIG. 35 is a simplified block diagram of a full monitor as shown in FIG. 8 above.

Figure 36:
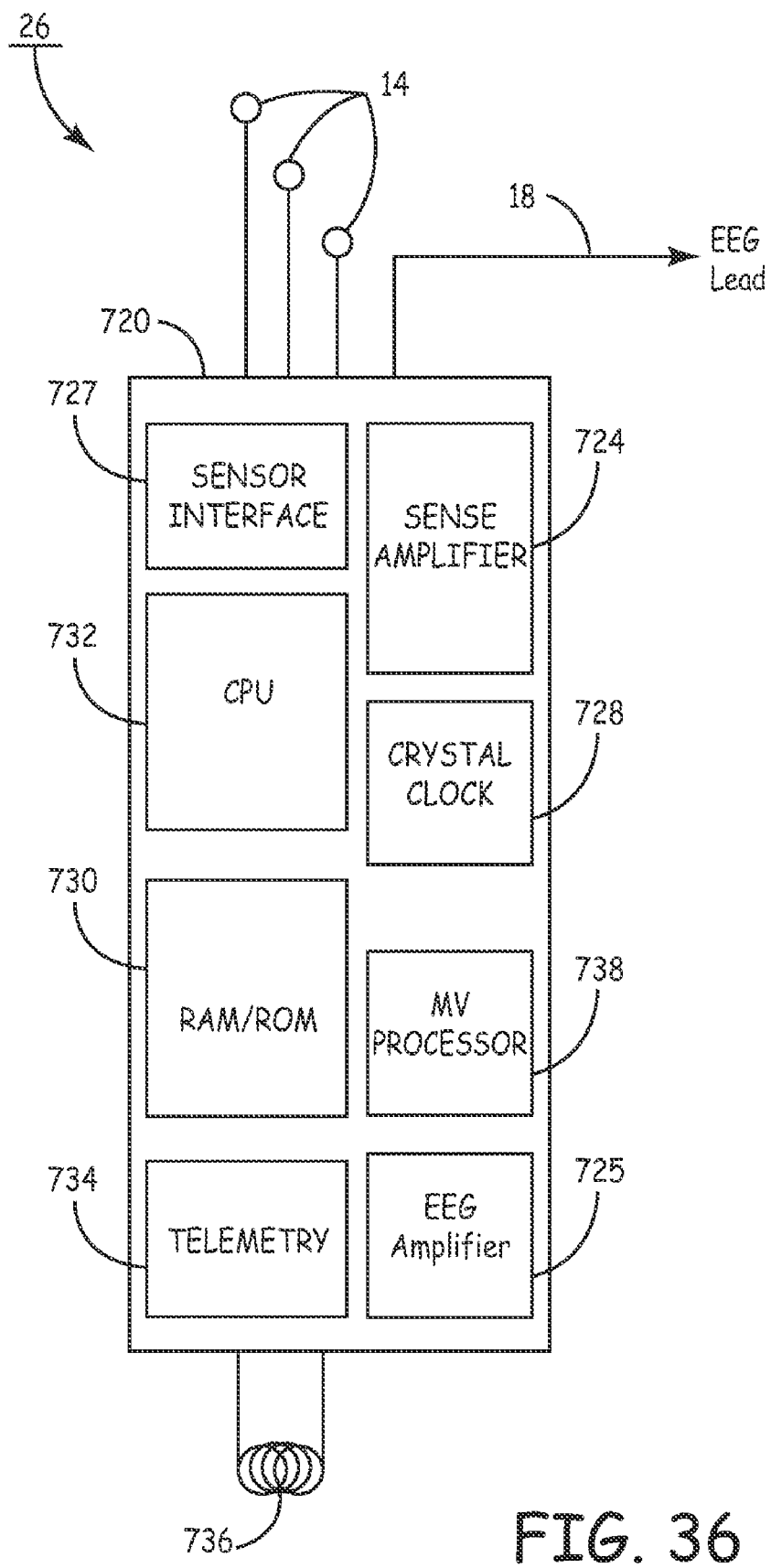

FIG. 36 is a simplified block diagram of a full monitor as shown in FIG. 10 above.

Figure 37:
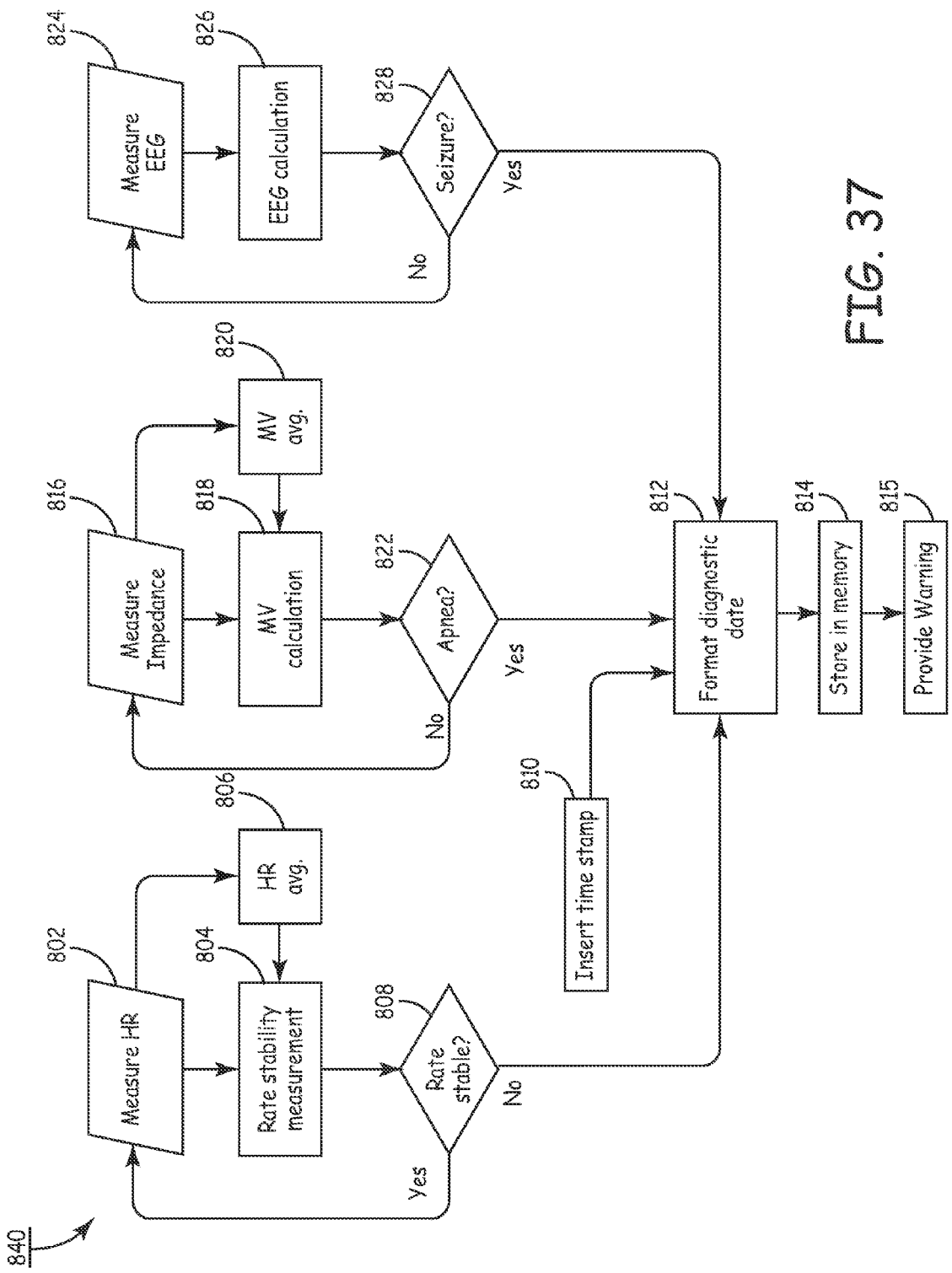

FIG. 37 is a flow diagram showing operation of a full monitor as shown in FIG. 5-10 above.

Figure 38:
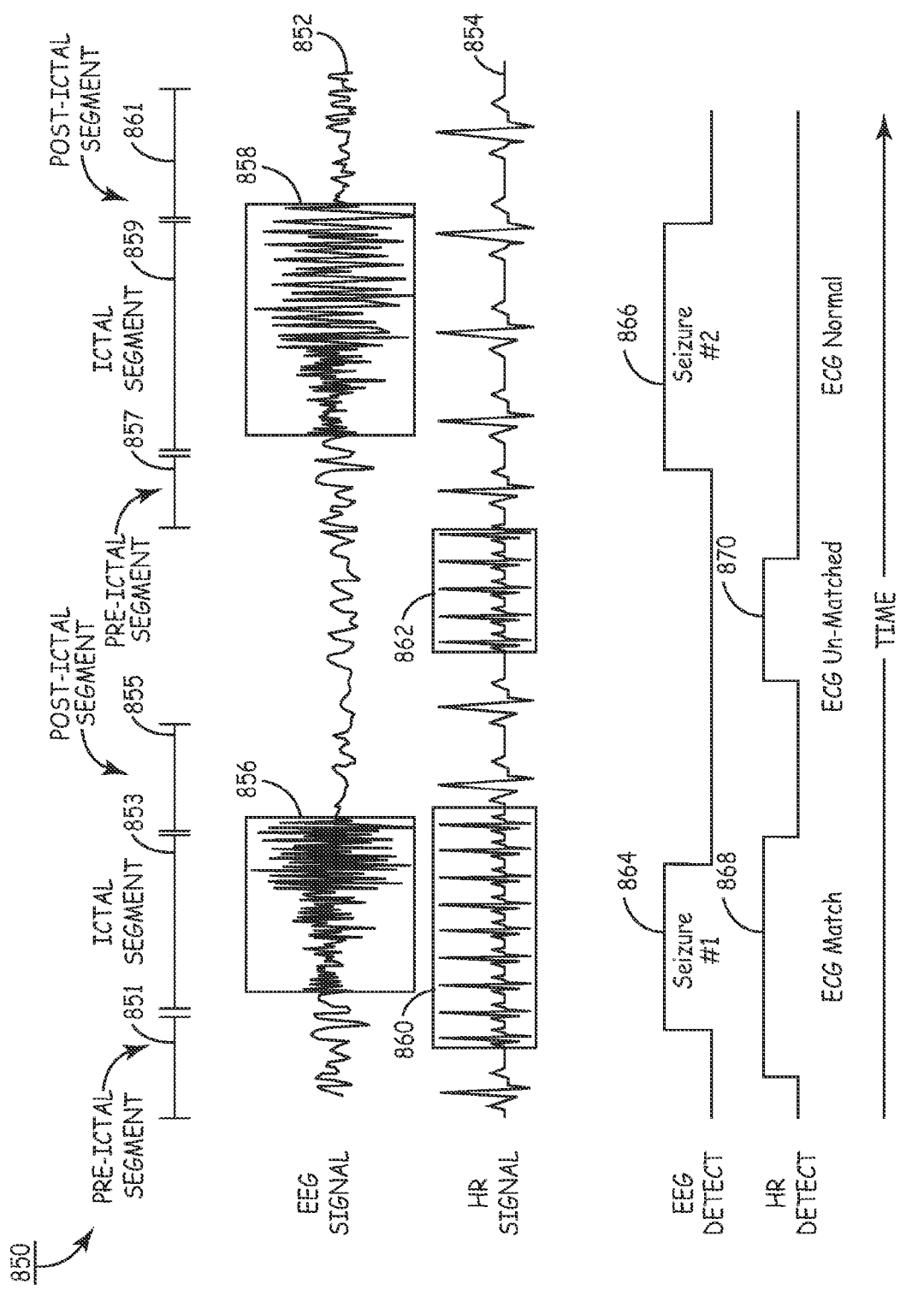

FIG. 38 is a diagram of exemplary physiologic data from a patient with a full monitor as shown in relation to FIG. 5-10 above.

Figure 39:
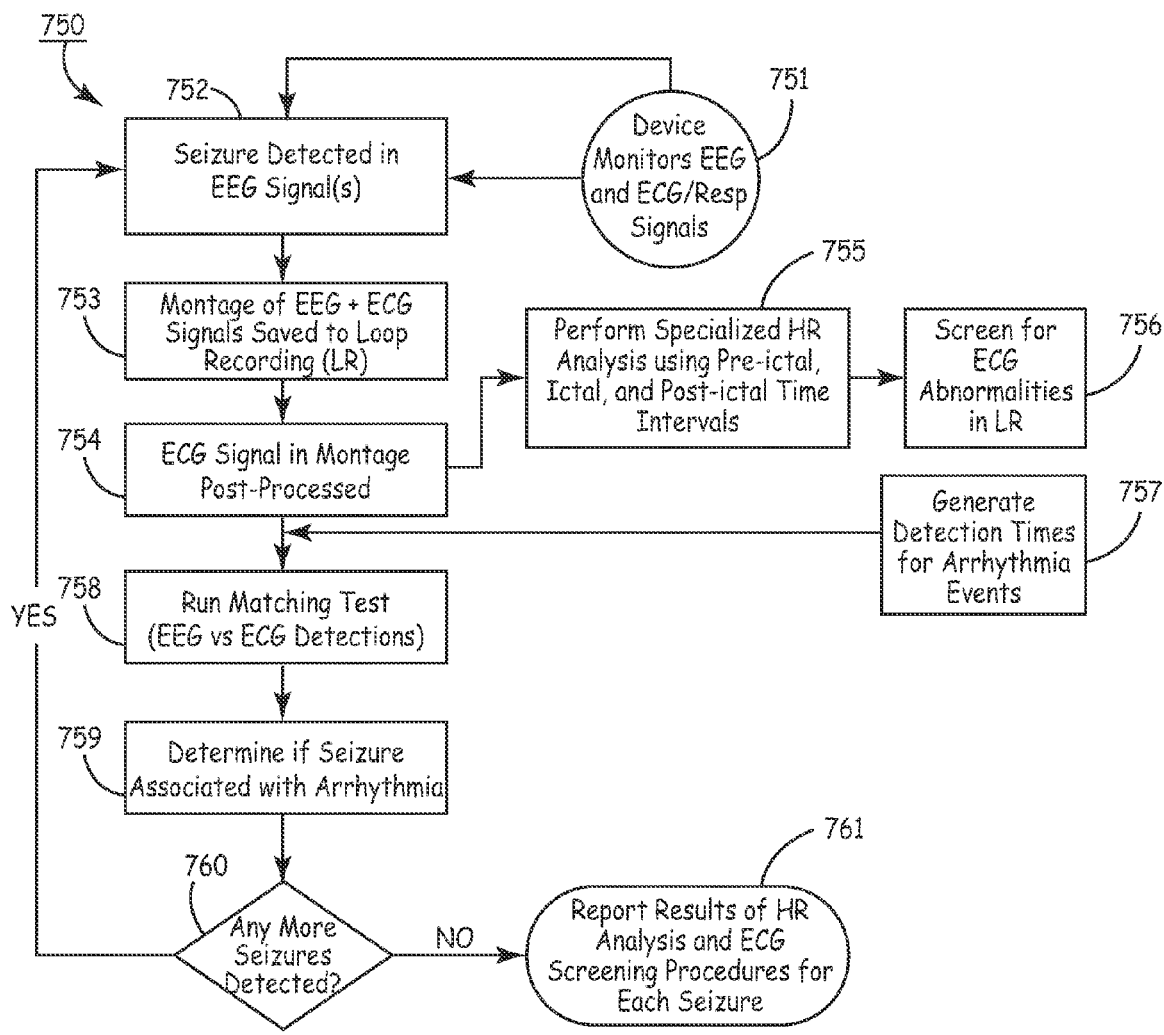

FIG. 39 shows a process for identifying ECG and respiratory abnormalities recorded during detected seizures in a full monitor as shown in relation to FIG. 5-10 above.

Figure 40A:
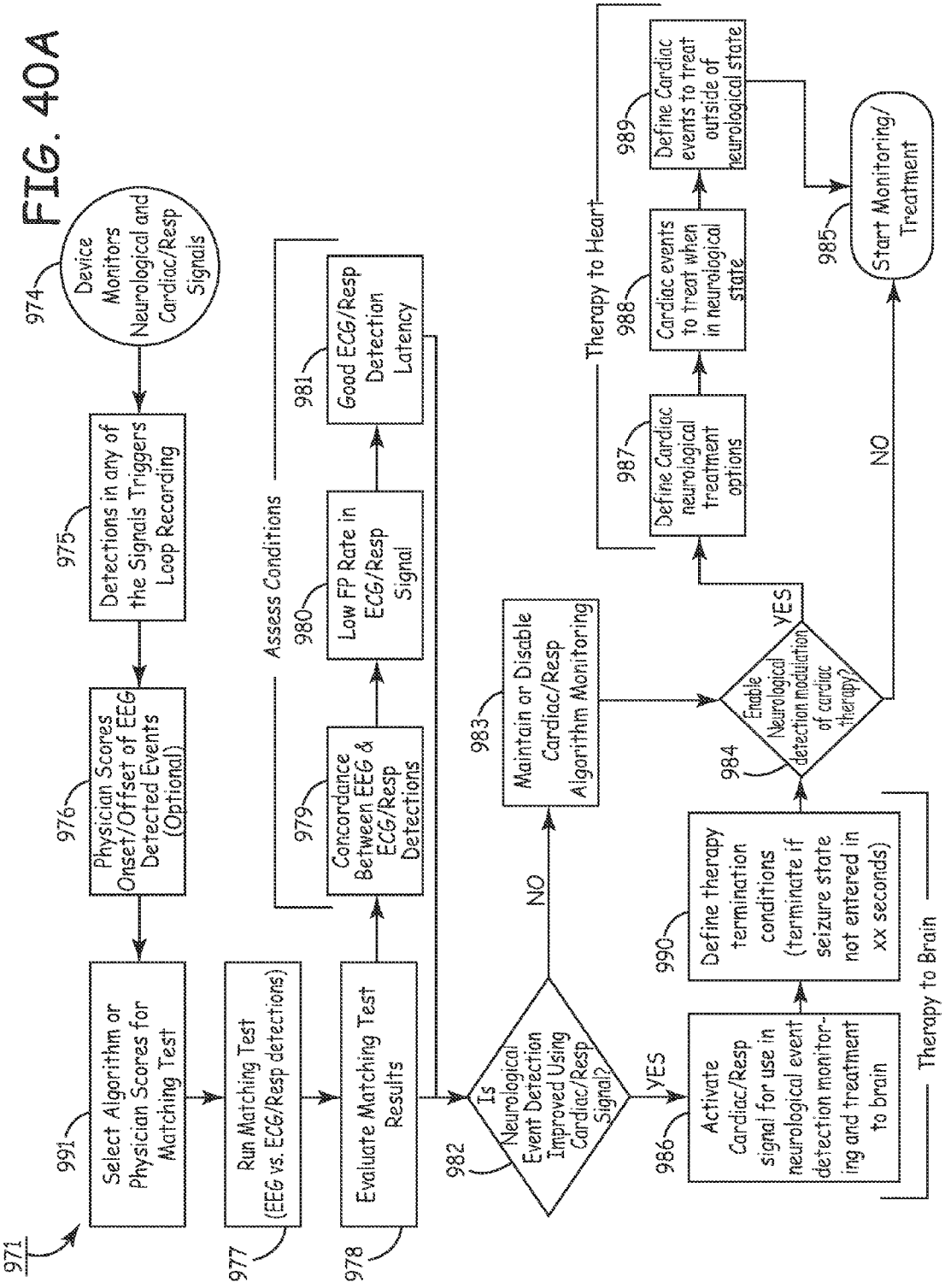

FIG. 40A shows a process for enabling the cardiac or respiratory detectors for neurological event detection in a full monitor as shown in relation to FIG. 5-10 above and detection/treatment as described in FIG. 41-51 below.

Figure 40B:
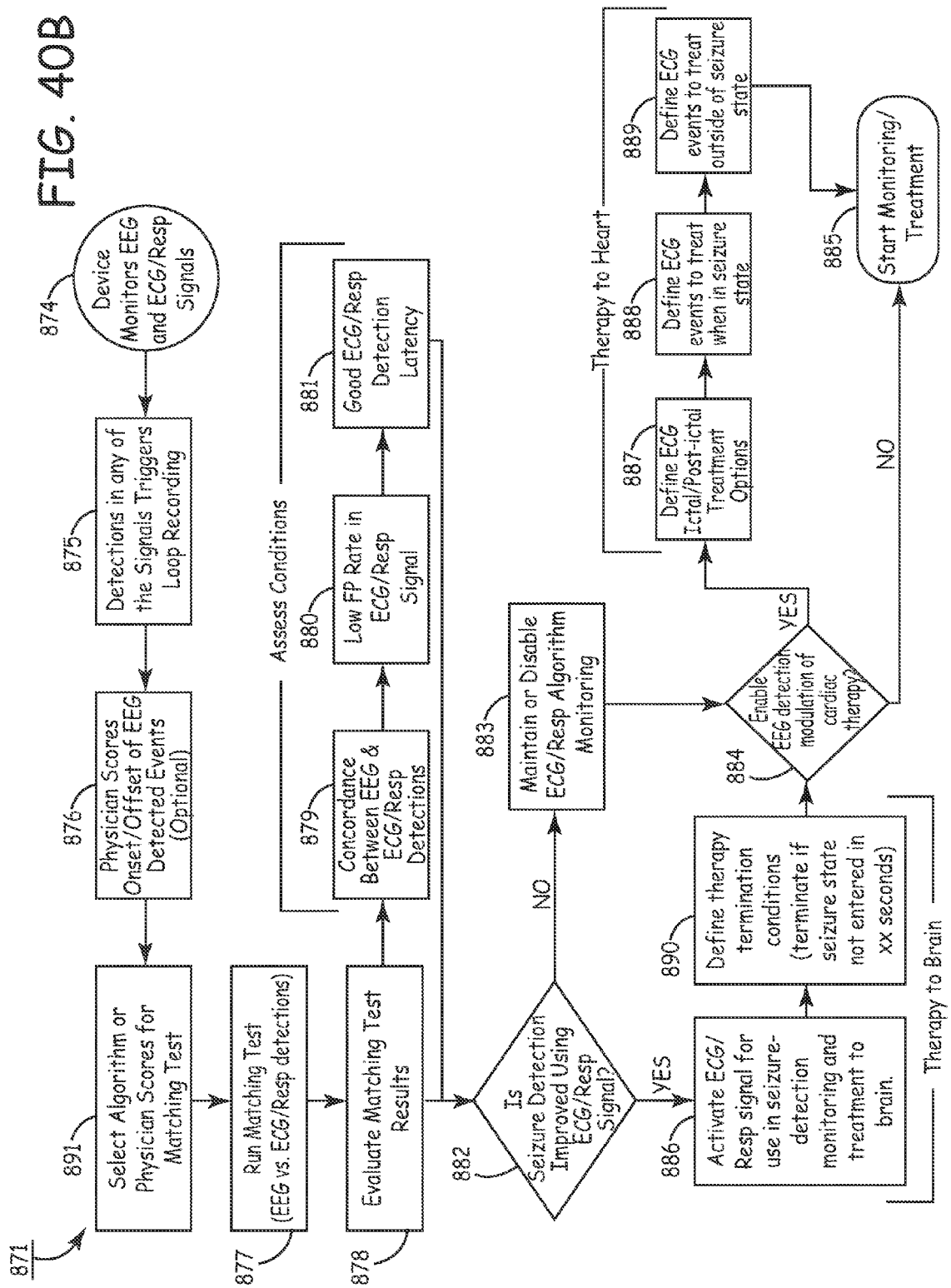

FIG. 40B shows a process for enabling the ECG or respiratory detectors for seizure detection in a full monitor as shown in relation to FIG. 5-10 above and detection/treatment as described in FIG. 41-51 below.

Figure 41:
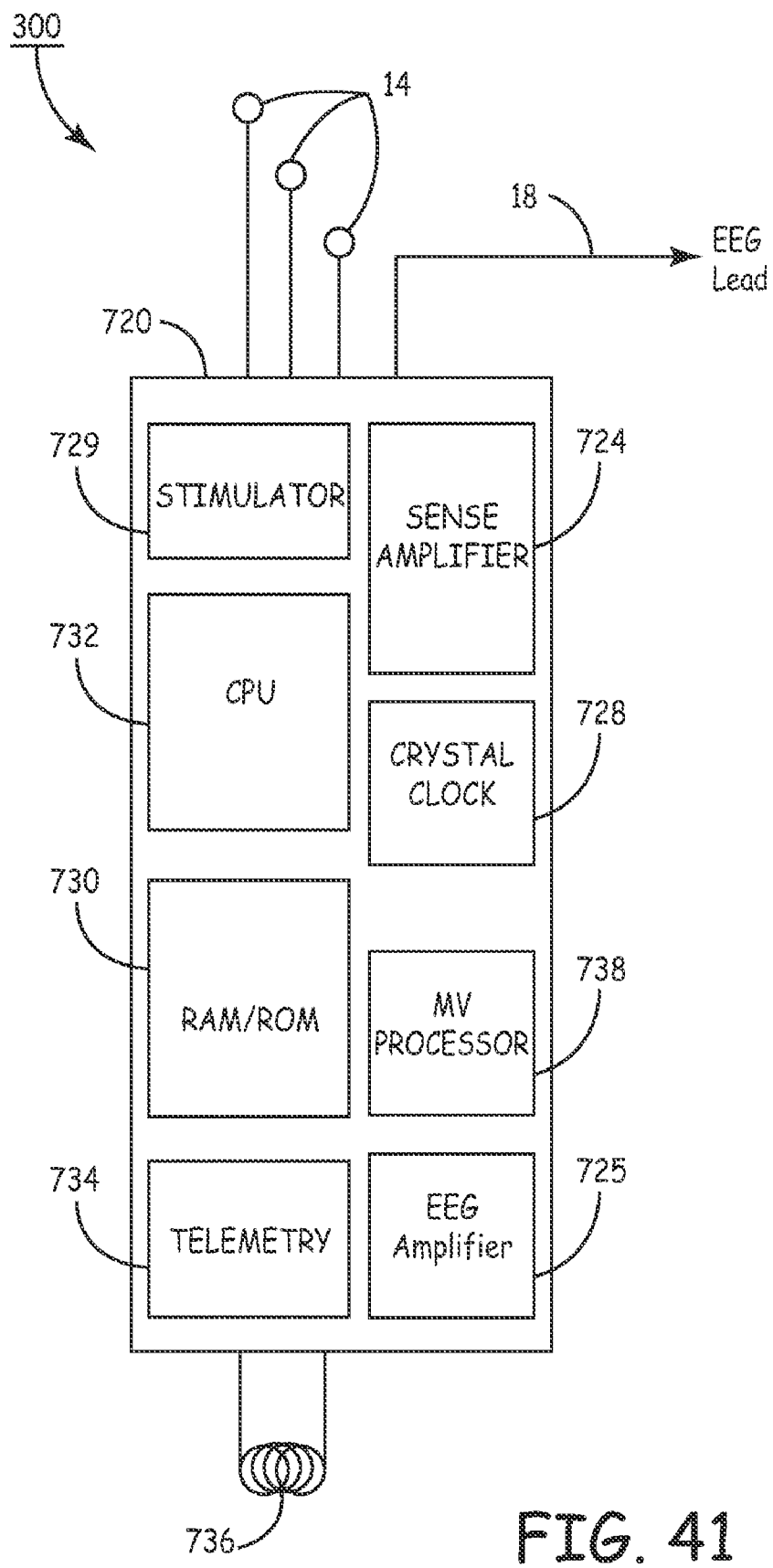

FIG. 41 is a simplified block diagram of a full monitor with brain stimulation therapy as shown in FIG. 11 above.

Figure 42:
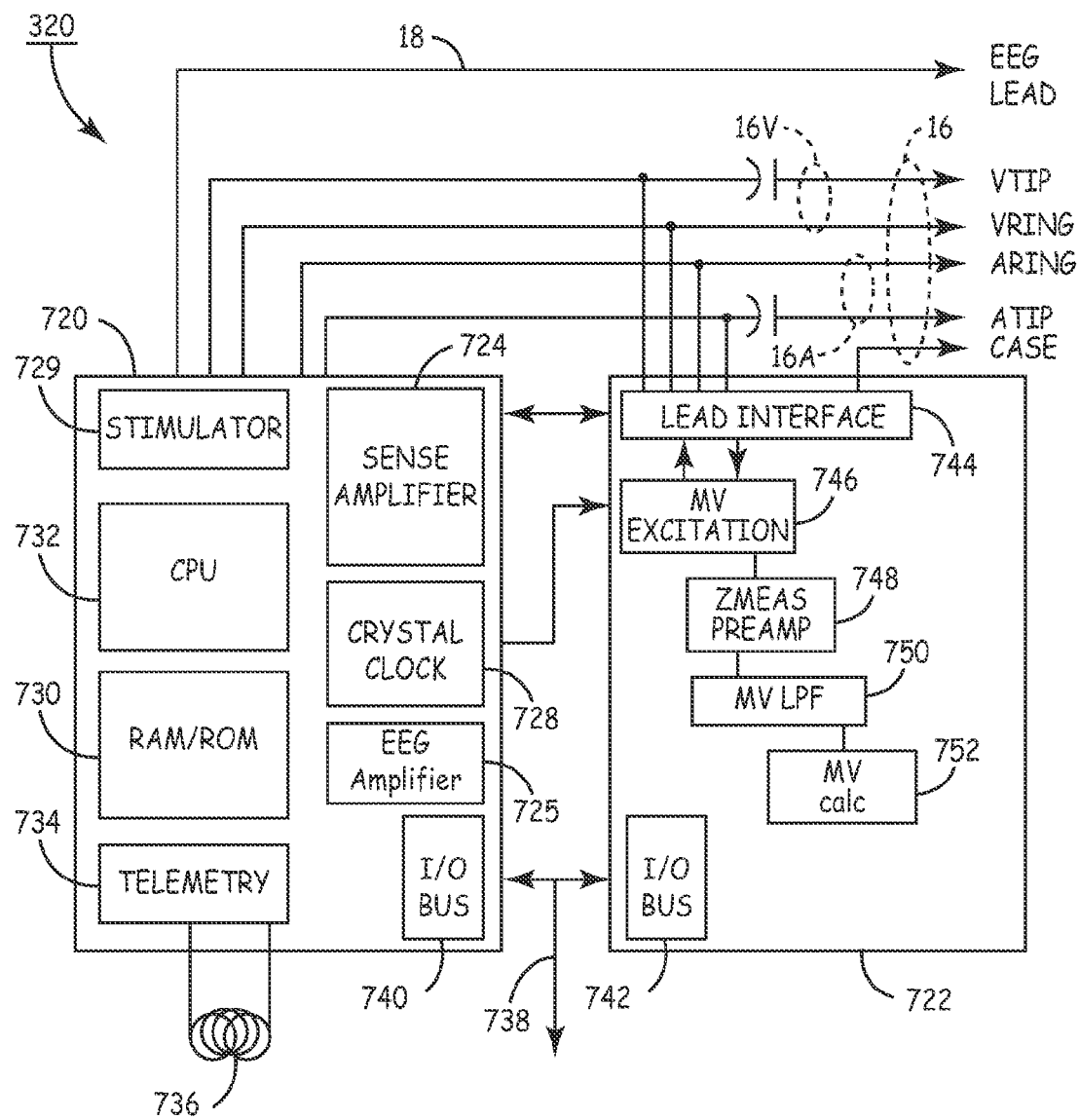

FIG. 42 is a simplified block diagram of a full monitor with brain stimulation therapy as shown in FIG. 12A above.

Figure 43:
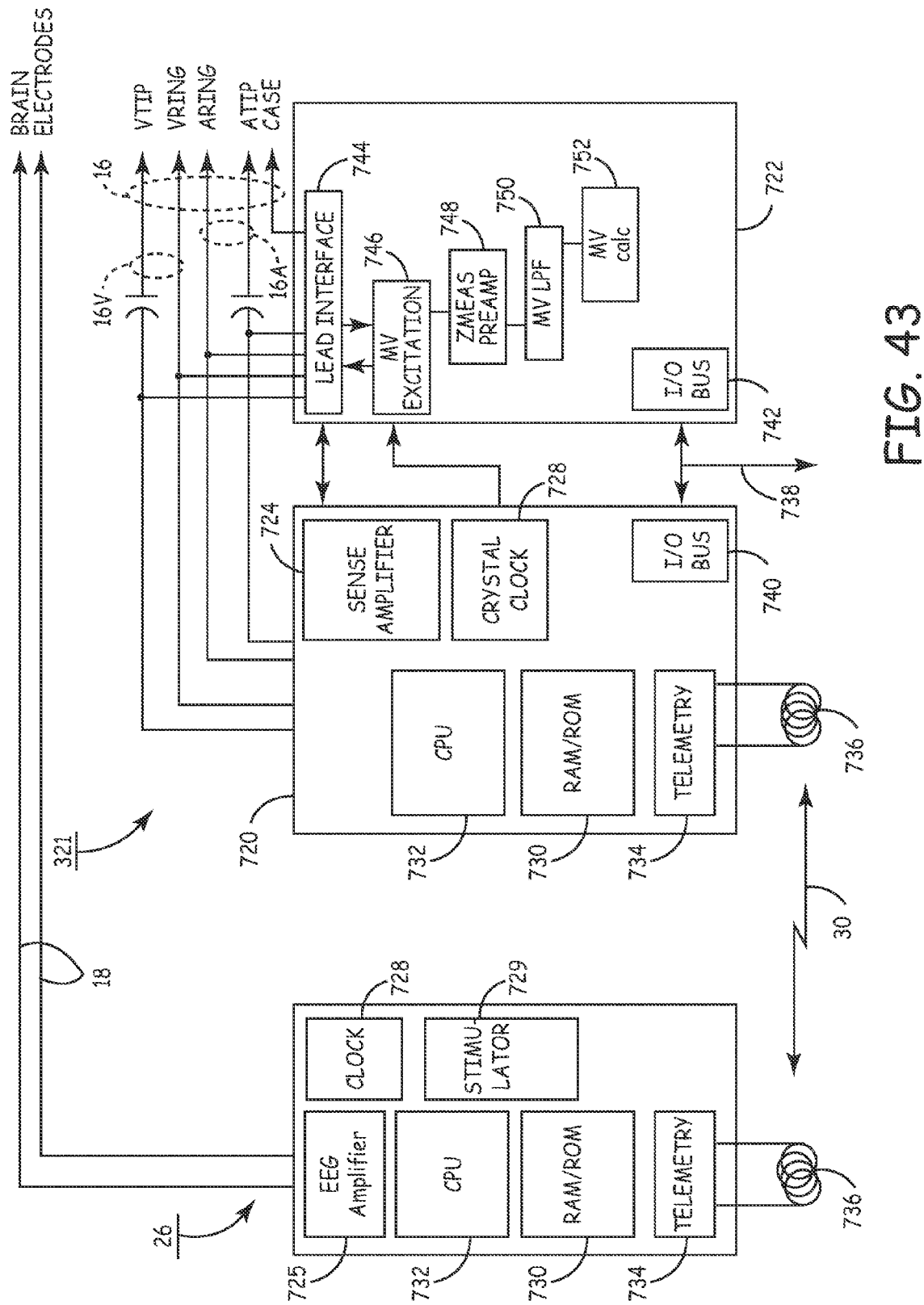

FIG. 43 is a simplified block diagram of a full monitor with brain stimulation therapy as shown in FIG. 12B above.

Figure 44:
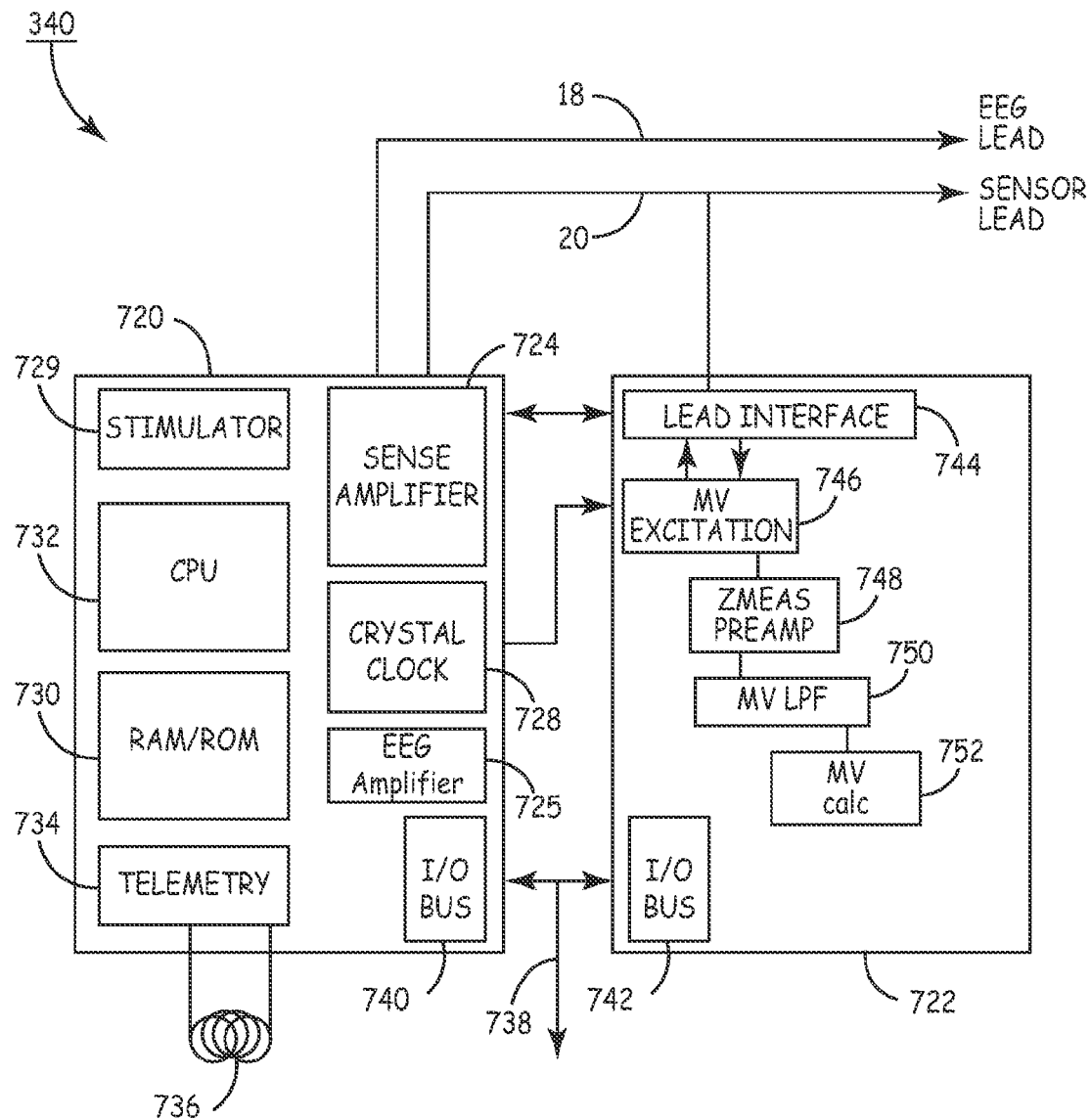

FIG. 44 is a simplified block diagram of a full monitor with brain stimulation therapy as shown in FIGS. 13 and 15 above.

Figure 45:
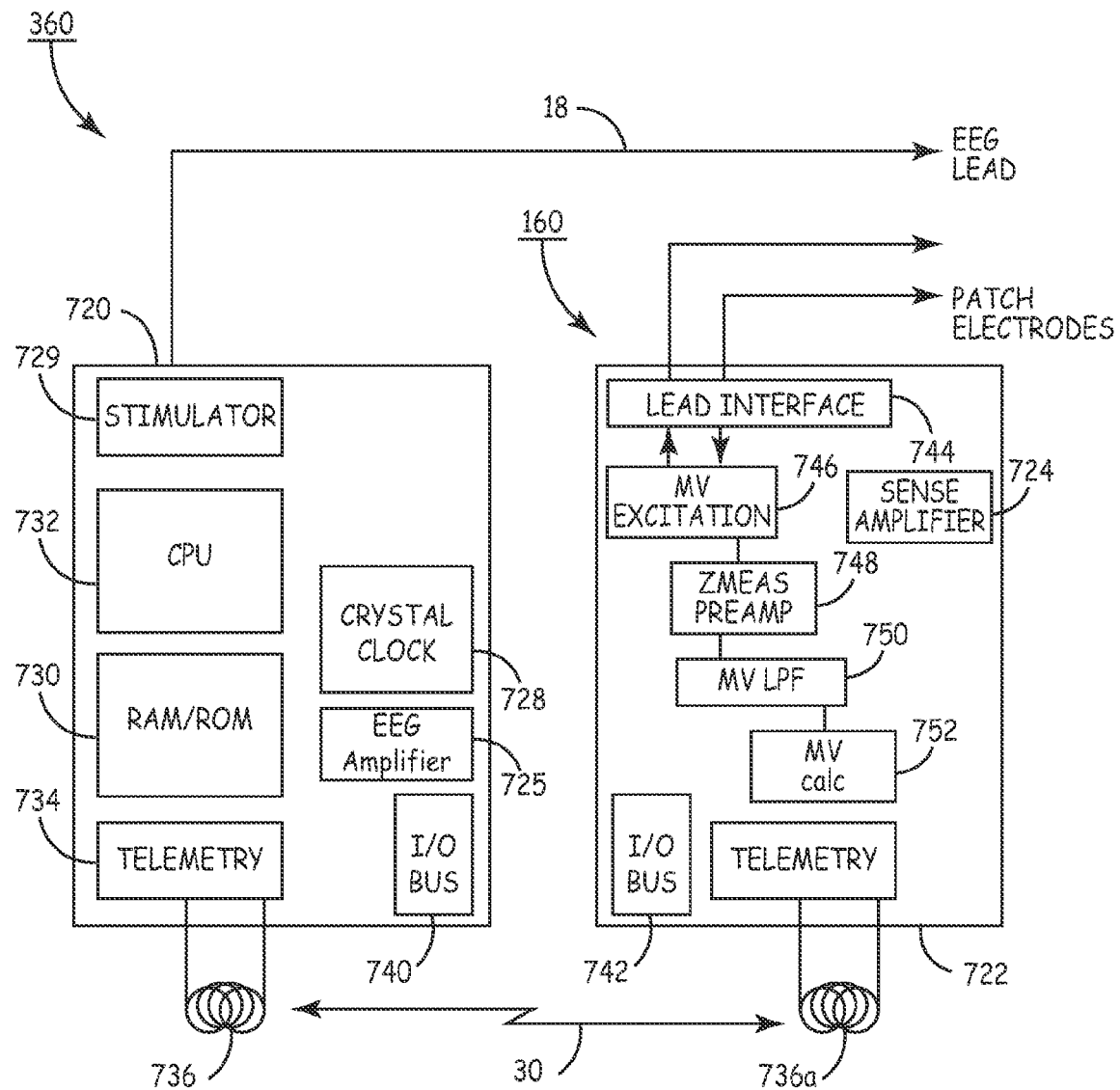

FIG. 45 is a simplified block diagram of a full monitor with brain stimulation therapy as shown in FIG. 14 above.

Figure 46:
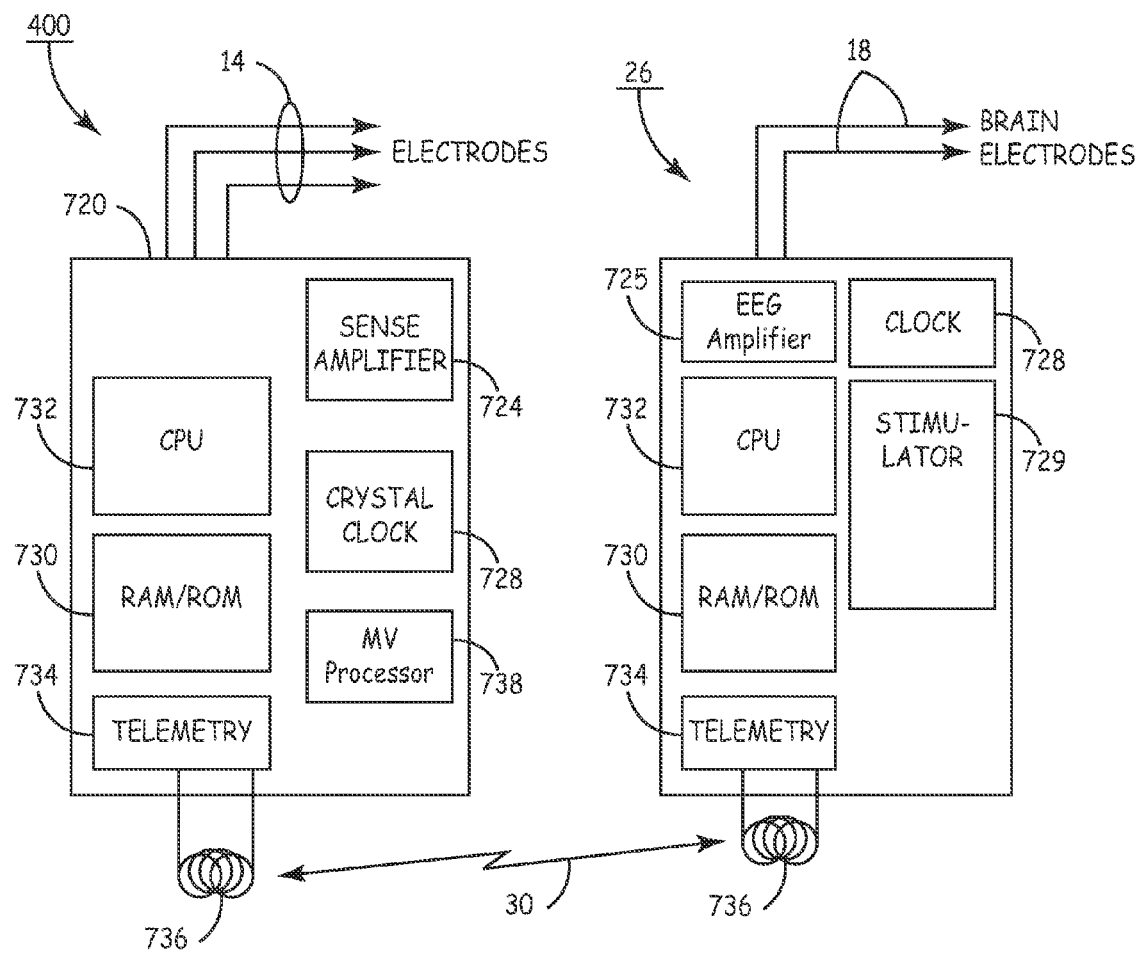

FIG. 46 is a simplified block diagram of a full monitor with brain stimulation therapy as shown in FIG. 20 above.

Figure 47:
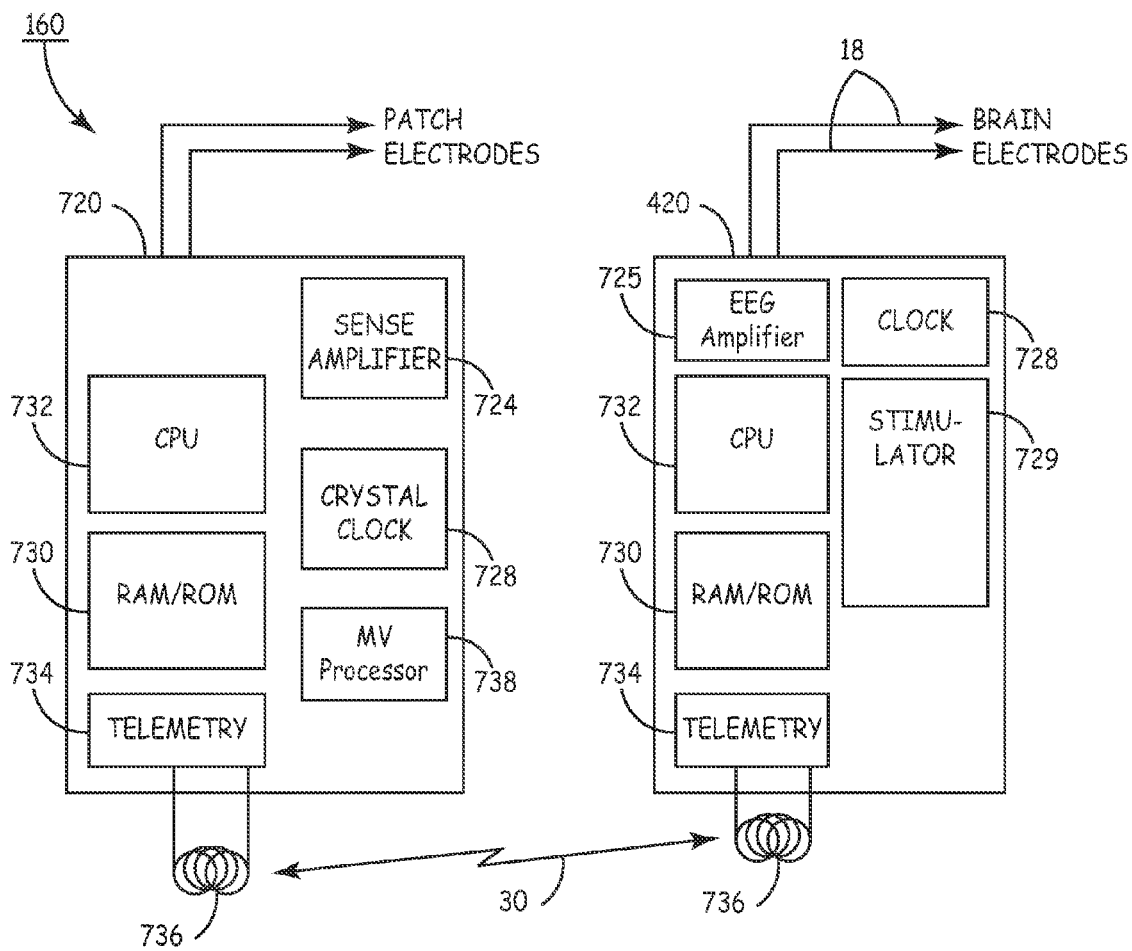

FIG. 47 is a simplified block diagram of a full monitor with brain stimulation therapy as shown in FIG. 21 above.

Figure 48:
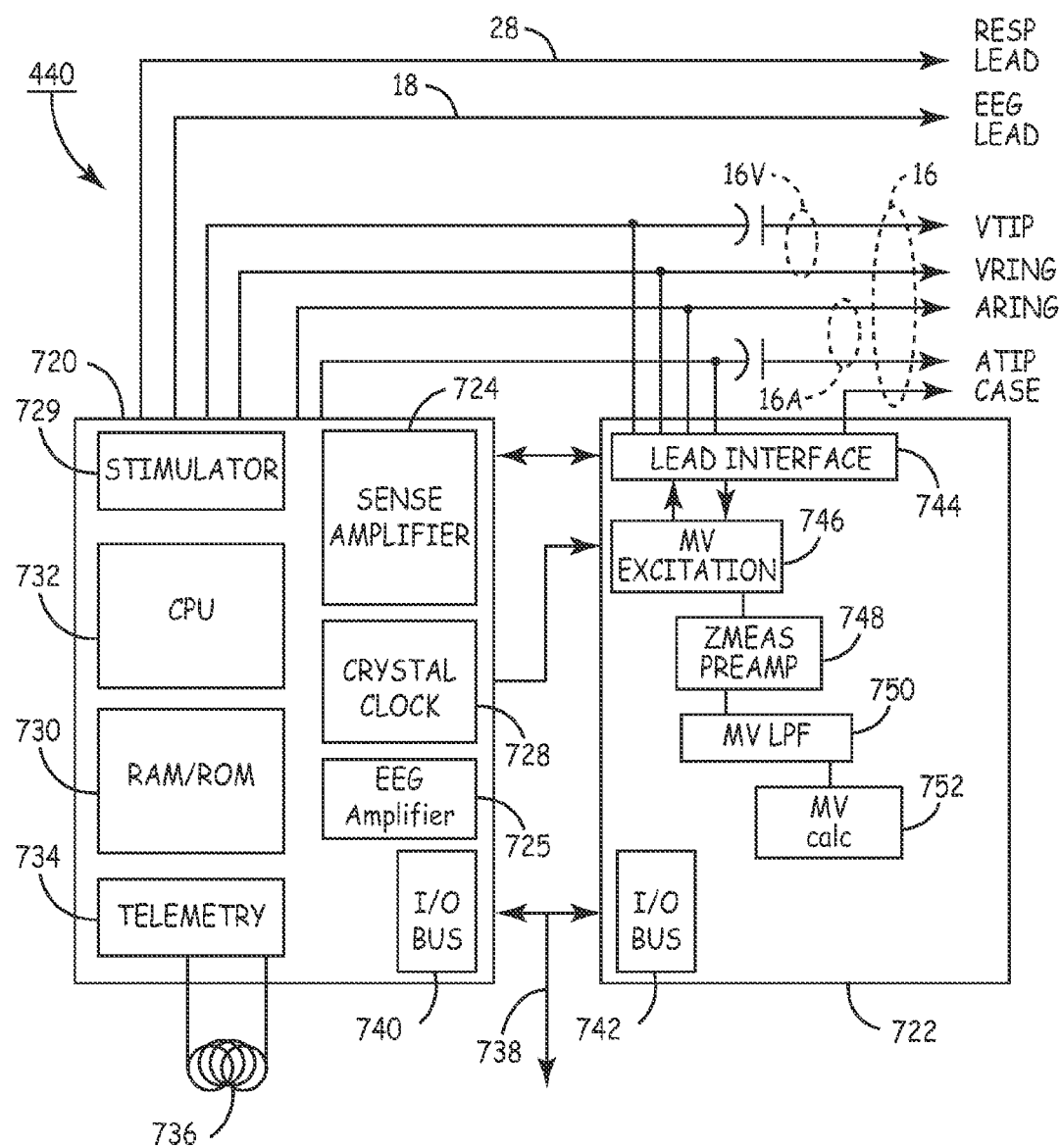

FIG. 48 is a simplified block diagram of a full monitor with brain and respiration stimulation therapy as shown in FIG. 16A above.

Figure 49:
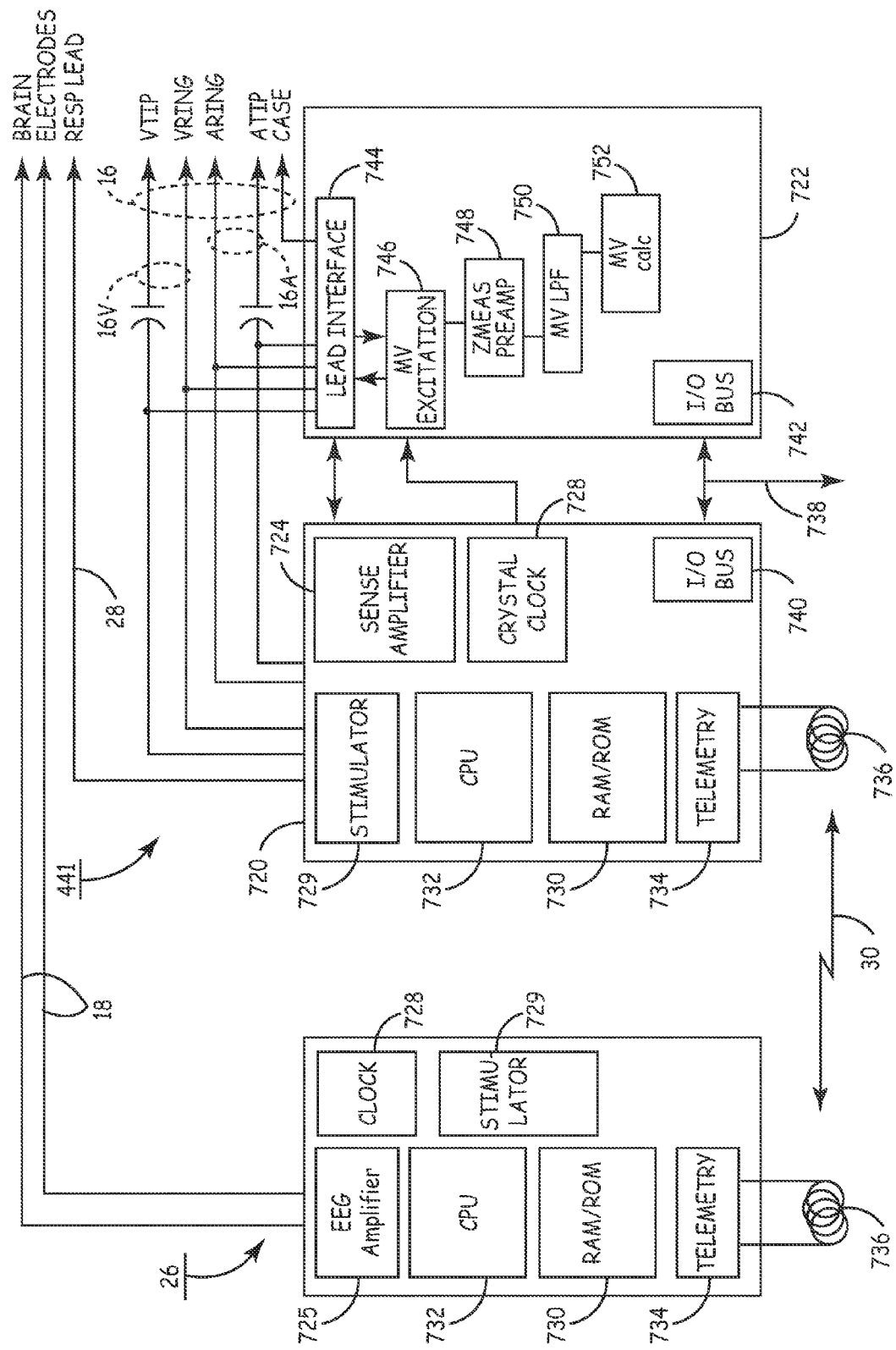

FIG. 49 is a simplified block diagram of a full monitor with brain and respiration stimulation therapy as shown in FIG. 16B above.

Figure 50:
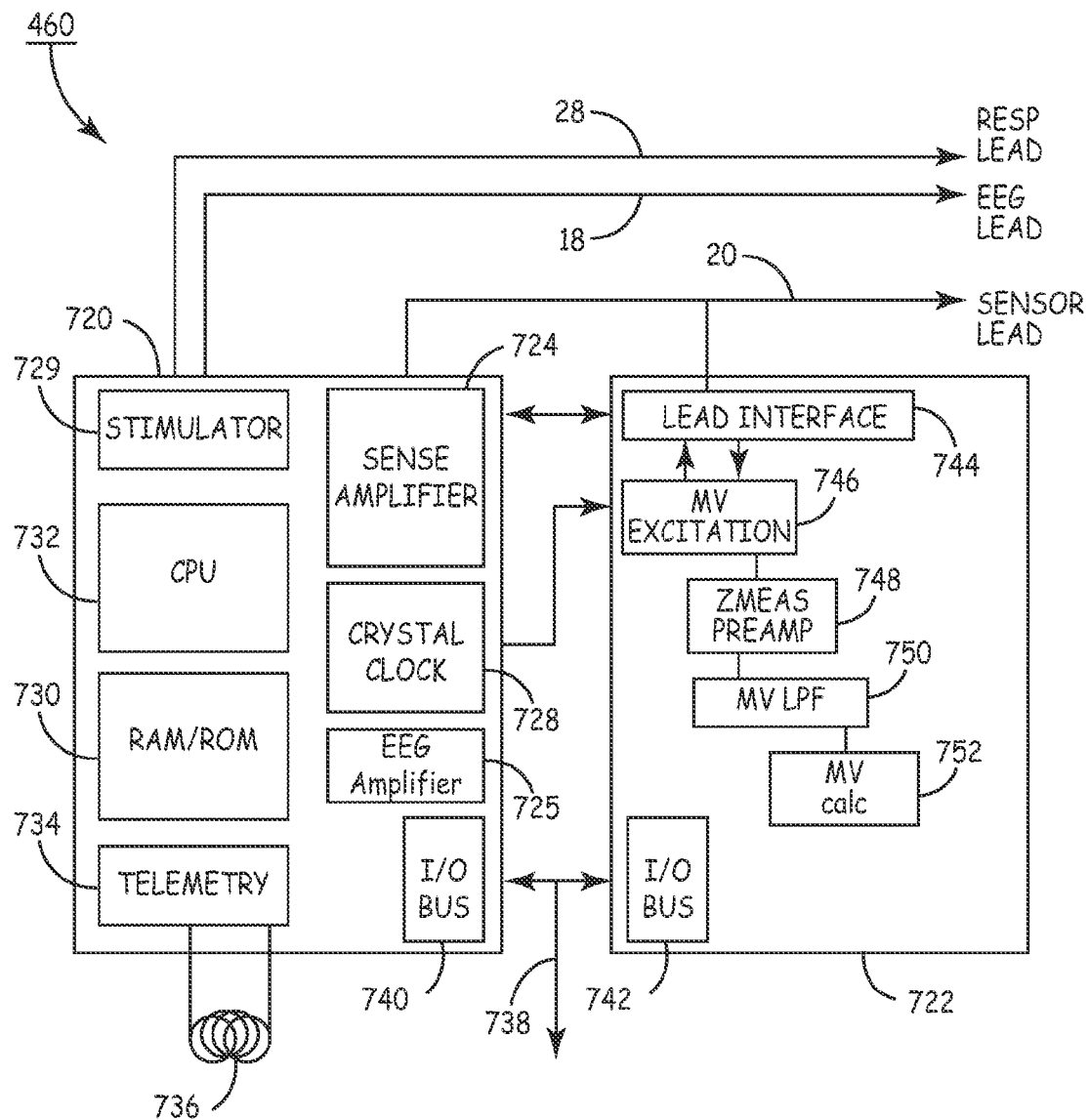

FIG. 50 is a simplified block diagram of a full monitor with brain and respiration stimulation therapy as shown in FIGS. 17, 18 and 19 above.

Figure 51:
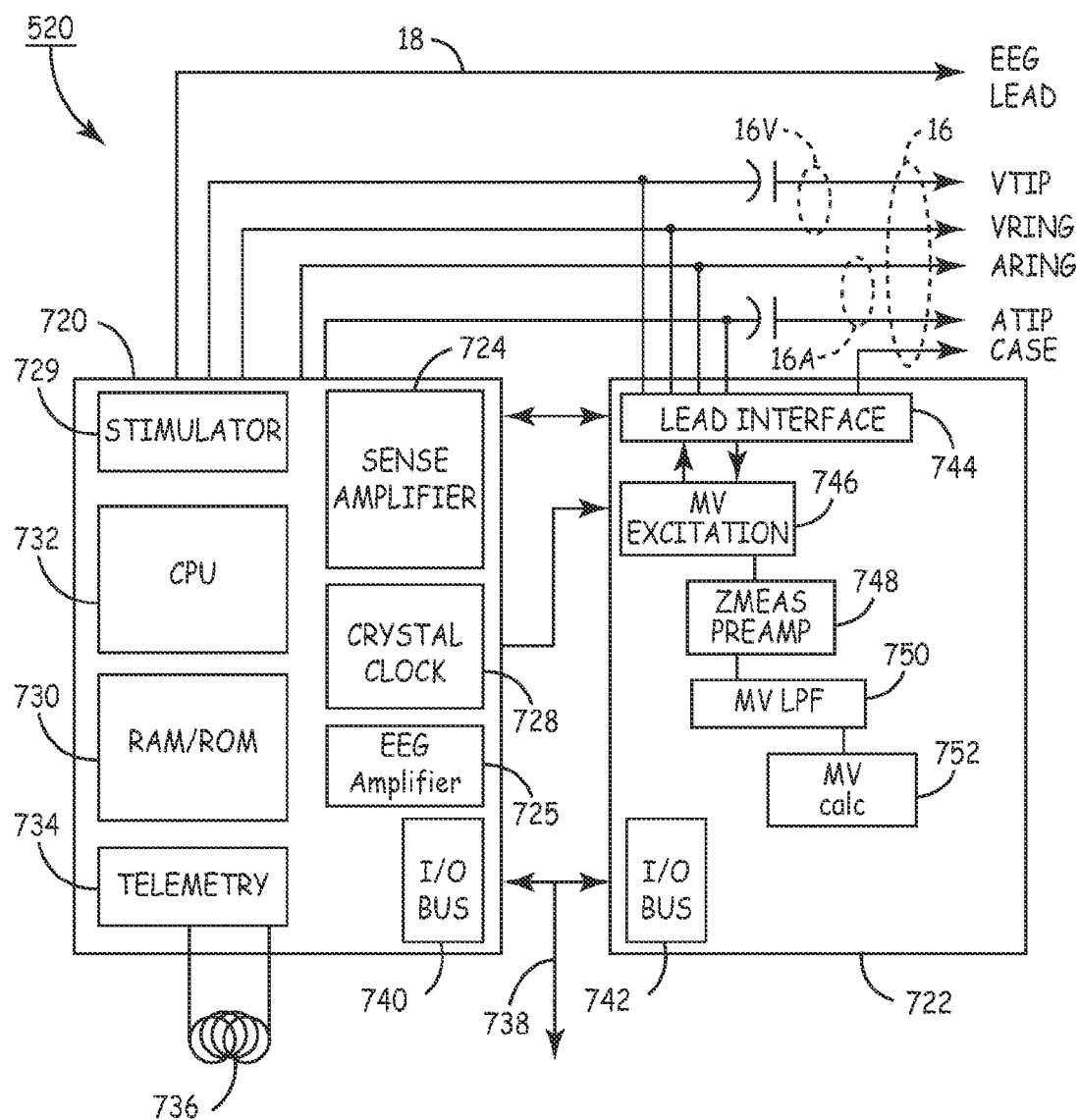

FIG. 51 is a simplified block diagram of a full monitor with brain and cardiac stimulation therapy as shown in FIG. 24A above.

Figure 52:
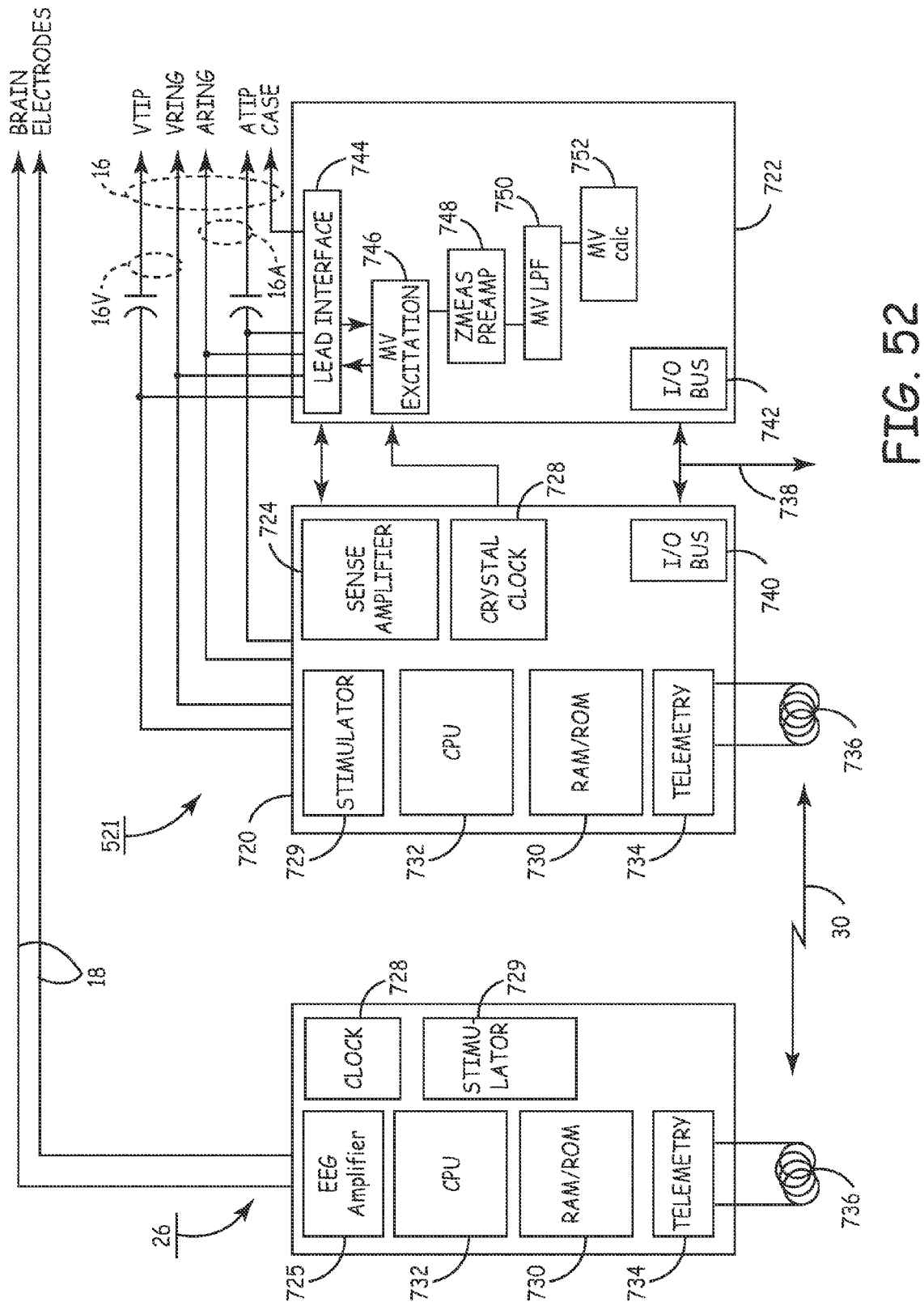

FIG. 52 is a simplified block diagram of a full monitor with brain and cardiac stimulation therapy as shown in FIG. 24B above.

Figure 53:
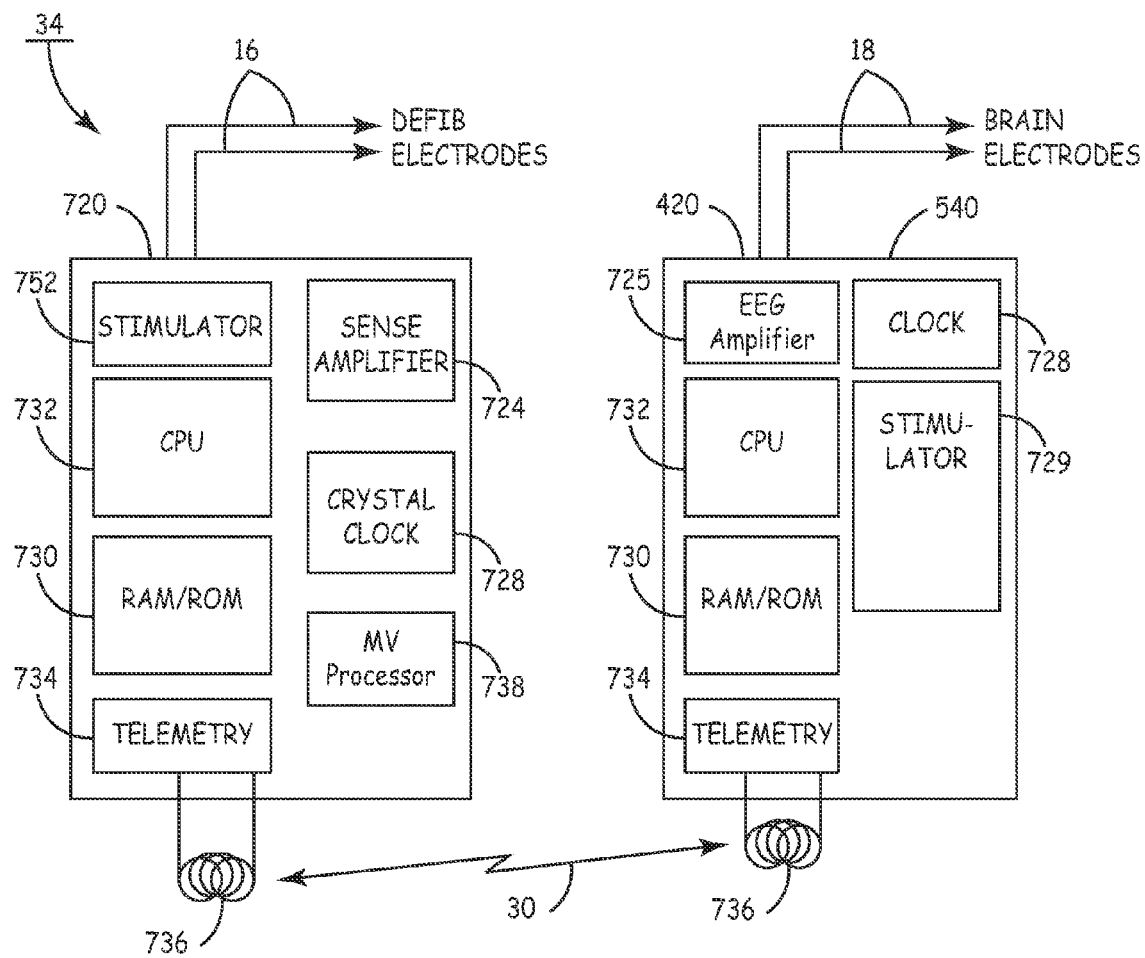

FIG. 53 is a simplified block diagram of a full monitor with brain and cardiac stimulation therapy as shown in FIGS. 22 and 23 above.

Figure 54:
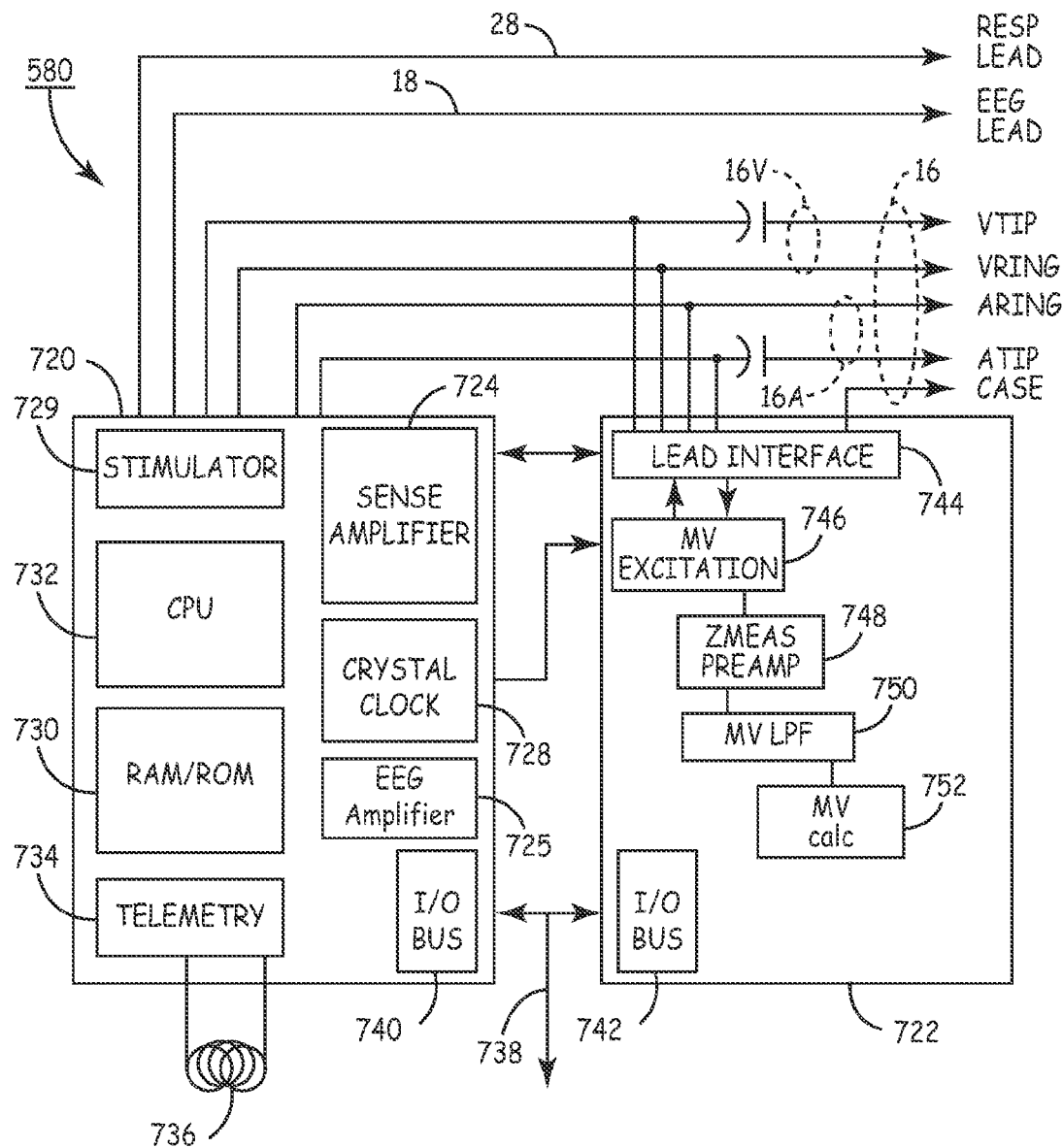

FIG. 54 is a simplified block diagram of a full monitor with brain, respiration and cardiac stimulation therapy as shown in FIG. 25A above.

Figure 55:
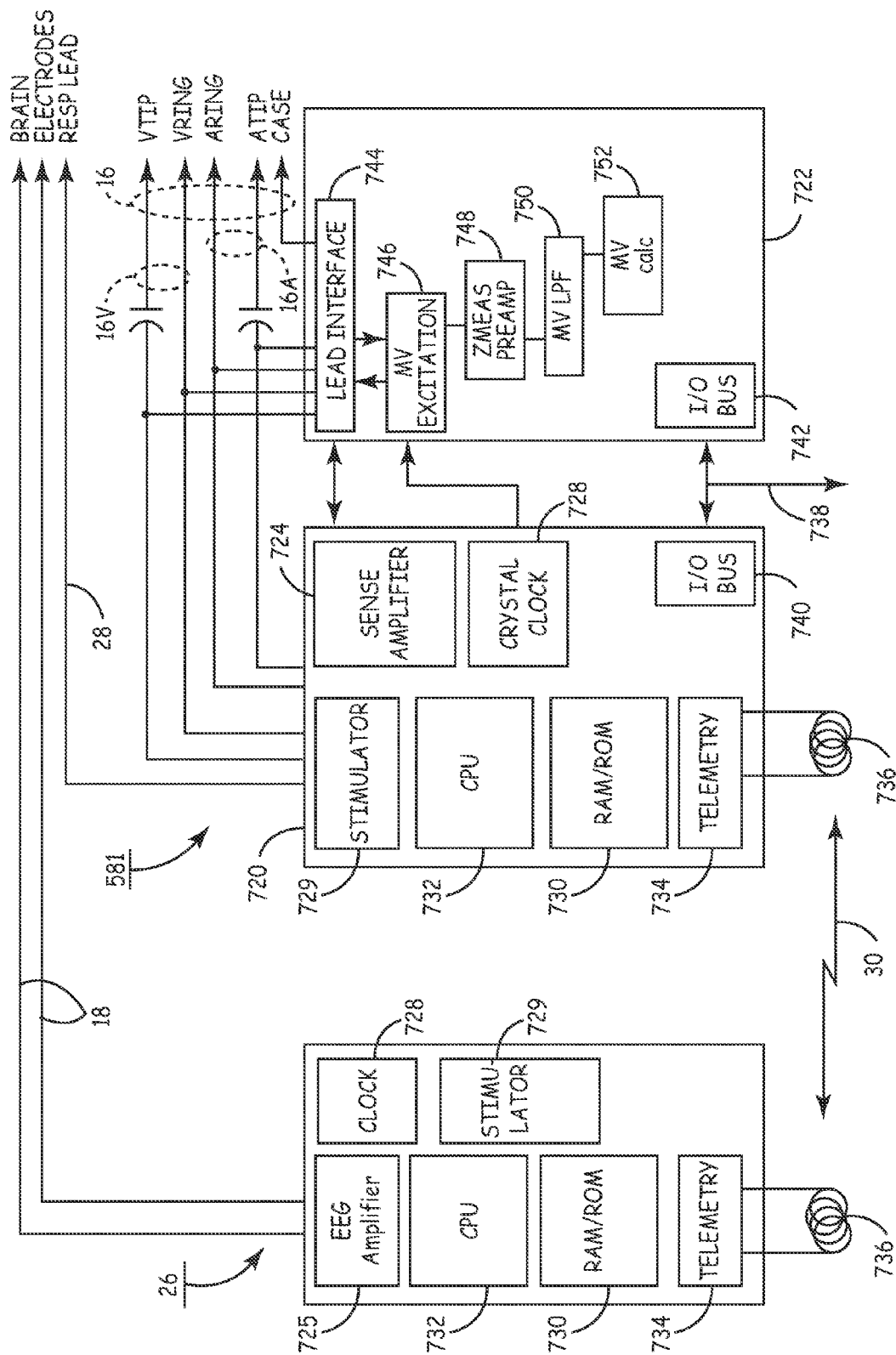

FIG. 55 is a simplified block diagram of a full monitor with brain, respiration and cardiac stimulation therapy as shown in FIG. 25B above.

Figure 56:
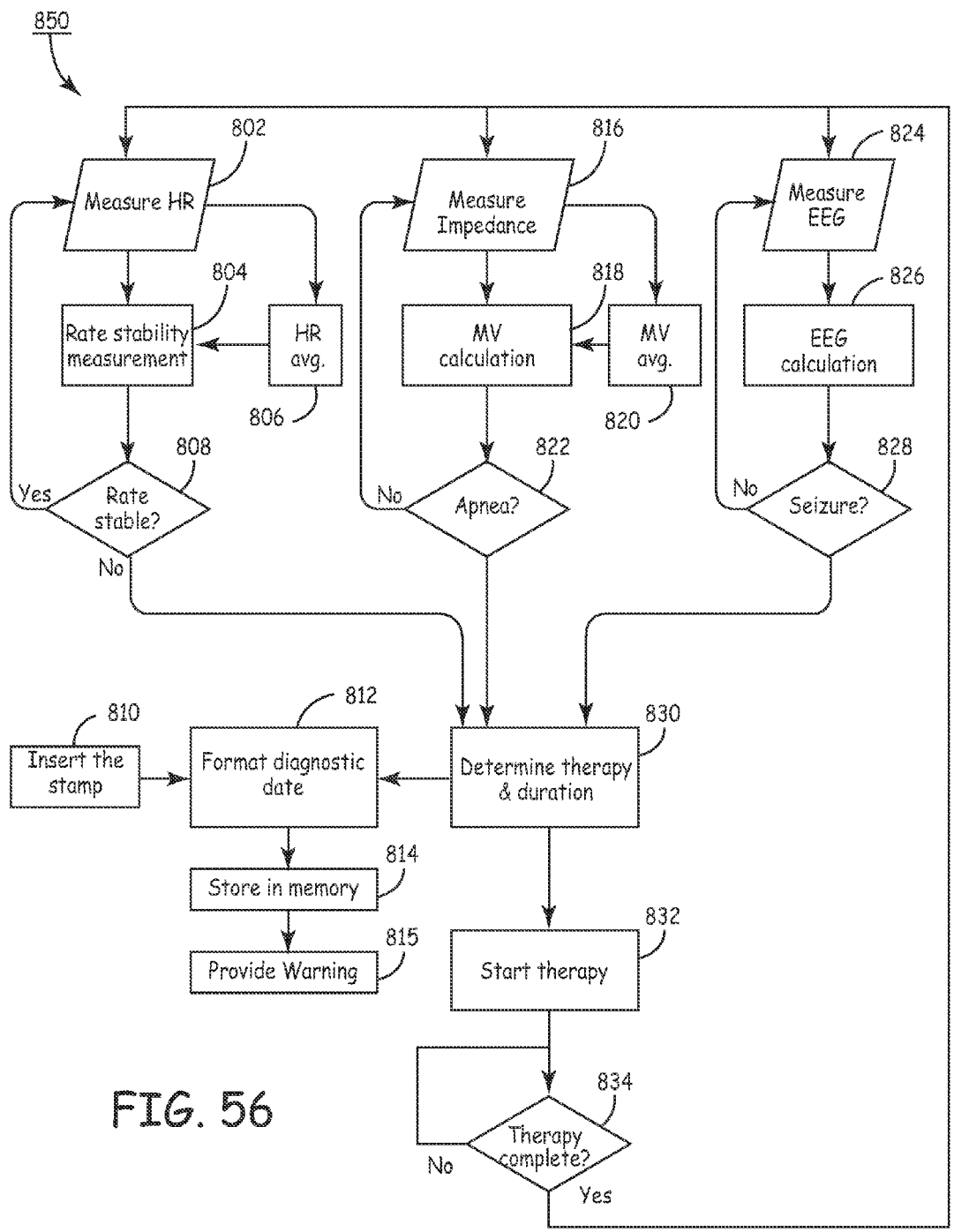

FIG. 56 is a flow diagram showing operation of a full monitor with therapy (including brain, respiration or cardiac stimulation therapy) as shown in FIG. 11-25 above.

Figure 57A:
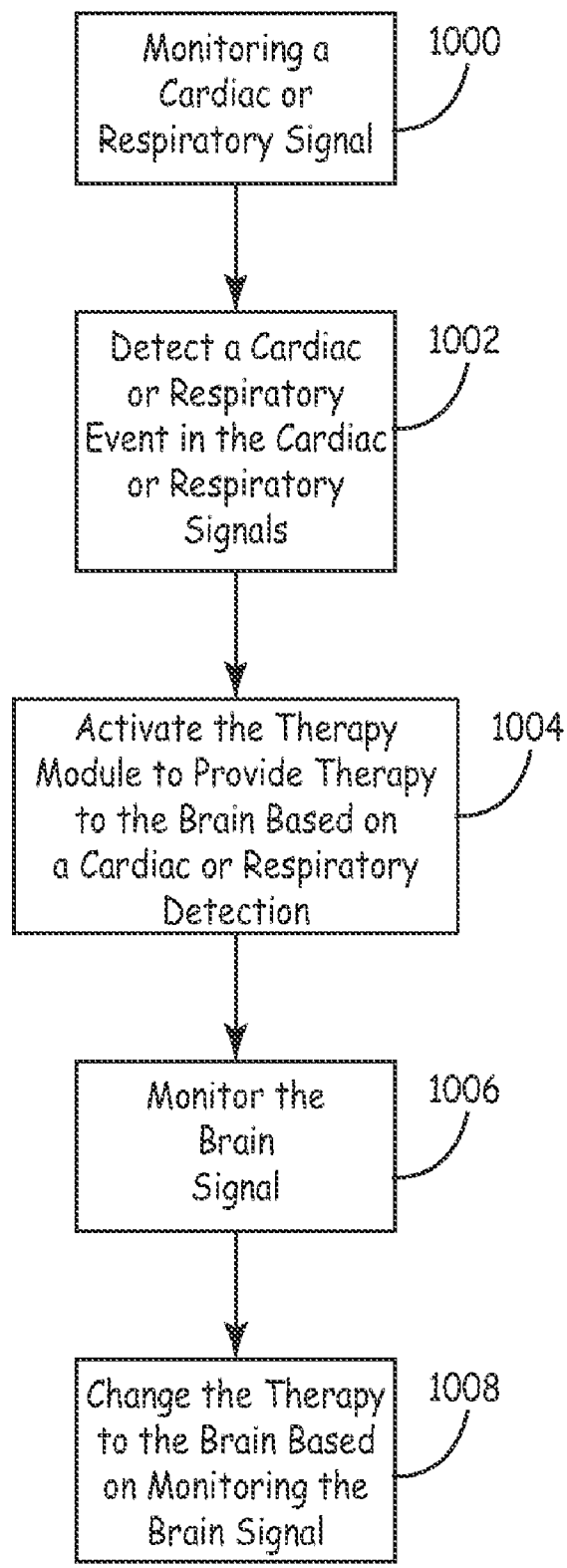

FIG. 57A is a flow diagram showing a process for enabling cardiac/respiratory detectors for neurological event detection and treatment including termination rules.

Figure 57B:
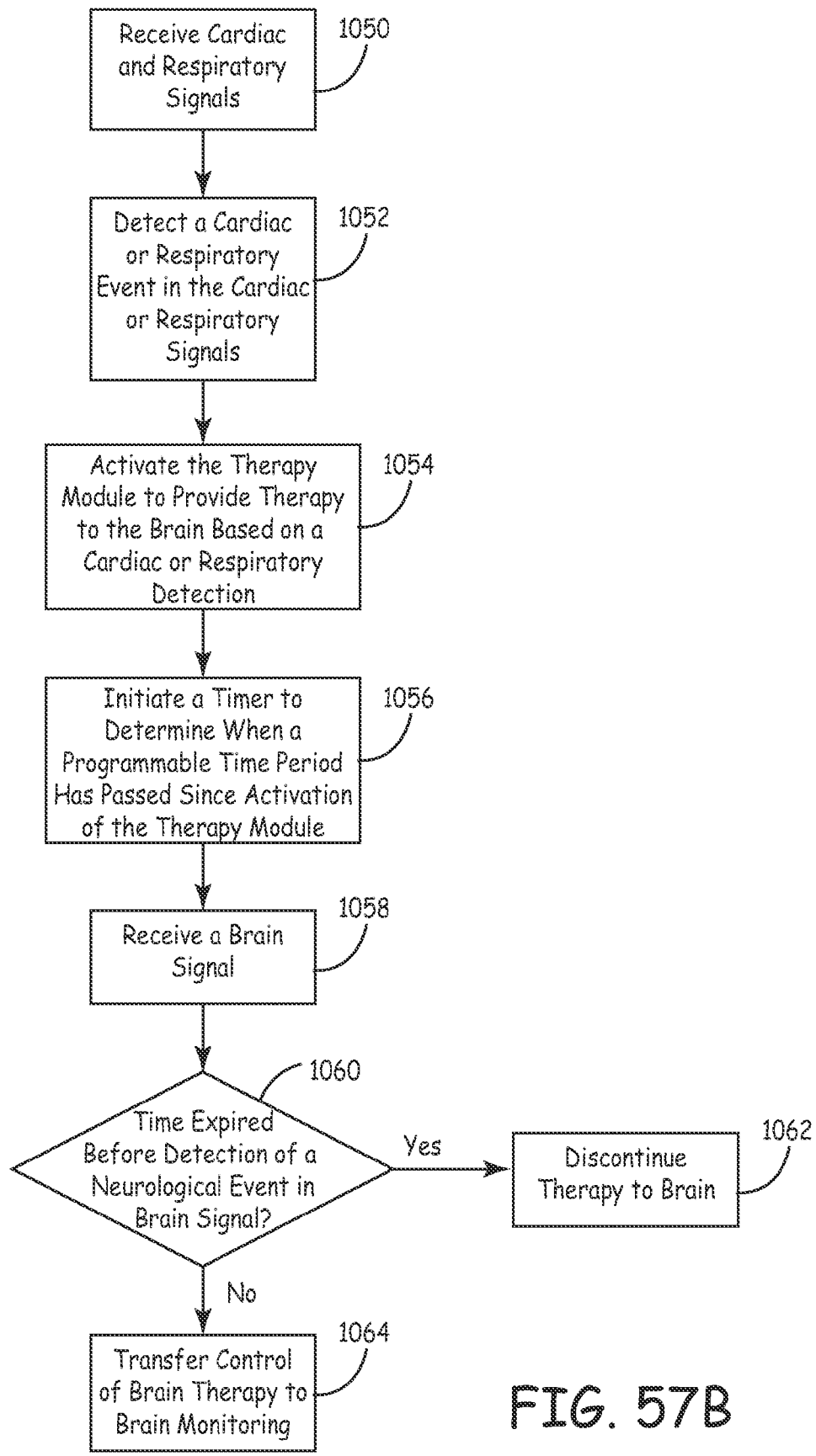

FIG. 57B is a flow diagram showing a process for enabling ECG/respiratory detectors for seizure detection and treatment including termination rules.

Figure 58:
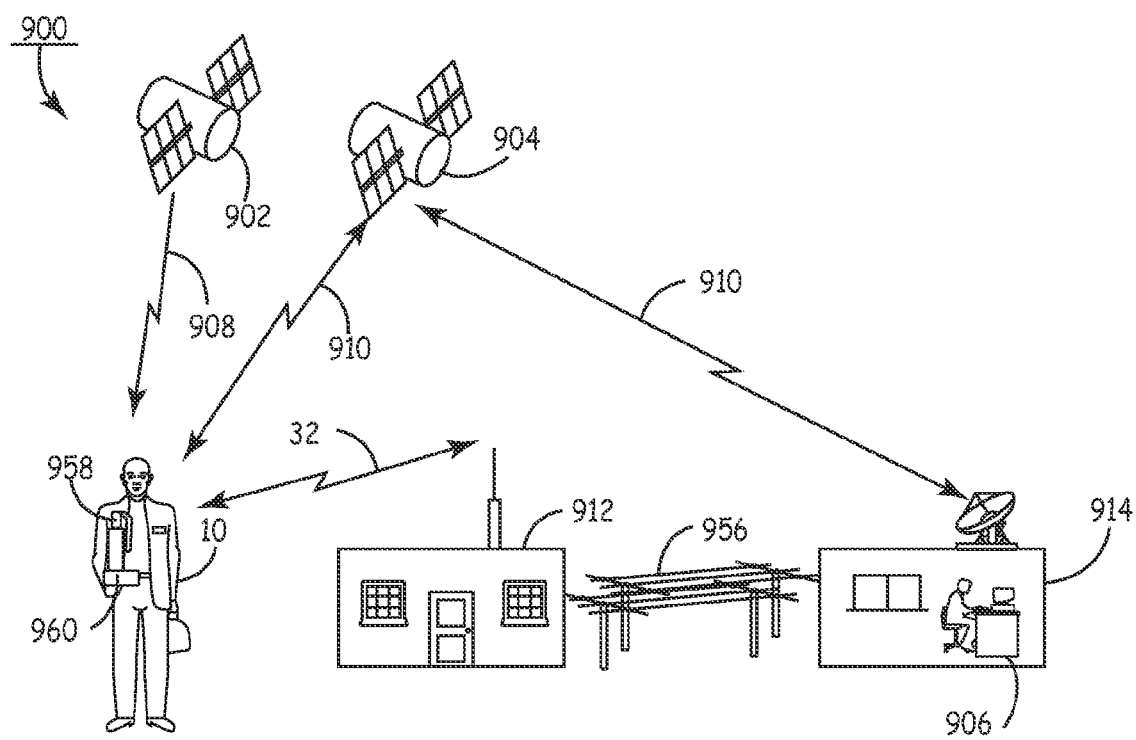

FIG. 58 is a schematic diagram of a system utilizing any of the above-described embodiments and allowing remote monitoring and diagnostic evaluation of at risk patients.

Figure 59:
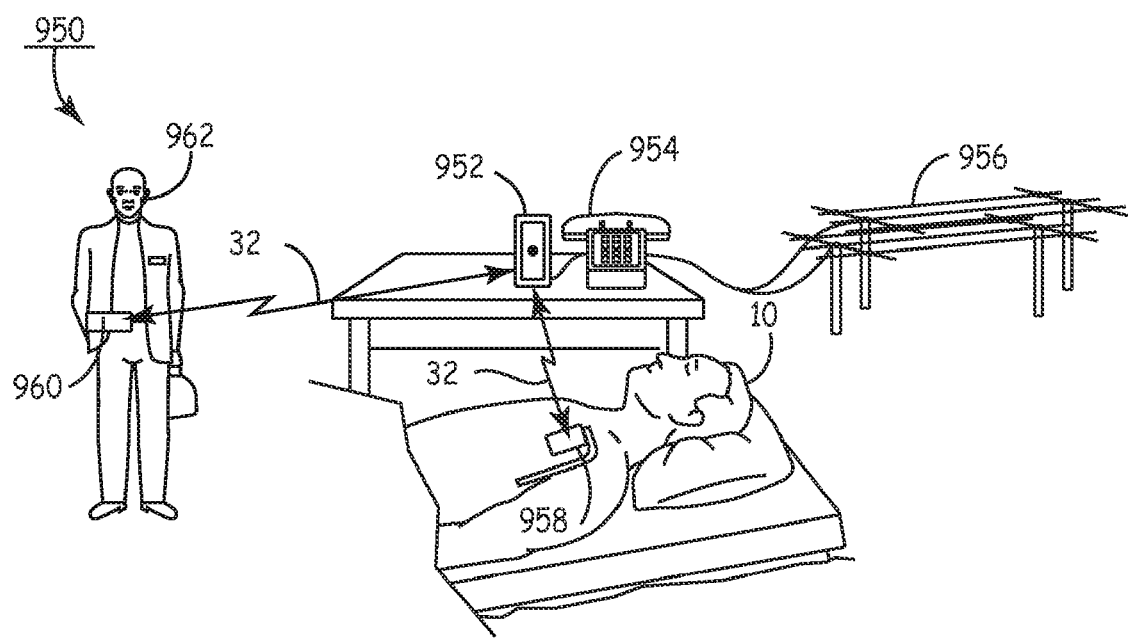

FIG. 59 is a schematic diagram of an alternative system utilizing any of the above-described embodiments and allowing remote monitoring and diagnostic evaluation of at risk patients.

Figure 60:
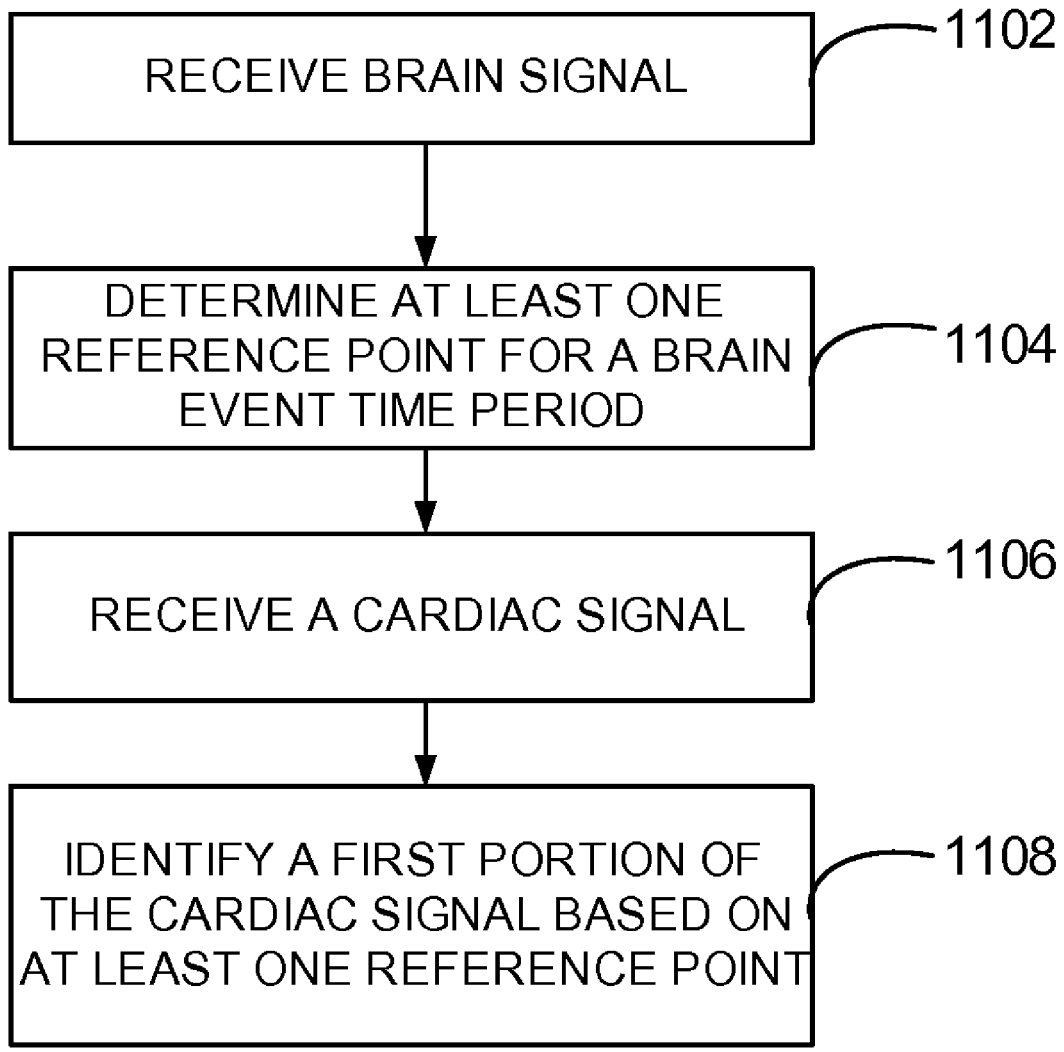

FIG. 60 is a flowchart illustrating one embodiment method of identifying a portion of a cardiac signal based on a reference point in a brain signal.

Figure 61:
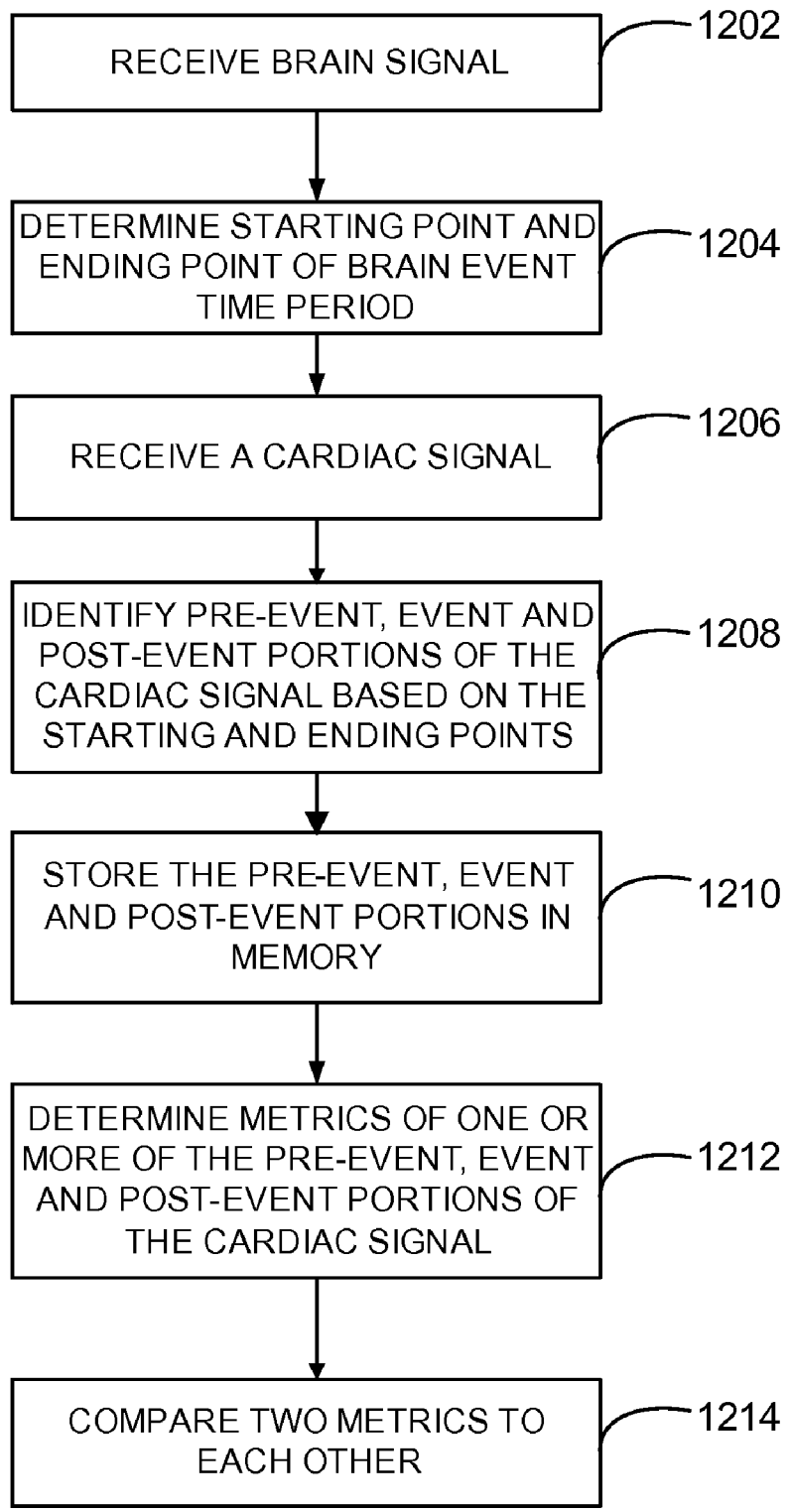

FIG. 61 is a flowchart illustrating a more detailed embodiment method of identifying a portion of a cardiac signal based on starting and ending points of a neurological event in a brain signal.

Figure 62:
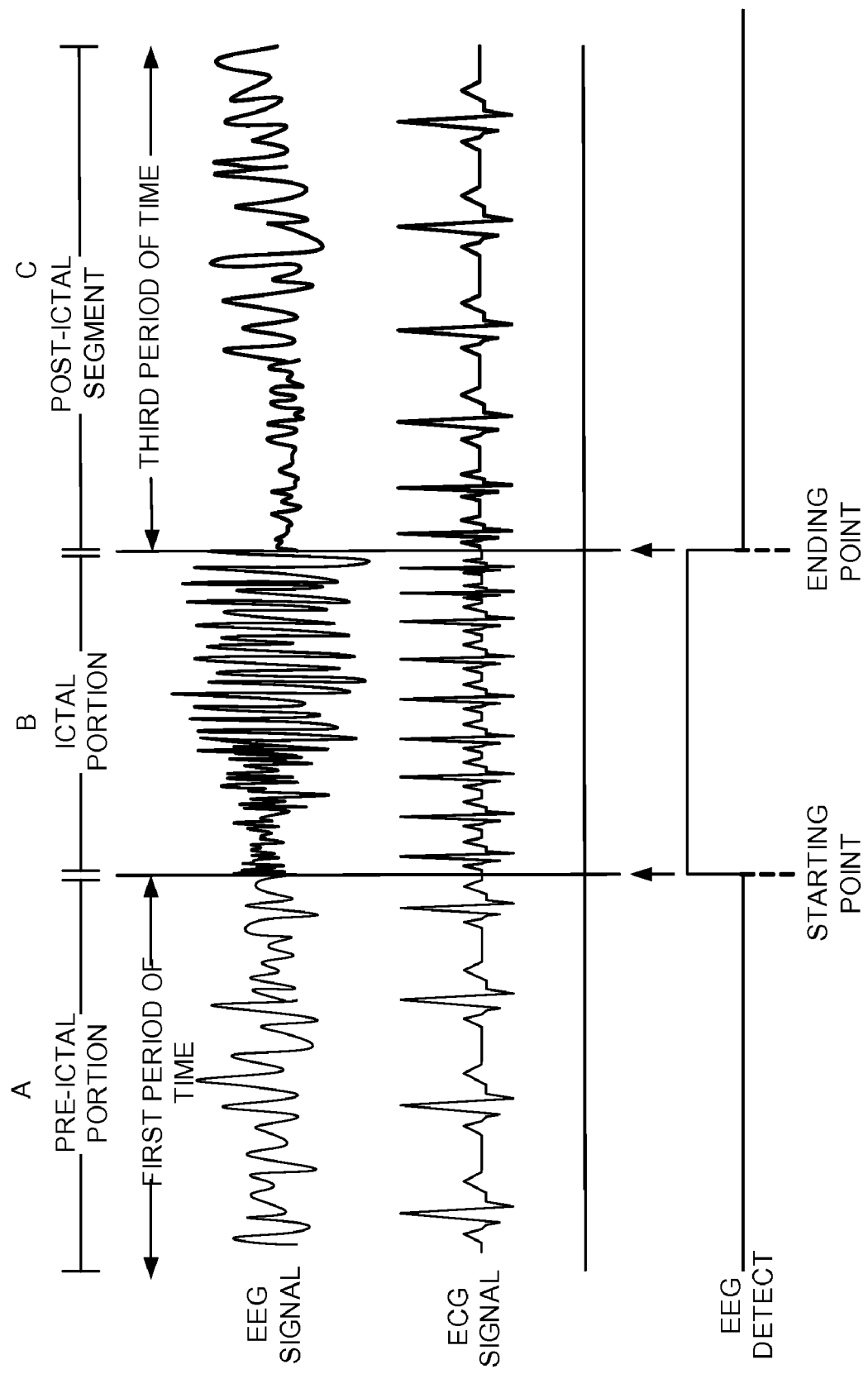

FIG. 62 is a chart of EEG and ECG signals showing exemplary relationships between the two signals.

Figure 63:
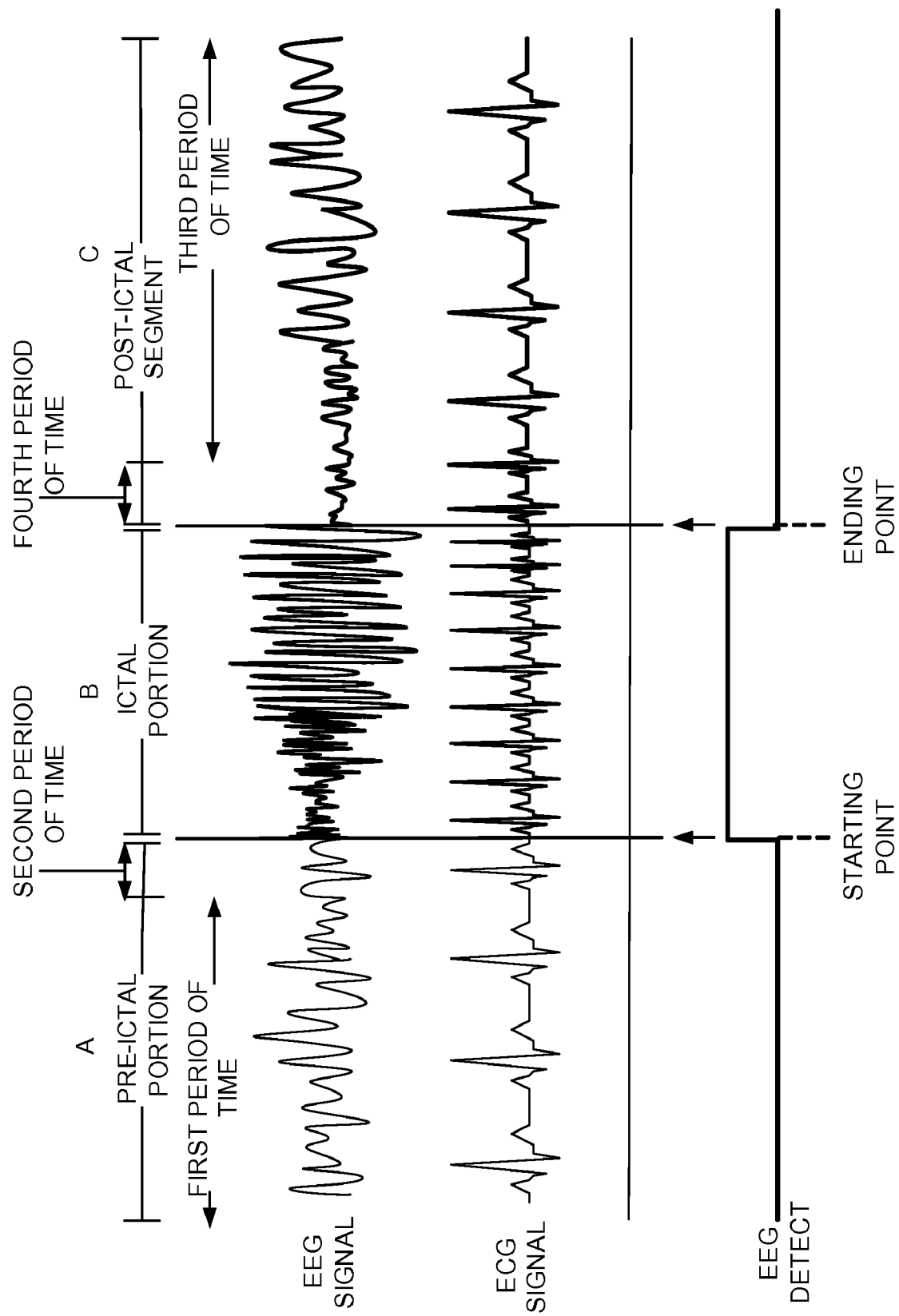

FIG. 63 is another chart of EEG and ECG signals showing exemplary relationships between the two signals.

FIG. 64 is a table describing criteria for a matching test in accordance with an embodiment of the invention.

Figure 65:
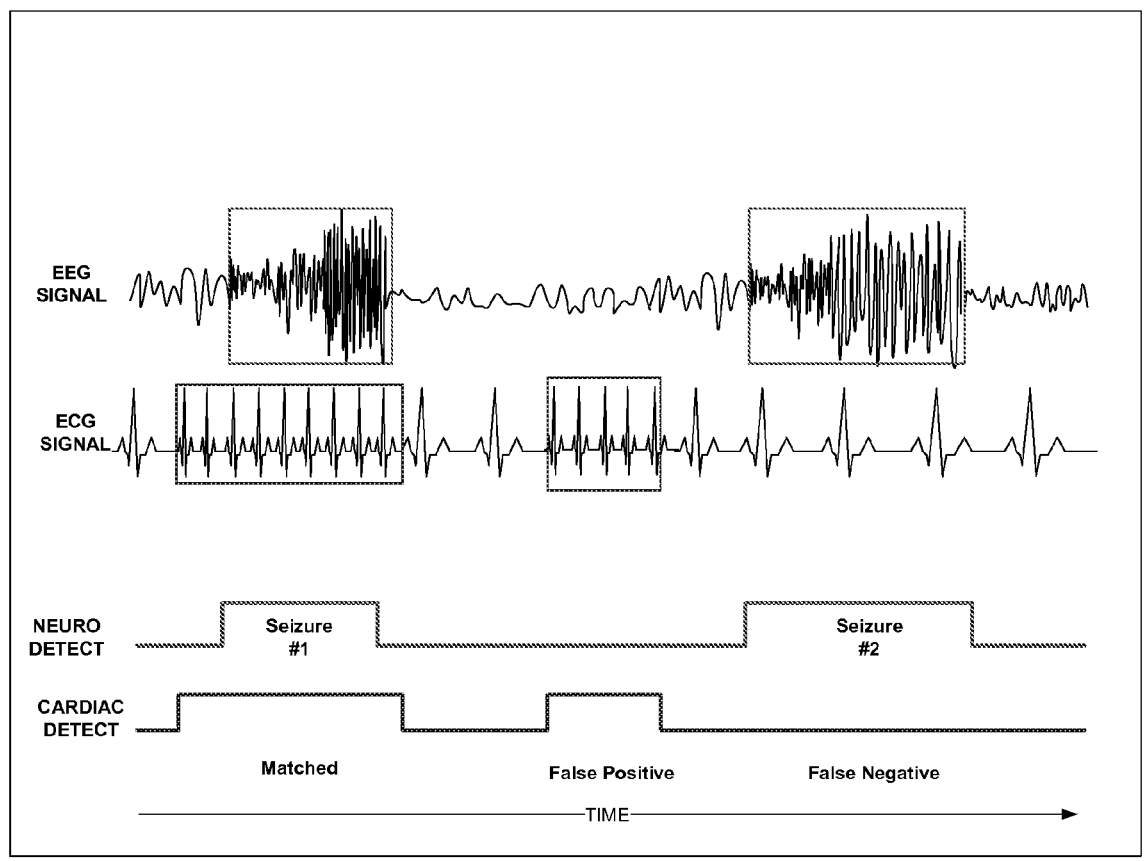

FIG. 65 illustrates a montage of EEG and ECG signals, and detected neurological and cardiac events from a patient, for applying a matching test in accordance with an embodiment of the invention.

Figure 66:
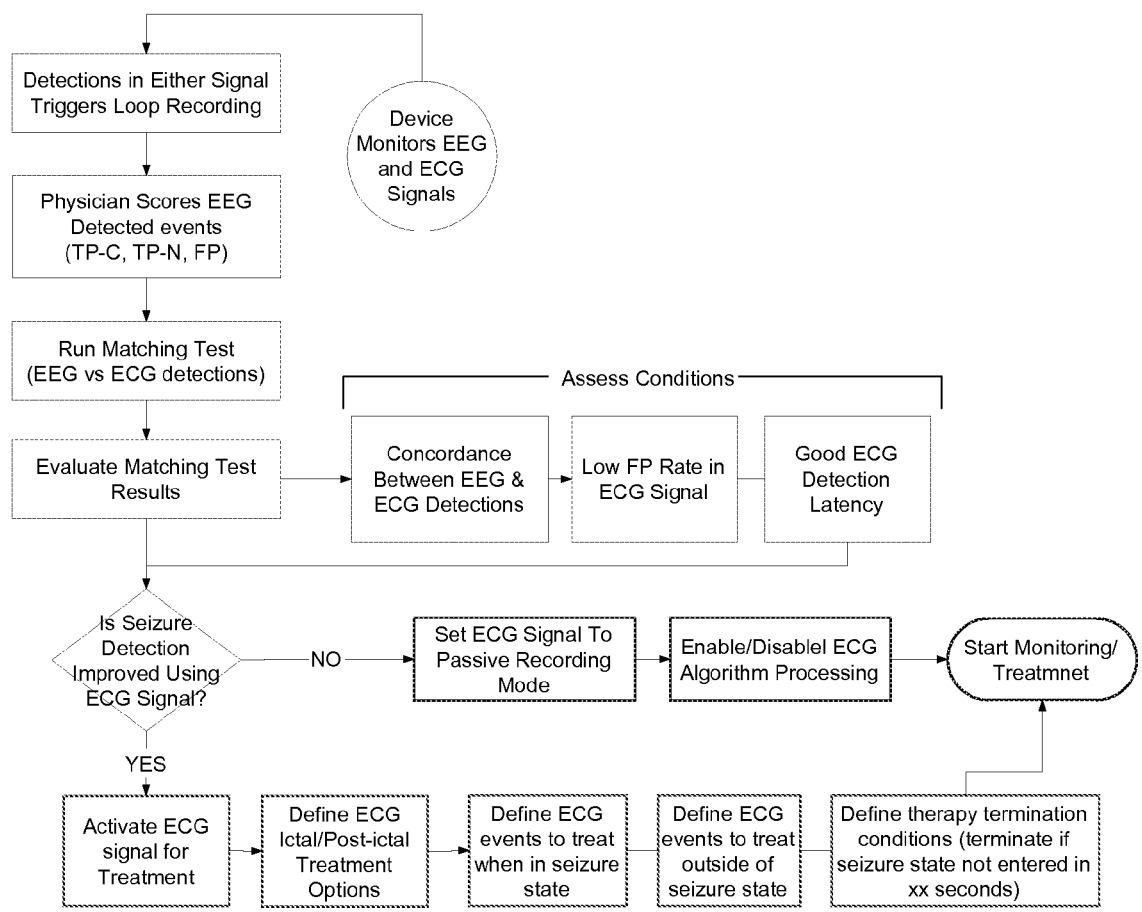

FIG. 66 is a flow chart describing a process for determining whether to activate cardiac event detection as a trigger for delivering therapy for treating a neurological event.

DETAILED DESCRIPTION OF THE INVENTION

The term "brain monitoring element" used herein means any device, component or sensor that receives a physiologic signal from the brain or head of a patient and outputs a brain signal that is based upon the sensed physiologic signal. Some examples of a brain monitoring element include leads, electrodes, chemical sensors, biological sensors, pressure sensors, and temperature sensors. A monitoring element does not have to be located in the brain to be a brain monitoring element. The term brain monitoring element is not the same as the term "monitor" also used herein, although a brain monitoring element could be a part of a monitor.

The term "cardiac monitoring element" used herein means any device, component or sensor that receives or infers a physiological signal from the heart of a patient and outputs a cardiac signal that is based upon sensed physiologic signal. Some examples of cardiac monitoring elements include leads, electrodes, chemical sensors, biological sensor, pressure sensors and temperature sensors. A monitoring element does not have to be located in the heart or adjacent to the heart to be a cardiac monitoring element. For example, a sensor or electrode adapted for sensing a cardiac signal and placed on the housing of an implantable device is a cardiac monitoring element. Furthermore, a cardiac monitoring element could be an externally placed sensor such as a holter monitoring system. The term "cardiac monitoring element" is not the same as the term "monitor" also used herein although a cardiac monitoring element could be a part of a monitor.

The term "respiratory monitoring element" used herein means any device, component or sensor that receives a physiologic signal indicative of activity or conditions in the lungs of a patient and outputs a respiration signal that is based upon the sensed physiologic signal. Some examples of respiration monitoring elements are provided below. A monitoring element does not have to be located in the lungs or adjacent to the lungs to be a respiratory monitoring element. The term "respiratory monitoring element" is not the same as the term "monitor" also used herein although a respiratory monitoring element could be a part of a monitor.

It is noted that many embodiments of the invention may reside on any hardware embodiment currently understood or conceived in the future. Many example hardware embodiments are provided in this specification. These examples are not meant to be limiting of the invention.

Core Monitor

Cardiopulmonary monitoring in the Core Monitor device (as described below in more detail in conjunction with FIGS. 1-4 and 26-30) monitors cardiac (e.g., ECG, blood pressure) or respiration signals continuously and records these signals in a loop recorder either automatically or manually when the patient indicates they have had a neurological event such as a seizure. Real-time analysis of the ECG signal evaluates rate disturbances (e.g., bradycardia; tachycardia; asystole) as well as any indications of cardiac ischemia (e.g., ST segment changes; T wave inversion, etc.). Real-time analysis of the respiration signal evaluates respiration disturbances (e.g., respiration rate, minute ventilation, apnea, prolonged pauses).

Abnormalities detected during real-time analysis will lead to an immediate patient alert. This alert can be audible (beeps, buzzers, tones, spoken voice, etc.), light, tactile, or other means.

Automatic loop recording may save the data for a programmable period of time. For example, the device may be programmed to save a period of time before a cardiac detection (e.g., 30 seconds of ECG raw or processed data before detection) and a second period of time after the detection (e.g., 3 minutes of ECG raw or processed data after detection).

The medical device system may also include a manual activation mode in which the patient provides an indication (e.g., push a button on a holter, patient programmer or other external patient activator device) when a neurological event is occurring or has just occurred. In manual activation mode, to allow for the fact that the patient may not mark the neurological event until the neurological event has ended, the ECG loop recording may begin a longer time period before the event is marked. For example, the medical device system may save ECG data beginning 15 minutes before the patient mark. This time period may be programmable. Post-processing of this saved signal will analyze the data to evaluate heart rate changes during the neurological event, heart rate variability and changes in ECG waveforms. Manual patient indication of a neurological event will be done through the patient external activator device 22. The patient (or caregiver) will push a button on the external device, while communicating with the implanted device. This will provide a marker and will initiate a loop recording. In addition, prolonged ECG loop recordings are possible (e.g., in the case of SUDEP, recording all data during sleep since the incidence of SUDEP is highest in patients during sleep).

Post-processing of the signal can occur in the implanted device, the patient's external device or in the clinician external device. Intermittently (e.g., every morning, once/week, following a neurological event), the patient may download data from the implantable device to the patient external device. This data will then be analyzed by the external device (or sent through a network to the physician) to assess any ECG or respiratory abnormalities. If an abnormality is detected, the device will notify the patient/caregiver. At that time, the patient/caregiver or device can inform the healthcare provider of the alert to allow a full assessment of the abnormality. The clinician external device is also capable of obtaining the data from the implanted device and conducting an analysis of the stored signals. If a potentially life-threatening abnormality is detected, the appropriate medical treatment can be prescribed (e.g., cardiac abnormality: a pacemaker, an implantable defibrillator, or a heart resynchronization device may be indicated or respiration abnormality: CPAP, patient positioning, or stimulation of respiration may be indicated).

FIG. 1 is a simplified schematic view of one embodiment of a core Monitor 100 implanted in a patient 10. Monitor 100 continuously senses and monitors the cardiac and respiration function of patient 10 via one or more monitoring elements 14 (e.g., cardiac electrodes) to allow detection of neurological events, the recording of data and signals pre and post event. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data.

Monitor 100, as stated above, typically includes one or more monitoring elements 14 such as several subcutaneous spiral electrodes that are embedded individually into three or four recessed casings placed in a compliant surround that is attached to the perimeter of implanted monitor 100 as substantially described in U.S. Pat. No. 6,512,940 "Subcutaneous Spiral Electrode for Sensing Electrical Signals of the Heart" to Brabec, et al and U.S. Pat. No. 6,522,915 "Surround Shroud Connector and Electrode Housings for a Subcutaneous Electrode Array and Leadless ECGS" to Ceballos, et al. These electrodes are electrically connected to the circuitry of the implanted Monitor 100 to allow the detection of cardiac depolarization waveforms (as substantially described in U.S. Pat. No. 6,505,067 "System and Method for Deriving a Virtual ECG or EGM Signal" to Lee, et al.) that may be further processed to detect cardiac electrical characteristics (e.g., heart rate, heart rate variability, arrhythmias, cardiac arrest, sinus arrest and sinus tachycardia). Further processing of the cardiac signal amplitudes may be used to detect respiration characteristics (e.g., respiration rate, minute ventilation, and apnea).

To aid in the implantation of Monitor 100 in a proper position and orientation, an implant aid may be used to allow the implanting physician to determine the proper location/orientation as substantially described in U.S. Pat. No. 6,496,715 "System and Method for Noninvasive Determination of Optimal Orientation of an Implantable Sensing Device" to Lee, et al.

FIG. 2 is a simplified schematic view of a second embodiment core Monitor 120 implanted in a patient 10. Monitor 120 continuously senses and monitors cardiac and respiration function of patient 10 via cardiac lead(s) 16 to allow detection of neurological events and the recording of data and signals pre and post event. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data. Monitor 120 senses both cardiac signals and respiration parameters via standard cardiac leads implanted in the heart. Monitor 120 measures intra-cardiac impedance, varying both with the intrathoracic pressure fluctuations during respiration and with cardiac contraction is representative of the pulmonary activity and of the cardiac activity as substantially described in U.S. Pat. No. 5,003,976 "Cardiac and Pulmonary Physiological Analysis via Intracardiac Measurements with a Single Sensor" to Alt. Cardiac leads 16 may consist of any typical lead configuration as is known in the art, such as, without limitation, right ventricular (RV) pacing or defibrillation leads, right atrial (RA) pacing or defibrillation leads, single pass RA/RV pacing or defibrillation leads, coronary sinus (CS) pacing or defibrillation leads, left ventricular pacing or defibrillation leads, pacing or defibrillation epicardial leads, subcutaneous defibrillation leads, unipolar or bipolar lead configurations, or any combinations of the above lead systems.

FIG. 3 is a simplified schematic view of a third embodiment core Monitor 140 implanted in a patient 10. Monitor 140 continuously senses and monitors cardiac and respiration function of patient 10 via an electrode (not shown) located distally on sensor stub 20 which is inserted subcutaneously in the thoracic area of the patient to allow detection of neurological events and the recording of data and signals pre and post event. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data. Monitor 140 senses cardiac signals between an electrode on the distal end of the sensor stub and the monitor case as described in conjunction with the embodiment shown in FIG. 5 in U.S. Pat. No. 5,987,352 "Minimally Invasive Implantable Device for Monitoring Physiologic Events" to Klein, et al. Monitor 140 also senses respiration parameters such as respiration rate, minute ventilation and apnea via measuring and analyzing the impedance variations measured from the implanted monitor 140 case to the electrode (not shown) located distally on sensor stub lead 20 as substantially described in U.S. Pat. No. 4,567,892 "Implantable Cardiac Pacemaker" and U.S. Pat. No. 4,596,251 "Minute Ventilation Dependent Rate Responsive Pacer" both to Plicchi, et al.

FIG. 4 is a simplified schematic view of a fourth embodiment core Monitor 160 attached to a patient 10. External patch Monitor 160 continuously senses and monitors cardiac and respiration function of patient 10 to allow detection of neurological events and the recording of data and signals pre and post event. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data. Also optionally, a button 38 on the external patch monitor 160 may be activated by the patient 10 to manually activate diagnostic data recording.

External patch Monitor 160 consists of a resilient substrate affixed to the patient's skin with the use of an adhesive which provides support for an amplifier, memory, microprocessor, receiver, transmitter and other electronic components as substantially described in U.S. Pat. No. 6,200,265 "Peripheral Memory Patch and Access Method for Use With an Implantable Medical Device" to Walsh, et al. The substrate flexes in a complimentary manner in response to a patient's body movements providing patient comfort and wearability. The low profile external patch Monitor 160 is preferably similar in size and shape to a standard bandage, and may be attached to the patient's skin in an inconspicuous location. Uplinking of stored physiologic telemetry data from the internal memory of external patch Monitor 160 may be employed to transfer information between the monitor and programmer 12.

Full Monitor

The term "full monitor" is used to describe a monitor that is capable of monitoring the brain (such as by monitoring a brain signal such as an electroencephalogram (EEG)) and additionally the heart or pulmonary system or both. This will allow the full monitor to collect neurological signals and at least one of the cardiovascular and respiratory signals in close proximity to neurological events detected (such as seizures) as well as notifying the patient/caregiver of a prolonged neurological event (such as status epilepticus). Cardiovascular and respiratory monitoring may occur around a neurological event (in the case of a seizure this is called peri-ictal). In distinction from the core monitor, in which patients/caregivers must notify the device that a neurological event has occurred, the full monitor device will detect the neurological event (based on the brain signal) and will automatically analyze the peri-ictal signals and initiate the loop recording. Monitoring of more than one physiologic signal allows for greater understanding of the total physiologic condition of the patient. For example, prolonged or generalized seizures put patients at higher risk for SUDEP, the EEG monitoring may be programmed to provide alerts when a neurological event has exceeded a pre-determined duration or severity.

FIG. 5 is a simplified schematic view of a full Monitor 200 implanted in a patient 10. Monitor 200 continuously senses and monitors cardiac, brain and respiration function of patient 10 via one or more brain monitoring elements 18 and one or more cardiac monitoring elements 14 or one or more respiratory monitoring elements 15. Brain monitoring elements 18 may be for example, one or more brain leads with one or more electrodes. Such a brain lead may be any lead capable of sensing brain activity such as EEG. For example, brain monitoring element 18 may be a deep brain lead, a cortical lead or an electrode placed on the head externally. Cardiac monitoring elements 14 may be cardiac leads or other types of sensors or electrodes capable of picking up cardiac signals. These monitoring elements allow detection of a neurological event and the recording of data and signals pre and post event. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data. An implant aid may be used with Monitor 200 to ensure a proper position and orientation during implant as described above in connection with the system of FIG. 1.

FIG. 6 is a simplified schematic view of a second embodiment of a full Monitor 220 implanted in a patient 10. Monitor 220 continuously senses and monitors cardiac, brain and respiration function of patient 10 via cardiac lead(s) 16 and a brain lead 18 to allow detection of a neurological event and the recording of data and signals pre and post event. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data.

FIG. 7 is a simplified schematic view of a third embodiment of a full Monitor 240 implanted in a patient 10. Monitor 240 continuously senses and monitors cardiac, brain and respiration function of patient 10 via sensor stub 20 and brain lead 18 to allow detection of a neurological event and the recording of data and signals pre and post event. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data.

FIG. 8 is a simplified schematic view of a fourth embodiment of a full Monitor 260 implanted in a patient 10. Monitor 260 in combination with external patch 160 continuously senses and monitors cardiac, brain and respiration function of patient 10 to allow detection of a neurological event and the recording of data and signals pre and post event. A 2-way wireless telemetry communication link 30 connects the Monitor unit 260 and external patch 160. The wireless communication link 30 may consist of an RF link (such as described in U.S. Pat. No. 5,683,432 "Adaptive Performance-Optimizing Communication System for Communicating with an Implantable Medical Device" to Goedeke, et al), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke). Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data. Also optionally, a button 38 on the external patch monitor 160 may be activated by the patient 10 to manually activate diagnostic data recording.

An alternative embodiment of the system of FIG. 8 consists of software "patches" or programs downloaded from a wearable patch 38 into an implanted neurostimulator, drug pump or monitor to allow research evaluation of new therapies, detection algorithms, clinical research and data gathering and the use of the patient as their own "control" by randomly downloading or enabling a new detection algorithm or therapy and gathering the resultant clinical data (as substantially described in U.S. Pat. No. 6,200,265 "Peripheral Memory Patch and Access Method for Use with an Implantable Medical Device" to Walsh, et al). The clinical and diagnostic data may be uploaded into the memory of the patch for later retrieval and review by the patient's physician or device clinical manager. This embodiment also allows the upgrading of the existing implant base with temporary new or additional therapeutic and diagnostic features.

FIG. 9 is a simplified schematic view of a fifth embodiment of a full Monitor 280 implanted in a patient 10. Monitor 280 continuously senses and monitors cardiac, brain and respiration function of patient 10 via brain lead 18 with integrated electrode 24 to allow detection of a neurological event and the recording of data and signals pre and post event. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data. Integrated electrode 24 senses ECG signals as described above in the referenced Klein '352 patent and respiration signals as described above in the referenced Plicchi '892 and '251 patents.

FIG. 10 is a simplified schematic view of a sixth embodiment of a full Monitor 26 implanted cranially in a patient 10. Monitor 26 continuously senses and monitors cardiac, brain and respiration function of patient 10 to allow detection of a neurological event and the recording of data and signals pre and post event. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data.

Monitor 26 may be constructed as substantially described in US Publication No. 20040176817 "Modular implantable medical device" to Wahlstrand et al. or U.S. Pat. No. 5,782,891 "Implantable Ceramic Enclosure for Pacing, Neurological and Other Medical Applications in the Human Body" to Hassler, et al. or U.S. Pat. No. 6,427,086 "Means and Method for the Intracranial Placement of a Neurostimulator" to Fischell et al. EEG sensing is accomplished by the use of integrated electrodes in the housing of monitor 26 or, alternatively, by cranially implanted leads.

ECG sensing in the cranium may be accomplished by leadless ECG sensing as described in the above Brabec '940, Ceballos '915 and Lee '067 referenced patents. Alternatively, ECG rate and asystole may be inferred (along with a blood pressure signal) from a capacitive dynamic pressure signal (ie, dP/dt) as substantially described in U.S. Pat. No. 4,485,813 "Implantable Dynamic Pressure Transducer System" to Anderson, et al. ECG rate and asystole may be inferred by monitoring an acoustic signal (i.e., sound) as substantially described in U.S. Pat. No. 5,554,177 "Method and Apparatus to Optimize Pacing Based on Intensity of Acoustic Signal" to Kieval, et al. The sensed acoustic signal is low pass filtered to limit ECG signals to 0.5-3 Hz while filtering out speech, swallowing and chewing sounds. ECG rate and asystole may be inferred (along with a blood saturation measurement) by monitoring a reflectance oximetry signal (i.e., $O_2sat$) as substantially described in U.S. Pat. No. 4,903,701 "Oxygen Sensing Pacemaker" to Moore, et al. ECG rate and asystole may be inferred by monitoring a blood temperature signal (i.e., dT/dt) as substantially described in U.S. Pat. No. 5,336,244 "Temperature Sensor Based Capture Detection for a Pacer" to Weijand. ECG rate and asystole may be inferred (along with an arterial flow measurement) by monitoring a blood flow signal (from an adjacent vein via impedance plethysmography, piezoelectric sensor or Doppler ultrasound) as substantially described in U.S. Pat. No. 5,409,009 "Methods for Measurement of Arterial Blood Flow" to Olson. ECG rate and asystole may be inferred (along with a blood pressure measurement) by monitoring a blood pressure signal utilizing a strain gauge substantially described in U.S. Pat. No. 5,168,759 "Strain Gauge for Medical Applications" to Bowman. ECG rate and asystole may be inferred by monitoring a blood parameter sensor (such as oxygen, pulse or flow) located on a V-shaped lead as substantially described in U.S. Pat. No. 5,354,318 "Method and Apparatus for Monitoring Brain Hemodynamics" to Taepke.

Monitor 26 may warn or alert the patient 10 via an annunciator such as buzzes, tones, beeps or spoken voice (as substantially described in U.S. Pat. No. 6,067,473 "Implantable Medical Device Using Audible Sound Communication to Provide Warnings" to Greeninger, et al.) via a piezo-electric transducer incorporated in the housing of monitor 26 and transmitting sound to the patient's 10 inner ear.

Monitor+Treatment (Brain)

FIG. 11 is a simplified schematic view of a full Monitor/Brain Therapy unit 300 implanted in a patient 10. Monitor/Brain Therapy unit 300 continuously senses and monitors cardiac, brain and respiration function of patient 10 via monitoring elements 14 and 18. Such monitoring elements may be subcutaneous electrodes and a brain lead to allow detection of a neurological event, the recording of data and signals pre and post event, and the delivery of therapy via brain lead. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy. An implant aid may be used with Monitor/Brain Therapy device 300 to assist with positioning and orientation during implant as described above in connection with the system of FIG. 1.

FIG. 12A is a simplified schematic view of a second embodiment of a full Monitor/Brain Therapy unit 320 implanted in a patient 10. Monitor/Brain Therapy unit 320 continuously senses and monitors cardiac, brain and respiration function of patient 10 via cardiac lead(s) 16 and a brain lead 18 to allow detection of a neurological event, the recording of data and signals pre and post event, and the delivery of therapy via brain lead 18. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy.

FIG. 12B is a simplified schematic view of a third embodiment of a full Monitor/Brain Therapy system consisting of a thoracically implanted Monitor unit 321 in combination with a cranially implanted brain Monitor/Therapy unit 26. Monitor unit 321 continuously senses and monitors the cardiac and respiration function of patient 10 via cardiac lead(s) 16 to allow detection of a neurological event, the recording of data and signals pre and post event, and the delivery of therapy via Monitor/Therapy unit 26. A 2-way wireless telemetry communication link 30 connects the Monitor/Therapy unit 26 and cardiac/respiration monitor 321. The wireless communication link 30 may consist of an RF link (such as described in U.S. Pat. No. 5,683,432 "Adaptive Performance-Optimizing Communication System for Communicating with an Implantable Medical Device" to Goedeke, et al), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke). Monitor 26 may be constructed as substantially described in US Publication No. 20040176817 "Modular implantable medical device" to Wahlstrand et al. or U.S. Pat. No. 5,782,891 "Implantable Ceramic Enclosure for Pacing, Neurological and Other Medical Applications in the Human Body" to Hassler, et al or U.S. Pat. No. 6,427,086 "Means and Method for the Intracranial Placement of a Neurostimulator" to Fischell. et al. EEG sensing and brain stimulation is accomplished by the use of integrated electrodes in the housing of Monitor/Therapy unit 26 or, alternatively, by cranially implanted leads (not shown in FIG. 12B). Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy.

FIG. 13 is a simplified schematic view of a fourth embodiment of a full Monitor/Brain Therapy unit 340 implanted in a patient 10. Monitor/Brain Therapy unit 340 continuously senses and monitors cardiac, brain and respiration function of patient 10 via sensor stub 20 and a brain lead 18 to allow detection of a neurological event such as a neurological event, the recording of data and signals pre and post event, and the delivery of therapy via brain lead 18. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy.

FIG. 14 is a simplified schematic view of a fifth embodiment of a full Monitor/Brain Therapy unit 360 implanted in a patient 10. Monitor/Brain Therapy unit 360 in combination with external patch 160 continuously senses and monitors cardiac, brain and respiration function of patient 10 via external patch 160 and a brain lead 18 to allow detection of neurological events, the recording of data and signals pre and post event, and the delivery of therapy via brain lead 18. A 2-way wireless telemetry communication link 30 connects the Monitor/Brain Therapy unit 360 and external patch 160. The wireless communication link 30 may consist of an RF link (such as described in U.S. Pat. No. 5,683,432 "Adaptive Performance-Optimizing Communication System for Communicating with an Implantable Medical Device" to Goedeke, et al), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke). Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy. Also optionally, a button 38 on the external patch monitor 160 may be activated by the patient 10 to manually activate diagnostic data recording and therapy delivery.

FIG. 15 is a simplified schematic view of a sixth embodiment of a full Monitor/Brain Therapy unit 380 implanted in a patient 10. Monitor/Brain Therapy unit 380 continuously senses and monitors cardiac, brain and respiration function of patient 10 via a brain lead 18 with integrated electrode 24 to allow detection of neurological events, the recording of data and signals pre and post event, and the delivery of therapy via brain lead 18. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy. Integrated electrode 24 senses ECG signals as described above in the referenced Klein '352 patent and respiration signals as described above in the referenced Plicchi '892 and '251 patents.

FIG. 20 is a simplified schematic view of a seventh embodiment of a full Monitor/Brain Therapy unit 26 implanted cranially in a patient 10. Monitor/Brain Therapy unit 26 in combination with leadless Monitor 400 continuously senses and monitors cardiac, brain and respiration function of patient 10 to allow detection of neurological events, the recording of data and signals pre and post event, and the delivery of therapy via brain lead 18. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy. A 2-way wireless telemetry communication link 30 connects the Monitor/Therapy unit 26 and leadless Monitor 400. The wireless communication link 30 may consist of an RF link (such as described in U.S. Pat. No. 5,683,432 "Adaptive Performance-Optimizing Communication System for Communicating with an Implantable Medical Device" to Goedeke, et al), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke). An implant aid may be used with Monitor device 400 to ensure a proper position and orientation during implant as described above in connection with the system of FIG. 1. Monitor 26 may be constructed as substantially described in US Publication No. 20040176817 "Modular implantable medical device" to Wahlstrand et al. or U.S. Pat. No. 5,782,891 "Implantable Ceramic Enclosure for Pacing, Neurological and Other Medical Applications in the Human Body" to Hassler, et al or U.S. Pat. No. 6,427,086 "Means and Method for the Intracranial Placement of a Neurostimulator" to Fischell. et al. EEG sensing is accomplished by the use of integrated electrodes in the housing of monitor 26 or, alternatively, by cranially implanted leads.

Monitor 26 may warn/alert the patient 10 via an annunciator such as, but not limited to, buzzes, tones, beeps or spoken voice (as substantially described in U.S. Pat. No. 6,067,473 "Implantable Medical Device Using Audible Sound Communication to Provide Warnings" to Greeninger, et al.) via a piezo-electric transducer incorporated in the housing of monitor 26 and transmitting sound to the patient's 10 inner ear.

FIG. 21 is a simplified schematic view of an eighth embodiment of a full Monitor/Brain Therapy unit 420 implanted cranially in a patient 10. Monitor/Brain Therapy unit 400 in combination with external patch core monitor 160 continuously senses and monitors cardiac, brain and respiration function of patient 10 to allow detection of neurological events, the recording of data and signals pre and post event, and the delivery of therapy via brain lead 18. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy. A 2-way wireless telemetry communication link 30 connects the Monitor/Therapy unit 26 and leadless Monitor 400. The wireless communication link 30 may consist of an RF link (such as described in U.S. Pat. No. 5,683,432 "Adaptive Performance-Optimizing Communication System for Communicating with an Implantable Medical Device" to Goedeke, et al), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke).

Monitor 26 may be constructed as substantially described in US Publication No. 20040176817 "Modular implantable medical device" to Wahlstrand et al. or U.S. Pat. No. 5,782,891 "Implantable Ceramic Enclosure for Pacing, Neurological and Other Medical Applications in the Human Body" to Hassler, et al or U.S. Pat. No. 6,427,086 "Means and Method for the Intracranial Placement of a Neurostimulator" to Fischell. et al. EEG sensing is accomplished by the use of integrated electrodes in the housing of monitor 26 or, alternatively, by cranially implanted leads.

Monitor 26 may warn/alert the patient 10 via an annunciator such as, but not limited to, buzzes, tones, beeps or spoken voice (as substantially described in U.S. Pat. No. 6,067,473 "Implantable Medical Device Using Audible Sound Communication to Provide Warnings" to Greeninger, et al.) via a piezo-electric transducer incorporated in the housing of monitor 26 and transmitting sound to the patient's 10 inner ear.

Monitor+Treatment (Brain+Respiration)

FIG. 16A is a simplified schematic view of a full Monitor/Brain and Respiration Therapy unit 440 implanted in a patient 10. Monitor/Brain and Respiration Therapy unit 440 continuously senses and monitors cardiac, brain and respiration function of patient 10 via cardiac lead(s) 16 and a brain lead 18 to allow detection of neurological events, the recording of data and signals pre and post event, and the delivery of therapy via brain lead 18 and phrenic nerve lead 28. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy. Optionally, lead 28 may connect to the diaphragm to provide direct diaphragmatic stimulation.

FIG. 16B is a simplified schematic view of a second embodiment of a full Monitor/Brain and Respiration Therapy system consisting of a thoracically implanted Monitor/Respiration Therapy unit 441 in combination with a cranially implanted brain Monitor/Therapy unit 26. Monitor unit 441 continuously senses and monitors the cardiac and respiration function of patient 10 via cardiac lead(s) 16 to allow detection of neurological events, the recording of data and signals pre and post event, the delivery of respiration therapy via phrenic nerve lead 28 and the delivery of brain stimulation via Monitor/Therapy unit 26. A 2-way wireless telemetry communication link 30 connects the Monitor/Therapy unit 26 and cardiac/respiration monitor and respiration therapy unit 441. The wireless communication link 30 may consist of an RF link (such as described in U.S. Pat. No. 5,683,432 "Adaptive Performance-Optimizing Communication System for Communicating with an Implantable Medical Device" to Goedeke, et al), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke). Monitor 26 may be constructed as substantially described in US Publication No. 20040176817 "Modular implantable medical device" to Wahlstrand et al. or U.S. Pat. No. 5,782,891 "Implantable Ceramic Enclosure for Pacing, Neurological and Other Medical Applications in the Human Body" to Hassler, et al or U.S. Pat. No. 6,427,086 "Means and Method for the Intracranial Placement of a Neurostimulator" to Fischell. et al. EEG sensing and brain stimulation is accomplished by the use of integrated electrodes in the housing of monitor 26 or, alternatively, by cranially implanted leads (not shown in FIG. 16B). Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy. Optionally, lead 28 may connect to the diaphragm to provide direct diaphragmatic stimulation.

FIG. 17 is a simplified schematic view of a third embodiment of a full Monitor/Brain and Respiration Therapy unit 460 implanted in a patient 10. Monitor/Brain and Respiration Therapy unit 460 continuously senses and monitors cardiac, brain and respiration function of patient 10 via sensor stub 20 and a brain lead 18 to allow detection of neurological events, the recording of data and signals pre and post event, and the delivery of therapy via brain lead 18 and phrenic nerve lead 28. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy. Optionally, lead 28 may connect to the diaphragm to provide direct diaphragmatic stimulation.

FIG. 18 is a simplified schematic view of a fourth embodiment of a full Monitor/Brain and Respiration Therapy unit 480 implanted in a patient 10. Monitor/Brain and Respiration Therapy unit 480 continuously senses and monitors cardiac, brain and respiration function of patient 10 via a brain lead 18 with integrated electrode 24 to allow detection of neurological events, the recording of data and signals pre and post event, and the delivery of therapy via brain lead 18 and phrenic nerve lead 28. Stored diagnostic data is uplinked and evaluated by the patient's physician utilizing programmer 12 via a 2 way telemetry link 32. An external patient activator 22 may optionally allow the patient 10, or other care provider (not shown), to manually activate the recording of diagnostic data and delivery of therapy. Optionally, lead 28 may connect to the diaphragm to provide direct diaphragmatic stimulation. Integrated electrode 24 senses ECG signals as described above in the referenced Klein '352 patent and respiration signals as described above in the referenced Plicchi '892 and '251 patents.

FIG. 19 is a simplified schematic view of a fifth embodiment of a full Monitor/Brain and Respiration Therapy unit 500 implanted in a patient 10. Monitor/Brain and Respiration Therapy unit 500 continuously senses and monitors cardiac, brain and respiration function of patient 10 via brain lead 18 and respiration lead 28 with integrated electrode 24 to allow detection of neurological events, the recording of data and signals pre and post event, and the delivery of therapy via brain lead 18 and phrenic nerve lead 28. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy. Optionally, lead 28 may connect to the diaphragm to provide direct diaphragmatic stimulation. Integrated electrode 24 senses ECG signals as described above in the referenced Klein '352 patent and respiration signals as described above in the referenced Plicchi '892 and '251 patents.

Monitor+Treatment (Brain+Cardiac)

FIG. 24A is a simplified schematic view of a full Monitor/Brain and Cardiac Therapy unit 520 implanted in a patient 10. Monitor/Brain and Cardiac Therapy unit 520 continuously senses and monitors cardiac, brain and respiration function of patient 10 via cardiac lead(s) 16 and a brain lead 18 to allow detection of neurological events, the recording of data and signals pre and post event, and the delivery of therapy via brain lead 18 and cardiac lead(s) 16. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy.

FIG. 24B is a simplified schematic view of a second embodiment of a full Monitor/Brain and Cardiac Therapy system consisting of a thoracically implanted Monitor/Therapy unit 521 implanted in patient 10 in combination with a cranially implanted brain Monitor/Therapy unit 26. Monitor/Therapy unit 521 continuously senses and monitors the cardiac and respiration function of patient 10 via cardiac lead(s) 16 to allow detection of neurological events, the recording of data and signals pre and post event, the delivery of cardiac therapy via Monitor/Therapy unit 521 and the delivery of therapy via Monitor/Therapy unit 26. A 2-way wireless telemetry communication link 30 connects the Monitor/Therapy unit 26 and cardiac/respiration Monitor/Therapy unit 521. The wireless communication link 30 may consist of an RF link (such as described in U.S. Pat. No. 5,683,432 "Adaptive Performance-Optimizing Communication System for Communicating with an Implantable Medical Device" to Goedeke, et al), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke). Monitor 26 may be constructed as substantially described in US Publication No. 20040176817 "Modular implantable medical device" to Wahlstrand et al. or U.S. Pat. No. 5,782,891 "Implantable Ceramic Enclosure for Pacing, Neurological and Other Medical Applications in the Human Body" to Hassler, et al or U.S. Pat. No. 6,427,086 "Means and Method for the Intracranial Placement of a Neurostimulator" to Fischell. et al. EEG sensing and brain stimulation is accomplished by the use of integrated electrodes in the housing of monitor 26 or, alternatively, by cranially implanted leads (not shown in FIG. 24B). Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy.

FIG. 22 is a simplified schematic view of a third embodiment of a full Monitor/Brain and Cardiac Therapy unit 540 implanted cranially in a patient 10. Monitor/Brain and Cardiac Therapy unit 540 in combination with external patient worn vest 34 continuously senses and monitors cardiac, brain and respiration function of patient 10 to allow detection of neurological events, the recording of data and signals pre and post event, and the delivery of therapy via brain lead 18 and vest 34. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy. A 2-way wireless telemetry communication link 30 connects the monitor/therapy unit 540 and patient worn vest 34. The wireless communication link 30 may consist of an RF link (such as described in U.S. Pat. No. 5,683,432 "Adaptive Performance-Optimizing Communication System for Communicating with an Implantable Medical Device" to Goedeke, et al), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke).

Monitor/Therapy unit 540 may be constructed as substantially described in US Publication No. 20040176817 "Modular implantable medical device" to Wahlstrand et al. or U.S. Pat. No. 5,782,891 "Implantable Ceramic Enclosure for Pacing, Neurological and Other Medical Applications in the Human Body" to Hassler, et al or U.S. Pat. No. 6,427,086 "Means and Method for the Intracranial Placement of a Neurostimulator" to Fischell. et al. EEG sensing is accomplished by the use of integrated electrodes in the housing of Monitor/Therapy unit 540 or, alternatively, by cranially implanted leads.

Monitor/Therapy unit 540 may warn/alert the patient 10 via an annunciator such as, but not limited to, buzzes, tones, beeps or spoken voice (as substantially described in U.S. Pat. No. 6,067,473 "Implantable Medical Device Using Audible Sound Communication to Provide Warnings" to Greeninger, et al.) via a piezo-electric transducer incorporated in the housing of monitor 26 and transmitting sound to the patient's 10 inner ear.

FIG. 23 is a simplified schematic view of a fourth embodiment of a full Monitor/Brain and Cardiac Therapy unit 560 implanted cranially in a patient 10. Monitor/Brain and Cardiac Therapy unit 560 in combination with leadless defibrillator 36 continuously senses and monitors cardiac, brain and respiration function of patient 10 to allow detection of neurological events, the recording of data and signals pre and post event, and the delivery of therapy via brain lead 18 and defibrillator 36. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy. A 2-way wireless telemetry communication link 30 connects the monitor/therapy unit 560 and leadless defibrillator 36. The wireless communication link 30 may consist of an RF link (such as described in U.S. Pat. No. 5,683,432 "Adaptive Performance-Optimizing Communication System for Communicating with an Implantable Medical Device" to Goedeke, et al), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke).

Monitor/Therapy unit 560 may be constructed as substantially described in US Publication No. 20040176817 "Modular implantable medical device" to Wahlstrand et al. or U.S. Pat. No. 5,782,891 "Implantable Ceramic Enclosure for Pacing, Neurological and Other Medical Applications in the Human Body" to Hassler, et al or U.S. Pat. No. 6,427,086 "Means and Method for the Intracranial Placement of a Neurostimulator" to Fischell. et al. EEG sensing is accomplished by the use of integrated electrodes in the housing of Monitor/Therapy unit 560 or, alternatively, by cranially implanted leads.

Monitor/Therapy unit 560 may warn/alert the patient 10 via an annunciator such as, but not limited to, buzzes, tones, beeps or spoken voice (as substantially described in U.S. Pat. No. 6,067,473 "Implantable Medical Device Using Audible Sound Communication to Provide Warnings" to Greeninger, et al.) via a piezo-electric transducer incorporated in the housing of Monitor/Therapy unit 560 and transmitting sound to the patient's 10 inner ear.

Monitor+Treatment (Brain+Respiration+Cardiac)

FIG. 25A is a simplified schematic view of a full Monitor/Brain, Respiration and Cardiac Therapy unit 580 implanted in a patient 10. Monitor/Brain, Respiration and Cardiac Therapy unit 580 continuously senses and monitors cardiac, brain and respiration function of patient 10 via cardiac lead(s) 16 and a brain lead 18 to allow detection of neurological events, the recording of data and signals pre and post event, and the delivery of therapy via brain lead 18, cardiac lead(s) 16 and phrenic nerve lead 28. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy. Optionally, lead 28 may connect to the diaphragm to provide direct diaphragmatic stimulation.

FIG. 25B is a simplified schematic view of a second embodiment of a full Monitor/Brain, Respiration and Cardiac Therapy system consisting of a thoracically implanted Monitor/Respiration Therapy unit 581 in combination with a cranially implanted brain Monitor/Therapy unit 26. Monitor/Therapy unit 581 continuously senses and monitors the cardiac and respiration function of patient 10 via cardiac lead(s) 16 to allow detection of neurological events, the recording of data and signals pre and post event, the delivery of respiration therapy via phrenic nerve lead 28 and the delivery of brain stimulation via Monitor/Therapy unit 26. A 2-way wireless telemetry communication link 30 connects the Monitor/Therapy unit 26 and cardiac/respiration monitor/therapy unit 581. The wireless communication link 30 may consist of an RF link (such as described in U.S. Pat. No. 5,683,432 "Adaptive Performance-Optimizing Communication System for Communicating with an Implantable Medical Device" to Goedeke, et al), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke). Monitor 26 may be constructed as substantially described in US Publication No. 20040176817 "Modular implantable medical device" to Wahlstrand et al. or U.S. Pat. No. 5,782,891 "Implantable Ceramic Enclosure for Pacing, Neurological and Other Medical Applications in the Human Body" to Hassler, et al or U.S. Pat. No. 6,427,086 "Means and Method for the Intracranial Placement of a Neurostimulator" to Fischell. et al. EEG sensing and brain stimulation is accomplished by the use of integrated electrodes in the housing of monitor 26 or, alternatively, by cranially implanted leads (not shown in FIG. 25B). Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy. Optionally, lead 28 may connect to the diaphragm to provide direct diaphragmatic stimulation.

Core Monitor Design

Turning now to FIG. 26, there is shown a block diagram of the electronic circuitry that makes up core Monitor 100 (FIG. 1) in accordance with one embodiment of the invention. As can be seen from FIG. 26, Monitor 100 comprises a primary control circuit 720. Much of the circuitry associated with primary control circuit 720 is of conventional design, in accordance, for example, with what is disclosed in U.S. Pat. No. 5,052,388 to Sivula et al, entitled "Method and Apparatus for Implementing Activity Sensing in a Pulse Generator." To the extent that certain components of Monitor 100 are purely conventional in their design and operation, such components will not be described herein in detail, as it is believed that design and implementation of such components would be a matter of routine to those of ordinary skill in the art. For example, primary control circuit 720 in FIG. 26 includes sense amplifier circuitry 724, a crystal clock 728, a random-access memory and read-only memory (RAM/ROM) unit 730, a central processing unit (CPU) 732, a MV Processor circuit 738 and a telemetry circuit 734, all of which are well-known in the art.

Monitor 100 preferably includes internal telemetry circuit 734 so that it is capable of being programmed by means of external programmer/control unit 12 via a 2-way telemetry link 32 (shown in FIG. 1). Programmers and telemetry systems suitable for use in the practice of the present invention have been well known for many years. Known programmers typically communicate with an implanted device via a bi-directional radio-frequency telemetry link, so that the programmer can transmit control commands and operational parameter values to be received by the implanted device, and so that the implanted device can communicate diagnostic and operational data to the programmer. Programmers believed to be suitable for the purposes of practicing the present invention include the Models 9790 and CareLink® programmers, commercially available from Medtronic, Inc., Minneapolis, Minn. Various telemetry systems for providing the necessary communications channels between an external programming unit and an implanted device have been developed and are well known in the art. Telemetry systems believed to be suitable for the purposes of practicing the present invention are disclosed, for example, in the following U.S. Pat. No. 5,127,404 to Wyborny et al. entitled "Telemetry Format for Implanted Medical Device"; U.S. Pat. No. 4,374,382 to Markowitz entitled "Marker Channel Telemetry System for a Medical Device"; and U.S. Pat. No. 4,556,063 to Thompson et al. entitled "Telemetry System for a Medical Device".

Typically, telemetry systems such as those described in the above referenced patents are employed in conjunction with an external programming/processing unit. Most commonly, telemetry systems for implantable medical devices employ a radio-frequency (RF) transmitter and receiver in the device, and a corresponding RF transmitter and receiver in the external programming unit. Within the implantable device, the transmitter and receiver utilize a wire coil as an antenna for receiving downlink telemetry signals and for radiating RF signals for uplink telemetry. The system is modeled as an air-core coupled transformer. An example of such a telemetry system is shown in the above-referenced Thompson et al. '063 patent.

In order to communicate digital data using RF telemetry, a digital encoding scheme such as is described in the above-reference Wyborny et al. '404 patent can be used. In particular, for downlink telemetry a pulse interval modulation scheme may be employed, wherein the external programmer transmits a series of short RF "bursts" or pulses in which the interval between successive pulses (e.g., the interval from the trailing edge of one pulse to the trailing edge of the next) is modulated according to the data to be transmitted. For example, a shorter interval may encode a digital "0" bit while a longer interval encodes a digital "1" bit.

For uplink telemetry, a pulse position modulation scheme may be employed to encode uplink telemetry data. For pulse position modulation, a plurality of time slots are defined in a data frame, and the presence or absence of pulses transmitted during each time slot encodes the data. For example, a sixteen-position data frame may be defined, wherein a pulse in one of the time slots represents a unique four-bit portion of data.

As depicted in FIG. 26, programming units such as the above-referenced Medtronic Models 9790 and CareLink® programmers typically interface with the implanted device through the use of a programming head or programming paddle, a handheld unit adapted to be placed on the patient's body over the implant site of the patient's implanted device. A magnet in the programming head effects reed switch closure in the implanted device to initiate a telemetry session. Thereafter, uplink and downlink communication takes place between the implanted device's transmitter and receiver and a receiver and transmitter disposed within the programming head.

As previously noted, primary control circuit 720 includes central processing unit 732 which may be an off-the-shelf programmable microprocessor or microcontroller, but in the presently preferred embodiment of the invention is a custom integrated circuit. Although specific connections between CPU 732 and other components of primary control circuit 720 are not shown in FIG. 26, it will be apparent to those of ordinary skill in the art that CPU 732 functions to control the timed operation of sense amplifier circuit 724 under control of programming stored in RAM/ROM unit 730. It is believed that those of ordinary skill in the art will be familiar with such an operative arrangement.

With continued reference to FIG. 26, crystal oscillator circuit 728, in the presently preferred embodiment a 32,768-Hz crystal controlled oscillator, provides main timing clock signals to primary control circuit 720.

It is to be understood that the various components of monitor 100 depicted in FIG. 26 are powered by means of a battery (not shown), which is contained within the hermetic enclosure of monitor 100, in accordance with common practice in the art. For the sake of clarity in the figures, the battery and the connections between it and the other components of monitor 100 are not shown.

With continued reference to FIG. 26, sense amplifier 724 is coupled to monitoring elements 14 such as subcutaneous electrodes. Cardiac intrinsic signals are sensed by sense amplifier 724 as substantially described in U.S. Pat. No. 6,505,067 "System and Method for Deriving a Virtual ECG or EGM Signal" to Lee, et al. Further processing by CPU 732 allows the detection of cardiac electrical characteristics/anomalies (e.g., heart rate, heart rate variability, arrhythmias, cardiac arrest, sinus arrest and sinus tachycardia) that would be a matter of routine to those of ordinary skill in the art.

Further processing of the cardiac signal amplitudes may be used to detect respiration characteristics/anomalies (e.g., respiration rate, tidal volume, minute ventilation, and apnea) in MV Processor 738. FIG. 27 shows the intracardiac signals 770 presented to sense amplifier 724 from monitoring elements 14. Note the amplitude variation of cardiac signals caused by the change in thoracic cavity pressure due to respiration (ie, inspiration and expiration). By low pass filtering the cardiac signals 770, a signal representing minute ventilation may be obtained as depicted in waveform 772 (FIG. 27). This respiration signal may further be examined to detect respiration rate and reduced or absence of inspiration and expiration (central apnea) by CPU 732 and software resident in RAM/ROM 730.

Upon detection of either a cardiac or respiration anomaly, CPU 732, under control of computer executable instruction in firmware resident in RAM/ROM 730, will initiate recording of the appropriate diagnostic information into RAM of RAM/ROM 730, initiate a warning or alert to the patient, patient caregiver, or remote monitoring location. See flow diagram and description as described below in association with FIG. 31.

Turning now to FIG. 28, there is shown a block diagram of the electronic circuitry that makes up core Monitor 120 (FIG. 2) in accordance with another disclosed embodiment of the invention. As can be seen from FIG. 28, Monitor 120 comprises a primary control circuit 720 and a minute ventilation circuit 722. Much of the circuitry associated with primary control circuit 720 is of conventional design, in accordance, for example, with what is disclosed in U.S. Pat. No. 5,052,388 to Sivula et al, entitled "Method and Apparatus for Implementing Activity Sensing in a Pulse Generator." To the extent that certain components of Monitor 120 are purely conventional in their design and operation, such components will not be described herein in detail, as it is believed that design and implementation of such components would be a matter of routine to those of ordinary skill in the art. For example, primary control circuit 720 in FIG. 28 includes sense amplifier circuitry 724, a crystal clock 728, a random-access memory and read-only memory (RAM/ROM) unit 730, a central processing unit (CPU) 732, and a telemetry circuit 734, all of which are well-known in the art.

Monitor 120 preferably includes internal telemetry circuit 734 so that it is capable of being programmed by means of external programmer/control unit 12 via a 2-way telemetry link 32 (shown in FIG. 2). Programmers and telemetry systems suitable for use in the practice of the present invention have been well known for many years. Known programmers typically communicate with an implanted device via a bi-directional radio-frequency telemetry link, so that the programmer can transmit control commands and operational parameter values to be received by the implanted device, and so that the implanted device can communicate diagnostic and operational data to the programmer. Programmers believed to be suitable for the purposes of practicing the present invention include the Models 9790 and CareLink® programmers, commercially available from Medtronic, Inc., Minneapolis, Minn. Various telemetry systems for providing the necessary communications channels between an external programming unit and an implanted device have been developed and are well known in the art. Telemetry systems believed to be suitable for the purposes of practicing the present invention are disclosed, for example, in the following U.S. Pat. No. 5,127,404 to Wyborny et al. entitled "Telemetry Format for Implanted Medical Device"; U.S. Pat. No. 4,374,382 to Markowitz entitled "Marker Channel Telemetry System for a Medical Device"; and U.S. Pat. No. 4,556,063 to Thompson et al. entitled "Telemetry System for a Medical Device".

Typically, telemetry systems such as those described in the above referenced patents are employed in conjunction with an external programming/processing unit. Most commonly, telemetry systems for implantable medical devices employ a radio-frequency (RF) transmitter and receiver in the device, and a corresponding RF transmitter and receiver in the external programming unit. Within the implantable device, the transmitter and receiver utilize a wire coil as an antenna for receiving downlink telemetry signals and for radiating RF signals for uplink telemetry. The system is modeled as an air-core coupled transformer. An example of such a telemetry system is shown in the above-referenced Thompson et al. '063 patent.

In order to communicate digital data using RF telemetry, a digital encoding scheme such as is described in the above-reference Wyborny et al. '404 patent can be used. In particular, for downlink telemetry a pulse interval modulation scheme may be employed, wherein the external programmer transmits a series of short RF "bursts" or pulses in which the interval between successive pulses (e.g., the interval from the trailing edge of one pulse to the trailing edge of the next) is modulated according to the data to be transmitted. For example, a shorter interval may encode a digital "0" bit while a longer interval encodes a digital "1" bit.

For uplink telemetry, a pulse position modulation scheme may be employed to encode uplink telemetry data. For pulse position modulation, a plurality of time slots are defined in a data frame, and the presence or absence of pulses transmitted during each time slot encodes the data. For example, a sixteen-position data frame may be defined, wherein a pulse in one of the time slots represents a unique four-bit portion of data.

As depicted in FIG. 28, programming units such as the above-referenced Medtronic Models 9790 and CareLink® programmers typically interface with the implanted device through the use of a programming head or programming paddle, a handheld unit adapted to be placed on the patient's body over the implant site of the patient's implanted device. A magnet in the programming head effects reed switch closure in the implanted device to initiate a telemetry session. Thereafter, uplink and downlink communication takes place between the implanted device's transmitter and receiver and a receiver and transmitter disposed within the programming head.

With continued reference to FIG. 28, Monitor 120 is coupled to leads 16 which, when implanted, extend transvenously between the implant site of Monitor 120 and the patient's heart (not shown). For the sake of clarity, the connections between leads 16 and the various components of Monitor 120 are not shown in FIG. 28, although it will be clear to those of ordinary skill in the art that, for example, leads 16 will necessarily be coupled, either directly or indirectly, to sense amplifier circuitry 724 in accordance with common practice, such that cardiac electrical signals may be conveyed to sensing circuitry 724, via leads 16. Cardiac leads 16 may consist of any typical lead configuration as is known in the art, such as, without limitation, right ventricular (RV) pacing or defibrillation leads, right atrial (RA) pacing or defibrillation leads, single pass RA/RV pacing or defibrillation leads, coronary sinus (CS) pacing or defibrillation leads, left ventricular pacing or defibrillation leads, pacing or defibrillation epicardial leads, subcutaneous defibrillation leads, unipolar or bipolar lead configurations, or any combinations of the above lead systems.

Sensed cardiac events are evaluated by CPU 732 and software stored in RAM/ROM unit 730. Cardiac anomalies detected include heart rate variability, QT variability, QT.sub.C, sinus arrest, syncope, ST segment elevation and various arrhythmias such as sinus, atrial and ventricular tachycardias.

Heart rate variability may be measured by the method and apparatus as described in U.S. Pat. No. 5,749,900 "Implantable Medical Device Responsive to Heart Rate Variability Analysis" to Schroeppel, et al and U.S. Pat. No. 6,035,233 "Implantable Medical Device Responsive to Heart Rate Variability Analysis" to Schroeppel, et al. Schroeppel '900 and '233 patents describe an implantable cardiac device that computes time intervals occurring between successive heartbeats and then derive a measurement of heart rate variability from epoch data for predetermined time periods. The Schroeppel device then compares measurement of heart rate variability with previously stored heart rate variability zones, which define normal and abnormal heart rate variability.

QT variability may be measured by the method and apparatus as described in U.S. Pat. No. 5,560,368 "Methodology for Automated QT Variability Measurement" to Berger. The Berger '368 patent utilizes a "stretchable" QT interval template started at the beginning of the QRS complex and terminating on the T-wave to determine beat-to-beat variability.

$QT_C$ may be measured by the method and apparatus as described in U.S. Pat. No. 6,721,599 "Pacemaker with Sudden Rate Drop Detection Based on QT Variations" to de Vries. The de Vries '599 patent measures QT interval real time and compares the instantaneous value to a calculated mean via a preprogrammed threshold change value.

Syncope may be detected by the methods and apparatus as described in U.S. Pat. No. 6,721,599 "Pacemaker with Sudden Rate Drop Detection Based on QT Variations" to de Vries. The de Vries '599 patent utilizes a sudden rate change and a real time QT interval measurement compared to a QT mean to detect sudden rate drop and neurally mediated syncope.

ST segment elevation (an indicator of myocardial ischemia) may be detected by the methods and apparatus as described in U.S. Pat. No. 6,128,526 "Method for Ischemia Detection and Apparatus for Using Same" to Stadler, et al and U.S. Pat. No. 6,115,630 "Determination of Orientation of Electrocardiogram Signal in Implantable Medical devices" to Stadler, et al. The Stadler '526 and '630 patents describe a system that compares a sampled data point prior to an R-wave complex peak amplitude to multiple samples post R-wave event to detect ST segment elevation.

Arrhythmias such as sinus, atrial and ventricular tachycardias may be detected by the methods and apparatus as described in U.S. Pat. No. 5,545,186 "Prioritized Rule Based Method and Apparatus for Diagnosis and Treatment of Arrhythmias" to Olson, et al. Sinus arrest may be detected by the methods and apparatus as described above in the Olson '186 patent.

In the presently disclosed embodiment, two leads are employed—an atrial lead 16A having atrial TIP and RING electrodes, and a ventricular lead 16V having ventricular TIP and RING electrodes. In addition, as noted above, the conductive hermetic canister of Monitor 120 serves as an indifferent electrode.

As previously noted, primary control circuit 720 includes central processing unit 732 which may be an off-the-shelf programmable microprocessor or microcontroller, but in the presently preferred embodiment of the invention is a custom integrated circuit. Although specific connections between CPU 732 and other components of primary control circuit 720 are not shown in FIG. 28, it will be apparent to those of ordinary skill in the art that CPU 732 functions to control the timed operation of sense amplifier circuit 724 under control of programming stored in RAM/ROM unit 730. It is believed that those of ordinary skill in the art will be familiar with such an operative arrangement.

With continued reference to FIG. 28, crystal oscillator circuit 728, in the presently preferred embodiment a 32,768-Hz crystal controlled oscillator, provides main timing clock signals to primary control circuit 720 and to minute ventilation circuit 722.

It is to be understood that the various components of Monitor 120 depicted in FIG. 28 are powered by means of a battery (not shown), which is contained within the hermetic enclosure of Monitor 120, in accordance with common practice in the art. For the sake of clarity in the figures, the battery and the connections between it and the other components of Monitor 120 are not shown.

As shown in FIG. 28, primary control circuit 720 is coupled to minute ventilation circuit 722 by means of multiple signal lines, designated collectively as 738 in FIG. 28. An I/O interface 740 in primary control circuit 720 and a corresponding I/O interface 742 in minute ventilation circuit 722, coordinate the transmission of signals between the two units via control lines 738.

Minute ventilation circuit 722 measures changes in transthoracic impedance, which has been shown to be proportional to minute ventilation. Minute ventilation is the product of tidal volume and respiration rate, and as such is a physiologic indicator of changes in metabolic demand.

Monitor 120, in accordance with the presently disclosed embodiment of the invention, measures transthoracic impedance using a bipolar lead 16 and a tripolar measurement system. As will be hereinafter described in greater detail, minute ventilation circuit 722 delivers 30-microSec biphasic current excitation pulses of 1-mA (peak-to-peak) between a RING electrode of bipolar lead 16 and the conductive canister of monitor 120, functioning as an indifferent electrode CASE, at a rate of 16-Hz. The resulting voltage is then measured between a TIP electrode of lead 16 and the monitor 120 CASE electrode. Such impedance measurement may be programmed to take place in either the atrium or ventricle of the patient's heart.

The impedance signal derived by minute ventilation circuit 722 has three main components: a DC offset voltage; a cardiac component resulting from the heart's function; and a respiratory component. The frequencies of the cardiac and respiratory components are assumed to be identical to their physiologic origin. Since the respiratory component of the impedance signal derived by minute ventilation circuit 722 is of primary interest for this aspect of the present invention, the impedance signal is subjected to filtering in minute ventilation low-pass filter (MV LPF) 750 having a passband of 0.05- to 0.8-Hz (corresponding to 3-48 breaths per minute) to remove the DC and cardiac components.

With continuing reference to FIG. 28, minute ventilation circuit 722 includes a Lead Interface circuit 744 which is essentially a multiplexer that functions to selectively couple and decouple minute ventilation circuit 722 to the VTIP, VRING, ATIP, ARING, and CASE electrodes, as will be hereinafter described in greater detail.

Coupled to lead interface circuit 744 is a minute ventilation (MV) Excitation circuit 746 which functions to deliver the biphasic constant-current pulses between various combinations of lead electrodes (VTIP, VRING, etc.) for the purpose of measuring cardiac impedance. In particular, MV Excitation circuit 746 delivers biphasic excitation pulses (at a rate of 16-Hz between the ventricular ring electrode VRING and the pacemaker canister CASE) of the type delivered in accordance with the method and apparatus described in U.S. Pat. No. 5,271,395 "Method and Apparatus for Rate Responsive Cardiac Pacing" to Wahlstrand et al.

To measure cardiac impedance, minute ventilation circuit 722 monitors the voltage differential present between pairs of electrodes as excitation pulses are being injected as described above. Again, the electrodes from which voltage differentials are monitored will vary depending upon whether atrial or ventricular measurements are being made. In one embodiment of the invention, the same electrodes (i.e., VRING and CASE for ventricular, ARING and CASE for atrial) are used for both delivery of excitation pulses and voltage differential monitoring. It is contemplated, however, that the electrode combinations for excitation and measurement may be among the programmable settings, which may be altered post-implant with the programming system.

With continued reference to FIG. 28, the 16-Hz sampled output voltages from ZMEAS PREAMP circuit 748 are presented to the minute ventilation low-pass filter circuit MV LPF 750, which has a passband of 0.05-0.8 Hz in the presently preferred embodiment of the invention. Again, it is believed that the design and implementation of MV LPF circuit 750 would be a matter of routine engineering to those of ordinary skill in the art. The output from MV LPF circuit 750 is a voltage waveform whose level at any given time is directly proportional to cardiac impedance measured between the selected electrodes. Thus, the MV LPF output signal will be referred to herein as an impedance waveform. MV Calculation 752 analyzes the impedance waveform to determine/detect respiration rate, tidal volume, minute ventilation and presence of apnea.

The circuit of FIG. 28 may additionally monitor pulmonary edema by measuring the DC impedance between the distal electrodes of cardiac leads 16 and the case of core monitor 120. Measurement technique may be as substantially described in U.S. Pat. No. 6,512,949 "Implantable Medical Device for Measuring Time Varying Physiologic Conditions Especially Edema and for Responding Thereto" by Combs, et al. Upon detection of a cardiac or respiration anomaly, CPU 732, under control of firmware resident in RAM/ROM 730, will initiate recording of the appropriate diagnostic information into RAM of RAM/ROM 730, initiate a warning or alert to the patient, patient caregiver, or remote monitoring location. See flow diagram and description as described below in association with FIG. 31.

Turning now to FIG. 29, there is shown a block diagram of the electronic circuitry that makes up core Monitor 140 with sensor stub 20 (FIG. 3) in accordance with another disclosed embodiment of the invention. As can be seen from FIG. 29, Monitor 140 comprises a primary control circuit 720 and a minute ventilation circuit 722, the function of which has been described in detail above in conjunction with the system of FIG. 28. Monitor 140 measures thoracic impedance from the case of monitor 140 to the distal end of a sensor stub lead 20 (a subcutaneously implanted sensor lead) via an impedance/voltage converter using a sampling frequency of approximately 16 Hz as substantially described in U.S. Pat. No. 4,596,251 "Minute Ventilation Dependant Rate Responsive Pacer" to Plicchi, et al. Respiration parameters are evaluated by CPU 732 and software resident in RAM/ROM 730.

Cardiac signals are sensed by sense amplifier 724 and evaluated by CPU 732 and software resident in RAM/ROM 730.

Upon detection of either/or a cardiac or respiration anomaly, CPU 732, under control of firmware resident in RAM/ROM 730, will initiate recording of the appropriate diagnostic information into RAM of RAM/ROM 730, initiate a warning or alert to the patient, patient caregiver, or remote monitoring location. See flow diagram and description as described below in association with FIG. 31.

Turning now to FIG. 30, there is shown a block diagram of the electronic circuitry that makes up external patch core Monitor 160 (FIG. 4) in accordance with another disclosed embodiment of the invention. As can be seen from FIG. 30, Monitor 160 comprises a primary control circuit 720 and a minute ventilation circuit 722, the function of which has been described in detail above in conjunction with the system of FIG. 28. Intrinsic cardiac signals are sensed by electrodes 161 affixed to the patient's skin, amplified by amplifier 724 and processed by CPU 732 and software program resident in RAM/ROM 730. Cardiac anomalies are detected such as heart rate variability, QT variability, QT.sub.C, sinus arrest, and various arrhythmias such as sinus, atrial and ventricular tachycardias. Respiration sensing is accomplished by low pass filtering the sensed and amplified intrinsic cardiac signals as shown in FIG. 27. Respiration anomalies (such as reduced or cessation of tidal volume and apnea) are evaluated and detected by CPU 732 and software resident in RAM/ROM 730.

Upon detection of either/or a cardiac or respiration anomaly, CPU 732, under control of firmware resident in RAM/ROM 730, will initiate recording of the appropriate diagnostic information into RAM of RAM/ROM 730, initiate a warning or alert to the patient, patient caregiver, or remote monitoring location. See flow diagram and description as described below in association with FIG. 31.

FIG. 31 is a flow diagram 800 showing operation of a core Monitor sensing/monitoring cardiac and respiration parameters for the detection of neurological events as shown and described in embodiments in FIG. 1-4 above. Beginning at block 802, the interval between sensed cardiac signals are measured. At block 804, a rate stability measurement is made on each cardiac interval utilizing a heart rate average from block 806. At block 808, a rate stable decision is made based upon preprogrammed parameters. If YES, the flow diagram returns to the HR Measurement block 802. If NO, the rate stability information is provided to Format Diagnostic Data block 812.

At block 816, thoracic impedance is continuously measured in a sampling operation. At block 818, a MV and respiration rate calculation is made. At block 822, a pulmonary apnea decision is made based upon preprogrammed criteria. If NO, the flow diagram returns to MV Measurement block 816. If YES, the occurrence of apnea and MV information is provided to Format Diagnostic Data block 812. Format Diagnostic Data block 812 formats the data from the cardiac and respiration monitoring channels, adds a time stamp (ie, date and time) and provides the data to block 814 where the data is stored in RAM, SRAM or MRAM memory for later retrieval by a clinician via telemetry. Optionally, block 812 may add examples of intrinsic ECG or respiration signals recorded during a sensed episode/seizure. Additionally, optionally, block 815 may initiate a warning or alert to the patient, patient caregiver, or remote monitoring location (as described in U.S. Pat. No. 5,752,976 "World Wide Patient Location and Data Telemetry System for Implantable Medical Devices" to Duffin, et al.

Full Monitor Design

FIG. 32 is a block diagram of the electronic circuitry that makes up full Monitor 200 (FIG. 5) in accordance with the presently disclosed alternative embodiment of the invention. As can be seen from FIG. 32, Monitor 200 includes a primary control circuit 720 that is described herein above in conjunction with FIG. 26. In addition the full monitor of FIG. 30 also includes an amplifier 725 to amplify and sense EEG signals from a cranially implanted lead 18. The CPU 732, in conjunction with a software program resident in RAM/ROM 730, evaluates the information from the sensed cardiac, respiration and EEG signals, detects the onset of cerebral, cardiac or respiratory anomalies, may perform one or more algorithms or methods as described in this specification (such as determination of concordance between EEG and cardiac or respiratory signals, comparison of heart rates associated with certain neurological event time periods, etc.), formats and stores diagnostic data for later retrieval by the patient's clinician and, optionally, may warn or alert the patient, patient caregiver or remote monitoring location. See flow diagram and description below in association with FIG. 37.

FIG. 33 is a block diagram of the electronic circuitry that makes up full Monitor 220 with brain 18 and cardiac 16 leads (FIG. 6) in accordance with the presently disclosed alternative embodiment of the invention. As can be seen from FIG. 33, Monitor 220 comprises a primary control circuit 720 and MV circuit 722 that are described herein above in conjunction with FIG. 28. In addition, the full Monitor 220 of FIG. 33 also includes an amplifier 725 to amplify and sense EEG signals from a cranially implanted lead 18. The CPU 732, in conjunction with a software program resident in RAM/ROM 730, integrates the information from the sensed cardiac, respiration and EEG signals, detects the onset of cerebral, cardiac or respiratory anomalies, formats and stores diagnostic data for later retrieval by the patient's clinician and, optionally, may warn or alert the patient, patient caregiver or remote monitoring location. See flow diagram and description as described below in association with FIG. 37.

FIG. 34 is a block diagram of the electronic circuitry that makes up full Monitor 240 with a brain lead 18 and sensor stub 20 (FIG. 7) in accordance with the presently disclosed alternative embodiment of the invention. As can be seen from FIG. 34, Monitor 240 comprises a primary control circuit 720 and MV circuit 722 that are described herein above in conjunction with FIG. 28. In addition, the full Monitor 240 of FIG. 34 also includes an amplifier 725 to amplify and sense EEG signals from a cranially implanted lead 18. The CPU 732, in conjunction with a software program resident in RAM/ROM 730, integrates the information from the sensed cardiac, respiration and EEG signals, detects the onset of cerebral, cardiac or respiratory anomalies, formats and stores diagnostic data for later retrieval by the patient's clinician and, optionally, may warn or alert the patient, patient caregiver or remote monitoring location. See flow diagram and description as described below in association with FIG. 37.

FIG. 35 is a block diagram of the electronic circuitry that makes up external patch 160/full Monitor 260 with a brain lead 18 (FIG. 8) in accordance with the presently disclosed alternative embodiment of the invention. As can be seen from FIG. 35, Monitor 260 comprises a primary control circuit 720 and external patch comprises a cardiac/MV (minute ventilation) circuit 160, the functions of which have been described in detail above in conjunction with the system of FIG. 28. Intrinsic cardiac signals are sensed by electrodes affixed to the patient's skin, amplified by amplifier 724, sent to primary control circuit 720 and processed by CPU 732 and software program resident in RAM/ROM 730. Cardiac anomalies are detected such as heart rate variability, QT variability, QT.sub.C, sinus arrest, and various arrhythmias such as sinus, atrial and ventricular tachycardias. Respiration sensing is accomplished by low pass filtering the sensed and amplified intrinsic cardiac signals as shown in FIG. 27 or, alternatively, by using the MV/Z measurement circuitry of external patch 160 as described above in connection with FIG. 28. Respiration anomalies (such as reduced or cessation of tidal volume and apnea) are evaluated and detected by CPU 732 and software resident in RAM/ROM 730.

The CPU 732, in conjunction with a software program resident in RAM/ROM 730, integrates the information from the sensed cardiac, respiration and EEG signals, detects the onset of cerebral, cardiac or respiratory anomalies, formats and stores diagnostic data for later retrieval by the patient's clinician and, optionally, may warn or alert the patient, patient caregiver or remote monitoring location. See flow diagram and description as described below in association with FIG. 37.

The circuitry and function of the device 240 shown in FIG. 34 and described herein above may also be used for the full Monitor 280 with integrated electrode 24 brain lead 18 (FIG. 9). As described above in association with core Monitor 240, thoracic impedance via impedance/voltage converter as measured from the case of monitor 240 to the sensor stub 20 using a sampling frequency of approximately 16 Hz as substantially described in U.S. Pat. No. 4,596,251 "Minute Ventilation Dependant Rate Responsive Pacer" to Plicchi, et al. The Monitor 280 of this alternative embodiment utilizes the same circuitry of Monitor 240 but connected to the integrated electrode 24 on brain lead 18 instead of the sensor stub of Monitor 240.

Upon detection of either/or a cardiac or respiration anomaly, CPU 732, under control of firmware resident in RAM/ROM 730, will initiate recording of the appropriate diagnostic information into RAM of RAM/ROM 730, initiate a warning or alert to the patient, patient caregiver, or remote monitoring location. See flow diagram and description as described below in association with FIG. 37.

FIG. 36 is a block diagram of the electronic circuitry that makes up full Monitor 26 (FIG. 10) in accordance with the presently disclosed alternative embodiment of the invention. As can be seen from FIG. 32, Monitor 26 comprises a primary control circuit 720 whose function is described herein above in conjunction with FIG. 26. In addition the full Monitor 26 of FIG. 32 also includes an EEG amplifier 725 to amplify and sense EEG signals from a cranially implanted lead 18 or, alternatively, device mounted electrodes. Additionally, Sensor Interface 727 powers up, amplifies and senses the cardiac and respiratory signals from anyone or more of the following cranially implanted sensors. ECG sensing in the cranium may be accomplished by leadless ECG sensing as described in the above Brabec '940, Ceballos '915 and Lee '067 referenced patents. Alternatively, cardiac rate and asystole may be inferred from a dP/dt signal described above in the Anderson '813 patent; an acoustic signal described above in the Kieval '177 patent; an O.sub.2sat signal described above in Moore '701 patent; a dT/dt signal described above in the Weijand '244 patent; a flow signal described above in the Olson '009; a strain gauge signal described above in the Bowman '759 patent; and a blood parameter sensor (such as oxygen, pulse or flow) located on a V-shaped lead described in the Taepke '318 patent.

The CPU 732, in conjunction with a software program resident in RAM/ROM 730, integrates the information from the sensed cardiac, respiration and EEG signals, detects the onset of cerebral, cardiac or respiratory anomalies, formats and stores diagnostic data for later retrieval by the patient's clinician and, optionally, may warn or alert the patient, patient caregiver or remote monitoring location. See flow diagram and description as described below in association with FIG. 37.

FIG. 37 is a flow diagram 840 showing operation of a full monitor sensing and monitoring cardiac, respiration and electroencephalogram parameters for the detection of neurological events as shown and described in embodiments in FIG. 5-10 above. Beginning at block 802, the interval between sensed cardiac signals are measured. At block 804, a rate stability measurement is made on each cardiac interval utilizing a heart rate average from block 806. At block 808, a rate stable decision is made based upon preprogrammed parameters. If YES, the flow diagram returns to the HR Measurement block 802. If NO, the rate stability information is provided to Format Diagnostic Data block 812.

At block 816, thoracic impedance is continuously measured in a sampling operation. At block 818, a MV and respiration rate calculation is made. At block 822, a pulmonary apnea decision is made based upon preprogrammed criteria. If NO, the flow diagram returns to MV Measurement block 816. If YES, the occurrence of apnea and MV information is provided to Format Diagnostic Data block 812.

At block 824, the electroencephalogram is sensed and measured. An EEG seizure determination is performed at block 826 as described in US published application 2004/0138536 "Clustering of Recorded Patient Neurological Activity to Determine Length of a Neurological Event" to Frei, et al incorporated herein by reference. At block 828, a seizure cluster episode is determined. If NO, the flow diagram returns to EEG Measurement block 824. If YES, the occurrence of a seizure cluster is provided to Format Diagnostic Data block 812. Format Diagnostic Data block 812 formats the data from the cardiac, respiration and EEG monitoring channels, adds a time stamp (ie, date and time) and provides the data to block 814 where the data is stored in RAM memory for later retrieval by a clinician via telemetry. Optionally, block 812 may add examples of intrinsic ECG, respiration or EEG signals recorded during a sensed episode/seizure. Additionally, optionally, block 815 may initiate a warning or alert to the patient, patient caregiver, or remote monitoring location (as described in U.S. Pat. No. 5,752,976 "World Wide Patient Location and Data Telemetry System for Implantable Medical Devices" to Duffin, et al.

FIG. 38 is a diagram 850 of exemplary physiologic data from a patient 10 with a full monitor as described herein above showing an EEG signal 852 and an ECG signal 854. A first epileptic seizure is shown at 856 (pre-ictal segment 851, ictal segment 853 and post-ictal segment 855) and detected at 864 and a second seizure is shown at 858 (pre-ictal segment 857, ictal segment 859 and post-ictal segment 861) and detected at 866 by the full monitor. The ECG signal 854 shows a first arrhythmic episode at 860 and detected at 868 and a second arrhythmic episode at 862 and detected at 870 by the full monitor. Note that the first epileptic seizure 864 and arrhythmic episode 868 are co-incident and "matched". Note that in the diagram 850 arrhythmic episode 870 and seizure episode 866 are not co-incident and are "unmatched".

Segmenting a Cardiac Signal According to Brain Detection Results.

One embodiment of the inventive system provides an automated method of processing cardiac and/or respiratory signals in a full monitoring device (brain-heart, brain-respiratory or brain, heart and respiratory) for a nervous system disorder, to screen for cardiac abnormalities/heart rate changes and respiratory abnormalities during or within a specified time period of a neurological event. This embodiment medical device system and method may report a patient's heart or pulmonary condition for each neurological event detected in the brain signal.

In the case of epilepsy for example, changes in cardiac rate, presence of ECG abnormalities, and respiratory conditions (i.e., pulmonary edema) have been associated with seizures. Such changes in autonomic functioning have been postulated as important factors in epilepsy patients at risk of sudden death (SUDEP). The capability to monitor cardiac or respiratory function during seizures is important, as it allows for identification of co-existing autonomic conditions that may underlie SUDEP.

To determine changes in cardiovascular function that may arise from seizures, a method called ictal-ECG segmentation has been developed for use in a medical device system. Upon detection of a brain event, as defined by a seizure-detection algorithm operating on EEG/ECoG signals, a corresponding portion of data in the ECG signal is identified. The identified portion of data may be further segmented into pre-ictal, ictal and post-ictal portions. For each portion, heart rate metrics (mean, median, min, max, and standard deviation) may be calculated and ECG abnormalities (bradycardia, tachycardia, asystole, ST segment depression, QTc prolongation, etc.) may be identified. Measures of change between indices are then calculated by comparing the metrics.

Desirable features of such a seizure-heart rate monitoring system includes the ability to monitor the following: (1) HR levels (R-R intervals) associated with the time-course of the seizure, including pre-ictal, ictal, and post-ictal periods; (2) HR changes associated with the onset and termination of the seizure; (3) time taken for heart rate to return to pre-ictal levels (within specified range) following seizure termination; and (4) presence of ECG abnormalities associated with the seizure and timing of occurrence (before, during, or after ictal period).

Such a system provides useful clinical information, in the form of an ECG seizure profile, for use in diagnosing and treating co-morbid cardiac conditions. For example, a physician would be able to determine the number and percentage of detected seizures for which there was an associated serious cardiac condition (e.g., tachycardia, asystolic pause, etc.), and be provided a detailed listing/summary of heart rate indices. Subsequent assessments could then determine whether the detected events necessitate cardiac treatment.

A seizure-heart rate monitoring system that employs ictal ECG segmentation may also be used to help determine whether cardiac function is affected by the patient's seizure type. In some patients, large changes in heart rate or specific types of arrhythmias may be triggered with certain seizure types and/or their location of onset. Assessments for trend over time may be made by comparing ECG seizure metrics between detected neurological events. For example, by plotting and comparing % change in heart rate metrics over time.

In one embodiment, the medical device system includes a brain monitoring element, a cardiac monitoring element and one or more processors in communication with the brain monitoring element and the cardiac monitoring element and configured to perform a variety of operations. The various processing steps discussed may be performed within any hardware embodiment envisioned including but not limited to the various hardware embodiments presented throughout this application. For example, all of the processing steps may be performed within one or more implantable devices. Alternatively, some processing steps may be performed within one or more implantable devices and other processing steps performed by an external component of the system such as a programmer or computer that receives the appropriate information from the implanted device(s) by telemetry.

The one or more processors perform a number of operations. In one embodiment shown in FIG. 60, the one or more processors receive a brain signal at block 1102. The brain signal comes from the brain monitoring element. For example, the brain signal could be the output of an electrode that senses an EEG signal from the brain. The one or more processors determine at least one reference point for a brain event time period at block 1104. A brain event time period is the time period over which a neurological event is detected in the brain signal. In the epilepsy example, the brain event is a seizure and the brain event time period is the period of time identified by the detection or prediction algorithm as the seizure event. An appropriate algorithm determines the reference point of the neurological event based on the analysis of the brain signal. It is noted that some neurological events may have a more abrupt onset and offset while other neurological events may have a more gradual onset and offset. A reference point for a brain event time period may be any point in time that has some relationship to a detected event in the brain signal. For example, the reference point may be the starting point or ending point of a seizure according to a seizure detection algorithm evaluating the brain signal. Alternatively, the reference point could be the midpoint of a neurological event. Alternatively, the reference point could be a maximum point in the brain event (e.g., highest reading of whatever quantitative measure being used to evaluate the brain signal). Alternatively the reference point could be some point in time before seizure onset that is identified by the detection or prediction algorithm and that has some relationship to the brain event. The one or more processors receive a cardiac signal from the cardiac monitoring element at block 1106. The one or more processors then identify a first portion of the cardiac signal based on the at least one reference point at block 1108. Identifying a portion of a cardiac signal involves determining a beginning and an end of the portion. Some examples of a portion of the cardiac signal include pre-event portion, event portion and post-event portion. A pre-event portion is some portion that occurs before the starting point of a brain event time period. An event portion is a portion that occurs during a brain event time period. A post-event portion is a portion that occurs after the ending point of a brain event time period. In the example of epilepsy, the pre-event, event and post-event portions are referred to as the pre-ictal, ictal and post-ictal portions respectively.

The flowchart at FIG. 61 illustrates an alternative embodiment of the operations performed by the one or more processors. At block 1202, the one or more processors receive a brain signal. An algorithm is performed by the one or more processors to determine at least one reference point (e.g., the starting point, the ending point or both) of the brain event time period at block 1204. Note that in the case of determining more than one reference point, the second reference point may be determined based on the first reference point. For example, if an algorithm detects the starting point of a neurological event, the algorithm may make an assumption that the ending point is a period of time after the starting point. Alternatively, both reference points may be determined by evaluation of the brain signal using a detection algorithm or other algorithm. The one or more processors receive a cardiac signal at block 1206. The one or more processors next identify two or more portions of the cardiac signal based on the starting and ending points of the brain event time period at block 1208. For example, one or more processors may identify a pre-event portion, event portion and post-event portion of the cardiac signal. Specifically in the case of epilepsy, the portions identified may be the pre-ictal, ictal and post-ictal portions of the cardiac signal. The identification of portions of the cardiac signal based on starting and ending points of the brain event time period may be by a simple relationship between the starting and ending points and the portions or it may be complex. Some examples of ways to identify portions of the cardiac signal are provided. In one embodiment illustrated in FIG. 62, identification of a pre-ictal portion of the cardiac signal involves identifying the portion of the cardiac signal between a programmable first period of time before the starting point to the starting point. The post-ictal portion of the cardiac signal may be identified as the portion of the cardiac signal between the ending point of the brain event time period and a third period of time after the ending point. Another exemplary embodiment method of identifying portions of a cardiac signal is illustrated in FIG. 63. Here, the pre-ictal portion is identified as the portion between a first period of time before the starting point to a second period of time before the starting point. Furthermore, the post-ictal portion is identified as the portion between a fourth period of time after the ending point to a third period of time after the ending point. In one embodiment, the time periods may be programmable. In another embodiment, they may be fixed.

The process may start with analysis of the brain signal. The terms "starting point" and "ending point" include points in time determined by an algorithm that may not necessarily correlate with a sharp or distinct change in the brain signal. For example a slight increase in features indicative of major depressive disorder may be sufficient for the algorithm to make the determination of a starting point even though a distinct or abrupt change in the brain signal is not observed. In the case of epilepsy a seizure detection algorithm may be used some of which have been cited elsewhere in this application. In the case of psychiatric disorders such as depression, a psychiatric monitoring algorithm may be used. For example, EEG asymmetry across different hemispheres of the brain may be evaluated to detect a depression event. One exemplary algorithm that may be used for depression is described in U.S. Published Patent Application 2005/0216071. The methods described in U.S. Pat. No. 6,622,036 may also be used.

Once one or more portions of the cardiac signal are identified, they may be stored in memory at block 1210. The phrase "stored in memory" means keeping the information so that it can be analyzed. For example, the phrase "stored in memory" includes retaining (rather than discarding) information in a circular buffer such as in a loop recording scheme. In one embodiment monitoring device for epilepsy, brain signals are monitored/processed with a seizure detection algorithm; the cardiac and respiratory signals are passively recorded during the brain signal processing. When a seizure has been detected in the brain signal data stream, a recording containing a montage of brain, cardiac and respiratory signals is created. The signals in the recording are then processed to evaluate the patient's heart and pulmonary condition.

At block 1212, the one or more processors may determine metrics of one or more of the pre-event, event and post-event portions of the cardiac signal. In one embodiment, the metrics may relate to heart rate. Some of the heart rate metrics that may be determined include the following that may be taken over the entire portion of the cardiac signal or over a subset of the portion: mean heart rate, median heart rate, maximum heart rate, minimum heart rate and standard deviation of the heart rate.

Once metrics are determined they may be compared at block 1214. Comparison of metrics means any comparison between two metrics. For example, percentage change from one metric to a second metric may be computed. In one embodiment, the pre-event metric may be compared to the post-event metric. In one embodiment the post-event portion may be divided into sub-portions, metrics computed for the sub-portions, and the sub-portion metrics compared to the pre-event metric. This may be done to determine how long it takes the patient's heart rate to return to normal after a brain event such as a seizure. In another embodiment, the pre-event metric may be compared to the event metric. In yet another embodiment, the event metric may be compared to the post-event metric.

In one embodiment, it may be desirable to have a processor in the implantable medical device portion of the system identify the portions of the cardiac signal (e.g., pre-ictal, ictal, post-ictal) and to store them, and to have a second processor in a programmer or other external device receive the portions of cardiac signal via telemetry and determine metrics and compare metrics. In yet another embodiment, the implanted processor may determine the metrics associated with the portions and send only the metrics to the external device via telemetry. The external device may then evaluate or compare the metrics. In yet another embodiment, the brain and cardiac signals may be telemetered to the external device and post-processed by the external device to identify the portions, determine the metrics and compare the metrics.

FIG. 39 shows one embodiment process 750 for identifying ECG and respiratory abnormalities recorded during detected seizures. At block 751, the full monitor monitors EEG and ECG or respiratory signals. At block 752, the monitor detects seizures in EEG signals. At block 753, seizure detection triggers recording and retention of EEG, ECG and respiratory signals. After uplinking to a programmer, the ECG/respiratory signals are post-processed. At this point one or more processors may identify an event portion, pre-event portion and post-event portion of the cardiac signal based on the starting point and the ending point of the brain event time period. The event portion of the cardiac signal may correspond in time exactly to the brain event time period such as an ictal period, or it may be different but computed based on the starting and ending points of the brain event time period. The pre-event portion of the cardiac signal may be everything before the event time period or it may be a period beginning a programmable period of time before the event time period to the beginning of the event time period. Likewise, the post-event time period may be everything after an event time period or it may be a period beginning at the end of the event time period and extending to a programmable period of time after the end of the event time period. For the seizure example, at block 755, ECG and respiratory signals are segmented into (a) pre-ictal, (b) ictal, and (c) post-ictal periods based upon the determined starting and ending points of the neurological event in the brain signal. The ictal periods are automatically derived from a seizure-detection algorithm operating on the EEG signals. For example, the beginning of the ictal period may be time-marked to detection cluster onset; the end of the ictal period by detection cluster offset (as described in published US Application No. 2004/0138536 "Clustering of Recorded Patient Neurological Activity to Determine Length of a Neurological Event" to Frei, et al incorporated herein by reference in its entirety). The durations of the pre-ictal and post-ictal periods are programmable. It may be desirable to program the pre-ictal period for purposes of a cardiac baseline or respiratory baseline as ending some period of time before or after the true ictal period as determined by the EEG detector. In this way a better baseline may be obtained that is not distorted by changes in cardiac or respiratory activity near in time to the neurological event.

At block 756, the loop-recorded data is screened for abnormalities. After the ECG and respiratory signals are segmented, the different intervals of ECG and respiratory data are separately processed to determine metrics associated with those signals. The term metric is used interchangeably herein with the term indices. These metrics may assist in detecting events or determining features or other activity reflected in those signals. Exemplary cardiac metrics that may be computed include indices of heart rate (HR) (i.e., mean, median, max, std. dev., etc.) or indications of abnormal heart activity such as an arrhythmia which are displayed in the physician programmer for each detected event. Exemplary respiratory metrics that may be computed include minute ventilation, respiration rate, apnea, or edema, which are displayed in the physician programmer for each detected event. Metrics from different segmented intervals or time periods of the cardiac or respiratory signal may be compared to one another. For example, to monitor changes in cardiovascular and pulmonary function that may arise from or cause seizures, percentage of change between indices/metrics may be calculated. For example, to indicate magnitude of change in heart rate from a baseline to seizure state, the percentage of change between the pre-ictal (baseline) and ictal (seizure) periods is computed/displayed.

% Chg. Detect Onset=(Ictal HR indices−Base HR indices)/Base HR indices

Comparison between the post-ictal and baseline periods is also performed to evaluate if and when a return to baseline is achieved.

% Chg. Detect End=(Post-Ictal HR indices=Base HR indices)/Base HR indices

During processing, the time at which the post-ictal heart rate returns to baseline, relative to the end of the ictal period, is identified. The physician may choose to increase the duration of the post-ictal period if, during detected seizures, the patient's HR indices do not consistently return to baseline levels.

At block 757, detection times for arrhythmic and respiratory anomalies are determined. The ECG and respiratory signals are further processed, via an arrhythmia/abnormality detection algorithm, to identify ECG and respiratory abnormalities (bradycardia, tachycardia, asystole, ST segment depression, QTc prolongation, apnea, edema, etc.). Such events may occur in different periods of data, and cross ictal boundaries (e.g., a tachy event may begin prior to seizure onset, and continue well after seizure termination, resulting in a detection that includes all intervals of data). Thus, during screening the entire ECG and respiration signals in the loop recording data is processed in a single step, without segmentation. The start and end times for each identified arrhythmia/abnormality in the loop recording data is stored and later retrieved for analysis.

The physician may further run a matching test (EEG detections versus ECG or respiratory detections) at block 758. The matching test is run to compare the EEG detections and ECG/respiratory detections in the loop recording data. The matching test reports whether each ECG/respiratory abnormality is coincident with (i.e., matched), or is temporally separated from, the detected seizure (i.e., unmatched). In the case of a match, the time difference between EEG detection onset and ECG/respiratory detection onset is computed.

At block 759, the matching test results are evaluated to determine if the seizure is associated with an arrhythmia or respiratory anomaly. At block 760, additional seizures are determined. If NO, block 761 reports results of ECG/respiratory screening procedures for each seizure. At block 760, if the result is YES the flow diagram returns to block 752.

ECG/respiratory post-processing may occur in the implantable device, after the loop recorded data has been stored to memory. Alternatively, the post-processing may occur on loop-recorded data transmitted to an external wearable device or physician programmer or other computer.

In another embodiment of cardiac signal segmentation it may be desirable to record the amount of time it takes a metric of the cardiac signal to return to some baseline metric after a change in the brain signal has been discovered. For example, the system may determine a first metric such as heart rate associated with a pre-event portion of the cardiac signal. The first metric is the baseline. The system then determines a second metric for the post-event portion and determines whether it meets predetermined criteria about its relationship to the first metric. The predetermined criteria may be any way of determining or estimating whether the second metric (e.g., heart rate after the seizure) has reached or is close enough to the first metric (e.g., the heart rate before the seizure). For example, the predetermined criteria may simply be to determine whether the second metric equals the first metric. Another example of predetermined criteria may be a determination of whether the second metric is within a specified range of the first metric. In another exemplary embodiment, the predetermined criteria may evaluate whether successive metrics cross from being greater than the first metric to less than the first metric or vice versa. Once the value of the first metric is crossed the predetermined criteria are met. If the predetermined criteria are met, a second metric time is recorded or otherwise transmitted. The second metric time means some time value related to the amount of time from the at least one reference point to the occurrence of the second portion. For example, in one embodiment, the second metric time is the amount of time from the ending point of the seizure to the point in time when the heart rate has returned to its pre-ictal level. In this way the clinician may learn for each event the amount of time it took a particular metric of the patient's cardiac signal to return to baseline. In one embodiment the second portion may be a short or very short period of time such as, for example, 10 seconds, 5 seconds, 2 seconds, 1 second, or less than 1 second, or even on a sample by sample basis (e.g., determine a new metric each time there is a heart beat). By using a short second portion, successive portions may be evaluated until the metric associated with the portions meets the predetermined criteria.

Determination of Improvements in Neurological Event Detection Using Cardiac or Respiratory Input Another embodiment of the invention is a medical device system and method for determining whether cardiac or respiratory signals may be used to improve neurological event detection. This medical device system includes a brain monitoring element (e.g., lead 18, external electrode), a cardiac monitoring element (e.g., lead 16, sensor stub 20, sensor 14, integrated electrode 24, external electrode, etc.) or respiratory monitoring element (e.g., lead 16, sensor stub 20, sensor 14, integrated electrode 24, external electrode, etc.) and a processor (e.g., CPU 732 or any other processor or combination of processors implanted or external). This determination of whether cardiac or respiratory signals may be used to improve neurological event detection may be very beneficial to understanding a patient's condition and that in turn is helpful to determining appropriate treatment or prevention options. The medical device system may include the ability to determine relationships between brain and heart only, brain and respiratory only, or both. Once these relationships are better understood, they may be utilized to make decisions about enabling the use of cardiac signals or cardiac detections or respiratory signals or respiratory detections in the monitoring or treatment of the neurological disorder. Note that this medical device system and method may be performed by many different types of hardware embodiments including the example hardware embodiments provided in this specification as well as in an external computer or programmer. The executable instructions executed by a processor may be stored in any computer readable medium such as, for example only, RAM 730.

The determination of improvements in neurological event detection using cardiac or respiratory input includes determination of concordance between brain and cardiac signals or between brain and respiratory signals, determination of detection latency, and the false positive rate in the cardiac or respiratory signal relative to a neurological event detected in the brain signal.

An example of the usefulness of this determination is provided here. If it is determined that a patient with epilepsy has improvement in neurological event detection based on a cardiac signal it may be desirable to enable the use of a cardiac activity detection algorithm to trigger application of therapy to the brain. Another example of the benefit of concordance information is that a high concordance between brain and heart (including perhaps concordance with a particular type of cardiac event) for an individual with epilepsy, may mean that the patient is more susceptible to SUDEP. Perhaps steps can be taken such as use or implantation of a heart assist device such as a pacemaker or defibrillator for this patient to reduce the likelihood of death. There are of course many other examples of situations that may be discovered by operation of this concordance system and method that result in better health care.

The medical device system with concordance capability may include a brain monitoring element 18 (e.g., EEG lead with one or more electrodes) for sensing activity of the brain and outputting a brain signal, and a cardiac or respiratory monitoring element 14 (e.g., electrodes or other sensors) or both, for sensing a cardiac or respiratory activity and outputting a cardiac or respiratory signal, and a processor. The processor is configured to receive the brain signal and one or more of the cardiac and respiratory signals and to compare the brain signal and one of the cardiac or respiratory signals to each other.

Comparison of the brain and cardiac signals to each other may take many different forms. In one embodiment, the processor is configured to obtain information identifying one or more neurological events in the brain signal, and to also obtain information identifying one or more cardiac events in the cardiac signal. "Obtain" means 1) automatically generating the information by executing an algorithm that evaluates the signal, or 2) receiving the information from a user such as a physician reviewing the brain and cardiac signals (this second aspect of obtain is hereinafter referred to as "manual identification of events"). The algorithm or physician may create or generate various features of the neurological event such as a determination of when the event begins and ends and hence a duration of the event. For example automatic generation of the information may be performed by a seizure detection algorithm such as described in US published application 2004/0138536 "Clustering of Recorded Patient Neurological Activity to Determine Length of a Neurological Event" to Frei, et al. Likewise in the case of a cardiac signal, any algorithm that evaluates a cardiac signal and outputs information about cardiac activity or abnormalities would be an automatic generation of the information. Some examples are presented above in the discussion of the core monitor. An example of a manual identification of an event includes a physician indicating to a physician programmer the temporal location of a neurological event and also indicating the temporal location of cardiac or respiratory events. This temporal location of an event may include marking of the beginning and end of the event.

In the case of manual identification of an event, the medical device system may include a user interface (for example, on a programmer or computer), for display of the brain, cardiac and respiration signals. The user, such as a physician, may mark events on the programmer. For example, the physician could mark the location by clicking a cursor over the location on the monitor. In another example, the physician could mark a location with a stylus on a touch sensitive screen. The physician markings may include marks that indicate the beginning and the end of an event.

In a more specific embodiment, the comparison of the brain signal to the cardiac or respiration signal includes for each neurological event, determining whether the neurological event is within a specified time period of one of the one or more cardiac or respiratory events, and for each of the one or more cardiac or respiratory events determining whether the cardiac or respiratory event is within a specified time period of one of the one or more neurological events. Two events are "within a specified time period" of each other if the two events are overlapping in time or the amount of time between two reference points of the two events is less than a time period that is previously determined and set in the device or that has been programmed or may be programmed into the device. Reference points of an event are some measure or indication of the temporal position of the event. For example, the two reference points may be the end of the first of the events to end and the beginning of the other event. Other reference points may be used such as, but not limited to, the midpoints of each of the events. An example of a specified time period that could be programmed into the device is 10 seconds. So in this example, the neurological event and the cardiac event would be within the specified time period of each other if a chosen reference point for the cardiac event (e.g., end of the cardiac event) was within 10 seconds of a chosen reference point (e.g., beginning of the neurological event) for the neurological event.

The comparison of brain signal to cardiac signal may include the following: determining the number of neurological events that are matched with a cardiac event (i.e., within a specified time period of a cardiac event); determining the number of neurological events that are matched with a cardiac event (i.e., not within the specified time period of a cardiac event); and determining the number of cardiac events that are not within the specified time period of a neurological event (the false positive rate in the ECG signal). The same steps may be applied in the case of comparison of a brain signal to a respiratory signal.

Furthermore for matched events (events that are within the specified time period of each other), the processor may determine the temporal relationship of the neurological event and the matched cardiac event or between the neurological event and the matched respiratory event. Because matched events may overlap or they may not overlap, the temporal relationship may be defined or described in many different ways. One embodiment of determining the temporal relationship is determining the temporal order (which event is first to occur) of the matched events. In order to determine the temporal order between two events, a reference point must be determined. As mentioned earlier the reference point may be the end, start or midpoint of an event, or the reference point may be computed in some other way. In general a reference point indicates some temporal information about the event. The reference points may then be compared to determine which occurred first. The event associated with the first to occur reference point is then the first to occur event.

In another embodiment of comparing the brain signal to a cardiac or respiratory signal, the processor is configured to compute a rate of concordance between the neurological events and the cardiac or respiratory events. In this embodiment, the processor is configured to categorize the neurological event as cardiac matched when there is a cardiac event within a specified time period of the neurological event. The processor computes the rate of concordance between the neurological events and the cardiac events based on the number of cardiac matched events and the number of neurological events. For example, the processor may compute the rate of concordance by calculating the number of cardiac matched events divided by the number of neurological events. The more matches the greater the concordance.

In another embodiment the processor is further configured to perform the following: dividing the neurological event into at least two segments (portions); and assigning the cardiac event to one or more of the segments according to when the cardiac event occurred relative to the segments. For example, if the neurological event is a seizure, then there may be three segments: a pre-ictal segment, an ictal segment, and a post ictal segment. Various methods may be used to assign a cardiac event to one of these segments. For example, an algorithm executed by the processor (e.g., any of the processors of the many hardware embodiments in this application such as CPU 732, or a processor in a programmer or other computer external to the body) may determine when the cardiac event started relative to the three segments and assign the cardiac event to the segment in which it started. Of course other methods, more complex or simple may be used to make this assignment.

The ECG algorithm may be automatically enabled/disabled for use in monitoring or treatment (as described herein below) if concordance, detection latency and false positive rates meet selected and programmable criteria, indicating an improvement in neurological event detection performance. Alternatively, the patient's clinician may choose to review matching results and manually enable/disable the ECG detector based on information provided. For example, detection of a cardiac event may result in turning a neurostimulator or drug delivery device on to prevent the onset of a seizure. Alternatively, detection of a cardiac event may result in modification of therapy parameters. In another alternative, the ECG detector may be enabled for purposes of recording ECG, EEG or some other data.

In the embodiment that includes therapeutic output, the medical device system further includes a neurological therapy delivery module configured to provide a therapeutic output to treat a neurological disorder when the cardiac event detection algorithm detects a cardiac event. A neurological therapy delivery module may be any module capable of delivery a therapy to the patient to treat a neurological disorder. For example, but not limited to, a neurological therapy delivery module may be an electrical stimulator (e.g., stimulator 729), drug delivery device, therapeutic patch, brain cooling module.

Depending on the individual patient, and depending on the particular neurological disorder of concern, there may be different levels of concordance between different types of cardiac events and the neurological events. Therefore, in another embodiment, the processor is further configured to obtain information categorizing each cardiac event as one or more of two or more types of cardiac events. Types of cardiac events are known by different signals or aspects of signals coming from the heart. Examples of different types of cardiac events include: tachyrhythmia, ST segment elevation, bradycardia, asystole. In this embodiment, the processor may then determine concordance between each type of cardiac event or subset of cardiac events and neurological events. One embodiment of such determination is a processor configured to categorize each neurological event as first type cardiac matched when there is a first type cardiac event within a specified time period of the neurological event. The processor further categorizes the neurological event as second type cardiac matched when there is a second type cardiac event within a specified time period of the neurological event. The processor further computes a first rate of concordance between the neurological events and the first type cardiac events based on the number of first type cardiac matched events and the number of neurological events. The processor also computes a second rate of concordance between the neurological events and the second type cardiac events based on the number of second type cardiac matched events and the number of neurological events. This computation of rate of concordance may be performed as many times as there are types of cardiac events. The categorization of events as well as the various computed rates of concordance may be stored in memory.

In the embodiment allowing for computation of specific type of cardiac event rates of concordance, the medical device system may further include the capability to enable the use of detection of a particular type of cardiac event to affect the provision of therapy to the patient for the neurological disorder. For example, if it is determined that a high rate of concordance exists between tachyarrythmia and seizure, the enablement of cardiac detection for affecting seizure therapy may be limited to the detection of tachyarrythmia. In this case the seizure therapy will not be affected by other types of cardiac events.

It is noted that the medical device system may be external to the patient's body, implanted or some combination. The processor itself may be either external or implanted. For example, the processor may be in a handheld unit such as a programmer, or the processor could be in a general purpose computer.

The various processor operations described above may be embodied in executable instructions and stored in a computer readable medium. The processor then operates to perform the various steps via execution of these instructions. At one level, the executable instructions cause the processor to receive a brain signal from a brain monitoring element, receive a cardiac signal from a hear monitoring element, and compare the brain signal to the cardiac signal.

As described above, in a full monitor device for epilepsy, EEG, respiratory and cardiac (ECG) physiologic signals are simultaneously monitored and processed by different algorithms. A seizure-detection algorithm detects seizure activity in the EEG signals. A second algorithm detects heart-rate changes, ECG abnormalities, or unique waveform patterns in the ECG signals, which may or may not be coincident with seizures. Additionally, a third algorithm detects minute ventilation, respiration rate and apnea, which also may or may not be coincident with seizures.

By default, the EEG is considered a 'primary signal'—detections from this signal are used to represent seizure. The ECG and respiratory signals are 'secondary signals'—it is not initially known whether events detected in these two signals are useful for seizure detection. In a treatment setting, the patient's clinician considers the stored signals and data to determine if processing the ECG and respiratory signals provides added benefit in improving detection performance.

To make this determination, the patient is monitored until a sufficient number of detections in one or both of the data streams are observed (number of required events is programmable). Events detected in the EEG data stream may be classified by the user, via the programmer interface, to indicate whether they are clinical seizures (TP-C), sub-clinical seizures (TP-N), or false positive detections (FP). Likewise, events detected in the ECG and respiratory signals may be classified to indicate type of abnormality detected.

The concordance between the EEG seizure detections and ECG and respiratory signals is then evaluated. This is accomplished in one of two ways:

The relation between the EEG and ECG detections is initially unknown. Determination of the relationship between EEG and ECG may be performed with post processing or in real time.

In the post processing embodiment, automated matching tests are performed to identify the temporal relationship of detections in the different data streams. The matching tests identify the number of EEG detections that are within a specified time period with ECG or respiratory abnormalities (EEG-ECG Match or EEG-Respiratory Match, see 864 and 868 FIG. 38), and those that are not (EEG detect-ECG Normal or EEG detect-Respiratory Normal). For matched detections, the time difference between EEG detection onset and ECG or respiratory detection onset is computed (detection latency). The number of detected events in the ECG or respiratory signals, independent of EEG triggered events, are also computed (ECG Un-matched or Respiratory Un-Matched, see 870 FIG. 38).

With the real time implementation, the device controls a flag set by the seizure-detection algorithm operating on EEG signals. The flag is a real-time indicator of the subject's seizure state (1=in EEG detection state; 0=out of EEG detection state). In real-time, the device monitors the co-occurrence of the EEG and ECG/respiratory detection states.

The following conditions are assessed:

Brain-Cardiac Match—The EEG event (e.g., seizure) is classified as matched with ECG event if the ECG detection state occurs during an EEG detection state or within a specified time period of an EEG detection state.

Brain-Respiratory Match—The EEG event (e.g., seizure) is classified as matched with respiratory event if the respiratory detection state occurs during an EEG detection state or within a specified time period of an EEG detection state.

Brain Detect-Cardiac Normal—The EEG event (e.g., seizure) is classified as matched with normal ECG if no ECG detection state occurs during an EEG detection state or within a specified time period of an EEG detection state.

Brain Detect-Respiratory Normal—The EEG event (e.g., seizure) is classified as matched with normal respiration if no respiratory detection state occurs during an EEG detection state or within a specified time period of the EEG detection state.

Cardiac Un-Matched—An ECG event is classified as unmatched to EEG event (e.g., seizure) if no EEG detection state occurs during the ECG detection state or within a specified time period of an ECG detection state.

Respiratory Un-Matched—A respiratory event is classified as unmatched to EEG event (e.g., seizure) if no EEG detection state occurs during the respiratory detection state or within a specified time period of the respiratory detection state.

After EEG-ECG or EEG-respiratory matching has been performed, the physician programmer indicates whether the following conditions are true: (1) a high rate of concordance between detections in the EEG and ECG data streams (or between the EEG and respiratory data streams); (2) earlier detection in the ECG signal (or respiratory signal) relative to neurological event onset as indicated in the EEG signal; and (3) a low rate of FP's in the ECG signal (or in the respiratory signal). If these conditions are all true, this may indicate that the ECG signal (or respiratory signal) provides value in neurological event detection (e.g., seizure detection).

Using this information, the physician may choose to activate the ECG algorithm or activate the respiration algorithm—that is, enable it as a primary signal for use in neurological event detection. Determination of whether to "add in" the ECG or respiratory signals (activate it in combination with the EEG signal) for seizure monitoring or treatment is based on satisfying one or more of the above stated conditions. This process can be automated by defining programmable threshold values for each of the stated conditions.

Note that ECG detection and respiratory detection may both be enabled or activated for neurological event detection if they both meet the conditions above.

The physician may decide not to enable the ECG/respiratory algorithms if the matching tests show no additional improvements in detection performance using the ECG or respiratory signals, or if specificity in the ECG/respiratory signals is low. In such cases, the physician may enable a mode of passive ECG recording, with the intended use of documenting cardiovascular changes during ictal periods in the EEG.

FIG. 40A shows a process 971 for determining whether to enable the cardiac or respiratory detection algorithms for neurological event detection. At block 974 the medical device system monitors a brain signal and, cardiac or respiratory signals. At block 975 detections in any of the 3 signals (brain, cardiac, respiratory) triggers loop recording. Determination of the bounds of the neurological, cardiac and respiratory events may be performed in various ways. In one embodiment this determination of the bounds of events may be performed by a physician. In another embodiment, such determination of the bounds of the events may be performed by detection algorithms executed by a processor. Block 991 represents this choice between physician marked events and algorithm marked events. In the physician marking embodiment, the loop recording stored data must be uplinked to an external device such as a programmer or other computer. Upon uplinking the loop recording stored data, the physician may score the onset, offset or other reference points in the brain signal at block 976. The physician may also classify the events as related or not to the particular neurological event being targeted. A matching test (brain detections versus cardiac or respiratory detections) is executed at block 977. The brain inputs to the matching test may be either physician markings (e.g., onset, offset of neurological event) or the automated scores from the neurological event detection algorithm. The matching test results from block 977 result in a summary of comparisons made between the brain and cardiac detections (or between the brain and respiratory detections). At block 978 the matching test results are evaluated. The evaluation at block 978 includes blocks 979, 980 and 981 (i.e., blocks 979, 980 and 981 are components of block 978. At block 979 concordance between brain and cardiac/respiratory detections is determined. At block 980 a cardiac or respiratory false positive rate (relative to the neurological signal) is evaluated using the cardiac unmatched events or the respiratory unmatched events in the cardiac or respiratory signals. At block 981 cardiac/respiratory latency is evaluated for the matched detections. At block 982, neurological event detection improvement using cardiac or respiration signals is considered based upon the above determinations. If use of cardiac signals or respiratory signals does not improve neurological event detection ("NO" condition), then the physician or other user may maintain or disable the cardiac event detection algorithm monitoring at block 983. If at block 982 the result is YES, the cardiac or respiratory signal is activated for neurological event monitoring or treatment.

Process 871 in FIG. 40B is one specific embodiment of process 971 in FIG. 40A. Process 871 is a process for determining whether to enable the ECG or respiratory detection algorithms for seizure detection. At block 874 the full monitor monitors EEG and ECG or respiratory signals. At block 875 detections in any of the 3 signals (EEG, ECG or respiratory) triggers loop recording. Determination of the bounds of the seizure, ECG and respiratory events may be performed in various ways. In one embodiment this determination of the bounds of a seizure may be performed by a physician. In another embodiment, such determination of the bounds of the events may be performed by detection algorithms executed by a processor. Block 891 represents this choice between physician marked events and algorithm marked events. In the physician marking embodiment, the loop recording stored data must be uplinked to an external device such as a programmer or other computer. Upon uplinking the loop recording stored data, the physician may score the onset, offset or other reference points in the EEG signal at block 876. The physician may also classify the events as seizure related or not. A matching test (EEG detections versus ECG or respiratory detections) is executed at block 877. The EEG inputs to the matching test may be either physician scores (e.g., onset, offset of seizure) or the automated scores from the neurological event detection algorithm. The matching test results from block 877 result in a summary of comparisons made between the EEG and ECG detections (or between the EEG and respiratory detections). At block 878 the matching test results are evaluated. The evaluation at block 878 includes blocks 879, 880 and 881 (i.e., blocks 879, 880 and 881 are components of block 878. At block 879 concordance between EEG and ECG/respiratory detections is determined. At block 880 an ECG false positive rate (relative to the neurological signal) is evaluated using the unmatched events in the ECG or respiratory signals. At block 881 ECG/respiratory latency is evaluated for the matched detections. At block 882, seizure detection improvement using ECG or respiration signals is considered based upon the above determinations. If use of ECG signals or respiratory signals does not improve seizure detection ("NO" condition), then the physician or other user may maintain or disable the ECG algorithm monitoring at block 883. The monitor begins monitoring or treatment at block 885. If at block 882 the result is YES, the ECG or respiratory signal is activated for seizure monitoring.

EEG-ECG/Respiration Event Detection Signal Matching

A matching test in accordance with embodiments of the invention compares the relative timing of events detected from different physiological signals obtained from a patient. The methods described may be implemented in either a physician programmer or in a monitoring device, and may be used, for example, to determine the suitability of enabling one type of event detection signal to facilitate detection of another type of event. For example, based on the results of the matching test, it may be determined that the detection of certain cardiac events (and/or respiratory events) may be useful in detecting, confirming, and/or predicting neurological events. In the discussion that follows, the examples and drawings make comparisons between cardiac and neurological event detection signals, for example, to determine whether a cardiac event detection signal may be enabled to facilitate detection of neurological events. Other similar types of comparisons may also be made (e.g., to determine whether a respiratory event detection signal may facilitate detection of cardiac events, or whether a neurological event detection signal may facilitate detection of respiratory events, etc.).

An event detection signal may be a signal that indicates the timing of certain events, such as the start and end times of a neurological event, for example. As used in the examples that follow, a neurological event detection signal may be a signal that indicates the start times and end times of neurological events, and a cardiac event detection signal may be a signal that indicates the beginning times and termination times of cardiac events. An event detection signal may be the output of a detection algorithm that operates, for example, on EEG/ECoG signals (e.g., in the case of neurological signals), on ECG signals (e.g., in the case of cardiac signals), and/or on signals related to breathing (e.g., in the case of respiratory signals). A cardiac event detection signal may, for example, indicate the occurrence of any of a number of different types of cardiac abnormalities, including heart rate changes, signal morphology changes, etc. It may be determined from the matching test that only a certain type (or only a few types) of cardiac event (e.g., the occurrence of PVCs, or a sudden increase in heart rate) may be useful to improve or augment neurological event detection (and in some cases, to predict neurological events), but that other types of cardiac events do not have a similar relationship. Thus, a cardiac event detection signal can be a signal that includes multiple types of cardiac events, or it may be particularized to a specific type of cardiac event.

FIG. 65 shows a montage of signals from a patient, including an EEG signal, an ECG signal, a neurological event detection signal, and a cardiac event detection signal. As shown in FIG. 65, the neurological event detection signal shows a seizure event occurring (Seizure #1), corresponding to a portion of the EEG signal enclosed by a rectangular box. Similarly, the cardiac event detection signal shows a detected cardiac event corresponding to a portion of the ECG signal enclosed by a rectangular box. In the particular example illustrated, the cardiac events being detected are of a particular type, namely, increases in heart rate, as shown by the faster ECG signal patterns enclosed by the rectangular boxes in FIG. 65. FIG. 65 also shows the occurrence of a detected cardiac event which is not matched with a neurological event (labeled "false positive" in FIG. 65). Similarly, FIG. 65 provides an example of a detected neurological event which is not matched with a cardiac event (labeled "false negative" in FIG. 65).

A matching test may analyze the timing relationships between detected neurological events and detected cardiac events, and categorize each event (or each matched pair of events) according to a series of defined rules. Exemplary matching test criteria and outcomes are presented in the table provided in FIG. 64. In its most simple form, events are classified as "matched events" when a detected neurological event is temporally related to one of the detected cardiac events. That is, a matched event may be determined to occur when the elapsed time between a reference point of a detected neurological event and a reference point of a detected cardiac event is less than some predetermined amount. The reference point for a given type of event can be defined in any number of ways. For example, the beginning time of a cardiac event and the start time of a neurological event may form the respective reference points for determining an elapsed time, or the elapsed time may be measured between the end time of a neurological event and the midpoint of a cardiac event (e.g., the midpoint may be half-way between the beginning and termination times of a cardiac event). Based on the choice of reference points selected, the elapsed time may then be measured and compared to a predetermined value to determine whether the events are matched.

Events that are unmatched may be further categorized, for example, unmatched cardiac events (e.g., cardiac events that are not temporally related to a neurological event) may be categorized as "false positives." Similarly, unmatched neurological events may be categorized as "false negatives." The choice of these terms may be somewhat arbitrary, and/or may be based on the assumption (in this example) that the neurological event detection signal would normally be the initial or primary way of identifying neurological events, and that a second signal, such as a cardiac event detection signal, would be considered a secondary signal being evaluated for potential use in detecting (or assisting in detecting) neurological events. Thus, a false negative in this context describes a situation where a neurological event, as indicated by the neurological event detection signal, is not temporally related to a cardiac event, as indicated by the cardiac event detection signal.

Events that are matched may be further categorized to provide additional information. For example, a matched event may comprise a detected cardiac event and a detected neurological event that are overlapping in time. An overlapping event may be defined to occur when, for example, the cardiac event has a beginning time that occurs before an end time of the matched neurological event, and the cardiac event has a termination time that occurs after a start time of the matched neurological event. Matched events that are non-overlapping would be events that do not meet the above criteria (e.g., some period of time elapses between the end of the first event and the beginning of the second event).

Overlapping and non-overlapping events may be further categorized according to the table of FIG. 64. A code representing the particular matching category or scenario may also be stored to facilitate further analysis. For example, in the case of a matched, overlapping event, the event may be further categorized into one of five possible matching scenarios, labeled with codes TP1 through TP5 in FIG. 64. In the case of a matched, non-overlapping event, the event may be further categorized into one of four possible matching scenarios, labeled with codes TP6 through TP9 in FIG. 64.

For overlapping events, the matching scenarios may be defined as follows:

TP1: Cardiac detections may be classified as "Equal-Equal" (e.g., the beginning time and termination time of the cardiac event are roughly equal to the start time and end time of the neurological event) if: (i) the cardiac event has a beginning time that roughly equals a start time of the matched neurological event, and (ii) the cardiac event has a termination time that roughly equals an end time of the matched neurological event. The timing of two events may be considered to be "roughly equal" if they occur within a small time window (e.g., less than about one second) of each other, according to some embodiments of the invention.

TP2: Cardiac detections may be classified as "Out-In" (e.g., the beginning time of the cardiac event occurs before the neurological event begins, and the termination time of the cardiac event occurs during the neurological event) if: (i) the cardiac event has a beginning time that occurs before a start time of the matched neurological event, and (ii) the cardiac event has a termination time that occurs after the start time of the matched neurological event, and (iii) the cardiac event termination time occurs before an end time of the matched neurological event.

TP3: Cardiac detections may be classified as "Out-Out" (e.g., the beginning time of the cardiac event occurs before the neurological event, and the termination time of the cardiac event occurs after the neurological event) if: (i) the cardiac event has a beginning time that occurs before a start time of the matched neurological event, and (ii) the cardiac event has a termination time that occurs after an end time of the matched neurological event.

TP4: Cardiac detections may be classified as "In-Out" if: (i) the cardiac event has a beginning time that occurs after a start time of the matched neurological event, and (ii) the cardiac event beginning time occurs before an end time of the matched neurological event, and (iii) the cardiac event has a termination time that occurs after the end time of the matched neurological event TP5: Cardiac detections may be classified as "In-In" if: (i) the cardiac event has a beginning time that occurs after a start time of the matched neurological event, and (ii) the cardiac event beginning time occurs before an end time of the matched neurological event, and (iii) the cardiac event has a termination time that occurs after the start time of the matched neurological event, and (iv) the cardiac event termination time occurs before the end time of the matched neurological event.

For non-overlapping events, the matching scenarios may be defined as follows:

TP6: Cardiac detections may be classified as "Out-Equal" if: (i) the cardiac event has a beginning time that occurs before a start time of the matched neurological event, and (ii) the cardiac event has a termination time that is equal to the start time of the matched neurological event.

TP7: Cardiac detections may be classified as "Equal-Out" if: (i) the cardiac event has a beginning time that is equal to an end time of the matched neurological event, and (ii) the cardiac event has a termination time that occurs after the end time of the matched neurological event.

TP8: Cardiac detections may be classified as "Out-Out After Detect" if the cardiac event has a beginning time that occurs within a predetermined window of time after an end time of the matched neurological event. The predetermined window of time may be a programmable setting, and may include values of time such as 2 seconds, for example, for considering a cardiac event to be matched with a neurological event. Such an event classification could be useful, for example, in situations where it may be desirable to have confirmation of a neurological event. This event classification may also be useful in conjunction with other event classifications, for example, in determining a rate of concordance between detected cardiac events and detected neurological events, since the inclusion of cardiac events that are "Out-Out After Detect" will tend to increase the rate of concordance. Thus, varying the predetermined window for TP8 events could have an impact on computed rates of concordance.

TP9: Cardiac detections may be classified as "Out-Out Before Detect" if the cardiac event has a termination time that occurs within a predetermined window of time before a start time of the matched neurological event. The predetermined window of time may be a programmable setting, and may include values of time such as 1 minute, for example, for considering a cardiac event to be matched with a neurological event. Such matched events may be further identified as "precursors," since they may provide the ability to identify (e.g., predict) a neurological event before it actually occurs. Some embodiments of the invention may additionally provide the ability to use precursors to trigger therapy prophylactically, which can potentially prevent a subsequent neurological event (such as a seizure) from occurring, or lessen the severity of any subsequent neurological event that does occur.

Thus, in a device for monitoring neurological events, EEG and ECG signals are obtained and processed by different algorithms. For example, a neurological event detection algorithm detects events (e.g., seizure activity) in the EEG signals, while a cardiac event detection algorithm detects events in the ECG signals such as heart-rate changes, ECG abnormalities, and/or unique waveform patterns, which may or may not be coincident with neurological events.

By convention, the EEG signal may be considered a 'primary signal'—event detections from this signal may be used to represent "actual" or "true" neurological events, since they will form a standard to which other event detection signals will be compared. In the various scenarios illustrated in FIG. 64, the neurological event detection signal is graphically shown as the upper signal in each of the examples shown in the left-hand column, while the cardiac event detection signal is graphically shown as the lower signal in each of the examples. The neurological event detection signal is typically the output of a detection algorithm (e.g., a seizure detection algorithm) that is based on an EEG input signal, and is basically an "ON-OFF" type signal that indicates the start times (STARTN in FIG. 64) and end times (ENDN) of detected neurological events (such as seizures). The ECG signal may be considered a 'secondary signal'—it is not initially known whether events detected from the ECG signal may be useful to facilitate neurological event detection. One goal of certain embodiments of the invention is to determine if processing the ECG signal provides added benefit in improving neurological event detection performance.

In some embodiments, the patient may be monitored until a sufficient number of detections in one or both of the data streams are observed (the number of required events may be programmable). In some embodiments, neurological events detected in the EEG data stream may be further classified by the user, via a programmer interface, to indicate whether they are clinical seizures (TP-C), sub-clinical seizures (TP-N), or false positive detections (FP), for example. Likewise, cardiac events detected in the ECG signal may be further classified to indicate the type of cardiac abnormality. The further classification of detected neurological and cardiac events may, in some cases, provide additional information helpful in determining whether (and how) a cardiac event detection signal may improve neurological event detection. For example, removing false positives from the neurological event detection signal might improve the quality of the information obtained from comparing a cardiac event detection signal to the neurological event detection signal. Similarly, comparing certain types of detected cardiac events (e.g., a defined subset of the detected cardiac events) to the detected neurological events might provide an indication of which types of cardiac events facilitate neurological event detection (and which do not).

In some embodiments, a number of comparisons may be made (e.g., a number of concordance calculations may be performed) between event detection signals simply by restricting one or both signals to certain event types (e.g., calculating concordance between TP-C neurological events and atrial fibrillation cardiac events).

The concordance between the neurological and cardiac event detection signals may be evaluated in a number of ways. The concordance may be defined as the number of matched events divided by the number of neurological events detected over a given period of time.

The concordance may also be defined as the number of matched events divided by the total number of detected events (both cardiac and neurological events). Other ways of defining the concordance calculation may produce useful information, and such variants may be deemed to fall within the scope of the invention as claimed.

Other ways of defining concordance may be similarly established, for example, by using information obtained from the matching test. For example, rather than counting the number of matched events uniformly, a weighting factor could be applied to each matched event according to the category assigned from the matching test. A weighting factor of 1.0 might be applied for TP1 (Equal-Equal) matched events, for example. A weighting factor less than 1.0 (e.g., 0.5) may be applied for matched events in which the cardiac event lags behind the neurological event somewhat (e.g., TP4, TP7, and TP8), for example. A weighting factor greater than 1.0 (e.g., 2.0) may be applied for matched events in which the cardiac event precedes the neurological event somewhat (e.g., TP2, TP3, TP6, and TP9), for example. The weighting factors themselves could be programmable parameters, for example, and could be modified by a physician/operator for the particular needs of an individual patient. Thus, a concordance value calculated using weighting factors as described above could produce a result that accounts for the timing of the cardiac events relative to the matched neurological events.

In some embodiments, the matching test may be performed in a "post-processing" mode, typically by an external programmer system and/or computer. For example, neurological and cardiac event detection signals may be stored in an implantable device, and may be subsequently retrieved for analysis and post-processing by a programmer via a telemetry link, as is known in the art. The programmer and/or other computing equipment may include software instructions that can perform the matching test on the retrieved event detection signals, and may also have the ability to compute a rate of concordance, for example, according to certain embodiments of the invention.

In some embodiments, "real-time" performance of the matching test may be performed, for example, by an implantable medical device. A device according to certain embodiments of the invention may obtain a predefined minimum number of detected events (e.g., 10 detected neurological events) before performing the matching test on stored cardiac and neurological events. In some embodiments, the results of the matching test (including measured rates of concordance, false positive rates, etc.) may be stored in memory in the device and may be retrieved by a programming system for subsequent analysis. In some embodiments, the device may determine that, based upon the matching test results, the cardiac signal (and the associated cardiac event detection signal) should be enabled for detecting neurological events. In an embodiment of the invention, the device may be further adapted to deliver therapy to treat a neurological event in response to a detected cardiac event based upon the results of the matching test.

Certain embodiments of the invention may include an implantable device adapted to deliver therapy for treating cardiac events (e.g., pacing pulses to treat a bradycardia episode, or defibrillation shocks to treat ventricular fibrillation). In such an embodiment, it may be desirable to employ different cardiac event detection parameters and/or cardiac therapy parameters based upon real-time matching test results. For example, a detected high heart rate cardiac event that is not matched with a neurological event may warrant a certain type of cardiac therapy (e.g., anti-tachycardia pacing to treat ventricular tachycardia), whereas a comparable detected high heart rate that is matched with a neurological event may warrant either (i) a different type or level of cardiac therapy, or (ii) a different threshold for triggering cardiac therapy, or (iii) both. Examples of cardiac therapy outputs that can be varied include pacing rate, amplitude, and pulse width, and energy levels of defibrillation shocks. Examples of thresholds for cardiac detection parameters that can be varied include heart rate, change in heart rate, and number of PVCs.

After the matching test has been performed, the physician (via a programmer, for example) may indicate whether the following conditions are true: (1) a high rate of concordance between detections in the EEG and ECG data streams; (2) earlier detection in the ECG signal relative to the EEG signal; and (3) a low rate of false positives and/or false negatives in the ECG signal. If true, this may indicate that the ECG provides value in neurological event detection.

Using this information, the physician may choose to activate the ECG algorithm—that is, to enable the cardiac event detection signal for use in neurological event detection. Determination of whether to "add in" the ECG signal (e.g., to activate it in combination with the EEG signal) for neurological event monitoring and/or treatment may be based on satisfying one or more of the above stated conditions. This process can be automated by defining programmable threshold values for each of the stated conditions. The process is described in FIG. 66.

Alternatively, the physician could also compare matching test results run on the EEG signals only (Test 1) vs. the combined EEG+ECG signals (Test 2). This method may, for example, require a physician to manually mark the electrographic onset (EO) and the electrographic termination (ET) (e.g., using a programmer) for all neurological events identified by the physician during the monitoring period. This would form the "primary" signal against which the Test 1 and Test 2 signals would be compared (e.g., using the matching test). Using the physician-marked neurological event detection signal as the primary signal, detections from the single (Test 1) and combined (Test 2) data streams are separately run through the matching test. The programmer may display matching test results for the two signals, providing values for concordance, sensitivity and specificity, for example, for both the single and combined algorithms, which can be compared.

The physician may decide not to enable the ECG algorithm for detecting neurological events if, for example, the matching tests show no additional improvement in neurological event detection performance using the ECG, or if the specificity using the ECG signal and detection algorithm is low. In such cases, the physician may enable a mode of passive ECG recording, substantially as described in U.S. Published Patent Application 2006/0224067 (P0021630.00), with the intended use of documenting cardiovascular changes during ictal periods in the EEG.

Monitor+Treatment (Brain)

FIG. 41 is a block diagram of the electronic circuitry that makes up full Monitor/Brain Therapy device 300 (FIG. 11) in accordance with the presently disclosed alternative embodiment of the invention. As can be seen from FIG. 41, Monitor/Brian Therapy device 300 comprises a primary control circuit 720 that is described herein above in conjunction with FIG. 26. In addition the Monitor/Brain Therapy device 300 of FIG. 41 also includes an amplifier 725 to amplify and sense EEG signals from a cranially implanted lead (one embodiment of a brain monitoring element 18) and a therapy module for providing therapy to the brain. The therapy module may be a drug delivery pump or an electrical stimulator or a brain cooling mechanism or other components depending on the treatment modality. In the embodiment of FIG. 41, the therapy module is an output stimulator 729 for stimulation of the brain. The CPU 732, in conjunction with software program in RAM/ROM 730, integrates the information from the sensed cardiac, respiration and EEG signals, detects the onset of cerebral, cardiac or respiratory anomalies, provides preprogrammed stimulation therapy to the patient's brain via a brain lead that may be the same as monitoring element 18, formats and stores diagnostic data for later retrieval by the patient's clinician and, optionally, may warn or alert the patient, patient caregiver or remote monitoring location. See flow diagram and description as described below in association with FIG. 56.

FIG. 42 is a block diagram of the electronic circuitry that makes up full Monitor/Brain Therapy device 320 (FIG. 12A) in accordance with the presently disclosed alternative embodiment of the invention. As can be seen from FIG. 42, Monitor/Brain Therapy device 320 comprises a primary control circuit 720 and MV circuit 722 that are described herein above in conjunction with FIG. 28. In addition the Monitor/Brain Therapy device of FIG. 42 also includes an amplifier 725 to amplify and sense EEG signals from a cranially implanted monitoring element 18 and an output stimulator 729 to provide brain stimulation. The CPU 732, in conjunction with software program in RAM/ROM 730, integrates the information from the sensed cardiac, respiration and EEG signals, detects the onset of cerebral, cardiac or respiratory anomalies, provides preprogrammed stimulation therapy to the patient's brain via a lead that may be the same as brain monitoring element 18, formats and stores diagnostic data for later retrieval by the patient's clinician and, optionally, may warn or alert the patient, patient caregiver or remote monitoring location. See flow diagram and description as described below in association with FIG. 56.

FIG. 43 is a block diagram of the electronic circuitry that makes up full Monitor/Brain Therapy device 321 (FIG. 12B) in accordance with the presently disclosed alternative embodiment of the invention. As can be seen from FIG. 43, Monitor/Brain Therapy device 321 in combination with a cranially implanted Monitor/Brain Therapy unit 26 in a patient 10 includes a primary control circuit 720 and MV circuit 722 that are described herein above in conjunction with FIG. 28. A 2-way wireless telemetry communication link 30 connects the Monitor/Therapy unit 26 and Monitor/Brain Therapy unit 321 via antennas 736. The wireless communication link 30 may consist of an RF link (such as described in U.S. Pat. No. 5,683,432 "Adaptive Performance-Optimizing Communication System for Communicating with an Implantable Medical Device" to Goedeke, et al, an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke). Monitor/Brain Therapy unit 26 contains an amplifier 725 to amplify and sense EEG signals from a cranially implanted brain monitoring element 18 such as a lead and an output stimulator 729 for stimulation of the brain. Monitor 26 may be constructed as substantially described in US Publication No. 20040176817 "Modular implantable medical device" to Wahlstrand et al. or U.S. Pat. No. 5,782,891 "Implantable Ceramic Enclosure for Pacing, Neurological and Other Medical Applications in the Human Body" to Hassler, et al or U.S. Pat. No. 6,427,086 "Means and Method for the Intracranial Placement of a Neurostimulator" to Fischell. et al. EEG sensing is accomplished by the use of integrated electrodes in the housing of monitor 26 or, alternatively, by a brain monitoring element 18 such as a cranially implanted leads.

Specifically, CPU 732, in conjunction with software program in RAM/ROM 730, integrates the information from the sensed cardiac, respiration and EEG signals, detects the onset of cerebral, cardiac or respiratory anomalies, provides preprogrammed stimulation therapy to the patient's brain via a lead or other therapy delivery device (that could be the same as brain monitoring element 18), formats and stores diagnostic data for later retrieval by the patient's clinician and, optionally, may warn or alert the patient, patient caregiver or remote monitoring location. See flow diagram and description as described below in association with FIG. 56.

FIG. 44 is a block diagram of one embodiment of the electronic circuitry that makes up full Monitor/Brain Therapy device 340 with a brain monitoring element 18 (e.g., lead) and cardiac or respiratory monitoring element 14 such as sensor stub 20 (FIG. 13) in accordance with the presently disclosed alternative embodiment of the invention. As can be seen from FIG. 44, Monitor/Brain Therapy device 340 comprises a primary control circuit 720 and MV circuit 722 that were described herein above in conjunction with FIG. 28. In addition, the full Monitor/Brain Therapy device 340 of FIG. 44 also includes an amplifier 725 to amplify and sense EEG signals from a brain monitoring element 18 such as a cranially implanted lead. Additionally, the full Monitor/Brain Therapy device 340 of FIG. 44 also includes a stimulator 729 for providing stimulation to the brain through brain monitoring element 18 such as a cranially implanted lead. The CPU 732, in conjunction with a software program resident in RAM/ROM 730, integrates the information from the sensed cardiac, respiration and EEG signals, detects the onset of cerebral, cardiac or respiratory anomalies, provides preprogrammed stimulation therapy to the patient's brain via a therapeutic element such as brain monitoring element 18 which may be a lead, formats and stores diagnostic data for later retrieval by the patient's clinician and, optionally, may warn or alert the patient, patient caregiver or remote monitoring location. See flow diagram and description as described below in association with FIG. 56.

FIG. 45 is a block diagram of one embodiment of the electronic circuitry that makes up external patch 160/full Monitor/Brain Therapy device 360 with a brain monitoring element 18 that may be used for sensing and application of therapy (in the case of therapy being electrical stimulation) (FIG. 8) in accordance with the presently disclosed alternative embodiment of the invention. As can be seen from FIG. 45, Monitor/Brain Therapy device 360 comprises a primary control circuit 720 and external patch comprises a cardiac/MV (minute ventilation) circuit 160, the functions of which have been described in detail above in conjunction with the system of FIG. 28. Intrinsic cardiac signals are sensed by electrodes affixed to the patient's skin, amplified by amplifier 724, sent to primary control circuit 720 and processed by CPU 732 and software program resident in RAM/ROM 730. Cardiac anomalies are detected such as heart rate variability, QT variability, QT.sub.C, sinus arrest, and various arrhythmias such as sinus, atrial and ventricular tachycardias. Respiration sensing is accomplished by low pass filtering the sensed and amplified intrinsic cardiac signals as shown in FIG. 27 or, alternatively, by using the MV/Z measurement circuitry of external patch 160 as described above in connection with FIG. 28. Respiration anomalies (such as reduced or cessation of tidal volume and apnea) are evaluated and detected by CPU 732 and software resident in RAM/ROM 730.

The CPU 732, in conjunction with a software program resident in RAM/ROM 730, integrates the information from the sensed cardiac, respiration and EEG signals, detects the onset of cerebral, cardiac or respiratory anomalies, provides preprogrammed stimulation therapy to the patient's brain via lead 18, formats and stores diagnostic data for later retrieval by the patient's clinician and, optionally, may warn or alert the patient, patient caregiver or remote monitoring location. See flow diagram and description as described below in association with FIG. 56.

The circuitry and function of the device 340 shown in FIG. 44 and described herein above may also be used for the full Monitor/Brain Therapy device 380 with integrated electrode 24 brain lead 18 (FIG. 15). As described above in association with core Monitor 340, thoracic impedance via impedance/voltage converter as measured from the case of monitor 340 to the integrated electrode 24 using a sampling frequency of approximately 16 Hz as substantially described in U.S. Pat. No. 4,596,251 "Minute Ventilation Dependant Rate Responsive Pacer" to Plicchi, et al. The Monitor 380 of this alternative embodiment utilizes the same circuitry of Monitor 340 but connected to the integrated electrode 24 on brain lead 18 instead of the sensor stub of Monitor 340.

Upon detection of either/or a cardiac or respiration anomaly, CPU 732, under control of firmware resident in RAM/ROM 730, will initiate recording of the appropriate diagnostic information into RAM of RAM/ROM 730, provides preprogrammed stimulation therapy to the patient's brain via lead 18, formats and stores diagnostic data for later retrieval by the patient's clinician and, optionally, may warn or alert the patient, patient caregiver or remote monitoring location. See flow diagram and description as described below in association with FIG. 56.

FIG. 46 is a block diagram of the electronic circuitry that makes up full Monitor/Brain Therapy device 400 (FIG. 20) in accordance with the presently disclosed alternative embodiment of the invention. As can be seen from FIG. 46, Monitor/Brian Therapy device 400 comprises a primary control circuit 720 (sensing cardiac and respiration parameters) that is described herein above in conjunction with FIG. 26. In addition the Monitor/Brain Therapy device 400 connects via a 2-way wireless communication link 30 to a cranially implanted EEG sensor and brain stimulator 26. EEG sensor and brain stimulator 26 contains an amplifier 725 to amplify and sense EEG signals from a cranially implanted lead 18 and an output stimulator 729 for stimulation of the brain. The CPU 732, in conjunction with software program in RAM/ROM 730, integrates the information from the sensed cardiac, respiration and EEG signals, detects the onset of cerebral, cardiac or respiratory anomalies, provides preprogrammed stimulation therapy to the patient's brain via lead 18, formats and stores diagnostic data for later retrieval by the patient's clinician and, optionally, may warn or alert the patient, patient caregiver or remote monitoring location. See flow diagram and description as described below in association with FIG. 56.

FIG. 47 is a block diagram of the electronic circuitry that makes up full Monitor/Brain Therapy device 420 (FIG. 21) in accordance with the presently disclosed alternative embodiment of the invention. As can be seen from FIG. 47, Monitor/Brian Therapy device 420 comprises a primary control circuit 720 (sensing cardiac and respiration parameters) that is configured as an external patch affixed to a patient and whose function is described herein above in conjunction with FIG. 26. In addition, the Monitor/Brain Therapy device 420 comprises to a cranially implanted EEG sensor and brain stimulator 26 connected to the primary control circuit 720 via a 2-way wireless communication link 30. The wireless communication link 30 may consist of an RF link (such as described in U.S. Pat. No. 5,683,432 "Adaptive Performance-Optimizing Communication System for Communicating with an Implantable Medical Device" to Goedeke, et al.), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke). EEG sensor and brain stimulator 26 contains an amplifier 725 to amplify and sense EEG signals from a cranially implanted lead 18 and an output stimulator 729 for stimulation of the brain. The CPU 732, in conjunction with software program in RAM/ROM 730, integrates the information from the sensed cardiac, respiration and EEG signals, detects the onset of cerebral, cardiac or respiratory anomalies, provides preprogrammed stimulation therapy to the patient's brain via lead 18, formats and stores diagnostic data for later retrieval by the patient's clinician and, optionally, may warn or alert the patient, patient caregiver or remote monitoring location. See flow diagram and description as described below in association with FIG. 56.

Monitor+Treatment (Brain+Respiration)

FIG. 48 is a block diagram of the electronic circuitry that makes up full Monitor/Brain and Respiration Therapy device 440 (FIG. 16A) in accordance with the presently disclosed alternative embodiment of the invention. As can be seen from FIG. 48, Monitor/Brain and Respiration Therapy device 440 comprises a primary control circuit 720 and MV circuit 722 whose function was described herein above in conjunction with FIG. 28. In addition the Monitor/Brain and Respiration Therapy device of FIG. 48 also includes an amplifier 725 to amplify and sense EEG signals from a cranially implanted lead 18 and an output stimulator 729 to provide brain stimulation via cranially implanted lead 18 and phrenic nerve stimulation via respiration lead 28. The CPU 732, in conjunction with software program in RAM/ROM 730, integrates the information from the sensed cardiac, respiration and EEG signals, detects the onset of cerebral, cardiac or respiratory anomalies, provides preprogrammed stimulation therapy to the patient's brain via lead 18 and stimulation of the patient's phrenic nerve via respiration lead 28, formats and stores diagnostic data for later retrieval by the patient's clinician and, optionally, may warn or alert the patient, patient caregiver or remote monitoring location. Optionally, lead 28 may connect to the diaphragm to provide direct diaphragmatic stimulation. See flow diagram and description as described below in association with FIG. 56.

FIG. 49 is a block diagram of the electronic circuitry that makes up full Monitor/Brain and Respiration Therapy device 441 (FIG. 16B) in accordance with the presently disclosed alternative embodiment of the invention. As can be seen from FIG. 49, Monitor/Brain and Respiration Therapy device 441 in combination with a cranially implanted Monitor/Brain Therapy unit 26 in a patient 10 includes a primary control circuit 720 and MV circuit 722 that are described herein above in conjunction with FIG. 28. A 2-way wireless telemetry communication link 30 connects the Monitor/Therapy unit 26 and Monitor/Brain and Respiration Therapy unit 441 via antennas 736. The wireless communication link 30 may consist of an RF link (such as described in U.S. Pat. No. 5,683,432 "Adaptive Performance-Optimizing Communication System for Communicating with an Implantable Medical Device" to Goedeke, et al), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke). Monitor/Brain Therapy unit 26 contains an amplifier 725 to amplify and sense EEG signals from a cranially implanted lead 18 and an output stimulator 729 for stimulation of the brain. Monitor 26 may be constructed as substantially described in US Publication No. 20040176817 "Modular implantable medical device" to Wahlstrand et al. or U.S. Pat. No. 5,782,891 "Implantable Ceramic Enclosure for Pacing, Neurological and Other Medical Applications in the Human Body" to Hassler, et al or U.S. Pat. No. 6,427,086 "Means and Method for the Intracranial Placement of a Neurostimulator" to Fischell. et al. EEG sensing is accomplished by the use of integrated electrodes in the housing of monitor 26 or, alternatively, by cranially implanted leads 18.

Specifically, CPU 732, in conjunction with software program in RAM/ROM 730, integrates the information from the sensed cardiac, respiration and EEG signals, detects the onset of cerebral, cardiac or respiratory anomalies, provides preprogrammed stimulation therapy to the patient's brain via lead 18 and to the phrenic nerve via respiration lead 28, formats and stores diagnostic data for later retrieval by the patient's clinician and, optionally, may warn or alert the patient, patient caregiver or remote monitoring location. Optionally, lead 28 may connect to the diaphragm to provide direct diaphragmatic stimulation. See flow diagram and description as described below in association with FIG. 56.

FIG. 50 is a block diagram of the electronic circuitry that makes up full Monitor/Brain and Respiration Therapy device 460 with a brain lead 18, phrenic nerve lead 28 and sensor stub 20 (FIG. 17) in accordance with the presently disclosed alternative embodiment of the invention. As can be seen from FIG. 50, Monitor/Brain and Respiration Therapy device 460 comprises a primary control circuit 720 and MV circuit 722 whose function was described herein above in conjunction with FIG. 28. In addition, the full Monitor/Brain and Respiration Therapy device 460 of FIG. 50 also includes an amplifier 725 to amplify and sense EEG signals from a cranially implanted lead 18. Additionally, the full Monitor/Brain Therapy device 340 of FIG. 44 also includes a stimulator 729 for providing stimulation to the brain through cranially implanted lead 18 and phrenic nerve stimulation via respiration lead 28. The CPU 732, in conjunction with a software program resident in RAM/ROM 730, integrates the information from the sensed cardiac, respiration and EEG signals, detects the onset of cerebral, cardiac or respiratory anomalies, provides preprogrammed stimulation therapy to the patient's brain via lead 18 and stimulation of the patient's phrenic nerve via respiration lead 28, formats and stores diagnostic data for later retrieval by the patient's clinician and, optionally, may warn or alert the patient, patient caregiver or remote monitoring location. See flow diagram and description as described below in association with FIG. 56.

The circuitry and function of the device 460 shown in FIG. 50 and described herein above may also be used for the full Monitor/Brain and Respiration Therapy device 480 with integrated electrode 24 brain lead 18 and phrenic nerve lead 28 (FIG. 18). As described above in association with Monitor/Brain and Respiration Therapy device 460, thoracic impedance via impedance/voltage converter as measured from the case of monitor 480 to the integrated electrode 24 using a sampling frequency of approximately 16 Hz as substantially described in U.S. Pat. No. 4,596,251 "Minute Ventilation Dependant Rate Responsive Pacer" to Plicchi, et al. The Monitor/Brain and Respiration Therapy device 480 of this alternative embodiment utilizes the same circuitry of Monitor/Brain and Respiration Therapy device 460 but connected to the integrated electrode 24 on brain lead 18 instead of the sensor stub 20 of Monitor/Brain and Respiration Therapy device 340.

Upon detection of either/or a cardiac or respiration anomaly, CPU 732, under control of firmware resident in RAM/ROM 730, will initiate recording of the appropriate diagnostic information into RAM of RAM/ROM 730, provides preprogrammed stimulation therapy to the patient's brain via lead 18 and stimulation of the patient's phrenic nerve via respiration lead 28, formats and stores diagnostic data for later retrieval by the patient's clinician and, optionally, may warn or alert the patient, patient caregiver or remote monitoring location. See flow diagram and description as described below in association with FIG. 56.

The circuitry and function of the device 460 shown in FIG. 50 and described herein above may also be used for the full Monitor/Brain and Respiration Therapy device 500 with brain lead 18 and integrated electrode 24 phrenic nerve lead 28 (FIG. 19). As described above in association with Monitor/Brain and Respiration Therapy device 460, thoracic impedance via impedance/voltage converter as measured from the case of monitor 500 to the integrated electrode 24 using a sampling frequency of approximately 16 Hz as substantially described in U.S. Pat. No. 4,596,251 "Minute Ventilation Dependant Rate Responsive Pacer" to Plicchi, et al. The Monitor/Brain and Respiration Therapy device 500 of this alternative embodiment utilizes the same circuitry of Monitor/Brain and Respiration Therapy device 460 but connected to the integrated electrode 24 on phrenic nerve lead 28 instead of the sensor stub 20 of Monitor/Brain and Respiration Therapy device 340.

Upon detection of either/or a cardiac or respiration anomaly, CPU 732, under control of firmware resident in RAM/ROM 730, will initiate recording of the appropriate diagnostic information into RAM of RAM/ROM 730, provides preprogrammed stimulation therapy to the patient's brain via lead 18 and stimulation of the patient's phrenic nerve via respiration lead 28, formats and stores diagnostic data for later retrieval by the patient's clinician and, optionally, may warn or alert the patient, patient caregiver or remote monitoring location. See flow diagram and description as described below in association with FIG. 56.

Monitor+Treatment (Brain+Cardiac)

FIG. 51 is a block diagram of the electronic circuitry that makes up full Monitor/Brain and Cardiac Therapy device 520 (FIG. 24A) in accordance with the presently disclosed alternative embodiment of the invention. As can be seen from FIG. 51, Monitor/Brain and Cardiac Therapy device 520 comprises a primary control circuit 720 and MV circuit 722 whose function is described herein above in conjunction with FIG. 28 and U.S. Pat. No. 5,271,395 "Method and Apparatus for Rate Responsive Cardiac Pacing" to Wahlstrand et al. In addition, the Monitor/Brain and Cardiac Therapy device of FIG. 51 also includes an amplifier 725 to amplify and sense EEG signals from a cranially implanted lead 18 and an output stimulator 729 to provide brain stimulation. The CPU 732, in conjunction with software program in RAM/ROM 730, integrates the information from the sensed cardiac, respiration and EEG signals, detects the onset of cerebral, cardiac or respiratory anomalies, provides preprogrammed stimulation therapy to the patient's brain via lead 18 and stimulation to the patient's heart via cardiac lead(s) 16, formats and stores diagnostic data for later retrieval by the patient's clinician and, optionally, may warn or alert the patient, patient caregiver or remote monitoring location. See flow diagram and description as described below in association with FIG. 54.

FIG. 52 is a block diagram of the electronic circuitry that makes up full Monitor/Brain and Cardiac Therapy device 521 (FIG. 24B) in accordance with the presently disclosed alternative embodiment of the invention. As can be seen from FIG. 52, Monitor/Brain and Cardiac Therapy device 521 in combination with a cranially implanted Monitor/Brain Therapy unit 26 in a patient 10 includes a primary control circuit 720 and MV circuit 722 that are described herein above in conjunction with FIG. 28. A 2-way wireless telemetry communication link 30 connects the Monitor/Therapy unit 26 and Monitor/Brain and Cardiac Therapy unit 521 via antennas 736. The wireless communication link 30 may consist of an RF link (such as described in U.S. Pat. No. 5,683,432 "Adaptive Performance-Optimizing Communication System for Communicating with an Implantable Medical Device" to Goedeke, et al), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke). Monitor/Brain Therapy unit 26 contains an amplifier 725 to amplify and sense EEG signals from a cranially implanted lead 18 and an output stimulator 729 for stimulation of the brain. Monitor 26 may be constructed as substantially described in US Publication No. 20040176817 "Modular implantable medical device" to Wahlstrand et al. or U.S. Pat. No. 5,782,891 "Implantable Ceramic Enclosure for Pacing, Neurological and Other Medical Applications in the Human Body" to Hassler, et al or U.S. Pat. No. 6,427,086 "Means and Method for the Intracranial Placement of a Neurostimulator" to Fischell. et al. EEG sensing is accomplished by the use of integrated electrodes in the housing of monitor 26 or, alternatively, by cranially implanted leads 18.

Specifically, CPU 732, in conjunction with software program in RAM/ROM 730, integrates the information from the sensed cardiac, respiration and EEG signals, detects the onset of cerebral, cardiac or respiratory anomalies, provides preprogrammed stimulation therapy to the patient's brain via lead 18 and cardiac stimulation via cardiac leads 16, formats and stores diagnostic data for later retrieval by the patient's clinician and, optionally, may warn or alert the patient, patient caregiver or remote monitoring location. See flow diagram and description as described below in association with FIG. 56.

Alternatively, the device as described above in connection to the Monitor and Treatment (Brain and Cardiac) system of FIG. 52 may include a pacemaker/cardioverter/defibrillator (PCD) to enable the termination of cardiac arrhythmias during, or prior to, neurological events. The PCD may be of the type as substantially described in U.S. Pat. No. 5,545,186 "Prioritized Rule Based Method and Apparatus for Diagnosis and Treatment of Arrhythmias" to Olson; U.S. Pat. No. 5,354, 316 "Method and Apparatus for Detection and Treatment of Tachycardia and fibrillation" to Kiemel or U.S. Pat. No. 5,314,430 "Atrial Defibrillator Employing Transvenous and Subcutaneous Electrodes and Method of Use" to Bardy. In one embodiment of the present invention, the PCD arrhythmia detection circuitry/algorithms are enabled upon the sensing of the onset or impending onset of a seizure. Upon seizure termination, the arrhythmia detection circuitry/algorithms are turned off.

FIG. 53 is a block diagram of the electronic circuitry that makes up full Monitor/Brain and Cardiac Therapy device 540 (FIG. 22) in accordance with the presently disclosed alternative embodiment of the invention. The system as shown in FIG. 53 is used for patients temporarily at risk of sudden death, for example, while the patient's physician is trying different epileptic drugs and titrating dosages to eliminate/minimize seizures or their severity. As can be seen from FIG. 53, Monitor/Brain and Cardiac Therapy device 540 comprises patient worn vest defibrillator 34 containing primary control circuit 720 whose function is described herein above in conjunction with FIG. 26 and in more detail in U.S. Pat. No. 6,280,461 "Patient-Worn Energy Delivery Apparatus" to Glegyak, et. In addition the Monitor/Brain and Cardiac Therapy device connects via a 2-way wireless communication link 30 to a cranially implanted brain stimulator 540. The wireless communication link 30 may consist of an RF link (such as described in U.S. Pat. No. 5,683,432 "Adaptive Performance-Optimizing Communication System for Communicating with an Implantable Medical Device" to Goedeke, et al), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke). EEG sensor and brain stimulator 540 contains an amplifier 725 to amplify and sense EEG signals from a cranially implanted lead 18 and an output stimulator 729. The CPU 732, in conjunction with software program in RAM/ROM 730, integrates the information from the sensed cardiac, respiration and EEG signals, detects the onset of cerebral, cardiac or respiratory anomalies, provides preprogrammed stimulation therapy to the patient's brain via lead 18 and defibrillation therapy via patient worn vest 34, formats and stores diagnostic data for later retrieval by the patient's clinician and, optionally, may warn or alert the patient, patient caregiver or remote monitoring location. See flow diagram and description as described below in association with FIG. 56.

The circuitry and function of the device 540 shown in FIG. 53 and described herein above may also be used for the full Monitor/Brain and Cardiac Therapy device 560 with a cranially implanted stimulator in 2-way communication with an leadless subcutaneous implantable defibrillator 36 (ie, "lifeboat", FIG. 23). The system described in connection with this embodiment is used for patients temporarily at risk of sudden death, for example, while the patient's physician is trying different epileptic drugs and titrating dosages to eliminate/ minimize seizures or their severity. As described above in conjunction with FIG. 53, Monitor/Brian and Cardiac Therapy device 560 comprises a leadless defibrillator 36 containing primary control circuit 720 whose function is described herein above in conjunction with FIG. 26 and in more detail in U.S. Pat. No. 6,647,292 "Unitary Subcutaneous only Implantable Cardioverter-Defibrillator and Optional Pacer" to Bardy.

The Monitor/Brain and Cardiac Therapy device connects via a 2-way wireless communication link 30 to a cranially implanted brain stimulator 560. The wireless communication link 30 may consist of an RF link (such as described in U.S. Pat. No. 5,683,432 "Adaptive Performance-Optimizing Communication System for Communicating with an Implantable Medical Device" to Goedeke, et al), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke). EEG sensor and brain stimulator 560 contains an amplifier 725 to amplify and sense EEG signals from a cranially implanted lead 18 and an output stimulator 729. The CPU 732, in conjunction with software program in RAM/ROM 730, integrates the information from the sensed cardiac, respiration and EEG signals, detects the onset of cerebral, cardiac or respiratory anomalies, provides preprogrammed stimulation therapy to the patient's brain via lead 18 and defibrillation therapy via implanted defibrillator 36, formats and stores diagnostic data for later retrieval by the patient's clinician and, optionally, may warn or alert the patient, patient caregiver or remote monitoring location. See flow diagram and description as described below in association with FIG. 56.

Monitor+Treatment (Brain+Respiration+Cardiac)

FIG. 54 is a block diagram of the electronic circuitry that makes up full Monitor/Brain, Respiration and Cardiac Therapy device 580 (FIG. 25A) in accordance with the presently disclosed alternative embodiment of the invention. As can be seen from FIG. 54, Monitor/Brain, Respiration and Cardiac Therapy device 580 comprises a primary control circuit 720 and MV circuit 722 whose function was described herein above in conjunction with FIG. 28. In addition the Monitor/Brain, Respiration and Cardiac Therapy device of FIG. 54 also includes an amplifier 725 to amplify and sense EEG signals from a cranially implanted lead 18 and an output stimulator 729 to provide brain stimulation via cranially implanted lead 18 and phrenic nerve stimulation via respiration lead 28. The CPU 732, in conjunction with software program in RAM/ROM 730, integrates the information from the sensed cardiac, respiration and EEG signals, detects the onset of cerebral, cardiac or respiratory anomalies, provides preprogrammed stimulation therapy to the patient's brain via lead 18, stimulation of the patient's phrenic nerve via respiration lead 28 and stimulation of the patient's heart via cardiac leads 16, formats and stores diagnostic data for later retrieval by the patient's clinician and, optionally, may warn or alert the patient, patient caregiver or remote monitoring location. Optionally, lead 28 may connect to the diaphragm to provide direct diaphragmatic stimulation. See flow diagram and description as described below in association with FIG. 56.

FIG. 55 is a block diagram of the electronic circuitry that makes up full Monitor/Brain, Respiration and Cardiac Therapy device 581 (FIG. 25B) in accordance with the presently disclosed alternative embodiment of the invention. As can be seen from FIG. 55, Monitor/Brain, Respiration and Cardiac Therapy device 581 in combination with a cranially implanted Monitor/Brain Therapy unit 26 in a patient 10 includes a primary control circuit 720 and MV circuit 722 that are described herein above in conjunction with FIG. 28. A 2-way wireless telemetry communication link 30 connects the Monitor/Therapy unit 26 and Monitor/Brain, Respiration and Cardiac Therapy unit 581 via antennas 736. The wireless communication link 30 may consist of an RF link (such as described in U.S. Pat. No. 5,683,432 "Adaptive Performance-Optimizing Communication System for Communicating with an Implantable Medical Device" to Goedeke, et al), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke). Monitor/Brain Therapy unit 26 contains an amplifier 725 to amplify and sense EEG signals from a cranially implanted lead 18 and an output stimulator 729 for stimulation of the brain. Monitor 26 may be constructed as substantially described in US Publication No. 20040176817 "Modular implantable medical device" to Wahlstrand et al. or U.S. Pat. No. 5,782,891 "Implantable Ceramic Enclosure for Pacing, Neurological and Other Medical Applications in the Human Body" to Hassler, et al or U.S. Pat. No. 6,427,086 "Means and Method for the Intracranial Placement of a Neurostimulator" to Fischell. et al. EEG sensing is accomplished by the use of integrated electrodes in the housing of monitor 26 or, alternatively, by cranially implanted leads 18.

Specifically, CPU 732, in conjunction with software program in RAM/ROM 730, integrates the information from the sensed cardiac, respiration and EEG signals, detects the onset of cerebral, cardiac or respiratory anomalies, provides preprogrammed stimulation therapy to the patient's brain via lead 18, to the phrenic nerve via respiration lead 28 and to the heart via cardiac leads 16, formats and stores diagnostic data for later retrieval by the patient's clinician and, optionally, may warn or alert the patient, patient caregiver or remote monitoring location. Optionally, lead 28 may connect to the diaphragm to provide direct diaphragmatic stimulation. See flow diagram and description as described below in association with FIG. 56.

FIG. 56 is a flow diagram 850 showing operation of a full monitor/therapy sensing and monitoring cardiac, respiration and electroencephalogram parameters for the detection of neurological events as shown and described in embodiments in FIG. 11-25 above. The blocks 802-808 relating to the identification of cardiac activity, and blocks 816-822 relating to identification of respiratory activity, may be activated or deactivated according to the determination of whether they improve the detection of the neurological disorder (see for example the discussion regarding determining concordance). It is noted that the particular detection scheme used for each of the physiologic signals (brain, heart, respiratory) is not restricted to the examples provided here.

In one embodiment, beginning at block 802, the interval between sensed cardiac signals are measured. At block 804, a rate stability measurement is made on each cardiac interval utilizing a heart rate average from block 806. At block 808, a rate stable decision is made based upon preprogrammed parameters. If YES (heart rate is determined to be stable), the flow diagram returns to the HR Measurement block 802. If NO, the rate stability information is provided to Determine Therapy and Duration block 830.

At block 816, thoracic impedance is continuously measured in a sampling operation. At block 818, a MV and respiration rate calculation is made. At block 822, a pulmonary apnea decision is made based upon preprogrammed criteria. If NO (no apnea detected), the flow diagram returns to MV Measurement block 816. If YES, the occurrence of apnea and MV information is provided to Determine Therapy and Duration block 830.

At block 824, the electroencephalogram is sensed and measured. An EEG calculation is performed at block 826. The seizure detection algorithm is executed at block 826. At block 828, a seizure episode is determined. If NO (no seizure detected), the flow diagram returns to EEG Measurement block 824. If YES, the occurrence of a seizure is provided to Determine Therapy and Duration block 830.

Based upon the data presented to it, Determine Therapy and Duration block 830 determines the type of therapy and the duration to block 832, which controls the start of the therapy by evaluating the severity and ranking of each event (i.e., maximum ratio, duration of seizure detection, spread, number of clusters per unit time, number of detections per cluster, duration of an event cluster, duration of a detection, and inter-seizure interval) per co-pending U.S. patent application Publication No. 20040133119 "Scoring of sensed neurological signals for use with a medical device system" to Osorio, et al incorporated herein by reference in its entirety. Block 834 monitors the completion of the determined therapy. If the therapy is not complete, control returns to block 834. If the therapy is determined to be complete, block 834 returns the flow diagram to blocks 802 (Measure HR), 816 (Measure Impedance) and 824 (Measure EEG) to continue the monitoring of cardiac, respiratory and brain signal parameters.

Therapy may consist of neural stimulation, cardiac pacing, cardioversion/defibrillation, and drug delivery via a pump, brain cooling, or any combination of therapies.

When block 830 determines that a therapy is to be initiated Format Diagnostic Data block 812 formats the data from the cardiac, respiration and EEG monitoring channels, adds a time stamp (ie, date and time), type and duration of therapy and provides the data to block 814 where the data is stored in RAM memory for later retrieval by a clinician via telemetry. Optionally, block 812 may add examples of intrinsic ECG, respiration or EEG signals recorded during a sensed episode/ seizure.

The physician may program the devices shown above in relation to FIGS. 11-25 and 41-55 to allow the ECG/respiratory detectors be enabled to trigger the delivery of therapy (i.e., stimulation or drug delivery) to the patient's brain, with goal of aborting seizures earlier or limiting their severity than if using EEG signal detection alone. Either EEG, respiratory or ECG detections may trigger therapy to the brain, depending on which occurs first. The physician may choose the type of ECG or respiratory event to use for triggering therapy to the brain.

Application of Therapy to the Brain Based on Cardiac or Respiratory Signals and Termination of Such Therapy In the present invention of the devices shown above in relation to FIGS. 11-25 and 41-55, the device is able to terminate or change the cardiac/respiratory initiated treatment, directed at the brain, if a neurological event is not entered within an expected time frame following cardiac detection. This feature allows the device to begin treating a patient's neurological event before its detection in the brain signal. These termination conditions are defined at block 990 of FIGS. 40A and 890 of FIG. 40B.

If the cardiac/respiratory initiated brain therapy has been ongoing for some time, and polling of the brain signal (i.e., processing the brain signal with a neurological event detection algorithm) has indicated the patient is not in a neurological event, then the following may be true: 1. Cardiac/respiratory triggered therapy was successful in aborting the neurological event, and therefore, the neurological event is not detectable in the brain signal. 2. The cardiac/respiratory event was not associated with a neurological event.

In either case, it would be appropriate to change (adjust or terminate) cardiac/respiratory initiated therapy directed specifically at aborting a neurological event. FIG. 57A is a flow chart illustrating the processing steps executed by a processor (e.g., CPU 732 or any other processor). At block 1000 the processor monitors the cardiac or respiratory signals. At block 1002, the processor detects a cardiac or respiratory event in the cardiac or respiratory signals. Based upon a cardiac or respiratory event detection at block 1002, the processor activates the therapy module to provide therapy to the brain at block 1004. The brain signal is monitored at block 1006. This may be a continuation of monitoring of the brain that was already ongoing or it may be initiation of brain monitoring. Once the therapy has been initiated from a cardiac or respiratory detection, the therapy may be changed at block 1008 based on the monitoring of the brain signal.

One embodiment of the process of FIG. 57A is illustrated in FIG. 57B. The processor receives the cardiac or respiratory signals at block 1050. A cardiac or respiratory event is detected at block 1052. The therapy module is activated at block 1054 to provide therapy to the brain based on a cardiac or respiratory detection. Once therapy has been initiated from a cardiac/respiratory detection, the device monitors the amount of time therapy has been delivered at block 1056. This time period is programmable. The processor continues to receive a brain signal at block 1058. At decision block 1060 the processor determines when the programmed time period has been exceeded without detection of a neurological event in the brain signal. If the answer is "Yes" (i.e., the cardiac or respiratory initiated brain therapy has been ongoing for the programmed time period without the occurrence of a neurological event in the brain signal), then therapy to the brain is discontinued at block 1062. If the patient has entered a neurological event while receiving cardiac/respiratory initiated therapy, control of therapy is transferred to the monitoring of the brain by the neurological event detection algorithm, and therapy decisions are made using the brain signals at block 1064. At this point therapy may continue until the EEG detection algorithm determines that the neurological event has ended. Then therapy may be terminated based on the detected end of the neurological event based on the EEG detection algorithm output.

FIG. 40A discussed above shows a process 971 for determining whether to enable the cardiac or respiratory detectors for neurological event detection and treatment. Once the cardiac or respiratory signals have been enabled for neurological event detection monitoring and treatment at block 986 and the neurological event detection algorithm has been enabled for modulation or other input into cardiac or respiratory therapy, the cardiac/respiratory parameters for ictal/post-ictal treatment options are defined at block 987. At block 988, cardiac/ respiratory events to treat when in a neurological state are defined. At block 989, cardiac/respiratory events to treat when outside a neurological event are defined. At block 990, therapy termination conditions (i.e., turn over control of brain therapy to the neurological event detection algorithm and terminate if a neurological event is not entered in a programmable period of time) are defined and the monitor starts monitoring or treatment at block 985.

If the matching test of the flow diagram of FIG. 40A shows that one type of cardiac event (type 1) is associated with neurological event onset while other types of cardiac events (type 2) occur frequently, but have no temporal relationship to the neurological event, then the physician may chose to direct therapy to the Brain (or Brain and Heart) upon type 1 event detection or direct therapy to the Heart on type 2 detection.

In the present invention as described in relation to the devices shown above in FIGS. 11-25 and 41-55, the physician is able to selectively choose which cardiac and respiratory events to treat in seizure and non-seizure states. For example, the device may be programmed to treat incidences of tachycardia in non-seizure states, but not in seizure states, where this type of cardiac behavior is expected and considered normal. Also, the patient may experience certain ECG or respiratory abnormalities, which are seizure induced, but cause no complications or increased health risk to the patient. In such cases, the physician may decide to suppress treatment for these events if detected during a seizure. This cannot be accomplished with existing pacemaker technology, which operates on ECG signals only.

There are other instances in which a detected ECG or respiratory abnormality does pose a health risk, regardless of when it occurs and how it was induced. For these events, the physician may choose a mode of operation that treats the ECG/respiratory abnormality in both seizure and non-seizure states (i.e., asystole, apnea).

Additionally, the physician may choose to treat the same ECG/respiratory event in both seizure and non-seizure states, but may define different thresholds (i.e., duration or intensity) for treating the event. For example, during a seizure state, a higher heart rate or sustained occurrence of tachycardia may be required before cardiac treatment is initiated, relative to a non-seizure state. This feature would enable cardiac therapy during status epilepticus, which is a prolonged condition, but suppress it for typical seizure behaviors.

If the matching test of the flow diagram of FIG. 57 shows that the ECG or respiratory signals do not improve seizure detection, but patient is at cardiac risk, the physician may choose to enable the ECG/respiratory detector to deliver therapy to the heart or diaphragm.

If the matching test of the flow diagram of FIG. 57 shows that the ECG or respiratory signals improves seizure detection, but the patient is also at cardiac risk, the physician may choose to treat the brain (for seizures) with EEG, ECG or respiratory detection, and heart (for cardiac problems) with ECG detection.

Preventative Pacing Therapy

Optionally, the therapy systems of FIGS. 11-25 and 41-55 may also have pre-emptive or preventative pacing capabilities. For example, upon EEG detection of seizure onset or imminent seizure onset, the pacing systems described in conjunction with FIGS. 11-25 and 41-55 may begin preventative overdrive pacing to prevent or mitigate sleep apnea such as described in U.S. Pat. No. 6,126,611 "Apparatus for Management of Sleep Apnea" to Bourgeois. The '611 patent detects sleep apnea and begins to pace the heart at a rate of 70-100 PPM (overdrive pacing the sleep intrinsic rate of typically 30-55 BPM) causing arousal and elimination/prevention of sleep apnea. The herein described invention uses the detection of the onset or impending onset of a seizure to trigger sleep apnea overdrive pacing to preemptively prevent the initiation of apnea. Upon the sensing of seizure termination or a preprogrammed timeout, the sleep apnea prevention overdrive pacing is terminated/inactivated.

Alternatively, the pacing systems may begin ventricular pacing overdrive upon sensing a ventricular premature contraction to prevent the initiation of ventricular arrhythmias such as described in U.S. Pat. No. 4,503,857 "Programmable Cardiac Pacemaker with Microprocessor Control of Pacer Rate" to Boute, et al and U.S. Pat. No. 5,312,451 "Apparatus and Methods for Controlling a Cardiac Pacemaker in the Event of a Ventricular Extrasystole" to Limousin, et al. Upon detection of the onset or impending onset of a seizure ventricular extrasystole overdrive pacing may be initiated, and subsequent to the programmed number of cycles, a slowing of the ventricular rate until either the programmed base rate is reached or a sinus detection occurs. Upon the sensing of seizure termination or a preprogrammed timeout, the sleep apnea prevention overdrive pacing is terminated/inactivated.

Additionally, the pacing systems described in conjunction with FIGS. 11-25 and 41-55 may include AF preventative pacing therapies as described in U.S. Pat. No. 6,185,459 "Method and Apparatus for Prevention of Atrial Tachyarrhythmias" to Mehra, et al or U.S. Pat. No. 6,650,938 "Method and System for Preventing Atrial Fibrillation by Rapid Pacing Intervention" to Boute. The '459 and '938 patents describe systems that sense premature atrial events and initiate overdrive pacing algorithms to prevent the initiation of atrial arrhythmias. In the present invention, upon detection of the onset or impending onset of a seizure, ventricular extrasystole AF overdrive pacing may be initiated, and subsequent to the programmed number of cycles, a slowing of the ventricular rate until either the programmed base rate is reached or a sinus detection occurs. Upon the sensing of seizure termination or a preprogrammed timeout, the sleep apnea prevention overdrive pacing is terminated/inactivated.

Signal Processing

The signal processing of cardiac, respiration or electroencephalogram signals of the above-described embodiments may include analog, continuous wave bandpass filtering as is well known in the art. Additionally, digital signal processing techniques as substantially described in U.S. Pat. No. 6,029,087 "Cardiac Pacing System with Improved Physiological Event Classification Based Upon DSP" to Wohlgemuth and U.S. Pat. No. 6,556,859 "System and Method for Classifying Sensed Atrial Events in a Cardiac Pacing System" to Wohlgemuth, et al may be used. Additionally, fuzzy logic processing techniques as described in U.S. Pat. No. 5,626,622 "Dual Sensor Rate Responsive Pacemaker" to Cooper and U.S. Pat. No. 5,836,988 "Rate Responsive Pacemaker with Exercise Recovery Using Minute Volume Determination" to Cooper, et al. may be used to determine/detect the occurrence or onset of seizures, respiratory or cardiac anomalies.

The devices of the above-described systems that contain 2 individual units in 2-way communication (e.g., the systems of FIG. 20-23) may optionally transmit events via the communication channel by one of several ways including, but not limited to, individual event logic signal, marker channel or processed signal.

Power Saving and Clock Synchronization

The devices of the above-described systems that contain 2 individual units in 2-way communication (e.g., the systems of FIGS. 20-23, 43, 45-47, 49, 52, 53, 55) may optionally have a reduced power capability during communication. The devices may communicate at a predefined specific time interval with clocks in each unit of the system updated/resynchronized on each communication (as described in U.S. Pat. No. 6,083,248 "World Wide Patient Location and Data Telemetry System for Implantable Medical Devices" to Thompson.

Optionally, a receiving unit may open a window at a period interval (e.g., 1 second) for a brief window (e.g., 100 mSec) to look for an incoming transmission from the other system unit.

Drug Pump

The therapy device in above devices as described in systems as described in conjunction with FIGS. 11-25 and 41-55 may optionally contain a drug pump to deliver liquid medicants in lieu of stimulation or in combination with stimulation. Medicants used could include epileptic drugs (examples of such drugs include, but are not limited to intrathecal delivery of CGX-1007 or Baclofen), mental health and mood disorder related drugs, cardiac drugs (examples of such drugs include, but are not limited to, pharmaceutical compositions comprising beta-adrenergic blocking agents, protain emide, type 1 antiarrhythmic agents such as disopyramide, class II agents such as propafenone, alphaagonists such as ephedrine and midodrine, and other antiarrhymic agents such as amiodarone, and combinations thereof) or respiratory drugs (examples of such drugs include, but are not limited to diuretics).

Remote Monitoring

The present invention also allows the residential, hospital or ambulatory monitoring of at-risk patients and their implanted medical devices at any time and anywhere in the world (see system 900 FIG. 58). Medical support staff 906 at a remote medical support center 914 may interrogate and read telemetry from the implanted medical device and reprogram its operation while the patient 10 is at very remote or even unknown locations anywhere in the world. Two-way voice communications 910 via satellite 904, cellular via link 32 or land lines 956 with the patient 10 and data/programming communications with the implanted medical device 958 via a belt worn transponder 960 may be initiated by the patient 10 or the medical support staff 906. The location of the patient 10 and the implanted medical device 958 may be determined via GPS 902 and link 908 and communicated to the medical support network in an emergency. Emergency response teams can be dispatched to the determined patient location with the necessary information to prepare for treatment and provide support after arrival on the scene. See for example, U.S. Pat. No. 5,752,976 "World Wide Patient Location and Data Telemetry System for Implantable Medical Devices" to Duffin et al. An alternative or addition to the remote monitoring system as described above in conjunction with FIG. 58 is shown in the system 950 of FIG. 59, which shows a patient 10 sleeping with an implantable Monitor 958 or optional therapy device as described above in connection with the systems of FIG. 1-57. The implantable device 958, upon detection of a neurological event (such as a seizure), respiratory apnea or cardiac conduction anomaly (ie, heart rate variability, QT extension, arrhythmia) may alert a remote monitoring location via local remote box 952 (as described in U.S. Pat. No. 5,752,976 "World Wide Patient Location and Data Telemetry System for Implantable Medical Devices" to Duffin, et al.) telephone 954 and phone lines 956 or the patient's care provider via an RF link 32 to a pager-sized remote monitor 960 placed in other locations in the house or carried (ie, belt worn) by the care provider 962. The remote caregiver monitor 960 may include audible buzzes/tones/beeps, vocal, light or vibration to alert the caregiver 962 of patient's monitor in an alarm/alert condition. The RF link may include RF portable phone frequencies, power line RF links, HomeRF, Bluetooth, ZigBee, WIFI, MICS band (medical implant communications service), or any other interconnect methods as appropriate. Often the care provider 962 may be able to take some action to help the patient 10. For example, the care provider may arouse the patient 10 from a neurological event (such as a SUDEP episode) by shaking them, arousing them, reposition the patient, or the like.

Patient Alert

The monitor (and optionally therapy) devices as described in systems described above in conjunction with FIG. 1-57 may optionally allow a patient alert to allow the patient an early warning of impending seizure, respiratory or cardiac anomalies via vibration (e.g., piezo buzzer in implanted device, a vibrator as used in a cell phone or pager in a "silent ring" mode in vest, patch or patient activator), audible buzzing or tones (e.g., audible in cranial implant, audible via external patch, patient activator or vest), light (e.g., external vest or patient activator) or vocal (e.g., spoken word in cranial, vest, external patch, or patient activator) indicators of the monitor in an alarm/alert condition.

It will be apparent from the foregoing that while particular embodiments of the invention have been illustrated and described, various modifications can be made without departing from the spirit and scope of the invention. Accordingly, it is not intended that the invention be limited, except as by the appended claims.

What is claimed is:

1. A method of treating a nervous system disorder in a patient, the method comprising:
    sensing a brain signal from the patient;
    obtaining a neurological event detection signal, the neurological event detection signal indicating neurological events detected from the brain signal;
    sensing a cardiac signal from the patient;
    obtaining a cardiac event detection signal, the cardiac event detection signal indicating cardiac events detected from the cardiac signal;
    analyzing timing relationships between detected events before enabling therapy delivery for treating a neurological disorder in response to a cardiac event, the detected events including detected neurological events and detected cardiac events;
    identifying a matched event when one of the detected neurological events is temporally related to one of the detected cardiac events;
    determining that the cardiac event detection signal facilitates detection of neurological events when the timing relationships between detected neurological events and detected cardiac events meet one or more predetermined criteria; and
    delivering a therapy to the patient for treating the neurological disorder in response to a cardiac event if the cardiac event detection signal is determined to facilitate detection of neurological events.

2. The method of claim 1 further comprising identifying a false positive event when one of the detected cardiac events is not temporally related to one of the detected neurological events, and determining that the cardiac event detection signal facilitates detection of neurological events when matched events and false positive events meet predetermined criteria.

3. The method of claim 1 further comprising identifying a false negative event when one of the detected neurological events is not temporally related to one of the detected cardiac events, and determining that the cardiac event detection signal facilitates detection of neurological events when matched events and false negative events meet predetermined criteria.

4. The method of claim 1 further comprising:
    identifying a false positive event when one of the detected cardiac events is not temporally related to one of the detected neurological events, identifying a false negative event when one of the detected neurological events is not temporally related to one of the detected cardiac events, and determining that the cardiac event detection signal facilitates detection of neurological events when matched events, false positive events, and false negative events meet predetermined criteria.

5. The method of claim 1 wherein a detected neurological event and a detected cardiac event are temporally related if an elapsed time between a reference point of the detected neurological event and a reference point of the detected cardiac event is less than a predetermined amount.

6. The method of claim 5 wherein the reference point of each of the detected events is a beginning time of the detected event.

7. The method of claim 5 wherein the reference point of each of the detected events is an ending time of the detected event.

8. The method of claim 5 wherein the reference point for a first event to occur of the temporally related detected events is a beginning time of the first event, and the reference point for a second event to occur of the temporally related detected events is an ending time of the second event.

9. The method of claim 5 wherein the reference point of each of the detected events is between a beginning time and an ending time for each of the detected events.

10. The method of claim 9 wherein the reference point of each of the detected events is a midpoint between a beginning time and an ending time for each of the detected events.

11. The method of claim 1 further comprising calculating a rate of concordance between the neurological event detection signal and cardiac event detection signal, and determining that the cardiac event detection signal facilitates detection of the neurological events when the rate of concordance exceeds a threshold.

12. The method of claim 11 further comprising enabling use of the cardiac event detection signal to detect neurological events when the rate of concordance between the neurological and cardiac event detection signals exceeds the threshold.

13. The method of claim 1 wherein the therapy comprises delivery of electrical stimulation to a brain of the patient.

14. The method of claim 1 wherein the therapy comprises delivery of a drug to the patient.

15. The method of claim 1 further comprising, for each of the matched events, determining a latency of the detected cardiac event with respect to a detected neurological event.

16. The method of claim 1 wherein the sensed brain signal is an EEG signal, and the neurological event detection signal is generated by a seizure detection algorithm which uses the EEG signal as an input.

17. The method of claim 1 wherein the sensed cardiac signal is an ECG signal, and the cardiac event detection signal is determined by a cardiac event detection algorithm which uses the ECG signal as an input.

18. The method of claim 17 wherein a cardiac event is detected by the cardiac event detection algorithm when a heart rate determined from the ECG signal exceeds a threshold.

19. The method of claim 18 wherein the cardiac event begins when the heart rate rises above a first threshold, and terminates when the heart rate decreases below a second threshold.

20. The method of claim 17 wherein the cardiac event is detected by the cardiac event detection algorithm when a change in heart rate determined from the ECG signal exceeds a threshold.

21. The method of claim 20 wherein the change in heart rate occurs within a predetermined window of time.

22. The method of claim 17 wherein the cardiac event is detected when one or more premature ventricular contractions (PVCs) occurs within a predetermined window of time.

23. The method of claim 17 wherein the cardiac event is detected when an arrhythmia occurs.

24. The method of claim 17 wherein each detected cardiac event is categorized as one or more of two or more types of cardiac events.

25. The method of claim 24 wherein each detected cardiac event is categorized as one or more of the following types: bradycardia, tachycardia, asystole, wandering pacemaker, multifocal atrial tachycardia, atrial fibrillation, sinus pause, premature atrial contractions (PAC), ST segment elevation, ST segment depression, T-wave inversion, QT interval prolongation, premature ventricular contractions (PVCs), AV-block (AVB) and bundle branch block (BBB).

26. The method of claim 24 wherein the step of identifying matched events is performed separately for each type of cardiac event.

27. The method of claim 26 wherein use of a given type of cardiac event is enabled for detecting neurological events based on the number of matched events for the given type of cardiac event.

28. The method of claim 26 wherein use of a given type of cardiac event is enabled for detecting neurological events based on a rate of concordance between the given type of cardiac event and the detected neurological events.

29. The method of claim 26 wherein the type of cardiac event is one of bradycardia, tachycardia, asystole, ST segment elevation, QT interval prolongation, premature ventricular contractions (PVCs), and atrial fibrillation.

30. The method of claim 17 wherein the cardiac event is detected when a measured heart rate variability falls outside of a defined range.

31. The method of claim 17 wherein the cardiac event is detected when a measured QT interval variability falls outside of a defined range.

32. The method of claim 17 wherein the cardiac event is detected when a rate-corrected QT interval ("$QT_C$") falls outside of a defined range.

33. The method of claim 17 wherein the cardiac event is detected when a sinus arrest episode is detected.

34. The method of claim 17 wherein the cardiac event is detected when a syncope episode is detected.

35. The method of claim 34 wherein the syncope episode comprises a sudden drop in heart rate.

36. The method of claim 1 wherein a minimum number of neurological events must be detected before determining that the cardiac event detection signal facilitates detection of neurological events.

37. The method of claim 1, further comprising changing the therapy delivered to the patient based on the brain signal.

38. The method of claim 37 wherein changing the therapy delivered to the patient based on the brain signal comprises discontinuing therapy to the patient when a period of time has passed after detection of the cardiac event without detection of a neurological event in the brain signal.

39. A method of treating a nervous system disorder in a patient, the method comprising:
sensing a brain signal from the patient;
obtaining a neurological event detection signal, the neurological event detection signal indicating neurological events detected from the brain signal;
sensing a cardiac signal from the patient;

obtaining a cardiac event detection signal, the cardiac event detection signal indicating cardiac events detected from the cardiac signal;

analyzing timing relationships between detected events, the detected events including detected neurological events and detected cardiac events;

identifying a matched event when one of the detected neurological events is temporally related to one of the detected cardiac events;

determining whether the cardiac event detection signal facilitates detection of neurological events based on matched events;

calculating a rate of concordance between the neurological event detection signal and cardiac event detection signal, and determining that the cardiac event detection signal facilitates detection of the neurological events when the rate of concordance exceeds a threshold, wherein calculating the rate of concordance comprises dividing a number of matched events by a number of detected neurological events; and delivering a therapy to the patient for treating a neurological disorder in response to a cardiac event if the cardiac event detection signal is determined to facilitate detection of neurological events.

40. A method of treating a nervous system disorder in a patient, the method comprising:

sensing a brain signal from the patient;

obtaining a neurological event detection signal, the neurological event detection signal indicating neurological events detected from the brain signal;

sensing a cardiac signal from the patient;

obtaining a cardiac event detection signal, the cardiac event detection signal indicating cardiac events detected from the cardiac signal;

analyzing timing relationships between detected events, the detected events including detected neurological events and detected cardiac events;

identifying a matched event when one of the detected neurological events is temporally related to one of the detected cardiac events;

determining whether the cardiac event detection signal facilitates detection of neurological events based on matched events;

identifying a false positive event when one of the detected cardiac events is not temporally related to one of the detected neurological events, and determining whether the cardiac event detection signal facilitates detection of neurological events based upon matched events and false positive events;

calculating a false positive rate, the false positive rate being equal to a number of false positive events divided by a number of detected neurological events, and delivering a therapy to the patient for treating a neurological disorder in response to a cardiac event if the cardiac event detection signal is determined to facilitate detection of neurological events.

41. The method of claim 40 wherein delivering the therapy to the patient further requires the false positive rate to be below a predetermined level.

42. A method of treating a nervous system disorder in a patient, the method comprising:

sensing a brain signal from the patient;

obtaining a neurological event detection signal, the neurological event detection signal indicating neurological events detected from the brain signal;

sensing a cardiac signal from the patient;

obtaining a cardiac event detection signal, the cardiac event detection signal indicating cardiac events detected from the cardiac signal;

analyzing timing relationships between detected events, the detected events including detected neurological events and detected cardiac events;

identifying a matched event when one of the detected neurological events is temporally related to one of the detected cardiac events;

determining whether the cardiac event detection signal facilitates detection of neurological events based on matched events;

identifying a false positive event when one of the detected cardiac events is not temporally related to one of the detected neurological events, and determining whether the cardiac event detection signal facilitates detection of neurological events based upon matched events and false positive events;

calculating a false positive rate, the false positive rate being equal to a number of false positive events per unit of time, and delivering a therapy to the patient for treating a neurological disorder in response to a cardiac event if the cardiac event detection signal is determined to facilitate detection of neurological events.

43. The method of claim 42 wherein delivering the therapy to the patient further requires the false positive rate to be below a predetermined level.

44. A method of treating a nervous system disorder in a patient, the method comprising:

sensing a brain signal from the patient;

obtaining a neurological event detection signal, the neurological event detection signal indicating neurological events detected from the brain signal;

sensing a cardiac signal from the patient;

obtaining a cardiac event detection signal, the cardiac event detection signal indicating cardiac events detected from the cardiac signal;

analyzing timing relationships between detected events, the detected events including detected neurological events and detected cardiac events;

identifying a matched event when one of the detected neurological events is temporally related to one of the detected cardiac events;

determining whether the cardiac event detection signal facilitates detection of neurological events based on matched events;

for each of the matched events, determining a latency of the detected cardiac event with respect to a detected neurological event, wherein determining latency comprises calculating a representative value of a time by which the matched cardiac events precede the corresponding matched neurological events; and delivering a therapy to the patient for treating a neurological disorder in response to a cardiac event if the cardiac event detection signal is determined to facilitate detection of neurological events.

45. A method of treating a nervous system disorder in a patient, the method comprising:

sensing a brain signal from the patient;

obtaining a neurological event detection signal, the neurological event detection signal indicating neurological events detected from the brain signal;

sensing a cardiac signal from the patient;

obtaining a cardiac event detection signal, the cardiac event detection signal indicating cardiac events detected from the cardiac signal;

analyzing timing relationships between detected events, the detected events including detected neurological events and detected cardiac events;

identifying a matched event when one of the detected neurological events is temporally related to one of the detected cardiac events;

determining whether the cardiac event detection signal facilitates detection of neurological events based on matched events;

for each of the matched events, determining a latency of the detected cardiac event with respect to a detected neurological event, wherein determining latency comprises calculating how frequently the matched cardiac events precede the corresponding matched neurological events; and delivering a therapy to the patient for treating a neurological disorder in response to a cardiac event if the cardiac event detection signal is determined to facilitate detection of neurological events.

46. A method of treating a nervous system disorder in a patient, the method comprising:

sensing a brain signal from the patient;

obtaining a neurological event detection signal, the neurological event detection signal indicating neurological events detected from the brain signal;

sensing a cardiac signal from the patient;

obtaining a cardiac event detection signal, the cardiac event detection signal indicating cardiac events detected from the cardiac signal;

analyzing timing relationships between detected events, the detected events including detected neurological events and detected cardiac events;

identifying a matched event when one of the detected neurological events is temporally related to one of the detected cardiac events;

determining whether the cardiac event detection signal facilitates detection of neurological events based on matched events;

for each of the matched events, determining a latency of the detected cardiac event with respect to a detected neurological event; and delivering a therapy to the patient for treating a neurological disorder in response to a cardiac event if the cardiac event detection signal is determined to facilitate detection of neurological events, wherein delivering the therapy to the patient further requires the latency of the detected cardiac events to meet a predetermined criterion.

47. A method of treating a nervous system disorder in a patient, the method comprising:

sensing a brain signal from the patient;

obtaining a neurological event detection signal, the neurological event detection signal indicating neurological events detected from the brain signal;

sensing a cardiac signal from the patient;

obtaining a cardiac event detection signal, the cardiac event detection signal indicating cardiac events detected from the cardiac signal;

analyzing timing relationships between detected events, the detected events including detected neurological events and detected cardiac events;

identifying a matched event when one of the detected neurological events is temporally related to one of the detected cardiac events;

calculating a false negative rate, the false negative rate being equal to a number of false negative events divided by a number of detected neurological events;

determining whether the cardiac event detection signal facilitates detection of neurological events based on matched events; and delivering a therapy to the patient for treating a neurological disorder in response to a cardiac event if the cardiac event detection signal is determined to facilitate detection of neurological events.

48. The method of claim 47 wherein delivering the therapy to the patient further requires the false negative rate be below a predetermined level.

49. A method of treating a nervous system disorder in a patient, the method comprising:

sensing a brain signal from the patient;

obtaining a neurological event detection signal, the neurological event detection signal indicating neurological events detected from the brain signal;

sensing a cardiac signal from the patient;

obtaining a cardiac event detection signal, the cardiac event detection signal indicating cardiac events detected from the cardiac signal;

analyzing timing relationships between detected events, the detected events including detected neurological events and detected cardiac events;

identifying a matched event when one of the detected neurological events is temporally related to one of the detected cardiac events;

determining whether the cardiac event detection signal facilitates detection of neurological events based on matched events;

calculating a rate of concordance between the neurological and cardiac event detection signals, the rate of concordance being equal to a number of matched events divided by a number of detected neurological events;

calculating a false positive rate, the false positive rate being equal to a number of false positive events divided by the number of detected neurological events;

calculating a false negative rate, the false negative rate being equal to a number of false negative events divided by the number of detected neurological events;

for each of the matched events, determining a latency of the detected cardiac event with respect to a detected neurological event; and delivering a therapy to the patient for treating a neurological disorder in response to a cardiac event if the cardiac event detection signal is determined to facilitate detection of neurological events, wherein delivering the therapy to the patient further requires a combination of the rate of concordance, false positive rate, false negative rate, and latency of the detected cardiac events to meet predetermined criteria.

50. A method of treating a nervous system disorder in a patient, the method comprising:

sensing a brain signal from the patient;

obtaining a neurological event detection signal, the neurological event detection signal indicating neurological events detected from the brain signal;

sensing a cardiac signal from the patient;

obtaining a cardiac event detection signal, the cardiac event detection signal indicating cardiac events detected from the cardiac signal;

analyzing timing relationships between detected events, the detected events including detected neurological events and detected cardiac events;

identifying a matched event when one of the detected neurological events is temporally related to one of the detected cardiac events;

determining whether the cardiac event detection signal facilitates detection of neurological events based on matched events;

calculating a rate of concordance between the neurological and cardiac event detection signals, the rate of concordance being equal to a number of matched events divided by a number of detected neurological events;

calculating a false positive rate, the false positive rate being equal to a number of false positive events per unit of time;

calculating a false negative rate, the false negative rate being equal to a number of false negative events per unit of time;

for each of the matched events, determining a latency of the detected cardiac event with respect to a detected neurological event; and delivering a therapy to the patient for treating a neurological disorder in response to a cardiac event if the cardiac event detection signal is determined to facilitate detection of neurological events, wherein delivering the therapy to the patient further requires a combination of the rate of concordance, false positive rate, false negative rate, and latency of the detected cardiac events to meet predetermined criteria.

51. A method of treating a nervous system disorder in a patient, the method comprising:

sensing a brain signal from the patient;

obtaining a neurological event detection signal, the neurological event detection signal indicating neurological events detected from the brain signal;

sensing a cardiac signal from the patient;

obtaining a cardiac event detection signal, the cardiac event detection signal indicating cardiac events detected from the cardiac signal;

analyzing timing relationships between detected events, the detected events including detected neurological events and detected cardiac events;

identifying a matched event when one of the detected neurological events is temporally related to one of the detected cardiac events;

determining whether the cardiac event detection signal facilitates detection of neurological events based on matched events;

delivering a therapy to the patient for treating a neurological disorder in response to a cardiac event if the cardiac event detection signal is determined to facilitate detection of neurological events; and for the cardiac events classified as matched, further classifying the cardiac events as either:
  (a) overlapping, if
    (i) the cardiac event has a beginning time that occurs before an end time of the matched neurological event,
    (ii) the cardiac event has a termination time that occurs after a start time of the matched neurological event; or
  (b) non-overlapping.

52. The method of claim 51 wherein, for cardiac events classified as overlapping, further classifying the cardiac events as Equal-Equal if
  (i) the cardiac event has a beginning time that equals a start time of the matched neurological event, and
  (ii) the cardiac event has a termination time that equals an end time of the matched neurological event.

53. The method of claim 51 wherein, for cardiac events classified as overlapping, further classifying the cardiac events as Out-In if
  (i) the cardiac event has a beginning time that occurs before a start time of the matched neurological event, and
  (ii) the cardiac event has a termination time that occurs after the start time of the matched neurological event, and
  (iii) the cardiac event termination time occurs before an end time of the matched neurological event.

54. The method of claim 51 wherein, for cardiac events classified as overlapping, further classifying the cardiac events as Out-Out if
  (i) the cardiac event has a beginning time that occurs before a start time of the matched neurological event, and
  (ii) the cardiac event has a termination time that occurs after an end time of the matched neurological event.

55. The method of claim 51 wherein, for cardiac events classified as overlapping, further classifying the cardiac events as In-Out if
  (i) the cardiac event has a beginning time that occurs after a start time of the matched neurological event, and
  (ii) the cardiac event beginning time occurs before an end time of the matched neurological event, and
  (iii) the cardiac event has a termination time that occurs after the end time of the matched neurological event.

56. The method of claim 51 wherein, for cardiac events classified as overlapping, further classifying the cardiac events as In-In if
  (i) the cardiac event has a beginning time that occurs after a start time of the matched neurological event, and
  (ii) the cardiac event beginning time occurs before an end time of the matched neurological event, and
  (iii) the cardiac event has a termination time that occurs after the start time of the matched neurological event, and
  (iv) the cardiac event termination time occurs before the end time of the matched neurological event.

57. The method of claim 51 wherein, for cardiac events classified as non-overlapping, further classifying the cardiac events as Out-Equal if
  (i) the cardiac event has a beginning time that occurs before a start time of the matched neurological event, and
  (ii) the cardiac event has a termination time that is equal to the start time of the matched neurological event.

58. The method of claim 51 wherein, for cardiac events classified as non-overlapping, further classifying the cardiac events as Equal-Out if
  (i) the cardiac event has a beginning time that is equal to an end time of the matched neurological event, and
  (ii) the cardiac event has a termination time that occurs after the end time of the matched neurological event.

59. The method of claim 51 wherein, for cardiac events classified as non-overlapping, further classifying the cardiac events as Out-Out After Detect if
  (i) the cardiac event has a beginning time that occurs within a predetermined window of time after an end time of the matched neurological event.

60. The method of claim 51 wherein, for cardiac events classified as non-overlapping, further classifying the cardiac events as Out-Out Before Detect if
  (i) the cardiac event has a termination time that occurs within a predetermined window of time before a start time of the matched neurological event.

61. The method of claim 51 wherein, for cardiac events classified as non-overlapping, determining that the cardiac event may be predictive of a neurological event if the cardiac event has a termination time that occurs within a predetermined window of time before a start time of the neurological event.

62. A method of treating a nervous system disorder in a patient, the method comprising:
   sensing a brain signal from the patient;
   obtaining a neurological event detection signal, the neurological event detection signal indicating neurological events detected from the brain signal;
   sensing a cardiac signal from the patient;
   obtaining a cardiac event detection signal, the cardiac event detection signal indicating cardiac events detected from the cardiac signal;
   analyzing timing relationships between detected events, the detected events including detected neurological events and detected cardiac events;
   identifying a matched event when one of the detected neurological events is temporally related to one of the detected cardiac events;
   determining whether the cardiac event detection signal facilitates detection of neurological events based on matched events;
   classifying each matched event into one of two or more categories based upon the timing relationship between the cardiac and neurological events;
   assigning a weighting factor to each matched event based upon the category for each matched event;
   calculating a rate of concordance between the neurological and cardiac event detection signals utilizing the weighting factors, wherein calculating the rate of concordance comprises dividing a weighted sum of matched events by a number of detected neurological events;
   determining that the cardiac event detection signal facilitates detection of the neurological events when the rate of concordance exceeds a threshold; and
   delivering a therapy to the patient for treating a neurological disorder in response to a cardiac event if the cardiac event detection signal is determined to facilitate detection of neurological events.

63. The method of claim 62 wherein the weighting factor for matched events in which the cardiac event precedes the neurological event is greater than 1.

64. The method of claim 62 wherein the weighting factor for matched events in which the cardiac event follows the neurological event is less than 1.

65. An implantable medical device (IMD) for treating a neurological disorder in a patient, the device comprising:
   a biocompatible housing adapted to be implanted in a patient;
   a power source;
   a therapy module; and
   a processor, the processor being configured to
      receive a brain signal from the patient,
      derive a neurological event detection signal from the brain signal, the neurological event detection signal indicating detected neurological events in the patient,
      receive a cardiac signal from the patient,
      derive a cardiac event detection signal, the cardiac event detection signal indicating detected cardiac events in the patient,
      analyze timing relationships between detected neurological events and cardiac events before enabling therapy delivery for treating a neurological disorder in response to a cardiac event,
      identify a matched event when one of the detected neurological events is temporally related to one of the detected cardiac events,
      determine that the cardiac event detection signal facilitates detection of neurological events when the timing relationships between detected neurological events and detected cardiac events meet one or more predetermined criteria, and
      cause the therapy module to deliver a therapy to the patient in response to a cardiac event if the cardiac event detection signal is determined to facilitate detection of neurological events.

66. The IMD of claim 65 wherein a detected neurological event and a detected cardiac event are temporally matched if an elapsed time between a reference point of the detected neurological event and a reference point of the detected cardiac event is less than a predetermined amount.

67. The IMD of claim 65 wherein the processor is further configured to calculate a rate of concordance between the neurological and cardiac event detection signals, and determine that the cardiac event detection signal facilitates detection of the neurological events when the rate of concordance exceeds a threshold.

68. The IMD of claim 67 wherein the processor is further configured to enable use of the cardiac event detection signal to detect neurological events when the rate of concordance between the neurological and cardiac event detection signals exceeds the threshold.

69. The IMD of claim 68 wherein the processor is further configured to cause the therapy to be delivered to the patient in response to the detected cardiac events.

70. The IMD of claim 69 wherein the therapy comprises delivery of electrical stimulation to a brain of the patient.

71. The IMD of claim 65 wherein the processor is further configured to determine, for each of the matched events, a latency of the detected cardiac event with respect to a detected neurological event, and enable use of the cardiac event detection signal to detect neurological events when the latency of the detected cardiac events meets a predetermined criterion.

72. The IMD of claim 65 wherein the neurological event detection signal is generated by a seizure detection algorithm which uses an EEG signal as an input, and wherein a matched event causes a modification of the seizure detection algorithm.

73. An implantable medical device (IMD) for treating a neurological disorder in a patient, the device comprising:
   a biocompatible housing adapted to be implanted in a patient;
   a power source;
   a therapy module; and
   a processor, the processor being configured to
      receive a brain signal from the patient,
      derive a neurological event detection signal from the brain signal, the neurological event detection signal indicating detected neurological events in the patient,
      receive a cardiac signal from the patient,
      derive a cardiac event detection signal, the cardiac event detection signal indicating detected cardiac events in the patient,
      analyze timing relationships between detected neurological events and cardiac events,
      identify a matched event when one of the detected neurological events is temporally related to one of the detected cardiac events,
      determine whether the cardiac event detection signal facilitates detection of neurological events based on the matched events,
      calculate a rate of concordance between the neurological and cardiac event detection signals and determine that the cardiac event detection signal facilitates detection of the neurological events when the rate of concordance exceeds a threshold, wherein calculating the rate of concordance comprises dividing a number of matched events by a number of detected neurological events, and cause the therapy module to deliver a therapy to the patient in response to a cardiac event if the cardiac event detection signal is determined to facilitate detection of neurological events.

74. An implantable medical device (IMD) for treating a neurological disorder in a patient, the device comprising:
a biocompatible housing adapted to be implanted in a patient;
a power source;
a therapy module; and
a processor, the processor being adapted configured to
receive a brain signal from the patient,
derive a neurological event detection signal from the brain signal, the neurological event detection signal indicating detected neurological events in the patient,
receive a cardiac signal from the patient,
derive a cardiac event detection signal, the cardiac event detection signal indicating detected cardiac events in the patient,
analyze timing relationships between detected neurological events and cardiac events,
identify a matched event when one of the detected neurological events is temporally related to one of the detected cardiac events,
determine whether the cardiac event detection signal facilitates detection of neurological events based on the matched events,
identify a false positive event when one of the detected cardiac events is not temporally related to one of the detected neurological events,
calculate a false positive rate, the false positive rate being equal to a number of false positive events divided by a number of detected neurological events,
enable use of the cardiac event detection signal to detect neurological events when the false positive rate is below a predetermined level, and
cause the therapy module to deliver a therapy to the patient in response to a cardiac event if the cardiac event detection signal is determined to facilitate detection of neurological events.

75. An implantable medical device (IMD) for treating a neurological disorder in a patient, the device comprising:
a biocompatible housing adapted to be implanted in a patient;
a power source;
a therapy module; and
a processor, the processor being configured to
receive a brain signal from the patient,
derive a neurological event detection signal from the brain signal, the neurological event detection signal indicating detected neurological events in the patient,
receive a cardiac signal from the patient,
derive a cardiac event detection signal, the cardiac event detection signal indicating detected cardiac events in the patient,
analyze timing relationships between detected neurological events and cardiac events,
identify a matched event when one of the detected neurological events is temporally related to one of the detected cardiac events,
determine whether the cardiac event detection signal facilitates detection of neurological events based on the matched events,
identify a false positive event when one of the detected cardiac events is not temporally related to one of the detected neurological events,
calculate a false positive rate, the false positive rate being equal to a number of false positive events per unit of time,
enable use of the cardiac event detection signal to detect neurological events when the false positive rate is below a predetermined level, and
cause the therapy module to deliver a therapy to the patient in response to a cardiac event if the cardiac event detection signal is determined to facilitate detection of neurological events.

76. An implantable medical device (IMD) for treating a neurological disorder in a patient, the device comprising:
a biocompatible housing adapted to be implanted in a patient;
a power source;
a therapy module; and
a processor, the processor being configured to
receive a brain signal from the patient,
derive a neurological event detection signal from the brain signal, the neurological event detection signal indicating detected neurological events in the patient,
receive a cardiac signal from the patient,
derive a cardiac event detection signal, the cardiac event detection signal indicating detected cardiac events in the patient,
analyze timing relationships between detected neurological events and cardiac events,
identify a matched event when one of the detected neurological events is temporally related to one of the detected cardiac events,
determine whether the cardiac event detection signal facilitates detection of neurological events based on the matched events,
calculate a false negative rate, the false negative rate being equal to a number of false negative events divided by a number of detected neurological events,
enable use of the cardiac event detection signal to detect neurological events when the false negative rate is below a predetermined level, and
cause the therapy module to deliver a therapy to the patient in response to a cardiac event if the cardiac event detection signal is determined to facilitate detection of neurological events.

77. A non-transitory computer-readable medium programmed with instructions for performing a method of treating a neurological disorder in a patient, the medium comprising instructions for causing a programmable processor to:
obtain a neurological event detection signal, the neurological event detection signal indicating neurological events detected in a brain signal from the patient;
obtain a cardiac event detection signal, the cardiac event detection signal indicating detected cardiac events in the patient;
analyze timing relationships between detected neurological events and cardiac events before enabling therapy delivery for treating a neurological disorder in response to a cardiac event;
identify a matched event when one of the detected neurological events is temporally related to one of the detected cardiac events;
determine that the cardiac event detection signal facilitates detection of neurological events when the timing relationships between detected neurological events and detected cardiac events meet one or more predetermined criteria; and cause a neurological therapy to be delivered to the patient in response to a detected cardiac event if the cardiac event detection signal is determined to facilitate detection of neurological events.

78. A system for treating a neurological disorder in a patient, the system comprising:

communication means for obtaining a neurological event detection signal and a cardiac event detection signal, the neurological event detection signal indicating detected neurological events in the patient, the cardiac event detection signal indicating detected cardiac events in the patient; and a processor for analyzing timing relationships between detected neurological events and cardiac events, said processor being configured to analyze timing relationships between detected neurological events and detected cardiac events before enabling therapy delivery for treating a neurological disorder in response to a cardiac event, identify a matched event when one of the detected neurological events is temporally related to one of the detected cardiac events, determine that the cardiac event detection signal facilitates detection of neurological events when the timing relationships between detected neurological events and detected cardiac events meet one or more predetermined criteria, and cause delivery of a therapy to the patient for treating the neurological disorder in response to a detected cardiac event if the cardiac event detection signal is determined to facilitate detection of neurological events.

79. A method of treating a nervous system disorder in a patient, the method comprising:

sensing a brain signal from the patient;

obtaining a neurological event detection signal, the neurological event detection signal indicating neurological events detected from the brain signal;

sensing a cardiac signal from the patient;

obtaining a cardiac event detection signal, the cardiac event detection signal indicating cardiac events detected from the cardiac signal;

analyzing timing relationships between a minimum number of detected neurological events and detected cardiac events before enabling therapy delivery for treating a nervous system disorder in response to a cardiac event;

determining whether the cardiac event detection signal facilitates detection of neurological events based on the timing relationships between detected neurological events and detected cardiac events; and delivering a therapy to the patient for treating the nervous system disorder in response to a cardiac event if the cardiac event detection signal is determined to facilitate detection of neurological events.

* * * * *